US010513686B2

(12) United States Patent
Ostertag et al.

(10) Patent No.: US 10,513,686 B2
(45) Date of Patent: Dec. 24, 2019

(54) MODIFIED STEM CELL MEMORY T CELLS, METHODS OF MAKING AND METHODS OF USING SAME

(71) Applicant: Poseida Therapeutics, Inc., San Diego, CA (US)

(72) Inventors: Eric Ostertag, San Diego, CA (US); Devon Shedlock, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/156,889

(22) Filed: Oct. 10, 2018

(65) Prior Publication Data
US 2019/0119640 A1  Apr. 25, 2019

Related U.S. Application Data

(63) Continuation of application No. 15/885,706, filed on Jan. 31, 2018, which is a continuation of application No. 15/790,792, filed on Oct. 23, 2017, which is a continuation of application No. PCT/US2017/054799, filed on Oct. 2, 2017.

(60) Provisional application No. 62/402,707, filed on Sep. 30, 2016, provisional application No. 62/502,508, filed on May 5, 2017, provisional application No. 62/553,058, filed on Aug. 31, 2017, provisional application No. 62/556,309, filed on Sep. 8, 2017.

(51) Int. Cl.
*C12N 15/85* (2006.01)
*C12N 5/0783* (2010.01)
*C12N 5/0789* (2010.01)
*C07K 14/725* (2006.01)

(52) U.S. Cl.
CPC ........ *C12N 5/0636* (2013.01); *C07K 14/7051* (2013.01); *C12N 5/0647* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,122,464 A | 6/1992 | Wilson et al. | |
| 5,168,062 A | 12/1992 | Stinski | |
| 5,266,491 A | 11/1993 | Nagata et al. | |
| 5,385,839 A | 1/1995 | Stinski | |
| 5,580,734 A | 12/1996 | Treco et al. | |
| 5,641,670 A | 6/1997 | Treco et al. | |
| 5,733,761 A | 3/1998 | Treco et al. | |
| 5,770,359 A | 6/1998 | Wilson et al. | |
| 5,827,739 A | 10/1998 | Wilson et al. | |
| 6,218,185 B1 | 4/2001 | Fraser et al. | |
| 6,551,825 B1 | 4/2003 | Fraser et al. | |
| 6,835,394 B1 | 12/2004 | Discher et al. | |
| 6,962,810 B2 | 11/2005 | Fraser et al. | |
| 7,105,343 B1 | 9/2006 | Fraser et al. | |
| 7,217,427 B2 | 5/2007 | Discher et al. | |
| 7,867,512 B2 | 1/2011 | Discher et al. | |
| 8,278,419 B2 | 10/2012 | Jacobs et al. | |
| 8,399,643 B2 | 3/2013 | Ostertag et al. | |
| 8,569,227 B2 | 10/2013 | Jabobs | |
| 9,200,059 B2 | 12/2015 | Jacobs et al. | |
| 9,234,029 B2 | 1/2016 | Jacobs | |
| 9,428,767 B2 | 8/2016 | Minshull et al. | |
| 9,534,234 B2 | 1/2017 | Minshull et al. | |
| 9,546,382 B2 | 1/2017 | Ostertag et al. | |
| 9,574,209 B2 | 2/2017 | Minshull et al. | |
| 9,580,697 B2 | 2/2017 | Minshull et al. | |
| 9,670,503 B2 | 6/2017 | Craig | |
| 9,783,790 B2 | 10/2017 | Craig | |
| 9,982,253 B2 | 5/2018 | Jacobs | |
| 10,040,842 B2 | 8/2018 | Jacobs et al. | |
| 10,041,077 B2 | 8/2018 | Minshull et al. | |
| 10,329,543 B2 | 6/2019 | Ostertag et al. | |
| 2010/0221824 A1 | 9/2010 | Fraser et al. | |
| 2015/0104808 A1 | 4/2015 | Jacobs et al. | |
| 2017/0166874 A1 | 6/2017 | Ostertag et al. | |
| 2017/0183407 A1 | 6/2017 | Cooper | |
| 2017/0226531 A1 | 8/2017 | Craig | |
| 2018/0009891 A1 | 1/2018 | Jensen | |
| 2018/0072999 A1 | 3/2018 | Craig | |
| 2018/0142219 A1 | 5/2018 | Ostertag et al. | |
| 2018/0289742 A1 | 10/2018 | Nishio et al. | |
| 2018/0318349 A1 | 11/2018 | Thompson | |
| 2019/0119636 A1 | 4/2019 | Ostertag et al. | |
| 2019/0119637 A1 | 4/2019 | Ostertag et al. | |

FOREIGN PATENT DOCUMENTS

| | | |
|---|---|---|
| EP | 3018200 A1 | 5/2016 |
| WO | WO 2010/051274 A2 | 5/2010 |
| WO | WO 2010/099296 | 9/2010 |
| WO | WO 2010/099301 A2 | 9/2010 |
| WO | WO 2011/133635 | 10/2011 |
| WO | WO 2011/137319 A2 | 11/2011 |
| WO | WO 2012/094679 | 7/2012 |
| WO | WO 2012/168304 A1 | 12/2012 |
| WO | WO 2013/012824 A2 | 1/2013 |
| WO | WO 2013/123061 A1 | 8/2013 |
| WO | WO 2014/078819 A2 | 5/2014 |
| WO | WO 2015/057545 A2 | 4/2015 |
| WO | WO 2015/195798 A1 | 12/2015 |
| WO | WO 2015/195803 A1 | 12/2015 |
| WO | WO 2016/011210 A2 | 1/2016 |
| WO | WO 2016/022805 | 2/2016 |
| WO | WO 2016/090111 | 6/2016 |
| WO | WO 2016/205554 A1 | 12/2016 |
| WO | WO 2017/004498 | 1/2017 |
| WO | WO 2017/004509 | 1/2017 |
| WO | WO 2017/061615 | 4/2017 |

(Continued)

OTHER PUBLICATIONS

US 5,733,746 A, 03/1998, Treco et al. (withdrawn)

(Continued)

*Primary Examiner* — Michail A Belyavskyi
(74) *Attorney, Agent, or Firm* — Cooley LLP; Ivor Elrifi; Matthew Pavao

(57) ABSTRACT

The disclosure provides a method of producing modified stem memory T cells (e.g. CAR-T cells) for administration to a subject as, for example an adoptive cell therapy.

30 Claims, 31 Drawing Sheets

Specification includes a Sequence Listing.

(56) References Cited

FOREIGN PATENT DOCUMENTS

| WO | WO 2017/079703 A1 | 5/2017 |
|----|-------------------|--------|
| WO | WO 2017/147538    | 8/2017 |
| WO | WO 2017/190091 A1 | 12/2017 |
| WO | WO 2018/014038 A1 | 1/2018 |
| WO | WO 2018/014039 A1 | 1/2018 |

OTHER PUBLICATIONS

Grabundzija, I., et al. "A Heltiron transposon reconstructed from bats reveals a novel mechanism of genome shuffling in eukaryotes", Nature Communications, Mar. 2, 2016; 7:10716.doi; 10.1038/ncomms10716.

Philip, B et al. A highly compact epitope-based marker/suicide gene for easier and safer T-cell therapy. Blood, Aug. 21, 2014; 124(8): 1277-87.

Sprague et al. Expression of a recombinant DNA gene coding for the vesicular stomatitis virus nucleocapsid protein. Feb. 1983; J. Virol 45: 773-781.

Yozo Nakazawa et al., "Evaluation of long-term transgene expression in piggyBac-modified human T lymphocytes", J of Immunotherapy, Jan. 2013 vol. 36, pp. 3-10.

Harjeet Singh, et al., "Third Generation Chimeric Antigen Receptors Containing CD137 or CD134 Signaling Endomains Augment CD19-Specific T-Cell Effector Function", Blood Journal, BLOOD, vol. 114, No. 22, Nov. 20, 2009, p. 4097.

Burton Earle Barnett, et al., "piggyBacTM-Produced CAR-T Cells Exhibit Stem-Cell Memory Phenotype", BLOOD, vol. 128, No. 22, Dec. 2, 2016, p. 2167.

Lenka V. Hurton, et al., "Tethered IL-15 augments antitumor activity and promotes a stem-cell memory subset in tumor-specific T cells", Proceedings of the National Academy of Sciences PNAS, vol. 113, No. 48, Nov. 14, 2016, pp. E7788-E7797.

Jennielle Jobson, et al., (May 11, 2017) "T Cells Can Serve as a Vehicle for Factor IX Gene Replacement" Poster presented at the American Society of Gene & Cell Therapy 20$^{th}$ Annual Meeting, Washington, DC, May 10-13, 2017, 1 page.

Jobson, J. et al. (May 2017) "T Cells can Serve as a Vehicle for Factor IX Gene Replacement", Mol Ther, 25(5SI):178, Abstract 385.

Sambrook et al., Molecular Cloning: A Laboratory Manual, 2$^{nd}$ Edition, Cold Spring Harbor, N.Y. (1989), sections 17.37-17.42.

Smith, L. J. et al. Human interleukin 4. The solution structure of a four-helix bundle protein, J. Mol. Biol. 224(4): 899-904; (Apr. 20, 1992).

de Vos, A.M. et al. Human growth hormone and extracellular domain of its receptor: crystal structure of the complex. Science 255(5042): 306-312; Jan. 17, (1992).

Kyte et al., A simple method for displaying the hydropathic character of a protein. J. Mol Biol. 157(1): 105-132; May 5, (1982).

Lehninger, Biochemistry, Second Edition; Worth Publishers, Inc. NY, N.Y. (1975), pp. 71-77.

Tatusova, T.A. and Madden, T. L. BLAST 2 Sequences, a new tool for comparing protein and nucleotide sequences. FEMS Microbiol Lett, 174(2): 247-250; May 15, (1999).

Gattinoni et al. A human memory T cell subset with stem cell-like properties. Nature Methods Sep. 18, (2011); 17(10): 1290-7.

Cunningham, B.C. and Wells, J.A. High-resolution epitope mapping of Hgh-Reptor interactions by alanine-scanning mutagenesis. Science 244(4908): 1081-1085; Jun. 2, 1989.

Sabatino, M. et al., (Jul. 2016) "Generation of clinical-grade CD19-specific CAR-modified CD8+memory stem cells for the treatment of human B-cell malignancies" Blood, 128(4): 519-528.

Sigma-Aldrich, Inc. (2019) "RPMI-1640 Media", Product Information Sheet [online]. Retrieved from the Internet: https://www.sigmaaldrich.com/content/dam/sigma-aldrich/docs/Sigma/Formulation/r8758for.pdf; retrieved on Jan. 9, 2019, 4 pages.

FIG. 6C

| | CARTyrin+ | GFP+ |
|---|---|---|
| WT piggyBac | 3.4% | 8.6% |
| Super piggyBac | 15.8% | 28.4% |
| Fold Increase | 4.7 | 3.3 |

FIG. 14D pHR-GFP.Selection Gene: (between 5' and 3' CRISPR Sites)
ggggccactagggacaggatcggcgtgcttcactcgctgggttccctttttccttctccttctggggcctgtgccat
ctctcgtttcttaggatggccttctccgacggatgtctcccttgcgtcccgcctcccttcttgtaggcctgcat
catcaccgttttctggacaaccccaaagtacccgtctccctggcttagccacctctccatcctcttgcttc
tttgcctggacaccccgttctcctgtggattcgggtcacctctcactccttcatttgggcagctccctacccc
ccttacctctctagtctgtgctagctcttccagcccctgtcatggcatcttccaggggtccgagagctcagcta
gtcttcttcctccaacccggggccctatgtccacttcaggacagcatgtttgctgcctccagggatcctgtgtcc
ccgagctgggaccacctatattcccagggccggttaatgtggctctggttctgggtactttatctgtcccgac
gtccgatcgaaccatggacagttagctttgcaaagatggataaagttttaaacagagaggaatctttgcagctaa
tggaccttctaggtcttgaaaggagtgggaattggctccggtgcccgtcagtgggcagagcgcacatcgcccaca
gtccccgagaagttggggggagggtcggcaattgaaccggtgcctagagaaggtggcgcggggtaaactgggaa
agtgatgtcgtgtactggctccgcctttttcccgagggtgggggagaaccgtatataagtgcagtagtcgccgtg
aacgttcttttcgcaacgggtttgccgccagaacacaggtaagtgccgtgtgtggttcccgcgggcctggcctc
tttacgggttatggcccttgcgtgccttgaattacttccacctggctgcagtacgtgattcttgatcccgagctt
cgggttggaagtgggtgggagagttcgaggccttgcgcttaaggagcccctcgcctcgtgcttgagttgaggcc
tggcctgggcgctggggccgccgcgtgcgaatctggtggcaccttcgcgcctgtctcgctgctttcgataagtct
ctagccatttaaaatttttgatgacctgctgcgacgcttttttctggcaagatagtcttgtaaatgcgggccaa
gatctgcacactggtatttcggttttttggggccgcgggcggcgacggggcccgtgcgtcccagcgcacatgttcg
gcgaggcggggcctgcgagcgcggccacccgagaatcggacggggggtagtctcaagctggccggcctgctctggtg
cctggcctcgcgccgccgtgtatcgccccgccctggcggcaaggctggccccggtcggcaccagttgcgtgagcg
gaaagatggccgcttcccggccctgctgcagggagctcaaaatggaggacgcggcgctcgggagagcgggcgggt
gagtcacccacacaaaggaaaaggggcctttccgtcctcagccgtcgcttcatgtgactccacggagtaccgggcg
ccgtccaggcacctcgattagttctcgagcttttggagtacgtcgtctttaggttgggggggaggggttttatgcg
atggagtttccccacactgagtgggtggagactgaagttaggccagcttggcacttgatgtaattctccttggaa
tttgcccttttttgagtttggatcttggttcattctcaagcctcagacagtggttcaaagttttttttcttccattt
caggtgtcgtgagaattctaatacgactcactatagggtgtgctgtctcatcatttggcaaagattggccacca
agcttaccgccatggtgagcaagggcgaggagctgttcaccggggtggtgcccatcctggtcgagctggacggcg
acgtaaacggccacaagttcagcgtgtccggcgagggcgagggcgatgccacctacggcaagctgaccctgaagt
tcatctgcaccaccggcaagctgcccgtgccctggcccaccctcgtgaccaccctgacctacggcgtgcagtgct
tcagccgctaccccgaccacatgaagcagcacgacttcttcaagtccgccatgcccgaaggctacgtccaggagc
gcaccatcttcttcaaggacgacggcaactacaagacccgcgccgaggtgaagttcgagggcgacacccctggtga
accgcatcgagctgaagggcatcgacttcaaggaggacggcaacatcctggggcacaagctggagtacaactaca
acagccacaacgtctatatcatggccgacaagcagaagaacggcatcaaggtgaacttcaagatccgccacaaca
tcgaggacggcagcgtgcagctcgccgaccactaccagcagaacacccccatcggcgacggccccgtgctgctgc
ccgacaaccactacctgagcacccagtccgccctgagcaaagaccccaacgagaagcgtgatcacatggtcctgc
tggagttcgtgaccgccgcgggatcactctcggcatggacgagctgtacaaggaaggaagaggcagcctgctga
catgtggcgacgtggaggagaaccctggcccaatggtgggcagcctgaattgtatcgtggccgtgtcccagaaca
tgggcatcggcaagaatggcgattttccttggccccctctgagaaatgagtccagatactttcagaggatgacca
caaccagctccgtggagggcaagcagaacctggtcatcatgggcaagaagacatggttctctatcccagagaaga
accgccccctgaagggccggatcaatctggtgctgagcagggagctgaaggagccaccccagggagcacactttc
tgtccaggtctctggacgatgccctgaagctgaccgagcagcctgagctggccaacaaggtggacatggtgtgga
tcgtgggcggctctagcgtgtataaggaggccatgaatcaccctggccacctgaagctgttcgtgacacggatca
tgcaggactttgagtccgatacctttcttccagagatcgacctggagaagtacaagctgctgcccgagtatcctg
gcgtgctgtctgatgtgcaggaggagaagggcatcaagtacaagttcgaggtgtatgagaagaacgattgataac
atatgcctttaattaaacactagttctatagtgtcacctaaattcccttagtgagggttaatggccgtaggccg
ccagaattgggtccagacatgataagatacattgatgagtttggacaaaccacaactagaatgcagtgaaaaaaa
tgctttatttgtgaaatttgtgatgctattgctttatttgtaaccattataagctgcaataaacaagttaacaac
aacaattgcattcatttatgtttcaggttcaggggggggtgtgggaggttttttcggactctaggacctgcgca
tgcgcttggggtacctaggatatcgacagaaaagccccatccttaggcctcctccttcctagtctcctgatattg
ggtctaaccccacctcctgttaggcagattccttatctggtgacacaccccatttcctggagccatctctctc
cttgccagaacctctaaggtttgcttacgatggagccagagaggatcctgggagggagagcttggcagggggtgg
gagggaagggggggatgcgtgacctgcccggttctcagtggccaccctgcgctaccctctcccagaacctgagct
gctctgacgcggccgtctggtgcgtttcactgatcctggtgctgcagcttccttacacttcccaagaggagaagc
agtttggaaaaacaaaatcagaataagttggtcctgagttctaactttggctcttcacctttctagtccccaatt
tatattgttcctccgtgcgtcagttttacctgtgagataaggccagtagccagccccgtcctggcagggctgtgc
ctctagggacaggattggtgacg (SEQ ID NO: 41)

FIG. 14E pMMEJ-GFP.Selection Gene: (between 5' and 3' CRISPR Sites)
ccaatcctgtccctagtggccccactgtggggacgtccgatcgaaccatggacagttagctttgcaaagatggat
aaagttttaaacagagaggaatctttgcagctaatggaccttctaggtcttgaaaggagtgggaattggctccgg
tgcccgtcagtgggcagagcgcacatcgcccacagtccccgagaagttgggggagggggtcggcaattgaaccgg
tgcctagagaaggtggcgcggggtaaactgggaaagtgatgtcgtgtactggctccgccttttttcccgagggtgg
gggagaaccgtatataagtgcagtagtcgccgtgaacgttcttttttcgcaacgggtttgccgccagaacacaggt
aagtgccgtgtgtggttcccgcggggcctggcctctttacgggttatggcccttgcgtgccttgaattacttccac
ctggctgcagtacgtgattcttgatcccgagcttcgggttggaagtgggtgggagagttcgaggccttgcgctta
aggagccccttcgcctcgtgcttgagttgaggcctggcctgggcgctggggccgccgcgtgcgaatctggtggca
ccttcgcgcctgtctcgctgctttcgataagtctctagccatttaaaattttttgatgacctgctgcgacgctttt
tttctggcaagatagtcttgtaaatgcgggccaagatctgcacactggtatttcggttttttggggccgcgggcgg
cgacggggcccgtgcgtcccagcgcacatgttcggcgaggcggggcctgcgagcgcggccaccgagaatcggacg
ggggtagtctcaagctggccggcctgctctggtgcctggcctcgcgccgcgtgtatcgccccgcctgggcggc
aaggctggccccggtcggcaccagttgcgtgagcggaaagatggccgcttccggccctgctgcagggagctcaaa
atggaggacgcggcgctcgggagagcgggcgggtgagtcacccacacaaaggaaaagggcctttccgtcctcagc
cgtcgcttcatgtgactccacggagtaccgggcgccgtccaggcacctcgattagttctcgagcttttggagtac
gtcgtctttaggttgggggaggggttttatgcgatggagtttccccacactgagtgggtggagactgaagttag
gccagcttggcacttgatgtaattctccttggaatttgccctttttgagtttggatcttggttcattctcaagcc
tcagacagtggttcaaagtttttttcttccatttcaggtgtcgtgagaattctaatacgactcactatagggtgt
gctgtctcatcatttggcaaagattggccaccaagcttaccgccatggtgagcaagggcgaggagctgttcacc
ggggtggtgcccatcctggtcgagctggacggcgacgtaaacggccacaagttcagcgtgtccggcgagggcgag
ggcgatgccacctacggcaagctgaccctgaagttcatctgcaccaccggcaagctgcccgtgccctggcccacc
ctcgtgaccaccctgacctacggcgtgcagtgcttcagccgctaccccgaccacatgaagcagcacgacttcttc
aagtccgccatgcccgaaggctacgtccaggagcgcaccatcttcttcaaggacgacggcaactacaagacccgc
gccgaggtgaagttcgagggcgacaccctggtgaaccgcatcgagctgaagggcatcgacttcaaggaggacggc
aacatcctggggcacaagctggagtacaactacaacagccacaacgtctatatcatggccgacaagcagaagaac
ggcatcaaggtgaacttcaagatccgccacaacatcgaggacggcagcgtgcagctcgccgaccactaccagcag
aacacccccatcggcgacggccccgtgctgctgcccgacaaccactacctgagcacccagtccgccctgagcaaa
gaccccaacgagaagcgtgatcacatggtcctgctggagttcgtgaccgccgccgggatcactctcggcatggac
gagctgtacaaggaaggaagaggcagcctgctgacatgtggcgacgtggaggagaaccctggcccaatggtgggc
agcctgaattgtatcgtggccgtgtcccagaacatgggcatcggcaagaatggcgattttccttggcccccctctg
agaaatgagtccagatactttcagaggatgaccacaaccagctccgtggagggcaagcagaacctggtcatcatg
ggcaagaagacatggttctctatcccagagaagaaccgccccctgaagggccggatcaatctggtgctgagcagg
gagctgaaggagccaccccagggagcacactttctgtccaggtctctggacgatgccctgaagctgaccgagcag
cctgagctggccaacaaggtggacatggtgtggatcgtgggcggctctagcgtgtataaggaggccatgaatcac
cctggccacctgaagctgttcgtgacacggatcatgcaggactttgagtccgataccttctttccagagatcgac
ctggagaagtacaagctgctgcccgagtatcctggcgtgctgtctgatgtgcaggaggagaagggcatcaagtac
aagttcgaggtgtatgagaagaacgattgataacatatgcctttaattaaacactagttctatagtgtcaccctaa
attccctttagtgagggttaatggccgtaggccgccagaattgggtccagacatgataagatacattgatgagtt
tggacaaaccacaactagaatgcagtgaaaaaatgctttatttgtgaaatttgtgatgctattgctttatttgt
aaccattataagctgcaataaacaagttaacaacaacaattgcattcatttatgtttcaggttcaggggaggt
gtgggaggttttttcggactctaggacctgcgcatgcgcttggggtacctaggatatcggatgggcttttctgt
caccaatcctgagg (SEQ ID NO: 42)

MODIFIED STEM CELL MEMORY T CELLS, METHODS OF MAKING AND METHODS OF USING SAME

RELATED APPLICATIONS

This application is a Continuation Application of U.S. application Ser. No. 15/885,706, filed on Jan. 31, 2018, which is a Continuation Application of U.S. application Ser. No. 15/790,792, filed on Oct. 23, 2017, which is a Continuation Application of International Application No. PCT/US2017/054799 filed on Oct. 2, 2017, which claims the benefit of US Provisional Applications U.S. Ser. No. 62/402,707 filed Sep. 30, 2016, U.S. Ser. No. 62/502,508 filed May 5, 2017, U.S. Ser. No. 62/553,058 filed Aug. 31, 2017 and U.S. Ser. No. 62/556,309 filed Sep. 8, 2017, the contents of each of which are herein incorporated by reference in their entirety.

INCORPORATION OF SEQUENCE LISTING

The contents of the text filed named "POTH-012_C04US_SeqList.txt", which was created on Oct. 10, 2018 and is 111 KB in size, are hereby incorporated by reference in their entirety.

FIELD OF THE DISCLOSURE

The disclosure is directed to molecular biology, and more, specifically, to methods of making and using modified stem-cell memory T cells.

BACKGROUND

There has been a long-felt but unmet need in the art for a method of producing modified stem-cell memory T cells for administration to a subject as, for example, an adoptive cell therapy. The disclosure provides a solution to this long-felt but unmet need.

SUMMARY

Unlike traditional biologics and chemotherapeutics, modified-T cells of the disclosure possess the capacity to rapidly reproduce upon antigen recognition, thereby potentially obviating the need for repeat treatments. To achieve this, modified-T cells of the disclosure must not only drive tumor destruction initially, but must also persist in the patient as a stable population of viable memory T cells to prevent potential cancer relapses. Thus, intensive efforts have been focused on the development of antigen receptor molecules that do not cause T cell exhaustion through antigen-independent (tonic) signaling, as well as of a modified-T cell product containing early memory cells, especially stem cell memory ($T_{SCM}$). Stem cell-like modified-T cells of the disclosure exhibit the greatest capacity for self-renewal and multipotent capacity to derive central memory ($T_{CM}$), effector memory ($T_{EM}$) and effector T cells ($T_E$), thereby producing better tumor eradication and long-term modified-T cell engraftment. Modified-T cells of the disclosure include, but are not limited to, those cells that express an antigen receptor comprising a protein scaffold of the disclosure. Modified-T cells of the disclosure include, but are not limited to, those cells that express a chimeric antigen receptor (CAR) (i.e. CAR-T cells of the disclosure). Chimeric antigen receptors (CARs) of the disclosure may comprise one or more sequences that each specifically bind an antigen, including, but not limited to, a single chain antibody (e.g. a scFv), a sequence comprising one or more fragments of an antibody (e.g. a VHH, referred to in the context of a CAR as a VCAR), an antibody mimic, and a Centyrin (referred to in the context of a CAR as a CARTyrin).

Modified cells of the disclosure may be further subjected to genomic editing. For example, a genomic editing construct may be introduced into the modified cells of the disclosure in a transposon or other means of delivery through electroporation or nucleofection and allowed to integrate into the genome of the cell during the following incubation phase. The resultant cell is a modified T cell with an edited genome that retains a stem-like phenotype. This modified T cell with an edited genome that retains a stem-like phenotype may be used as a cellular therapy. Alternatively, or in addition, modified cells of the disclosure may be subject to a first electroporation or nucleofection and a subsequent electroporation or nucleofection to introduce a genomic editing construct.

Specifically, the disclosure provides a method of producing a modified stem memory T cell ($T_{SCM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified T cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising introducing into a plurality of primary human T cell (a) a transposon composition comprising a transposon comprising an antigen receptor or a therapeutic protein and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 25% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 50% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 60% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 75% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 80% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 85% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 90% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 95% of the plurality of modified T cells expresses one or more cell-surface marker(s) of a stem memory T cell ($T_{SCM}$), thereby producing a plurality of modified stem memory T cells ($T_{SCM}$). In certain embodiments, the cell-surface markers comprise CD62L and CD45RA. In certain embodiments, the cell-surface markers of the CAR-$T_{SCM}$ comprise one or more of CD62L, CD45RA, CD28, CCR7, CD127, CD45RO, CD95, CD95 and IL-2Rβ. In certain embodiments, the cell-surface markers of the CAR-$T_{SCM}$ comprise one or more of CD45RA, CD95, IL-2Rβ, CR7, and CD62L. In certain embodiments of this method, the transposon is a plasmid DNA transposon with a sequence encoding the antigen receptor or the therapeutic protein is flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase.

In certain embodiments of the methods of the disclosure, the transposon is a plasmid DNA transposon with a sequence encoding the antigen receptor or the therapeutic protein is flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

```
                                                               (SEQ ID NO: 4)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substitution at one or more of positions 30, 165, 282, or 538 of the sequence:

```
                                                               (SEQ ID NO: 4)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments, the transposase enzyme is a piggyBac™ (PB) transposase enzyme that comprises or consists of an amino acid sequence having an amino acid substitution at two or more of positions 30, 165, 282, or 538 of the sequence of SEQ ID NO: 4. In certain embodiments, the transposase enzyme is a piggyBac™ (PB) transposase enzyme that comprises or consists of an amino acid sequence having an amino acid substitution at three or more of positions 30, 165, 282, or 538 of the sequence of SEQ ID NO: 4. In certain embodiments, the transposase enzyme is a piggyBac™ (PB) transposase enzyme that comprises or consists of an amino acid sequence having an amino acid substitution at each of the following positions 30, 165, 282, and 538 of the sequence of SEQ ID NO: 4. In certain embodiments, the amino acid substitution at position 30 of the sequence of SEQ ID NO: 4 is a substitution of a valine (V) for an isoleucine (I). In certain embodiments, the amino acid substitution at position 165 of the sequence of SEQ ID NO: 4 is a substitution of a serine (S) for a glycine (G). In certain embodiments, the amino acid substitution at position 282 of the sequence of SEQ ID NO: 4 is a substitution of a valine (V) for a methionine (M). In certain embodiments, the amino acid substitution at position 538 of the sequence of SEQ ID NO: 4 is a substitution of a lysine (K) for an asparagine (N).

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 4 wherein the amino acid substitution at position 30 is a substitution of a valine (V) for an isoleucine (I), the amino acid substitution at position 165 is a substitution of a serine (S) for a glycine (G), the amino acid substitution at position 282 is a substitution of a valine (V) for a methionine (M), and the amino acid substitution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

```
                                                                     (SEQ ID NO: 5)
  1 MGSSLDDEHI LSALLQSDDE LVGEDSDSEV SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTSATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RVYIPNKPSK YGIKILMMCD

301 SGTKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPKEV

541 PGTSDDSTEE PVMKKRTYCT YCPSKIRRKA NASCKKCKKV ICREHNIDMC QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 4 or SEQ ID NO: 5. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 4 or SEQ ID NO: 5 is a substitution of an asparagine (N) for a serine (S). In certain embodiments, the amino acid substitution at position 46 of SEQ ID NO: 4 or SEQ ID NO: 5 is a substitution of a serine (S) for an alanine (A). In certain embodiments, the amino acid substitution at position 46 of SEQ ID NO: 4 or SEQ ID NO: 5 is a substitution of a threonine (T) for an alanine (A). In certain embodiments, the amino acid substitution at position 82 of SEQ ID NO: 4 or SEQ ID NO: 5 is a substitution of a tryptophan (W) for an isoleucine (I). In certain embodiments, the amino acid substitution at position 103 of SEQ ID NO: 4 or SEQ ID NO: 5 is a substitution of a proline (P) for a serine (S). In certain embodiments, the amino acid substitution at position 119 of SEQ ID NO: 4 or SEQ ID NO: 5 is a substitution of a proline (P) for an arginine (R). In certain embodiments, the amino acid substitution at position 125 of SEQ ID NO: 4 or SEQ ID NO: 5 is a substitution of an alanine (A) a cysteine (C). In certain embodiments, the amino acid substitution at position 125 of SEQ ID NO: 4 or SEQ ID NO: 5 is a substitution of a leucine (L) for a cysteine (C). In certain embodiments, the amino acid substitution at position 177 of SEQ ID NO: 4 or SEQ ID NO: 5 is a substitution of a lysine (K) for a tyrosine (Y). In certain embodiments, the amino acid substitution at position 177 of SEQ ID NO: 4 or SEQ ID NO: 5 is a substitution of a histidine (H) for a tyrosine (Y). In certain embodiments, the amino acid substitution at position 180 of SEQ ID NO: 4 or SEQ ID NO: 5 is a substitution of a leucine (L) for a phenylalanine (F). In certain embodiments, the amino acid substitution at position 180 of SEQ ID NO: 4 or SEQ ID NO: 5 is a substitution of an isoleucine (I) for a phenylalanine (F). In certain embodiments, the amino acid substitution at position 180 of SEQ ID NO: 4 or SEQ ID NO: 5 is a substitution of a valine (V) for a phenylalanine (F). In certain embodiments, the amino acid substitution at position 185 of SEQ ID NO: 4 or SEQ ID NO: 5 is a substitution of a leucine (L) for a methionine (M). In certain embodiments, the amino acid substitution at position 187 of SEQ ID NO: 4 or SEQ ID NO: 5 is a substitution of a glycine (G) for an alanine (A). In certain embodiments, the amino acid substitution at position 200 of SEQ ID NO: 4 or SEQ ID NO: 5 is a substitution of a tryptophan (W) for a phenylalanine (F), In certain embodiments, the amino acid substitution at position 207 of SEQ ID NO: 4 or SEQ ID NO: 5 is a substitution of a proline (P) for a valine (V). In certain embodiments, the amino acid substitution at position 209 of SEQ ID NO: 4 or SEQ ID NO: 5 is a substitution of a phenylalanine (F) for a valine (V). In certain embodiments, the amino acid substitution at position 226 of SEQ ID NO: 4 or SEQ ID NO: 5 is a substitution of a phenylalanine (F) for a methionine (M). In certain embodiments, the amino acid substitution at position 235 of SEQ ID NO: 4 or SEQ ID NO: 5 is a substitution of an arginine (R) for a leucine (L). In certain embodiments, the amino acid substitution at position 240 of SEQ ID NO: 4 or SEQ ID NO: 5 is a substitution of a lysine (K) for a valine (V). In certain embodiments, the amino acid substitution at position 241 of SEQ ID NO: 4 or SEQ ID NO: 5 is a substitution of a leucine (L) for a phenylalanine (F). In certain embodiments, the amino acid substitution at position 243 of SEQ ID NO: 4 or SEQ ID NO: 5 is a substitution of a lysine (K) for a proline (P). In certain embodiments, the amino acid substitution at position 258 of SEQ ID NO: 4 or SEQ ID NO: 5 is a substitution of a serine (S) for an asparagine (N). In certain embodiments, the amino acid substitution at position 296 of SEQ ID NO: 4 or SEQ ID NO: 5 is a substitution of a tryptophan (W) for a leucine (L). In certain embodiments, the amino acid substitution at position 296 of SEQ ID NO: 4 or SEQ ID NO: 5 is a substitution of a tyrosine (Y) for a leucine (L). In certain embodiments, the amino acid substitution at position 296 of SEQ ID NO: 4 or SEQ ID NO: 5 is a substitution of a phenylalanine (F) for a leucine (L). In certain embodiments, the amino acid substitution at position 298 of SEQ ID NO: 4 or SEQ ID NO: 5 is a substitution of a leucine (L) for a methionine (M). In certain embodiments, the amino acid substitution at position 298 of SEQ ID NO: 4 or SEQ ID NO: 5 is a substitution of an alanine (A) for a methionine (M). In certain embodiments, the amino acid substitution at position 298 of SEQ ID NO: 4 or SEQ ID NO: 5 is a substitution of a valine (V) for a methionine (M). In certain embodiments, the amino acid substitution at position 311 of SEQ ID NO: 4 or SEQ ID NO: 5 is a substitution of an isoleucine (I) for a proline (P). In certain embodiments, the amino acid substitution at position 311 of SEQ ID NO: 4 or SEQ ID NO: 5 is a substitution of a valine for a proline (P). In certain embodiments, the amino acid substitution at position 315 of SEQ ID NO: 4 or SEQ ID NO: 5 is a substitution of a lysine (K) for an arginine (R), In certain embodiments, the amino acid substitution at position 319 of SEQ ID NO: 4 or SEQ ID NO: 5 is a substitution of a glycine (G) for a threonine (T). In certain embodiments, the amino acid substitution at position 327 of SEQ ID NO: 4 or SEQ ID NO: 5 is a substitution of an arginine (R) for a tyrosine (Y). In certain embodiments, the amino acid substitution at position 328 of SEQ ID NO: 4 or SEQ ID NO: 5 is a substitution of a valine (V) for a tyrosine (Y). In certain embodiments, the amino acid substitution at position 340 of SEQ ID NO: 4 or SEQ ID NO: 5 is a substitution of a glycine (G) for a cysteine (C). In certain embodiments, the amino acid substitution at position 340 of SEQ ID NO: 4 or SEQ ID NO: 5 is a substitution of a leucine (L) for a cysteine (C). In certain embodiments, the amino acid substitution at position 421 of SEQ ID NO: 4 or SEQ ID NO: 5 is a substitution of a histidine (H) for the aspartic acid (D). In certain embodiments, the amino acid substitution at position 436 of SEQ ID NO: 4 or SEQ ID NO: 5 is a substitution of an isoleucine (I) for a valine (V). In certain embodiments, the amino acid substitution at position 456 of SEQ ID NO: 4 or SEQ ID NO: 5 is a substitution of a tyrosine (Y) for a methionine (M). In certain embodiments, the amino acid substitution at position 470 of SEQ ID NO: 4 or SEQ ID NO: 5 is a substitution of a phenylalanine (F) for a leucine (L). In certain embodiments, the amino acid substitution at position 485 of SEQ ID NO: 4 or SEQ ID NO: 5 is a substitution of a lysine (K) for a serine (S). In certain embodiments, the amino acid substitution at position 503 of SEQ ID NO: 4 or SEQ ID NO: 5 is a substitution of a leucine (L) for a methionine (M). In certain embodiments, the amino acid substitution at position 503 of SEQ ID NO: 4 or SEQ ID NO: 5 is a substitution of an isoleucine (I) for a methionine (M). In certain embodiments, the amino acid substitution at position 552 of SEQ ID NO: 4 or SEQ ID NO: 5 is a substitution of a lysine (K) for a valine (V). In certain embodiments, the amino acid substitution at position 570 of SEQ ID NO: 4 or SEQ ID NO: 5 is a substitution of a threonine (T) for an alanine (A). In certain embodiments, the amino acid substitution at position 591 of SEQ ID NO: 4 or SEQ ID NO: 5 is a substitution of a proline (P) for a glutamine (Q). In certain embodiments, the amino acid substitution at position 591 of SEQ ID NO: 4 or SEQ ID NO: 5 is a substitution of an arginine (R) for a glutamine (Q).

In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 4 or SEQ ID NO: 5. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 4 or SEQ ID NO: 5. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 4 or SEQ ID NO: 5. In certain embodiments, the amino acid substitution at position 103 of SEQ ID NO: 4 or SEQ ID NO: 5 is a substitution of a proline (P) for a serine (S). In certain embodiments, the amino acid substitution at position 194 of SEQ ID NO: 4 or SEQ ID NO: 5 is a substitution of a valine (V) for a methionine (M). In certain embodiments, the amino acid substitution at position 372 of SEQ ID NO: 4 or SEQ ID NO: 5 is a substitution of an alanine (A) for an arginine (R). In certain embodiments, the amino acid substitution at position 375 of SEQ ID NO: 4 or SEQ ID NO: 5 is a substitution of an alanine (A) for a lysine (K). In certain embodiments, the amino acid substitution at position 450 of SEQ ID NO: 4 or SEQ ID NO: 5 is a substitution of an asparagine (N) for an aspartic acid (D). In certain embodiments, the amino acid substitution at position 509 of SEQ ID NO: 4 or SEQ ID NO: 5 is a substitution of a glycine (G) for a serine (S). In certain embodiments, the amino acid substitution at position 570 of SEQ ID NO: 4 or SEQ ID NO: 5 is a substitution of a serine (S) for an asparagine (N). In certain embodiments, the piggyBac™ transposase enzyme may comprise a substitution of a valine (V) for a methionine (M) at position 194 of SEQ ID NO: 4. In certain embodiments, including those embodiments wherein the piggyBac™ transposase enzyme may comprise a substitution of a valine (V) for a methionine (M) at position 194 of SEQ ID NO: 4, the piggyBac™ transposase enzyme may further comprise an amino acid substitution at positions 372, 375 and 450 of the sequence of SEQ ID NO: 4 or SEQ ID NO: 5. In certain embodiments, the piggyBac™ transposase enzyme may comprise a substitution of a valine (V) for a methionine (M) at position 194 of SEQ ID NO: 4, a substitution of an alanine (A) for an arginine (R) at position 372 of SEQ ID NO: 4, and a substitution of an alanine (A) for a lysine (K) at position 375 of SEQ ID NO: 4. In certain embodiments, the piggyBac™ transposase enzyme may comprise a substitution of a valine (V) for a methionine (M) at position 194 of SEQ ID NO: 4, a substitution of an alanine (A) for an arginine (R) at position 372 of SEQ ID NO: 4, a substitution of an alanine (A) for a lysine (K) at position 375 of SEQ ID NO: 4 and a substitution of an asparagine (N) for an aspartic acid (D) at position 450 of SEQ ID NO: 4.

The disclosure provides a method of producing a modified stem memory T cell ($T_{SCM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified T cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising introducing into a plurality of primary human T cell (a) a transposon composition comprising a transposon comprising an antigen receptor or a therapeutic protein and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 25% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 50% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 60% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 75% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 80% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 85% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 90% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 95% of the plurality of modified T cells expresses one or more cell-surface marker(s) of a stem memory T cell ($T_{SCM}$), thereby producing a plurality of modified stem memory T cells ($T_{SCM}$). In certain embodiments, the cell-surface markers comprise CD62L and CD45RA. In certain embodiments, the cell-surface markers of the CAR-$T_{SCM}$ comprise one or more of CD62L, CD45RA, CD28, CCR7, CD127, CD45RO, CD95, CD95 and IL-2Rβ. In certain embodiments, the cell-surface markers of the CAR-$T_{SCM}$ comprise one or more of CD45RA, CD95, IL-2Rβ, CR7, and CD62L. In certain embodiments of this method, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X).

In certain embodiments of the methods of the disclosure, the Sleeping Beauty transposase enzyme comprises an amino acid sequence at least 75%, 80%, 85%, 90%, 95%, 99% or any percentage in between identical to:

(SEQ ID NO: 6)
```
  1 MGKSKEISQD LRKKIVDLHK SGSSLGAISK RLKVPRSSVQ TIVRKYKHHG TTQPSYRSGR

61 RRYLSPRDER TLVRKVQINP RTTAKDLVKM LEETGTKVSI STVKRVLYRH NLKGRSARKK

121 PLLQNRHKKA RLRFATAHGD KDRTFWRNVL WSDETKIELF GHNDHRYVWR KKGEACKPKN

181 TIPTVKHGGG SIMLWGCFAA GGTGALHKID GIMRKENYVD ILKQHLKTSV RKLKLGRKWV

241 FQMDNDPKHT SKVVAKWLKD NKVKVLEWPS QSPDLNPIEN LWAELKKRVR ARRPTNLTQL

301 HQLCQEEWAK IHPTYCGKLV EGYPKRLTQV KQFKGNATKY.
```

In certain embodiments of the methods of the disclosure, the hyperactive Sleeping Beauty (SB100X) transposase enzyme comprises an amino acid sequence at least 75%, 80%, 85%, 90%, 95%, 99% or any percentage in between identical to:

(SEQ ID NO: 7)
```
  1 MGKSKEISQD LRKRIVDLHK SGSSLGAISK RLAVPRSSVQ TIVRKYKHHG TTQPSYRSGR

61 RRYLSPRDER TLVRKVQINP RTTAKDLVKM LEETGTKVSI STVKRVLYRH NLKGHSARKK

121 PLLQNRHKKA RLRFATAHGD KDRTFWRNVL WSDETKIELF GHNDHRYVWR KKGEACKPKN

181 TIPTVKHGGG SIMLWGCFAA GGTGALHKID GIMDAVQYVD ILKQHLKTSV RKLKLGRKWV

241 FQHDNDPKHT SKVVAKWLKD NKVKVLEWPS QSPDLNPIEN LWAELKKRVR ARRPTNLTQL

301 HQLCQEEWAK IHPNYCGKLV EGYPKRLTQV KQFKGNATKY.
```

The disclosure provides a method of producing a modified stem memory T cell ($T_{SCM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified T cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising introducing into a plurality of primary human T cell (a) a transposon composition comprising a transposon comprising an antigen receptor and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 25% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 50% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 60% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 75% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 80% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 85% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 90% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 95% of the plurality of modified T cells expresses one or more cell-surface marker(s) of a stem memory T cell ($T_{SCM}$), thereby producing a plurality of modified stem memory T cells ($T_{SCM}$). In certain embodiments, the cell-surface markers comprise CD62L and CD45RA. In certain embodiments, the cell-surface markers of the CAR-$T_{SCM}$ comprise one or more of CD62L, CD45RA, CD28, CCR7, CD127, CD45RO, CD95, CD95 and IL-2Rβ. In certain embodiments, the cell-surface markers of the CAR-$T_{SCM}$ comprise one or more of CD45RA, CD95, IL-2Rβ, CR7, and CD62L. In certain embodiments of this method, the transposon is a Helraiser transposon. In certain embodiments, and, in particular, those embodiments wherein the transposon is a Helraiser transposon, the transposase is a Helitron transposase.

In certain embodiments of the methods of the disclosure, the transposase is a Helitron transposase. Helitron transposases mobilize the Helraiser transposon, an ancient element from the bat genome that was active about 30 to 36 million years ago. An exemplary Helraiser transposon of the disclosure includes Helibat1, which comprises a nucleic acid sequence comprising:

(SEQ ID NO: 27)
```
  1 TCCTATATAA TAAAAGAGAA ACATGCAAAT TGACCATCCC TCCGCTACGC TCAAGCCACG

61 CCCACCAGCC AATCAGAAGT GACTATGCAA ATTAACCCAA CAAAGATGGC AGTTAAATTT

121 GCATACGCAG GTGTCAAGCG CCCCAGGAGG CAACGGCGGC CGCGGGCTCC CAGGACCTTC

181 GCTGGCCCCG GGAGGCGAGG CCGGCCGCGC CTAGCCACAC CCGCGGGCTC CCGGGACCTT

241 CGCCAGCAGA GAGCAGAGCG GGAGAGCGGG CGGAGAGCGG GAGGTTTGGA GGACTTGGCA

301 GAGCAGGAGG CCGCTGGACA TAGAGCAGAG CGAGAGAGAG GGTGGCTTGG AGGGCGTGGC

361 TCCCTCTGTC ACCCCAGCTT CCTCATCACA GCTGTGGAAA CTGACAGCAG GGAGGAGGAA
```

-continued

```
 421 GTCCCACCCC CACAGAATCA GCCAGAATCA GCCGTTGGTC AGACAGCTCT CAGCGGCCTG

481 ACAGCCAGGA CTCTCATTCA CCTGCATCTC AGACCGTGAC AGTAGAGAGG TGGGACTATG

541 TCTAAAGAAC AACTGTTGAT ACAACGTAGC TCTGCAGCCG AAAGATGCCG GCGTTATCGA

601 CAGAAAATGT CTGCAGAGCA ACGTGCGTCT GATCTTGAAA GAAGGCGGCG CCTGCAACAG

661 AATGTATCTG AAGAGCAGCT ACTGGAAAAA CGTCGCTCTG AAGCCGAAAA ACAGCGGCGT

721 CATCGACAGA AAATGTCTAA AGACCAACGT GCCTTTGAAG TTGAAAGAAG GCGGTGGCGA

781 CGACAGAATA TGTCTAGAGA ACAGTCATCA ACAAGTACTA CCAATACCGG TAGGAACTGC

841 CTTCTCAGCA AAAATGGAGT ACATGAGGAT GCAATTCTCG AACATAGTTG TGGTGGAATG

901 ACTGTTCGAT GTGAATTTTG CCTATCACTA AATTTCTCTG ATGAAAAACC ATCCGATGGG

961 AAATTTACTC GATGTTGTAG CAAAGGGAAA GTCTGTCCAA ATGATATACA TTTTCCAGAT

1021 TACCCGGCAT ATTTAAAAAG ATTAATGACA AACGAAGATT CTGACAGTAA AAATTTCATG

1081 GAAAATATTC GTTCCATAAA TAGTTCTTTT GCTTTTGCTT CCATGGGTGC AAATATTGCA

1141 TCGCCATCAG GATATGGGCC ATACTGTTTT AGAATACACG GACAAGTTTA TCACCGTACT

1201 GGAACTTTAC ATCCTTCGGA TGGTGTTTCT CGGAAGTTTG CTCAACTCTA TATTTTGGAT

1261 ACAGCCGAAG CTACAAGTAA AAGATTAGCA ATGCCAGAAA ACCAGGGCTG CTCAGAAAGA

1321 CTCATGATCA ACATCAACAA CCTCATGCAT GAAATAAATG AATTAACAAA ATCGTACAAG

1381 ATGCTACATG AGGTAGAAAA GGAAGCCCAA TCTGAAGCAG CAGCAAAAGG TATTGCTCCC

1441 ACAGAAGTAA CAATGGCGAT TAAATACGAT CGTAACAGTG ACCCAGGTAG ATATAATTCT

1501 CCCCGTGTAA CCGAGGTTGC TGTCATATTC AGAAACGAAG ATGGAGAACC TCCTTTTGAA

1561 AGGGACTTGC TCATTCATTG TAAACCAGAT CCCAATAATC CAAATGCCAC TAAAATGAAA

1621 CAAATCAGTA TCCTGTTTCC TACATTAGAT GCAATGACAT ATCCTATTCT TTTTCCACAT

1681 GGTGAAAAAG GCTGGGGAAC AGATATTGCA TTAAGACTCA GAGACAACAG TGTAATCGAC

1741 AATAATACTA GACAAAATGT AAGGACACGA GTCACACAAA TGCAGTATTA TGGATTTCAT

1801 CTCTCTGTGC GGGACACGTT CAATCCTATT TTAAATGCAG GAAAATTAAC TCAACAGTTT

1861 ATTGTGGATT CATATTCAAA AATGGAGGCC AATCGGATAA ATTTCATCAA AGCAAACCAA

1921 TCTAAGTTGA GAGTTGAAAA ATATAGTGGT TTGATGGATT ATCTCAAATC TAGATCTGAA

1981 AATGACAATG TGCCGATTGG TAAAATGATA ATACTTCCAT CATCTTTTGA GGGTAGTCCC

2041 AGAAATATGC AGCAGCGATA TCAGGATGCT ATGGCAATTG TAACGAAGTA TGGCAAGCCC

2101 GATTTATTCA TAACCATGAC ATGCAACCCC AAATGGGCAG ATATTACAAA CAATTTACAA

2161 CGCTGGCAAA AAGTTGAAAA CAGACCTGAC TTGGTAGCCA GAGTTTTTAA TATTAAGCTG

2221 AATGCTCTTT TAAATGATAT ATGTAAATTC CATTTATTTG GCAAAGTAAT AGCTAAAATT

2281 CATGTCATTG AATTTCAGAA ACGCGGACTG CCTCACGCTC ACATATTATT GATATTAGAT

2341 AGTGAGTCCA AATTACGTTC AGAAGATGAC ATTGACCGTA TAGTTAAGGC AGAAATTCCA

2401 GATGAAGACC AGTGTCCTCG ACTTTTTCAA ATTGTAAAAT CAAATATGGT ACATGGACCA

2461 TGTGGAATAC AAAATCCAAA TAGTCCATGT ATGGAAAATG GAAATGTTC AAAGGGATAT

2521 CCAAAAGAAT TTCAAAATGC GACCATTGGA AATATTGATG GATATCCCAA ATACAAACGA

2581 AGATCTGGTA GCACCATGTC TATTGGAAAT AAAGTTGTCG ATAACACTTG GATTGTCCCT

2641 TATAACCCGT ATTTGTGCCT TAAATATAAC TGTCATATAA ATGTTGAAGT CTGTGCATCA

2701 ATTAAAGTG TCAAATATTT ATTTAAATAC ATCTATAAAG GGCACGATTG TGCAAATATT

2761 CAAATTTCTG AAAAAAATAT TATCAATCAT GACGAAGTAC AGGACTTCAT TGACTCCAGG

2821 TATGTGAGCG CTCCTGAGGC TGTTTGGAGA CTTTTTGCAA TGCGAATGCA TGACCAATCT
```

-continued

```
2881 CATGCAATCA CAAGATTAGC TATTCATTTG CCAAATGATC AGAATTTGTA TTTTCATACC
2941 GATGATTTTG CTGAAGTTTT AGATAGGGCT AAAAGGCATA ACTCGACTTT GATGGCTTGG
3001 TTCTTATTGA ATAGAGAAGA TTCTGATGCA CGTAATTATT ATTATTGGGA GATTCCACAG
3061 CATTATGTGT TTAATAATTC TTTGTGGACA AAACGCCGAA AGGGTGGGAA TAAAGTATTA
3121 GGTAGACTGT TCACTGTGAG CTTTAGAGAA CCAGAACGAT ATTACCTTAG ACTTTTGCTT
3181 CTGCATGTAA AAGGTGCGAT AAGTTTTGAG GATCTGCGAA CTGTAGGAGG TGTAACTTAT
3241 GATACATTTC ATGAAGCTGC TAAACACCGA GGATTATTAC TTGATGACAC TATCTGGAAA
3301 GATACGATTG ACGATGCAAT CATCCTTAAT ATGCCCAAAC AACTACGGCA ACTTTTTGCA
3361 TATATATGTG TGTTTGGATG TCCTTCTGCT GCAGACAAAT TATGGGATGA GAATAAATCT
3421 CATTTTATTG AAGATTTCTG TTGGAAATTA CACCGAAGAG AAGGTGCCTG TGTGAACTGT
3481 GAAATGCATG CCCTTAACGA AATTCAGGAG GTATTCACAT TGCATGGAAT GAAATGTTCA
3541 CATTTCAAAC TTCCGGACTA TCCTTTATTA ATGAATGCAA ATACATGTGA TCAATTGTAC
3601 GAGCAACAAC AGGCAGAGGT TTTGATAAAT TCTCTGAATG ATGAACAGTT GGCAGCCTTT
3661 CAGACTATAA CTTCAGCCAT CGAAGATCAA ACTGTACACC CCAAATGCTT TTTCTTGGAT
3721 GGTCCAGGTG GTAGTGGAAA AACATATCTG TATAAAGTTT TAACACATTA TATTAGAGGT
3781 CGTGGTGGTA CTGTTTTACC CACAGCATCT ACAGGAATTG CTGCAAATTT ACTTCTTGGT
3841 GGAAGAACCT TTCATTCCCA ATATAAATTA CCAATTCCAT TAAATGAAAC TTCAATTTCT
3901 AGACTCGATA TAAAGAGTGA AGTTGCTAAA ACCATTAAAA AGGCCCAACT TCTCATTATT
3961 GATGAATGCA CCATGGCATC CAGTCATGCT ATAAACGCCA TAGATAGATT ACTAAGAGAA
4021 ATTATGAATT TGAATGTTGC ATTTGGTGGG AAAGTTCTCC TTCTCGGAGG GGATTTTCGA
4081 CAATGTCTCA GTATTGTACC ACATGCTATG CGATCGGCCA TAGTACAAAC GAGTTTAAAG
4141 TACTGTAATG TTTGGGGATG TTTCAGAAAG TTGTCTCTTA AAACAAATAT GAGATCAGAG
4201 GATTCTGCTT ATAGTGAATG GTTAGTAAAA CTTGGAGATG GCAAACTTGA TAGCAGTTTT
4261 CATTTAGGAA TGGATATTAT TGAAATCCCC CATGAAATGA TTTGTAACGG ATCTATTATT
4321 GAAGCTACCT TTGGAAATAG TATATCTATA GATAATATTA AAAATATATC TAAACGTGCA
4381 ATTCTTTGTC CAAAAAATGA GCATGTTCAA AAATTAAATG AAGAAATTTT GGATATACTT
4441 GATGGAGATT TCACACATA TTTGAGTGAT GATTCCATTG ATTCAACAGA TGATGCTGAA
4501 AAGGAAAATT TTCCCATCGA ATTTCTTAAT AGTATTACTC CTTCGGGAAT GCCGTGTCAT
4561 AAATTAAAAT TGAAAGTGGG TGCAATCATC ATGCTATTGA GAAATCTTAA TAGTAAATGG
4621 GGTCTTTGTA ATGGTACTAG ATTTATTATC AAAAGATTAC GACCTAACAT TATCGAAGCT
4681 GAAGTATTAA CAGGATCTGC AGAGGGAGAG GTTGTTCTGA TTCCAAGAAT TGATTTGTCC
4741 CCATCTGACA CTGGCCTCCC ATTTAAATTA ATTCGAAGAC AGTTTCCCGT GATGCCAGCA
4801 TTTGCGATGA CTATTAATAA ATCACAAGGA CAAACTCTAG ACAGAGTAGG AATATTCCTA
4861 CCTGAACCCG TTTTCGCACA TGGTCAGTTA TATGTTGCTT TCTCTCGAGT TCGAAGAGCA
4921 TGTGACGTTA AAGTTAAAGT TGTAAATACT TCATCACAAG GGAAATTAGT CAAGCACTCT
4981 GAAAGTGTTT TTACTCTTAA TGTGGTATAC AGGGAGATAT TAGAATAAGT TTAATCACTT
5041 TATCAGTCAT TGTTTGCATC AATGTTGTTT TTATATCATG TTTTTGTTGT TTTTATATCA
5101 TGTCTTTGTT GTTGTTATAT CATGTTGTTA TTGTTTATTT ATTAATAAAT TTATGTATTA
5161 TTTTCATATA CATTTACTC ATTTCCTTTC ATCTCTCACA CTTCTATTAT AGAGAAAGGG
5221 CAAATAGCAA TATTAAAATA TTTCCTCTAA TTAATTCCCT TTCAATGTGC ACGAATTTCG
5281 TGCACCGGGC CACTAG.
```

Unlike other transposases, the Helitron transposase does not contain an RNase-H like catalytic domain, but instead comprises a RepHel motif made up of a replication initiator domain (Rep) and a DNA helicase domain. The Rep domain is a nuclease domain of the HUH superfamily of nucleases.

An exemplary Helitron transposase of the disclosure comprises an amino acid sequence comprising:

The disclosure provides a method of producing a modified stem memory T cell ($T_{SCM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified

```
                                                              (SEQ ID NO: 28)
   1 MSKEQLLIQR SSAAERCRRY RQKMSAEQRA SDLERRRRLQ QNVSEEQLLE KRRSEAEKQR

61 RHRQKMSKDQ RAFEVERRRW RRQNMSREQS STSTTNTGRN CLLSKNGVHE DAILEHSCGG

121 MTVRCEFCLS LNFSDEKPSD GKFTRCCSKG KVCPNDIHFP DYPAYLKRLM TNEDSDSKNF

181 MENIRSINSS FAFASMGANI ASPSGYGPYC FRIHGQVYHR TGTLHPSDGV SRKFAQLYIL

241 DTAEATSKRL AMPENQGCSE RLMININNLM HEINELTKSY KMLHEVEKEA QSEAAAKGIA

301 PTEVTMAIKY DRNSDPGRYN SPRVTEVAVI FRNEDGEPPF ERDLLIHCKP DPNNPNATKM

361 KQISILFPTL DAMTYPILFP HGEKGWGTDI ALRLRDNSVI DNNTRQNVRT RVTQMQYYGF

421 HLSVRDTFNP ILNAGKLTQQ FIVDSYSKME ANRINFIKAN QSKLRVEKYS GLMDYLKSRS

481 ENDNVPIGKM IILPSSFEGS PRNMQQRYQD AMAIVTKYGK PDLFITMTCN PKWADITNNL

541 QRWQKVENRP DLVARVFNIK LNALLNDICK FHLFGKVIAK IHVIEFQKRG LPHAHILLIL

601 DSESKLRSED DIDRIVKAEI PDEDQCPRLF QIVKSNMVHG PCGIQNPNSP CMENGKCSKG

661 YPKEFQNATI GNIDGYPKYK RRSGSTMSIG NKVVDNTWIV PYNPYLCLKY NCHINVEVCA

721 SIKSVKYLFK YIYKGHDCAN IQISEKNIIN HDEVQDFIDS RYVSAPEAVW RLFAMRMHDQ

781 SHAITRLAIH LPNDQNLYFH TDDFAEVLDR AKRHNSTLMA WFLLNREDSD ARNYYYWEIP

841 QHYVFNNSLW TKRRKGGNKV LGRLFTVSFR EPERYYLRLL LLHVKGAISF EDLRTVGGVT

901 YDTFHEAAKH RGLLLDDTIW KDTIDDAIIL NMPKQLRQLF AYICVFGCPS AADKLWDENK

961 SHFIEDFCWK LHRREGACVN CEMHALNEIQ EVFTLHGMKC SHFKLPDYPL LMNANTCDQL

1021 YEQQQAEVLI NSLNDEQLAA FQTITSAIED QTVHPKCFFL DGPGGSGKTY LYKVLTHYIR

1081 GRGGTVLPTA STGIAANLLL GGRTFHSQYK LPIPLNETSI SRLDIKSEVA KTIKKAQLLI

1141 IDECTMASSH AINAIDRLLR EIMNLNVAFG GKVLLLGGDF RQCLSIVPHA MRSAIVQTSL

1201 KYCNVWGCFR KLSLKTNMRS EDSAYSEWLV KLGDGKLDSS FHLGMDIIEI PHEMICNGSI

1261 IEATFGNSIS IDNIKNISKR AILCPKNEHV QKLNEEILDI LDGDFHTYLS DDSIDSTDDA

1321 EKENFPIEFL NSITPSGMPC HKLKLKVGAI IMLLRNLNSK WGLCNGTRFI IKRLRPNIIE

1381 AEVLTGSAEG EVVLIPRIDL SPSDTGLPFK LIRRQFPVMP AFAMTINKSQ GQTLDRVGIF

1441 LPEPVFAHGQ LYVAFSRVRR ACDVKVKVVN TSSQGKLVKH SESVFTLNVV YREILE.
```

In Helitron transpositions, a hairpin close to the 3' end of the transposon functions as a terminator. However, this hairpin can be bypassed by the transposase, resulting in the transduction of flanking sequences. In addition, Helraiser transposition generates covalently closed circular intermediates. Furthermore, Helitron transpositions can lack target site duplications. In the Helraiser sequence, the transposase is flanked by left and right terminal sequences termed LTS and RTS. These sequences terminate with a conserved 5'-TC/CTAG-3' motif. A 19 bp palindromic sequence with the potential to form the hairpin termination structure is located 11 nucleotides upstream of the RTS and consists of the sequence (SEQ ID NO: 29)
GTGCACGAATTTCGTGCACCGGGCCACTAG.

T cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising introducing into a plurality of primary human T cell (a) a transposon composition comprising a transposon comprising an antigen receptor and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 25% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 50% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 60% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 75% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 80% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 85% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 90% of the plurality of modified T cells expresses one or more cell-surface marker(s) of a stem memory T cell ($T_{SCM}$), thereby producing a plurality of modified stem memory T cells ($T_{SCM}$). In certain embodiments, the method produces a plurality of modified T cells, wherein at least 95% of the plurality of modified T cells expresses one or more cell-surface marker(s) of a stem memory T cell ($T_{SCM}$), thereby producing a plurality of modified stem memory T cells ($T_{SCM}$). In certain embodiments, the cell-surface markers comprise CD62L and CD45RA. In certain embodiments, the cell-surface markers of the CAR-$T_{SCM}$ comprise one or more of CD62L, CD45RA, CD28, CCR7, CD127, CD45RO, CD95, CD95 and IL-2Rβ. In certain embodiments, the cell-surface markers of the CAR-$T_{SCM}$ comprise one or more of CD45RA, CD95, IL-2Rβ, CR7, and CD62L. In certain embodiments of this method, the transposon is a Tol2 transposon. In certain embodiments, including those embodiments wherein the transposon is a Tol2 transposon, the transposase is a Tol2 transposase.

In certain embodiments of the methods of the disclosure, the transposase is a Tol2 transposase. Tol2 transposons may be isolated or derived from the genome of the medaka fish, and may be similar to transposons of the hAT family. Exemplary Tol2 transposons of the disclosure are encoded by a sequence comprising about 4.7 kilobases and contain a gene encoding the Tol2 transposase, which contains four exons. An exemplary Tol2 transposase of the disclosure comprises an amino acid sequence comprising the following:

```
                                                            (SEQ ID NO: 30)
  1 MEEVCDSSAA ASSTVQNQPQ DQEHPWPYLR EFFSLSGVNK DSFKMKCVLC LPLNKEISAF

61 KSSPSNLRKH IERMHPNYLK NYSKLTAQKR KIGTSTHASS SKQLKVDSVF PVKHVSPVTV

121 NKAILRYIIQ GLHPFSTVDL PSFKELISTL QPGISVITRP TLRSKIAEAA LIMKQKVTAA

181 MSEVEWIATT TDCWTARRKS FIGVTAHWIN PGSLERHSAA LACKRLMGSH TFEVLASAMN

241 DIHSEYEIRD KVVCTTTDSG SNFMKAFRVF GVENNDIETE ARRCESDDTD SEGCGEGSDG

301 VEFQDASRVL DQDDGFEFQL PKHQKCACHL LNLVSSVDAQ KALSNEHYKK LYRSVFGKCQ

361 ALWNKSSRSA LAAEAVESES RLQLLRPNQT RWNSTFMAVD RILQICKEAG EGALRNICTS

421 LEVPMFNPAE MLFLTEWANT MRPVAKVLDI LQAETNTQLG WLLPSVHQLS LKLQRLHHSL

481 RYCDPLVDAL QQGIQTRFKH MFEDPEIIAA AILLPKFRTS WTNDETIIKR GMDYIRVHLE

541 PLDHKKELAN SSSDDEDFFA SLKPTTHEAS KELDGYLACV SDTRESLLTF PAICSLSIKT

601 NTPLPASAAC ERLFSTAGLL FSPKRARLDT NNFENQLLLK LNLRFYNFE.
```

An exemplary Tol2 transposon of the disclosure, including inverted repeats, subterminal sequences and the Tol2 transposase, is encoded by a nucleic acid sequence comprising the following:

```
                                                            (SEQ ID NO: 31)
  1 CAGAGGTGTA AAGTACTTGA GTAATTTTAC TTGATTACTG TACTTAAGTA TTATTTTTGG

61 GGATTTTTAC TTTACTTGAG TACAATTAAA AATCAATACT TTTACTTTTA CTTAATTACA

121 TTTTTTTAGA AAAAAAGTA CTTTTTACTC CTTACAATTT TATTTACAGT CAAAAAGTAC

181 TTATTTTTTG GAGATCACTT CATTCTATTT TCCCTTGCTA TTACCAAACC AATTGAATTG

241 CGCTGATGCC CAGTTAATT TAAATGTTAT TTATTCTGCC TATGAAAATC GTTTTCACAT

301 TATATGAAAT TGGTCAGACA TGTTCATTGG TCCTTTGGAA GTGACGTCAT GTCACATCTA
```

```
 361 TTACCACAAT GCACAGCACC TTGACCTGGA AATTAGGGAA ATTATAACAG TCAATCAGTG
 421 GAAGAAAATG GAGGAAGTAT GTGATTCATC AGCAGCTGCG AGCAGCACAG TCCAAAATCA
 481 GCCACAGGAT CAAGAGCACC CGTGGCCGTA TCTTCGCGAA TTCTTTTCTT TAAGTGGTGT
 541 AAATAAAGAT TCATTCAAGA TGAAATGTGT CCTCTGTCTC CCGCTTAATA AGAAATATC
 601 GGCCTTCAAA AGTTCGCCAT CAAACCTAAG GAAGCATATT GAGGTAAGTA CATTAAGTAT
 661 TTTGTTTTAC TGATAGTTTT TTTTTTTTTT TTTTTTTTTT TTTTTGGGTG TGCATGTTTT
 721 GACGTTGATG GCGCGCCTTT TATATGTGTA GTAGGCCTAT TTTCACTAAT GCATGCGATT
 781 GACAATATAA GGCTCACGTA ATAAAATGCT AAAATGCATT TGTAATTGGT AACGTTAGGT
 841 CCACGGGAAA TTTGGCGCCT ATTGCAGCTT TGAATAATCA TTATCATTCC GTGCTCTCAT
 901 TGTGTTTGAA TTCATGCAAA ACACAAGAAA ACCAAGCGAG AAATTTTTTT CCAAACATGT
 961 TGTATTGTCA AAACGGTAAC ACTTTACAAT GAGGTTGATT AGTTCATGTA TTAACTAACA
1021 TTAAATAACC ATGAGCAATA CATTTGTTAC TGTATCTGTT AATCTTTGTT AACGTTAGTT
1081 AATAGAAATA CAGATGTTCA TTGTTTGTTC ATGTTAGTTC ACAGTGCATT AACTAATGTT
1141 AACAAGATAT AAAGTATTAG TAAATGTTGA AATTAACATG TATACGTGCA GTTCATTATT
1201 AGTTCATGTT AACTAATGTA GTTAACTAAC GAACCTTATT GTAAAAGTGT TACCATCAAA
1261 ACTAATGTAA TGAAATCAAT TCACCCTGTC ATGTCAGCCT TACAGTCCTG TGTTTTTGTC
1321 AATATAATCA GAAATAAAAT TAATGTTTGA TTGTCACTAA ATGCTACTGT ATTTCTAAAA
1381 TCAACAAGTA TTTAACATTA TAAAGTGTGC AATTGGCTGC AAATGTCAGT TTTATTAAAG
1441 GGTTAGTTCA CCCAAAAATG AAAATAATGT CATTAATGAC TCGCCCTCAT GTCGTTCCAA
1501 GCCCGTAAGA CCTCCGTTCA TCTTCAGAAC ACAGTTTAAG ATATTTTAGA TTTAGTCCGA
1561 GAGCTTTCTG TGCCTCCATT GAGAATGTAT GTACGGTATA CTGTCCATGT CCAGAAAGGT
1621 AATAAAAACA TCAAAGTAGT CCATGTGACA TCAGTGGGTT AGTTAGAATT TTTTGAAGCA
1681 TCGAATACAT TTTGGTCCAA AAATAACAAA ACCTACGACT TTATTCGGCA TTGTATTCTC
1741 TTCCGGGTCT GTTGTCAATC CGCGTTCACG ACTTCGCAGT GACGCTACAA TGCTGAATAA
1801 AGTCGTAGGT TTTGTTATTT TTGGACCAAA ATGTATTTTC GATGCTTCAA ATAATTCTAC
1861 CTAACCCACT GATGTCACAT GGACTACTTT GATGTTTTTA TTACCTTTCT GGACATGGAC
1921 AGTATACCGT ACATACATTT TCAGTGGAGG GACAGAAAGC TCTCGGACTA AATCTAAAAT
1981 ATCTTAAACT GTGTTCCGAA GATGAACGGA GGTGTTACGG GCTTGGAACG ACATGAGGGT
2041 GAGTCATTAA TGACATCTTT TCATTTTTGG GTGAACTAAC CCTTTAATGC TGTAATCAGA
2101 GAGTGTATGT GTAATTGTTA CATTTATTGC ATACAATATA AATATTTATT TGTTGTTTTT
2161 ACAGAGAATG CACCCAAATT ACCTCAAAAA CTACTCTAAA TTGACAGCAC AGAAGAGAAA
2221 GATCGGGACC TCCACCCATG CTTCCAGCAG TAAGCAACTG AAAGTTGACT CAGTTTTCCC
2281 AGTCAAACAT GTGTCTCCAG TCACTGTGAA CAAAGCTATA TTAAGGTACA TCATTCAAGG
2341 ACTTCATCCT TTCAGCACTG TTGATCTGCC ATCATTTAAA GAGCTGATTA GTACACTGCA
2401 GCCTGGCATT TCTGTCATTA CAAGGCCTAC TTTACGCTCC AAGATAGCTG AAGCTGCTCT
2461 GATCATGAAA CAGAAAGTGA CTGCTGCCAT GAGTGAAGTT GAATGGATTG CAACCACAAC
2521 GGATTGTTGG ACTGCACGTA GAAAGTCATT CATTGGTGTA ACTGCTCACT GGATCAACCC
2581 TGGAAGTCTT GAAAGACATT CCGCTGCACT TGCCTGCAAA AGATTAATGG GCTCTCATAC
2641 TTTTGAGGTA CTGGCCAGTG CCATGAATGA TATCCACTCA GAGTATGAAA TACGTGACAA
2701 GGTTGTTTGC ACAACCACAG ACAGTGGTTC CAACTTTATG AAGGCTTTCA GAGTTTTTGG
2761 TGTGGAAAAC AATGATATCG AGACTGAGGC AAGAAGGTGT GAAAGTGATG ACACTGATTC
```

-continued

```
2821 TGAAGGCTGT GGTGAGGGAA GTGATGGTGT GGAATTCCAA GATGCCTCAC GAGTCCTGGA

2881 CCAAGACGAT GGCTTCGAAT TCCAGCTACC AAAACATCAA AAGTGTGCCT GTCACTTACT

2941 TAACCTAGTC TCAAGCGTTG ATGCCCAAAA AGCTCTCTCA AATGAACACT ACAAGAAACT

3001 CTACAGATCT GTCTTTGGCA AATGCCAAGC TTTATGGAAT AAAAGCAGCC GATCGGCTCT

3061 AGCAGCTGAA GCTGTTGAAT CAGAAAGCCG GCTTCAGCTT TTAAGGCCAA ACCAAACGCG

3121 GTGGAATTCA ACTTTTATGG CTGTTGACAG AATTCTTCAA ATTTGCAAAG AAGCAGGAGA

3181 AGGCGCACTT CGGAATATAT GCACCTCTCT TGAGGTTCCA ATGTAAGTGT TTTTCCCCTC

3241 TATCGATGTA AACAAATGTG GGTTGTTTTT GTTTAATACT CTTTGATTAT GCTGATTTCT

3301 CCTGTAGGTT TAATCCAGCA GAAATGCTGT TCTTGACAGA GTGGGCCAAC ACAATGCGTC

3361 CAGTTGCAAA AGTACTCGAC ATCTTGCAAG CGGAAACGAA TACACAGCTG GGGTGGCTGC

3421 TGCCTAGTGT CCATCAGTTA AGCTTGAAAC TTCAGCGACT CCACCATTCT CTCAGGTACT

3481 GTGACCCACT TGTGGATGCC CTACAACAAG GAATCCAAAC ACGATTCAAG CATATGTTTG

3541 AAGATCCTGA GATCATAGCA GCTGCCATCC TTCTCCCTAA ATTTCGGACC TCTTGGACAA

3601 ATGATGAAAC CATCATAAAA CGAGGTAAAT GAATGCAAGC AACATACACT TGACGAATTC

3661 TAATCTGGGC AACCTTTGAG CCATACCAAA ATTATTCTTT TATTTATTTA TTTTTGCACT

3721 TTTTAGGAAT GTTATATCCC ATCTTTGGCT GTGATCTCAA TATGAATATT GATGTAAAGT

3781 ATTCTTGCAG CAGGTTGTAG TTATCCCTCA GTGTTTCTTG AAACCAAACT CATATGTATC

3841 ATATGTGGTT TGGAAATGCA GTTAGATTTT ATGCTAAAAT AAGGGATTTG CATGATTTTA

3901 GATGTAGATG ACTGCACGTA AATGTAGTTA ATGACAAAAT CCATAAAATT TGTTCCCAGT

3961 CAGAAGCCCC TCAACCAAAC TTTTCTTTGT GTCTGCTCAC TGTGCTTGTA GGCATGGACT

4021 ACATCAGAGT GCATCTGGAG CCTTTGGACC ACAAGAAGGA ATTGGCCAAC AGTTCATCTG

4081 ATGATGAAGA TTTTTTCGCT TCTTTGAAAC CGACAACACA TGAAGCCAGC AAAGAGTTGG

4141 ATGGATATCT GGCCTGTGTT TCAGACACCA GGGAGTCTCT GCTCACGTTT CCTGCTATTT

4201 GCAGCCTCTC TATCAAGACT AATACACCTC TTCCCGCATC GGCTGCCTGT GAGAGGCTTT

4261 TCAGCACTGC AGGATTGCTT TTCAGCCCCA AAAGAGCTAG GCTTGACACT AACAATTTTG

4321 AGAATCAGCT TCTACTGAAG TTAAATCTGA GGTTTTACAA CTTTGAGTAG CGTGTACTGG

4381 CATTAGATTG TCTGTCTTAT AGTTTGATAA TTAAATACAA ACAGTTCTAA AGCAGGATAA

4441 AACCTTGTAT GCATTTCATT TAATGTTTTT TGAGATTAAA AGCTTAAACA AGAATCTCTA

4501 GTTTTCTTTC TTGCTTTTAC TTTTACTTCC TTAATACTCA AGTACAATTT TAATGGAGTA

4561 CTTTTTTACT TTTACTCAAG TAAGATTCTA GCCAGATACT TTTACTTTTA ATTGAGTAAA

4621 ATTTTCCCTA AGTACTTGTA CTTTCACTTG AGTAAAATTT TTGAGTACTT TTTACACCTC

4681 TG.
```

The disclosure provides a method of producing a modified central memory T-cell (T$_{CM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified T cell expresses one or more cell-surface marker(s) of a central memory T-cell (T$_{CM}$), thereby producing a modified central memory T-cell (T$_{CM}$). The disclosure provides a method of producing a plurality of modified central memory T-cells (T$_{CM}$), comprising introducing into a plurality of primary human T cell (a) a transposon composition comprising a transposon comprising an antigen receptor and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a central memory T-cell (T$_{CM}$), thereby producing a plurality of modified central memory T-cells (T$_{CM}$). In certain embodiments, the method produces a plurality of modified T cells, wherein at least 25% of the plurality of modified T cells expresses one or more cell-surface marker(s) of central memory T-cell (T$_{CM}$), thereby producing a plurality of modified central memory T-cells (T$_{CM}$). In certain embodiments, the method produces a plurality of modified T cells, wherein at least 50% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 60% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 75% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 80% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 85% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 90% of the plurality of modified T cells expresses one or more cell-surface marker(s) of central memory T-cell ($T_{CM}$), thereby producing a plurality of modified central memory T-cells ($T_{CM}$). In certain embodiments, the method produces a plurality of modified T cells, wherein at least 95% of the plurality of modified T cells expresses one or more cell-surface marker(s) of central memory T-cell ($T_{CM}$), thereby producing a plurality of modified central memory T-cells ($T_{CM}$). In certain embodiments, the cell-surface markers comprise one or more of CD45RO, CD95, CCR7, and CD62L. In certain embodiments of this method, the transposon is a plasmid DNA transposon with a sequence encoding the antigen receptor or the therapeutic protein is flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments of this method, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X). In certain embodiments of this method, the transposon is a Helraiser transposon. In certain embodiments, and, in particular, those embodiments wherein the transposon is a Helraiser transposon, the transposase is a Helitron transposase. In certain embodiments of this method, the transposon is a Tol2 transposon. In certain embodiments, including those embodiments wherein the transposon is a Tol2 transposon, the transposase is a Tol2 transposase.

The disclosure provides a method of producing a composition comprising a plurality of modified stem memory T-cells ($T_{SCM}$) and a plurality of modified central memory T-cells ($T_{CM}$), comprising introducing into a plurality of primary human T cell (a) a transposon composition comprising a transposon comprising an antigen receptor or a therapeutic protein and (b) a transposase composition comprising a transposase or a sequence encoding the transposase; to produce a composition comprising a plurality of modified $T_{SCM}$ and a plurality of modified $T_{CM}$, wherein the plurality of modified $T_{SCM}$ expresses one or more CD62L, CD45RA, CD28, CCR7, CD127, CD45RO, CD95, CD95 and IL-2Rβ and the plurality of modified $T_{CM}$ expresses one or more CD45RO, CD95, IL-2Rβ, CCR7, and CD62L, thereby producing a composition comprising a plurality of modified $T_{SCM}$ and a plurality of modified $T_{CM}$. In certain embodiments of this method, the modified stem memory T-cells ($T_{SCM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified central memory T-cells ($T_{CM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified stem memory T-cells ($T_{SCM}$) comprise at least 10% of the total number of cells of the composition and the modified central memory T-cells ($T_{CM}$) comprise at least 90% of the total number of cells of the composition. In certain embodiments of this method, the modified stem memory T-cells ($T_{SCM}$) comprise at least 90% of the total number of cells of the composition and the modified central memory T-cells ($T_{CM}$) comprise at least 10% of the total number of cells of the composition. In certain embodiments of this method, the modified stem memory T-cells ($T_{SCM}$) comprise at least 20% of the total number of cells of the composition and the modified central memory T-cells ($T_{CM}$) comprise at least 80% of the total number of cells of the composition. In certain embodiments of this method, the modified stem memory T-cells ($T_{SCM}$) comprise at least 80% of the total number of cells of the composition and the modified central memory T-cells ($T_{CM}$) comprise at least 20% of the total number of cells of the composition. In certain embodiments of this method, the modified stem memory T-cells ($T_{SCM}$) comprise at least 30% of the total number of cells of the composition and the modified central memory T-cells ($T_{CM}$) comprise at least 70% of the total number of cells of the composition. In certain embodiments of this method, the modified stem memory T-cells ($T_{SCM}$) comprise at least 70% of the total number of cells of the composition and the modified central memory T-cells ($T_{CM}$) comprise at least 30% of the total number of cells of the composition. In certain embodiments of this method, the modified stem memory T-cells ($T_{SCM}$) comprise at least 40% of the total number of cells of the composition and the modified central memory T-cells ($T_{CM}$) comprise at least 60% of the total number of cells of the composition. In certain embodiments of this method, the modified stem memory T-cells ($T_{SCM}$) comprise at least 60% of the total number of cells of the composition and the modified central memory T-cells ($T_{CM}$) comprise at least 40% of the total number of cells of the composition. In certain embodiments of this method, the modified stem memory T-cells ($T_{SCM}$) comprise at least 50% of the total number of cells of the composition and the modified central memory T-cells ($T_{CM}$) comprise at least 50% of the total number of cells of the composition. In certain embodiments of this method, the transposon is a plasmid DNA transposon with a sequence encoding the antigen receptor or the therapeutic protein is flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments of this method, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X). In certain embodiments of this method, the transposon is a Helraiser transposon. In certain embodiments, and, in particular, those embodiments wherein the transposon is a Helraiser transposon, the transposase is a Helitron transposase. In certain embodiments of this method, the transposon is a Tol2 transposon. In certain embodiments, including those embodiments wherein the transposon is a Tol2 transposon, the transposase is a Tol2 transposase.

In certain embodiments of the methods of the disclosure, the transposon may be derived or recombined from any species. Alternatively, or in addition, the transposon may be synthetic.

In certain embodiments of the methods of the disclosure, the antigen receptor is a T-cell receptor. In certain embodiments, the T-cell receptor is naturally-occurring. In certain embodiments, the T-cell receptor is not naturally-occurring. In certain embodiments, and, in particular, those embodiments wherein the T-cell receptor is not naturally-occurring, the T-cell receptor comprises one or more mutation(s) compared to a wild-type T-cell receptor. In certain embodiments, and, in particular, those embodiments wherein the T-cell receptor is not naturally-occurring, the T-cell receptor is a recombinant T-cell receptor. In certain embodiments of this method, the antigen receptor is a Chimeric Antigen Receptor (CAR). In certain embodiments, the CAR is a CARTyrin. In certain embodiments, the CAR comprises one or more VHH sequence(s). In certain embodiments, the CAR is a VCAR.

In certain embodiments of the methods of the disclosure, including those wherein the method comprises introducing into a primary human T cell (a) a transposon composition comprising a transposon comprising an antigen receptor and (b) a transposase composition comprising a transposase or a sequence encoding the transposase, the methods further comprise introducing into a primary human T cell (c) a second transposon composition comprising a transposon comprising a therapeutic protein, to produce a modified T cell, wherein the modified T cell is capable of expressing the therapeutic protein. In certain embodiments, the therapeutic protein is a secretable protein and the method produces a modified T cell capable of secreting the therapeutic protein. In certain embodiments, the transposase composition of (b) transposes the transposon of (a) and the transposon of (c). In certain embodiments, this methods further comprises introducing into the primary human T cell (d) a second transposase composition comprising a transposase or a sequence encoding the transposase. In certain embodiments, the second transposase composition transposes the transposon of (c). In certain embodiments, the transposase composition of (b) transposes the transposon of (a) and the transposase composition of (d) transposes the transposon of (c). In certain embodiments of this method, the transposon is a plasmid DNA transposon with a sequence encoding the antigen receptor or the therapeutic protein flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments of this method, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X). In certain embodiments of this method, the transposon is a Helraiser transposon. In certain embodiments, and, in particular, those embodiments wherein the transposon is a Helraiser transposon, the transposase is a Helitron transposase. In certain embodiments of this method, the transposon is a Tol2 transposon. In certain embodiments, including those embodiments wherein the transposon is a Tol2 transposon, the transposase is a Tol2 transposase.

The disclosure provides a method of producing a modified stem memory T cell ($T_{SCM}$), comprising: (a) introducing into a primary human T cell a composition comprising an antigen receptor to produce a modified T cell, wherein the antigen receptor or the therapeutic protein is not contained in a transposon, and (b) contacting the modified T-cell and a T-cell activator composition comprising one or more of an anti-human CD3 monospecific tetrameric antibody complex, an anti-human CD28 monospecific tetrameric antibody complex and an activation supplement to produce an activated modified T-cell, wherein the activated modified T-cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising: (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement to produce a plurality of activated modified T-cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 25% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 50% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 60% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 75% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 80% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 85% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 90% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the method produces a plurality of activated modified T cells, wherein at least 95% of the plurality of activated modified T cells expresses one or more cell-surface marker(s) of a stem memory T cell ($T_{SCM}$), thereby producing a plurality of activated modified stem memory T cells ($T_{SCM}$). In certain embodiments, the cell-surface markers comprise CD62L and CD45RA. In certain embodiments, the cell-surface markers of the activated modified $T_{SCM}$ comprise one or more of CD62L, CD45RA, CD28, CCR7, CD127, CD45RO, CD95, CD95 and IL-2Rβ. In certain embodiments, the cell-surface markers of the activated modified $T_{SCM}$ comprise one or more of CD45RA, CD95, IL-2Rβ, CR7, and CD62L.

In certain embodiments of the methods of the disclosure of producing a modified stem memory T cell ($T_{SCM}$), comprising: (a) introducing into a primary human T cell a composition comprising an antigen receptor to produce a modified T cell, wherein the antigen receptor or the therapeutic protein is not contained in a transposon, and (b) contacting the modified T-cell and a T-cell activator composition comprising one or more of an anti-human CD3 monospecific tetrameric antibody complex, an anti-human CD28 monospecific tetrameric antibody complex and an activation supplement to produce an activated modified T-cell, the T-cell activator composition of (b) further comprises an anti-human CD2 monospecific tetrameric antibody complex. In certain embodiments, this method further comprises the step of (c) contacting the activated modified T-cell and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the plurality of expanded modified T-cells expresses one or more cell-surface marker(s) of a stem memory T cell ($T_{SCM}$). In certain embodiments of this method, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of expanded modified T-cells expresses cell-surface marker(s) of a stem memory T cell ($T_{SCM}$). In certain embodiments of this method, at least 60% of the plurality of expanded modified T-cells expresses cell-surface marker(s) of a stem memory T cell ($T_{SCM}$). In certain embodiments, this method further comprises the step of (d) enriching the plurality of expanded modified T-cells to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a stem memory T cell ($T_{SCM}$). In certain embodiments, this method further comprises the step of (d) enriching the plurality of expanded modified T-cells to produce a composition comprising at least 60% of modified T-cells that express cell-surface marker(s) of a stem memory T cell ($T_{SCM}$). In certain embodiments of this method, the enriching step comprises isolating modified T-cells that express one or more cell-surface marker(s) of a stem memory T cell ($T_{SCM}$) from the plurality of enriched modified T-cells. In certain embodiments of this method, the enriching step further comprises contacting the isolated modified $T_{SCM}$ and a T-cell expansion composition comprising one or more of human serum albumin, recombinant human insulin, human transferrin, 2-Mercaptoethanol, Iscove's MDM, and an expansion supplement to produce a plurality of expanded enriched modified $T_{SCM}$. In certain embodiments of this method, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments of this method, the T-cell expansion composition further comprises one or more of octanoic acid, palmitic acid, linoleic acid, oleic acid and a sterol. In certain embodiments of this method, the T-cell expansion composition further comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints. In certain embodiments of this method, the T-cell expansion composition further comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg and a sterol at a concentration of about 1 mg/kg. In certain embodiments of this method, the T-cell expansion composition further comprises one or more of octanoic acid at a concentration of between 6.4 μmol/kg and 640 μmol/kg, inclusive of the endpoints; palmitic acid at a concentration of between 0.7 μmol/kg and 70 μmol/kg, inclusive of the endpoints; linoleic acid at a concentration of between 0.75 μmol/kg and 75 μmol/kg, inclusive of the endpoints; oleic acid at a concentration of between 0.75 μmol/kg and 75 μmol/kg, inclusive of the endpoints; and a sterol at a concentration of between 0.25 μmol/kg and 25 μmol/kg, inclusive of the endpoints. In certain embodiments of this method, the T-cell expansion composition further comprises one or more of octanoic acid at a concentration of about 64 μmol/kg, palmitic acid at a concentration of about 7 μmol/kg, linoleic acid at a concentration of about 7.5 μmol/kg, oleic acid at a concentration of about 7.5 μmol/kg and a sterol at a concentration of about 2.5 μmol/kg.

The disclosure provides a method of producing a modified central memory T-cell ($T_{CM}$), comprising: (a) introducing into a primary human T cell a composition comprising an antigen receptor to produce a modified T cell, wherein the antigen receptor or the therapeutic protein is not contained in a transposon, and (b) contacting the modified T-cell and a T-cell activator composition comprising one or more of an anti-human CD3 monospecific tetrameric antibody complex, an anti-human CD28 monospecific tetrameric antibody complex and an activation supplement to produce an activated modified T-cell, wherein the activated modified T-cell expresses one or more cell-surface marker(s) of a central memory T-cell ($T_{CM}$), thereby producing a central memory T-cell ($T_{CM}$). The disclosure provides a method of producing a plurality of modified central memory T-cell ($T_{CM}$), comprising: (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement to produce a plurality of activated modified T-cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated modified T cells expresses one or more cell-surface marker(s) of a central memory T-cell ($T_{CM}$), thereby producing a plurality of activated modified central memory T-cell ($T_{CM}$). In certain embodiments, the method produces a plurality of activated modified T cells, wherein at least 25% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 50% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 60% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 75% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 80% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 85% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 90% of the plurality of activated modified T cells expresses one or more cell-surface marker(s) of a central memory T cell ($T_{CM}$), thereby producing a plurality of activated modified central memory T cell ($T_{CM}$). In certain embodiments, the method produces a plurality of activated modified T cells, wherein at least 95% of the plurality of activated modified T cells expresses one or more cell-surface marker(s) of a central memory T cell ($T_{CM}$), thereby producing a plurality of activated modified central memory T cell ($T_{CM}$). In certain embodiments, the cell-surface markers of the activated modified $T_{CM}$ comprise one or more of CD45RO, CD95, IL-2Rβ, CCR7, and CD62L.

In certain embodiments of the methods of the disclosure of producing a modified central memory T-cell ($T_{CM}$), comprising: (a) introducing into a primary human T cell a composition comprising an antigen receptor to produce a modified T cell, wherein the antigen receptor or the therapeutic protein is not contained in a transposon, and (b) contacting the modified T-cell and a T-cell activator composition comprising one or more of an anti-human CD3 monospecific tetrameric antibody complex, an anti-human CD28 monospecific tetrameric antibody complex and an activation supplement to produce an activated modified T-cell, the T-cell activator composition of (b) further comprises an anti-human CD2 monospecific tetrameric antibody complex. In certain embodiments, this method further comprises the step of (c) contacting the activated modified T-cell and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the plurality of expanded modified T-cells expresses one or more cell-surface marker(s) of a central memory T cell ($T_{CM}$). In certain embodiments of this method, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of expanded modified T-cells expresses cell-surface marker(s) of a central memory T cell ($T_{CM}$). In certain embodiments of this method, at least 60% of the plurality of expanded modified T-cells expresses cell-surface marker(s) of a central memory T cell ($T_{CM}$). In certain embodiments, this method further comprises the step of (d) enriching the plurality of expanded modified T-cells to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a central memory T cell ($T_{CM}$). In certain embodiments, this method further comprises the step of (d) enriching the plurality of expanded modified T-cells to produce a composition comprising at least 60% of modified T-cells that express cell-surface marker(s) of a central memory T cell ($T_{CM}$). In certain embodiments of this method, the enriching step comprises isolating modified T-cells that express one or more cell-surface marker(s) of a central memory T cell ($T_{CM}$) from the plurality of enriched modified T-cells. In certain embodiments of this method, the enriching step further comprises contacting the isolated modified $T_{CM}$ and a T-cell expansion composition comprising one or more of human serum albumin, recombinant human insulin, human transferrin, 2-Mercaptoethanol, Iscove's MDM, and an expansion supplement to produce a plurality of expanded enriched modified $T_{CM}$. In certain embodiments of this method, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments of this method, the T-cell expansion composition further comprises one or more of octanoic acid, palmitic acid, linoleic acid, oleic acid and a sterol. In certain embodiments of this method, the T-cell expansion composition further comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints. In certain embodiments of this method, the T-cell expansion composition further comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg and a sterol at a concentration of about 1 mg/kg. In certain embodiments of this method, the T-cell expansion composition further comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments of this method, the T-cell expansion composition further comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg.

The disclosure provides a method of producing a composition comprising a plurality of modified stem memory T-cells ($T_{SCM}$) and a plurality of modified central memory T-cells ($T_{CM}$), comprising: (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement to produce a composition comprising a plurality of activated modified stem memory T-cells ($T_{SCM}$) and a plurality of activated modified central memory T-cells ($T_{CM}$), wherein the plurality of activated modified $T_{SCM}$ expresses one or more CD62L, CD45RA, CD28, CCR7, CD127, CD45RO, CD95, CD95 and IL-2Rβ and the plurality of activated modified $T_{CM}$ expresses one or more CD45RO, CD95, IL-2Rβ, CCR7, and CD62L, thereby producing a composition comprising a plurality of modified $T_{SCM}$ and a plurality of modified $T_{CM}$. In certain embodiments of this method, the modified stem memory T-cells ($T_{SCM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified central memory T-cells ($T_{CM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified stem memory T-cells ($T_{SCM}$) comprise at least 10% of the total number of cells of the composition and the modified central memory T-cells ($T_{CM}$) comprise at least 90% of the total number of cells of the composition. In certain embodiments of this method, the modified stem memory T-cells ($T_{SCM}$) comprise at least 90% of the total number of cells of the composition and the modified central memory T-cells ($T_{CM}$) comprise at least 10% of the total number of cells of the composition. In certain embodiments of this method, the modified stem memory T-cells ($T_{SCM}$) comprise at least 20% of the total number of cells of the composition and the modified central memory T-cells ($T_{CM}$) comprise at least 80% of the total number of cells of the composition. In certain embodiments of this method, the modified stem memory T-cells ($T_{SCM}$) comprise at least 80% of the total number of cells of the composition and the modified central memory T-cells ($T_{CM}$) comprise at least 20% of the total number of cells of the composition. In certain embodiments of this method, the modified stem memory T-cells ($T_{SCM}$) comprise at least 30% of the total number of cells of the composition and the modified central memory T-cells ($T_{CM}$) comprise at least 70% of the total number of cells of the composition. In certain embodiments of this method, the modified stem memory T-cells ($T_{SCM}$) comprise at least 70% of the total number of cells of the composition and the modified central memory T-cells ($T_{CM}$) comprise at least 30% of the total number of cells of the composition. In certain embodiments of this method, the modified stem memory T-cells ($T_{SCM}$) comprise at least 40% of the total number of cells of the composition and the modified central memory T-cells ($T_{CM}$) comprise at least 60% of the total number of cells of the composition. In certain embodiments of this method, the modified stem memory T-cells ($T_{SCM}$) comprise at least 60% of the total number of cells of the composition and the modified central memory T-cells ($T_{CM}$) comprise at least 40% of the total number of cells of the composition. In certain embodiments of this method, the modified stem memory T-cells ($T_{SCM}$) comprise at least 50% of the total number of cells of the composition and the modified central memory T-cells ($T_{CM}$) comprise at least 50% of the total number of cells of the composition.

In certain embodiments of methods of the disclosure of producing a composition comprising a plurality of modified stem memory T-cells ($T_{SCM}$) and a plurality of modified central memory T-cells ($T_{CM}$), comprising: (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement to produce a composition comprising a plurality of activated modified stem memory T-cells ($T_{SCM}$) and a plurality of activated modified central memory T-cells ($T_{CM}$), the T-cell activator composition of (b) further comprises an anti-human CD2 monospecific tetrameric antibody complex. In certain embodiments, this method further comprises the step of (c) contacting the composition the plurality of activated modified stem memory T-cells ($T_{SCM}$) and the plurality of activated modified central memory T-cells ($T_{CM}$) with a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein the plurality of expanded modified $T_{SCM}$ expresses one or more CD62L, CD45RA, CD28, CCR7, CD127, CD45RO, CD95, CD95 and IL-2Rβ and the plurality of expanded modified $T_{CM}$ expresses one or more CD45RO, CD95, IL-2Rβ, CCR7, and CD62L, thereby producing a composition comprising a plurality of expanded modified $T_{SCM}$ and a plurality of expanded modified $T_{CM}$. In certain embodiments of this method, the enriching step comprises isolating modified T-cells that express one or more cell-surface marker(s) of a stem memory T cell ($T_{SCM}$) from the plurality of enriched modified T-cells or isolating modified T-cells that express one or more cell-surface marker(s) of a central memory T cell ($T_{CM}$) from the plurality of enriched modified T-cells. In certain embodiments of this method, the enriching step comprises isolating modified T-cells that express one or more cell-surface marker(s) of a stem memory T cell ($T_{SCM}$) from the plurality of enriched modified T-cells and isolating modified T-cells that express one or more cell-surface marker(s) of a central memory T cell ($T_{CM}$) from the plurality of enriched modified T-cells. In certain embodiments of this method, the enriching step further comprises contacting the composition comprising the isolated modified TSCM and the isolated modified $T_{CM}$ with a T-cell expansion composition comprising one or more of human serum albumin, recombinant human insulin, human transferrin, 2-Mercaptoethanol, Iscove's MDM, and an expansion supplement to produce a composition comprising a plurality of expanded enriched modified $T_{SCM}$ and a plurality of expanded enriched modified $T_{CM}$. In certain embodiments of this method, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments of this method, the T-cell expansion composition further comprises one or more of octanoic acid, palmitic acid, linoleic acid, oleic acid and a sterol. In certain embodiments of this method, the T-cell expansion composition further comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints. In certain embodiments of this method, the T-cell expansion composition further comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg and a sterol at a concentration of about 1 mg/kg. In certain embodiments of this method, the T-cell expansion composition further comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments of this method, the T-cell expansion composition further comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments of this method, the modified stem memory T-cells ($T_{SCM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified central memory T-cells ($T_{CM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified stem memory T-cells ($T_{SCM}$) comprise at least 10% of the total number of cells of the composition and the modified central memory T-cells ($T_{CM}$) comprise at least 90% of the total number of cells of the composition. In certain embodiments of this method, the modified stem memory T-cells ($T_{SCM}$) comprise at least 90% of the total number of cells of the composition and the modified central memory T-cells ($T_{CM}$) comprise at least 10% of the total number of cells of the composition. In certain embodiments of this method, the modified stem memory T-cells ($T_{SCM}$) comprise at least 20% of the total number of cells of the composition and the modified central memory T-cells ($T_{CM}$) comprise at least 80% of the total number of cells of the composition. In certain embodiments of this method, the modified stem memory T-cells ($T_{SCM}$) comprise at least 80% of the total number of cells of the composition and the modified central memory T-cells ($T_{CM}$) comprise at least 20% of the total number of cells of the composition. In certain embodiments of this method, the modified stem memory T-cells ($T_{SCM}$) comprise at least 30% of the total number of cells of the composition and the modified central memory T-cells ($T_{CM}$) comprise at least 70% of the total number of cells of the composition. In certain embodiments of this method, the modified stem memory T-cells ($T_{SCM}$) comprise at least 70% of the total number of cells of the composition and the modified central memory T-cells ($T_{CM}$) comprise at least 30% of the total number of cells of the composition. In certain embodiments of this method, the modified stem memory T-cells ($T_{SCM}$) comprise at least 40% of the total number of cells of the composition and the modified central memory T-cells ($T_{CM}$) comprise at least 60% of the total number of cells of the composition. In certain embodiments of this method, the modified stem memory T-cells ($T_{SCM}$) comprise at least 60% of the total number of cells of the composition and the modified central memory T-cells ($T_{CM}$) comprise at least 40% of the total number of cells of the composition. In certain embodiments of this method, the modified stem memory T-cells ($T_{SCM}$) comprise at least 50% of the total number of cells of the composition and the modified central memory T-cells ($T_{CM}$) comprise at least 50% of the total number of cells of the composition.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, the introducing step comprises a homologous recombination. In certain embodiments of the introduction step comprising a homologous recombination, a genomic editing composition contacts a genomic sequence of at least one primary T cell of the plurality of T cells. In certain embodiments of the introduction step comprising a homologous recombination, a genomic editing composition contacts a genomic sequence of a portion of primary T cells of the plurality of T cells. In certain embodiments, the portion of primary T cells is at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage in between of the total number of primary T cells in the plurality of T cells. In certain embodiments of the introduction step comprising a homologous recombination, a genomic editing composition contacts a genomic sequence of each primary T cell of the plurality of T cells. In certain embodiments of the introduction step comprising a homologous recombination, a genomic editing composition induces a single strand break. In certain embodiments of the introduction step comprising a homologous recombination, a genomic editing composition induces a double strand break. In certain embodiments of the introduction step comprising a homologous recombination, the introduction step further comprises a donor sequence composition. In certain embodiments, the donor sequence composition comprises a sequence encoding the antigen receptor. In certain embodiments, the donor sequence composition comprises a sequence encoding the antigen receptor, a 5' genomic sequence and a 3' genomic sequence, wherein the 5' genomic sequence is homologous or identical to a genomic sequence of the primary T cell that is 5' to the break point induced by the genomic editing composition and the 3' genomic sequence is homologous or identical to a genomic sequence of the primary T cell that is 3' to the break point induced by the genomic editing composition. In certain embodiments of the introduction step comprising a homologous recombination, the genomic editing composition and donor sequence composition are contacted with the genomic sequence simultaneously or sequentially. In certain embodiments of the introduction step comprising a homologous recombination, the genomic editing composition and donor sequence composition are contacted with the genomic sequence sequentially, and the genomic editing composition is provided first. In certain embodiments of the introduction step comprising a homologous recombination, the genomic editing composition comprises a sequence encoding a DNA binding domain and a sequence encoding a nuclease domain. In certain embodiments of the introduction step comprising a homologous recombination, the genomic editing composition comprises a DNA binding domain and a nuclease domain. In certain embodiments of the genomic editing composition, the DNA binding domain comprises a guide RNA (gRNA). In certain embodiments of the genomic editing composition, the DNA binding domain comprises a DNA-binding domain of a TALEN. In certain embodiments of the genomic editing composition, the DNA binding domain comprises a DNA-binding domain of a ZFN. In certain embodiments of the genomic editing composition, the nuclease domain comprises a Cas9 nuclease or a sequence thereof. In certain embodiments of the genomic editing composition, the nuclease domain comprises an inactive Cas9 (SEQ ID NO: 33, comprising a substitution of a Alanine (A) for Aspartic Acid (D) at position 10 (D10A) and a substitution of Alanine (A) for Histidine (H) at position 840 (H840A)). In certain embodiments of the genomic editing composition, the nuclease domain comprises a short and inactive Cas9 (SEQ ID NO: 32, comprising a substitution of an Alanine (A) for an Aspartic Acid (D) at position 10 (D10A) and a substitution of an Alanine (A) for an Asparagine (N) at position 540 (N540A)). In certain embodiments of the genomic editing composition, the nuclease domain comprises or further comprises a type IIS endonuclease. In certain embodiments of the genomic editing composition, the type IIS endonuclease comprises AciI, MnlI, AlwI, BbvI, BccI, BceAI, BsmAI, BsmFI, BspCNI, BsrI, BtsCI, HgaI, HphI, HpyAV, MboII, MylI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the type IIS endonuclease comprises Clo051. In certain embodiments of the genomic editing composition, the nuclease domain comprises or further comprises a TALEN or a nuclease domain thereof. In certain embodiments of the genomic editing composition, the nuclease domain comprises or further comprises a ZFN or a nuclease domain thereof. In certain embodiments of the introduction step comprising a homologous recombination, the genomic editing composition induces a break in a genomic sequence and the donor sequence composition is inserted using the endogenous DNA repair mechanisms of the primary T cell. In certain embodiments of the introduction step comprising a homologous recombination, the insertion of the donor sequence composition eliminates a DNA binding site of the genomic editing composition, thereby preventing further activity of the genomic editing composition.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement, a viral vector comprises the antigen receptor. In certain embodiments, the viral vector comprises one or more sequences isolated, derived, or recombined from an RNA virus. In certain embodiments, the RNA virus is a single-stranded or a double-stranded virus. In certain embodiments, the viral vector comprises one or more sequences isolated, derived, or recombined from a DNA virus. In certain embodiments, the DNA virus is a single-stranded or a double-stranded virus. In certain embodiments, the virus is replication-defective.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement, a viral vector comprises the antigen receptor. In certain embodiments, the viral vector comprises a sequence isolated or derived from a retrovirus. In certain embodiments, the viral vector comprises a sequence isolated or derived from a lentivirus.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement, a viral vector comprises the antigen receptor. In certain embodiments, the viral vector comprises a sequence isolated or derived from a retrovirus. In certain embodiments, the viral vector comprises a sequence isolated or derived from a gamma retrovirus.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement, a viral vector comprises the antigen receptor. In certain embodiments, the viral vector comprises a sequence isolated or derived from an adeno-associated virus (AAV). In certain embodiments, the AAV is a serotype AAV1, AAV2, AAV3, AAV4, AAV5, AAV6, AAV7, AAV8, AAV9, AAV10 or AAV11. In certain embodiments, the AAV comprises a sequence from one or more of AAV1, AAV2, AAV3, AAV4, AAV5, AAV6, AAV7, AAV8, AAV9, AAV10 or AAV11. In certain embodiments, the AAV comprises a sequence isolated, derived, or recombined from one or more of AAV1, AAV2, AAV3, AAV4, AAV5, AAV6, AAV7, AAV8, AAV9, AAV10 or AAV11. In certain embodiments, the AAV comprises a sequence isolated, derived, or recombined from AAV2. In certain embodiments, including those in which the vector crosses the blood brain barrier (BBB), the AAV comprises a sequence isolated, derived, or recombined from AAV9. Exemplary adeno-associated viruses and recombinant adeno-associated viruses of the disclosure include, but are not limited to, self-complementary AAV (scAAV) and AAV hybrids containing the genome of one serotype and the capsid of another serotype (e.g. AAV2/5, AAV-DJ and AAV-DJ8). Exemplary adeno-associated viruses and recombinant adeno-associated viruses of the disclosure include, but are not limited to, rAAV-LK03, rAAV-NP59 and rAAV-NP84.

In certain embodiments of the methods of producing an activated modified $T_{SCM}$ or $T_{CM}$ of the disclosure, a nucleic acid vector comprises the antigen receptor. In certain embodiments, a DNA vector comprises the antigen receptor. In certain embodiments, an mRNA vector comprises the antigen receptor. In certain embodiments, the nucleic acid vector is a plasmid or a minicircle vector.

In certain embodiments of the methods of producing an activated modified $T_{SCM}$ or $T_{CM}$ of the disclosure, a nanoparticle vector comprises the antigen receptor. Nanoparticles may be comprised of polymers disclosed in, for example, International Patent Publication No. WO 2012/094679, International Patent Publication No. WO 2016/022805, International Patent Publication No. WO/2011/133635, International Patent Publication No. WO/2016/090111, International Patent Publication No. WO/2017/004498, WO/2017/004509, International Patent Application No. PCT/US2017/030271, U.S. Pat. Nos. 6,835,394, 7,217,427, and 7,867,512.

In certain embodiments of the methods of producing an activated modified $T_{SCM}$ or $T_{CM}$ of the disclosure, the antigen receptor is a T-cell receptor. In certain embodiments, the T-cell receptor is naturally-occurring. In certain embodiments, the T-cell receptor is not naturally-occurring. In certain embodiments, and, in particular, those embodiments wherein the T-cell receptor is not naturally-occurring, the T-cell receptor comprises one or more mutation(s) compared to a wild-type T-cell receptor. In certain embodiments, and, in particular, those embodiments wherein the T-cell receptor is not naturally-occurring, the T-cell receptor is a recombinant T-cell receptor. In certain embodiments of this method, the antigen receptor is a Chimeric Antigen Receptor (CAR). In certain embodiments, the CAR is a CARTyrin. In certain embodiments, the CAR comprises one or more VHH sequence(s). In certain embodiments, the CAR is a VCAR.

In certain embodiments of the methods of producing an activated modified $T_{SCM}$ or $T_{CM}$ of the disclosure, including those methods comprising (a) introducing into a plurality of primary human T cells a composition comprising an antigen receptor to produce a plurality of modified T cells, wherein the antigen receptor or the therapeutic protein is not contained in a transposon, and (b) contacting the plurality of modified T-cells and a T-cell activator composition comprising one or more of an anti-human CD3 monospecific tetrameric antibody complex, an anti-human CD28 monospecific tetrameric antibody complex and an activation supplement, the method further comprises introducing into the primary human T cell, a composition comprising a therapeutic protein to produce a modified T cell capable of expressing the therapeutic protein. In certain embodiments, the therapeutic protein is a secretable protein and the method produces a modified T cell capable of secreting the therapeutic protein. In certain embodiments, the introducing step comprises a homologous recombination and a donor sequence comprises a sequence encoding the therapeutic protein. In certain embodiments, the donor sequence that comprises the antigen receptor further comprises the therapeutic protein. In certain embodiments, a first donor sequence comprises the antigen receptor and a second donor sequence comprises the therapeutic protein. In certain embodiments, a vector comprises a sequence encoding the therapeutic protein. In certain embodiments, the vector is a viral vector. In certain embodiments, the vector is a nanoparticle. In certain embodiments, the vector that comprises the antigen receptor further comprises the therapeutic protein. In certain embodiments, a first vector comprises the antigen receptor and a second vector template comprises the therapeutic protein.

The disclosure provides a method of producing a modified stem memory T cell ($T_{SCM}$), comprising: (a) introducing into a primary human T cell a composition comprising an antigen receptor to produce a modified T cell, wherein a transposon comprises the antigen receptor, and (b) contacting the modified T cell and a T-cell activator composition comprising one or more of an anti-human CD3 monospecific tetrameric antibody complex, an anti-human CD28 monospecific tetrameric antibody complex and an activation supplement to produce an activated modified T-cell, wherein the activated modified-T cell expresses one or more cell-surface marker(s) of a stem memory T cell ($T_{SCM}$), thereby producing a modified stem memory T cell ($T_{SCM}$). The disclosure provides a method of producing a plurality of modified stem memory T cells ($T_{SCM}$), comprising: (a) introducing into a plurality of primary human T cells a composition comprising an antigen receptor to produce a plurality of modified T cells, wherein a transposon comprises the antigen receptor, and (b) contacting the plurality of modified T cells and a T-cell activator composition comprising one or more of an anti-human CD3 monospecific tetrameric antibody complex, an anti-human CD28 monospecific tetrameric antibody complex and an activation supplement to produce a plurality of activated modified T-cells, wherein at least 25%, 50%, 60%, 75%, 80%, 85%, 90%, 95% or 99% of the plurality of activated modified –T cells expresses one or more cell-surface marker(s) of a stem memory T cell ($T_{SCM}$), thereby producing a modified stem memory T cell ($T_{SCM}$). In certain embodiments of this method, at least 60% of the plurality of activated modified –T cells expresses one or more cell-surface marker(s) of a stem memory T cell ($T_{SCM}$). In certain embodiments of this method, the T-cell activator composition of (b) further comprises an anti-human CD2 monospecific tetrameric antibody complex. The disclosure provides a method of producing a modified stem memory T cell ($T_{SCM}$), comprising: (a) introducing into a primary human T cell a composition comprising a chimeric antigen receptor (CAR) to produce a CAR-T cell and (b) contacting the CAR-T cell and a T-cell activator composition comprising one or more of an anti-human CD3 monospecific tetrameric antibody complex, an anti-human CD28 monospecific tetrameric antibody complex, an anti-human CD2 monospecific tetrameric antibody complex and an activation supplement to produce an activated CAR-T cell, wherein the activated CAR-T cell expresses one or more cell-surface marker(s) of a stem memory T cell ($T_{SCM}$), thereby producing a CAR-expressing stem memory T cell ($T_{SCM}$) (CAR-$T_{SCM}$). The disclosure provides a method of producing a plurality of modified stem memory T cells ($T_{SCM}$), comprising: (a) introducing into a plurality of primary human T cells a composition comprising a chimeric antigen receptor (CAR) to produce a plurality of CAR-T cells and (b) contacting the plurality of CAR-T cells and a T-cell activator composition comprising one or more of an anti-human CD3 monospecific tetrameric antibody complex, an anti-human CD28 monospecific tetrameric antibody complex, an anti-human CD2 monospecific tetrameric antibody complex and an activation supplement to produce a plurality of activated CAR-T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the methods further comprises the step of: (c) contacting the activated modified T cell and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the plurality of expanded modified T-cells expresses one or more cell-surface marker(s) of a stem memory T cell ($T_{SCM}$). In certain embodiments, the T-cell expansion composition comprises or further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg. In certain embodiments, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of expanded modified T-cells expresses cell-surface marker(s) of a stem memory T cell ($T_{SCM}$). In certain embodiments, at least 60% of the plurality of expanded modified T-cells expresses cell-surface marker(s) of a stem memory T cell ($T_{SCM}$). In certain embodiments, the method further comprises the step of: (d) enriching the plurality of expanded modified T-cells to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a stem memory T cell ($T_{SCM}$). In certain embodiments, the method further comprises the step of: (d) enriching the plurality of expanded modified T-cells to produce a composition comprising at least 60% of modified T-cells that express cell-surface marker(s) of a stem memory T cell ($T_{SCM}$). In certain embodiments, the enriching step further comprises isolating modified T-cells that express one or more cell-surface marker(s) of a stem memory T cell ($T_{SCM}$) from the plurality of enriched modified T-cells. In certain embodiments, the enriching step further comprises contacting the isolated modified $T_{SCM}$ and a T-cell expansion composition comprising one or more of human serum albumin, recombinant human insulin, human transferrin, 2-Mercaptoethanol, Iscove's MDM, and an expansion supplement to produce a plurality of expanded enriched modified $T_{SCM}$. In certain embodiments, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg.

The disclosure provides a method of producing a modified central memory T cell ($T_{CM}$), comprising: (a) introducing into a primary human T cell a composition comprising an antigen receptor to produce a modified T cell, wherein a transposon comprises the antigen receptor, and (b) contacting the modified T cell and a T-cell activator composition comprising one or more of an anti-human CD3 monospecific tetrameric antibody complex, an anti-human CD28 monospecific tetrameric antibody complex and an activation supplement to produce an activated modified T-cell, wherein the activated modified-T cell expresses one or more cell-surface marker(s) of a central memory T cell ($T_{CM}$), thereby producing a modified central memory T cell ($T_{CM}$). The disclosure provides a method of producing a plurality of modified central memory T cells ($T_{CM}$), comprising: (a) introducing into a plurality of primary human T cells a composition comprising an antigen receptor to produce a plurality of modified T cells, wherein a transposon comprises the antigen receptor, and (b) contacting the plurality of modified T cells and a T-cell activator composition comprising one or more of an anti-human CD3 monospecific tetrameric antibody complex, an anti-human CD28 monospecific tetrameric antibody complex and an activation supplement to produce a plurality of activated modified T-cells, wherein at least 25%, 50%, 60%, 75%, 80%, 85%, 90%, 95% or 99% of the plurality of activated modified –T cells expresses one or more cell-surface marker(s) of a central memory T cell ($T_{CM}$), thereby producing a modified central memory T cell ($T_{CM}$). In certain embodiments of this method, at least 60% of the plurality of activated modified –T cells expresses one or more cell-surface marker(s) of a central memory T cell ($T_{CM}$). In certain embodiments of this method, the T-cell activator composition of (b) further comprises an anti-human CD2 monospecific tetrameric antibody complex. In certain embodiments, the methods further comprises the step of: (c) contacting the activated modified T cell and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the plurality of expanded modified T-cells expresses one or more cell-surface marker(s) of a central memory T cell ($T_{CM}$). In certain embodiments, the T-cell expansion composition comprises or further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg. In certain embodiments, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of expanded modified T-cells expresses cell-surface marker(s) of a central memory T cell ($T_{CM}$). In certain embodiments, at least 60% of the plurality of expanded modified T-cells expresses cell-surface marker(s) of a central memory T cell ($T_{CM}$). In certain embodiments, the method further comprises the step of: (d) enriching the plurality of expanded modified T-cells to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a central memory T cell ($T_{CM}$). In certain embodiments, the method further comprises the step of: (d) enriching the plurality of expanded modified T-cells to produce a composition comprising at least 60% of modified T-cells that express cell-surface marker(s) of a central memory T cell ($T_{CM}$). In certain embodiments, the enriching step further comprises isolating modified T-cells that express one or more cell-surface marker(s) of a central memory T cell ($T_{CM}$) from the plurality of enriched modified T-cells. In certain embodiments, the enriching step further comprises contacting the isolated modified $T_{CM}$ and a T-cell expansion composition comprising one or more of human serum albumin, recombinant human insulin, human transferrin, 2-Mercaptoethanol, Iscove's MDM, and an expansion supplement to produce a plurality of expanded enriched modified $T_{CM}$. In certain embodiments, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg.

The disclosure provides a method of producing a composition comprising a plurality of modified stem memory T-cells ($T_{SCM}$) and a plurality of modified central memory T-cells ($T_{CM}$), comprising: (a) introducing into a plurality of primary human T cells a composition comprising an antigen receptor to produce a composition comprising a plurality of modified stem memory T-cells ($T_{SCM}$) and a plurality of modified central memory T-cells ($T_{CM}$), wherein a transposon comprises the antigen receptor, and (b) contacting the composition and a T-cell activator composition comprising one or more of an anti-human CD3 monospecific tetrameric antibody complex, an anti-human CD28 monospecific tetrameric antibody complex and an activation supplement to produce a composition comprising a plurality of activated modified stem memory T-cells ($T_{SCM}$) and a plurality of activated modified central memory T-cells ($T_{CM}$), wherein the plurality of activated modified $T_{SCM}$ expresses one or more CD62L, CD45RA, CD28, CCR7, CD127, CD45RO, CD95, CD95 and IL-2Rβ and the plurality of activated modified $T_{CM}$ expresses one or more CD45RO, CD95, IL-2Rβ, CCR7, and CD62L, thereby producing a composition comprising a plurality of modified $T_{SCM}$ and a plurality of modified $T_{CM}$. In certain embodiments of this method, the T-cell activator composition of (b) further comprises an anti-human CD2 monospecific tetrameric antibody complex. In certain embodiments, the methods further comprises the step of: (c) contacting the composition and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the composition comprising a plurality of expanded modified T-cells expresses one or more cell-surface marker(s) of a stem memory T cell ($T_{SCM}$). In certain embodiments, the methods further comprises the step of: (c) contacting the composition and a T-cell expansion composition comprising one or more of human serum albumin, recombinant human insulin, human transferrin, 2-Mercaptoethanol, Iscove's MDM, and an expansion supplement to produce a plurality of expanded modified T-cells, wherein at least 2% of the composition comprising a plurality of expanded modified T-cells expresses one or more cell-surface marker(s) of a central memory T cell ($T_{CM}$). In certain embodiments, the T-cell expansion composition comprises or further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg. In certain embodiments, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of cells the composition comprising a plurality of expanded modified $T_{SCM}$ and a plurality of expanded modified $T_{CM}$ expresses cell-surface marker(s) of a stem memory T cell ($T_{SCM}$). In certain embodiments, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of cells the composition comprising a plurality of expanded modified $T_{SCM}$ and a plurality of expanded modified $T_{CM}$ expresses cell-surface marker(s) of a central memory T cell ($T_{CM}$). In certain embodiments, the method further comprises the step of: (d) enriching the composition to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a stem memory T cell ($T_{SCM}$). In certain embodiments, the method further comprises the step of: (d) enriching the composition to produce a composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of modified T-cells that express cell-surface marker(s) of a central memory T cell ($T_{CM}$). In certain embodiments, the enriching step further comprises isolating modified T-cells that express one or more cell-surface marker(s) of a stem memory T cell ($T_{SCM}$) from the composition or isolating modified T-cells that express one or more cell-surface marker(s) of a central memory T cell ($T_{CM}$) from the composition. In certain embodiments, the enriching step further comprises isolating modified T-cells that express one or more cell-surface marker(s) of a stem memory T cell ($T_{SCM}$) from the composition and isolating modified T-cells that express one or more cell-surface marker(s) of a central memory T cell ($T_{CM}$) from the composition. In certain embodiments, the enriching step further comprises contacting the isolated modified $T_{SCM}$ and/or $T_{CM}$ and a T-cell expansion composition comprising one or more of human serum albumin, recombinant human insulin, human transferrin, 2-Mercaptoethanol, Iscove's MDM, and an expansion supplement to produce a composition comprising a plurality of expanded enriched modified $T_{SCM}$ and/or $T_{CM}$. In certain embodiments, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg. In certain embodiments of this method, the modified stem memory T-cells ($T_{SCM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified central memory T-cells ($T_{CM}$) comprise at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage of cells in between of the total number of cells of the composition. In certain embodiments of this method, the modified stem memory T-cells ($T_{SCM}$) comprise at least 10% of the total number of cells of the composition and the modified central memory T-cells ($T_{CM}$) comprise at least 90% of the total number of cells of the composition. In certain embodiments of this method, the modified stem memory T-cells ($T_{SCM}$) comprise at least 90% of the total number of cells of the composition and the modified central memory T-cells ($T_{CM}$) comprise at least 10% of the total number of cells of the composition. In certain embodiments of this method, the modified stem memory T-cells ($T_{SCM}$) comprise at least 20% of the total number of cells of the composition and the modified central memory T-cells ($T_{CM}$) comprise at least 80% of the total number of cells of the composition. In certain embodiments of this method, the modified stem memory T-cells ($T_{SCM}$) comprise at least 80% of the total number of cells of the composition and the modified central memory T-cells ($T_{CM}$) comprise at least 20% of the total number of cells of the composition. In certain embodiments of this method, the modified stem memory T-cells ($T_{SCM}$) comprise at least 30% of the total number of cells of the composition and the modified central memory T-cells ($T_{CM}$) comprise at least 70% of the total number of cells of the composition. In certain embodiments of this method, the modified stem memory T-cells ($T_{SCM}$) comprise at least 70% of the total number of cells of the composition and the modified central memory T-cells ($T_{CM}$) comprise at least 30% of the total number of cells of the composition. In certain embodiments of this method, the modified stem memory T-cells ($T_{SCM}$) comprise at least 40% of the total number of cells of the composition and the modified central memory T-cells ($T_{CM}$) comprise at least 60% of the total number of cells of the composition. In certain embodiments of this method, the modified stem memory T-cells ($T_{SCM}$) comprise at least 60% of the total number of cells of the composition and the modified central memory T-cells ($T_{CM}$) comprise at least 40% of the total number of cells of the composition. In certain embodiments of this method, the modified stem memory T-cells ($T_{SCM}$) comprise at least 50% of the total number of cells of the composition and the modified central memory T-cells ($T_{CM}$) comprise at least 50% of the total number of cells of the composition.

In certain embodiments of the methods of the disclosure, including those wherein the method comprises introducing into a primary human T cell (a) introducing into a primary human T cell a composition comprising an antigen receptor to produce a modified T cell, wherein a transposon comprises the antigen receptor, and (b) contacting the modified T cell and a T-cell activator composition comprising one or more of an anti-human CD3 monospecific tetrameric antibody complex, an anti-human CD28 monospecific tetrameric antibody complex and an activation supplement to produce an activated modified T-cell, the method further comprises introducing into the primary human T cell (c) a second transposon composition comprising a transposon comprising a therapeutic protein, to produce a modified T cell, wherein the modified T cell is capable of expressing the therapeutic protein. In certain embodiments, the therapeutic protein is a secretable protein and the method produces a modified T cell capable of secreting the therapeutic protein. In certain embodiments, the method further comprises introducing a transposase composition. In certain embodiments, the transposase composition transposes the transposon of (a) and the second transposon. In certain embodiments, the method comprises introducing a first transposase composition and a second transposase composition. In certain embodiments, including those wherein the method comprises introducing a first transposase composition and a second transposase composition, the first transposase composition transposes the transposon of (a) and the second transposase composition transposes the second transposon. In certain embodiments of this method, the transposon is a plasmid DNA transposon with a sequence encoding the antigen receptor or the therapeutic protein flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments of this method, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X). In certain embodiments of this method, the transposon is a Helraiser transposon. In certain embodiments, and, in particular, those embodiments wherein the transposon is a Helraiser transposon, the transposase is a Helitron transposase. In certain embodiments of this method, the transposon is a Tol2 transposon. In certain embodiments, including those embodiments wherein the transposon is a Tol2 transposon, the transposase is a Tol2 transposase.

In certain embodiments of the methods of the disclosure, including those wherein the method comprises introducing into a primary human T cell (a) introducing into a primary human T cell a composition comprising an antigen receptor to produce a modified T cell, wherein a transposon comprises the antigen receptor, and (b) contacting the modified T cell and a T-cell activator composition comprising one or more of an anti-human CD3 monospecific tetrameric antibody complex, an anti-human CD28 monospecific tetrameric antibody complex and an activation supplement to produce an activated modified T-cell, the method further comprises introducing into the primary human T cell a sequence encoding a therapeutic protein, to produce a modified T cell, wherein the modified T cell is capable of expressing the therapeutic protein. In certain embodiments of introducing a sequence encoding a therapeutic protein, the introducing step comprises a homologous recombination. In certain embodiments of introducing a sequence encoding a therapeutic protein, a vector comprises the sequence encoding the therapeutic protein. In certain embodiments, the vector is a viral vector. In certain embodiments, the vector is a nanoparticle.

In certain embodiments of the methods of the disclosure, the introducing step further comprises a composition comprising a genomic editing construct. In certain embodiments, the genomic editing construct comprises a guide RNA and a clustered regularly interspaced short palindromic repeats (CRISPR) associated protein 9 (Cas9) DNA endonuclease. In certain embodiments, the genomic editing construct comprises a DNA binding domain and a type IIS endonuclease. In certain embodiments, the genomic editing construct encodes a fusion protein. In certain embodiments, the genomic editing construct encodes the DNA binding domain and the type IIS endonuclease and wherein the expressed DNA binding domain and the expressed type IIS endonuclease are non-covalently linked. In certain embodiments, including those embodiments wherein the genomic editing construct comprises a DNA binding domain and a type IIS endonuclease, the genomic editing construct comprises a sequence derived from a Cas9 endonuclease. In certain embodiments, including those embodiments wherein the genomic editing construct comprises a DNA binding domain and a type IIS endonuclease, the sequence derived from a Cas9 endonuclease is the DNA binding domain. In certain embodiments, including those embodiments wherein the sequence derived from a Cas9 endonuclease is the DNA binding domain, the sequence derived from a Cas9 endonuclease encodes an inactive Cas9. In certain embodiments, including those embodiments wherein the sequence derived from a Cas9 endonuclease is the DNA binding domain, the sequence derived from a Cas9 endonuclease encodes a truncated Cas9. In certain embodiments, the sequence derived from a Cas9 endonuclease comprises an amino acid substitution of an Alanine (A) for an Aspartic Acid (D) at position 10 (D10A). In certain embodiments, the sequence derived from a Cas9 endonuclease comprises an amino acid substitution of an Alanine (A) for a Histidine (H) at position 840 (H840A). In certain embodiments, the sequence derived from a Cas9 endonuclease comprises dCas9 (SEQ ID NO: 33). In certain embodiments, the sequence derived from a Cas9 endonuclease comprises an amino acid substitution of an Alanine (A) for an Asparagine (N) at position 580 (N580A). In certain embodiments, the sequence derived from a Cas9 endonuclease comprises dSaCas9 (SEQ ID NO:

32). In certain embodiments, including those embodiments wherein the genomic editing construct comprises a DNA binding domain and a type IIS endonuclease, the genomic editing construct comprises a sequence derived from a transcription activator-like effector nuclease (TALEN). In certain embodiments, including those embodiments wherein the genomic editing construct comprises a DNA binding domain and a type IIS endonuclease, the sequence derived from a TALEN is the DNA binding domain. In certain embodiments, the genomic editing construct comprises a TALEN. In certain embodiments, including those embodiments wherein the genomic editing construct comprises a DNA binding domain and a type IIS endonuclease, the genomic editing construct comprises a sequence derived from a zinc-finger nuclease (ZFN). In certain embodiments, including those embodiments wherein the genomic editing construct comprises a DNA binding domain and a type IIS endonuclease, the sequence derived from a ZFN is the DNA binding domain. In certain embodiments, the genomic editing construct comprises a zinc-finger nuclease (ZFN).

In certain embodiments of the methods of the disclosure, the transposon is a plasmid DNA transposon with a sequence encoding the antigen receptor or the therapeutic protein flanked by two cis-regulatory insulator elements. In certain embodiments of this method, the introducing step further comprises a composition comprising an mRNA sequence encoding a transposase. In certain embodiments, the transposon is a piggyBac transposon. In certain embodiments, and, in particular, those embodiments wherein the transposon is a piggyBac transposon, the transposase is a Super piggyBac™ (SPB) transposase. In certain embodiments, and, in particular, those embodiments wherein the transposase is a Super piggyBac™ (SPB) transposase, the sequence encoding the transposase is an mRNA sequence. In certain embodiments, the piggyBac transposase comprises an amino acid sequence comprising SEQ ID NO: 4. In certain embodiments, the piggyBac transposase is a hyperactive variant and the hyperactive variant comprises an amino acid substitution at one or more of positions 30, 165, 282 and 538 of SEQ ID NO: 4. In certain embodiments, the amino acid substitution at position 30 of SEQ ID NO: 4 is a substitution of a valine (V) for an isoleucine (I) (I30V). In certain embodiments, the amino acid substitution at position 165 of SEQ ID NO: 4 is a substitution of a serine (S) for a glycine (G) (G165S). In certain embodiments, the amino acid substitution at position 282 of SEQ ID NO: 4 is a substitution of a valine (V) for a methionine (M) (M282V). In certain embodiments, the amino acid substitution at position 538 of SEQ ID NO: 4 is a substitution of a lysine (K) for an asparagine (N) (N538K). In certain embodiments, the Super piggyBac (SPB) transposase comprises an amino acid sequence comprising SEQ ID NO: 5. In certain embodiments, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X). In certain embodiments, the transposon is a Helraiser transposon. In certain embodiments, in particular those embodiments wherein the transposon is a Helraiser transposon, the transposase is a Helitron transposase. In certain embodiments, the transposon is a Tol2 transposon. In certain embodiments, in particular those embodiments wherein the transposon is a Tol2 transposon, the transposase is a Tol2 transposase. In certain embodiments, the sequence encoding the transposase is an mRNA sequence. In certain embodiments, the transposon may be derived or recombined from any species. Alternatively, or in addition, the transposon may be synthetic.

In certain embodiments of the methods of the disclosure, the transposon further comprises a selection gene. In certain embodiments, the T-cell expansion composition further comprises a selection agent.

In certain embodiments of the methods of the disclosure, the antigen receptor is a T-cell receptor. In certain embodiments, the T-cell receptor is naturally-occurring. In certain embodiments, the T-cell receptor is not naturally-occurring. In certain embodiments, and, in particular, those embodiments wherein the T-cell receptor is not naturally-occurring, the T-cell receptor comprises one or more mutation(s) compared to a wild-type T-cell receptor. In certain embodiments, and, in particular, those embodiments wherein the T-cell receptor is not naturally-occurring, the T-cell receptor is a recombinant T-cell receptor. In certain embodiments of this method, the antigen receptor is a Chimeric Antigen Receptor (CAR). In certain embodiments, the CAR is a CARTyrin. In certain embodiments, the CAR comprises one or more VHH sequence(s). In certain embodiments, the CAR is a VCAR.

In certain embodiments of the methods of the disclosure, the cell-surface markers of the modified $T_{SCM}$ comprise CD62L and CD45RA. In certain embodiments, the cell-surface markers of the modified $T_{SCM}$ comprise one or more of CD62L, CD45RA, CD28, CCR7, CD127, CD45RO, CD95, CD95 and IL-2Rβ. In certain embodiments, the cell-surface markers of the modified $T_{SCM}$ comprise one or more of CD45RA, CD95, IL-2Rβ, CR7, and CD62L.

In certain embodiments of the methods of the disclosure, the plurality of expanded modified T-cells comprises a naïve T-cell (modified $T_N$) and the cell-surface markers of the CAR-$T_N$ comprise one or more of CD45RA, CCR7 and CD62L. In certain embodiments, the plurality of expanded modified T-cells comprises a central memory T-cell (modified $T_{CM}$) and the cell-surface markers of the CAR-$T_{CM}$ comprise one or more of CD45RO, CD95, CCR7, and CD62L. In certain embodiments, the plurality of expanded modified T-cells comprises an effector memory T-cell (modified $T_{EM}$) and the cell-surface markers of the CAR-$T_{EM}$ comprise one or more of CD45RO, CD95, and IL-2Rβ. In certain embodiments, plurality of expanded modified T-cells comprises an effector T-cell (modified $T_{EFF}$) and the cell-surface markers of the CAR-$T_{EFF}$ comprise one or more of CD45RA, CD95, and IL-2Rβ.

In certain embodiments of the methods of the disclosure, the plurality of expanded modified T-cells comprises a central memory T-cell (modified $T_{CM}$) and the cell-surface markers of the CAR-$T_{CM}$ comprise one or more of CD45RO, CD95, IL-2Rβ, CCR7, and CD62L. In certain embodiments, the most abundant cell in the plurality of expanded modified T-cells is a central memory T-cell (modified $T_{CM}$) and the cell-surface markers of the CAR-$T_{CM}$ comprise one or more of CD45RO, CD95, IL-2Rβ, CCR7, and CD62L. In certain embodiments, wherein the most abundant cell in the plurality of expanded modified T-cells is a central memory T-cell (modified $T_{CM}$), the plurality of expanded modified T-cells comprises a $T_{SCM}$ cell and the cell-surface markers of the $T_{SCM}$ cell comprise one or more of CD62L, CD45RA, CD28, CCR7, CD127, CD45RO, CD95, CD95 and IL-2Rβ.

The disclosure provides a method of producing a modified stem memory T cell ($T_{SCM}$), comprising: (a) introducing into a primary human T cell a composition comprising a chimeric antigen receptor (CAR) to produce a CAR-T cell and (b) contacting the CAR-T cell and a T-cell activator composition comprising one or more of an anti-human CD3 monospecific tetrameric antibody complex, an anti-human CD28 monospecific tetrameric antibody complex, an anti-human CD2 monospecific tetrameric antibody complex and an activation supplement to produce an activated CAR-T cell, wherein the activated CAR-T cell expresses one or more cell-surface marker(s) of a stem memory T cell ($T_{SCM}$), thereby producing a CAR-expressing stem memory T cell ($T_{SCM}$) (CAR-$T_{SCM}$). The disclosure provides a method of producing a plurality of modified stem memory T cells ($T_{SCM}$), comprising: (a) introducing into a plurality of primary human T cells a composition comprising a chimeric antigen receptor (CAR) to produce a plurality of CAR-T cells and (b) contacting the plurality of CAR-T cells and a T-cell activator composition comprising one or more of an anti-human CD3 monospecific tetrameric antibody complex, an anti-human CD28 monospecific tetrameric antibody complex, an anti-human CD2 monospecific tetrameric antibody complex and an activation supplement to produce a plurality of activated CAR-T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 25% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 50% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 60% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 75% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 80% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 85% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 90% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 95% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the cell-surface markers comprise CD62L and CD45RA. In certain embodiments, the cell-surface markers of the activated CAR $T_{SCM}$ comprise one or more of CD62L, CD45RA, CD28, CCR7, CD127, CD45RO, CD95, CD95 and IL-2Rβ. In certain embodiments, the cell-surface markers of the activated CAR $T_{SCM}$ comprise one or more of CD45RA, CD95, IL-2Rβ, CR7, and CD62L. The disclosure provides a method of producing a modified stem memory T cell ($T_{SCM}$), comprising: (a) introducing into a primary human T cell a composition comprising a chimeric antigen receptor (CAR) to produce a CAR-T cell and (b) contacting the CAR-T cell and a T-cell activator composition comprising one or more of an anti-human CD3 monospecific tetrameric antibody complex, an anti-human CD28 monospecific tetrameric antibody complex and an activation supplement to produce an activated CAR-T cell, wherein the activated CAR-T cell expresses one or more cell-surface marker(s) of a stem memory T cell ($T_{SCM}$), thereby producing a CAR-expressing stem memory T cell ($T_{SCM}$) (CAR-$T_{SCM}$).

The disclosure provides a method of producing a plurality of modified stem memory T cells ($T_{SCM}$), comprising: (a) introducing into a plurality of primary human T cells a composition comprising a chimeric antigen receptor (CAR) to produce a plurality of CAR-T cells and (b) contacting the plurality of CAR-T cells and a T-cell activator composition comprising one or more of an anti-human CD3 monospecific tetrameric antibody complex, an anti-human CD28 monospecific tetrameric antibody complex and an activation supplement to produce a plurality of activated CAR-T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 25% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 50% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 60% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 75% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 80% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 85% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 90% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 95% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the cell-surface markers comprise CD62L and CD45RA. In certain embodiments, the cell-surface markers of the activated CAR $T_{SCM}$ comprise one or more of CD62L, CD45RA, CD28, CCR7, CD127, CD45RO, CD95, CD95 and IL-2Rβ. In certain embodiments, the cell-surface markers of the activated CAR $T_{SCM}$ comprise one or more of CD45RA, CD95, IL-2Rβ, CR7, and CD62L.

In certain embodiments, this method may further comprise the step of: (c) contacting the activated CAR-T cell and a T-cell expansion composition comprising one or more of human serum albumin, recombinant human insulin, human transferrin, 2-Mercaptoethanol, Iscove's MDM, and an expansion supplement to produce a plurality of expanded CAR-T cells, wherein at least 2% of the plurality of expanded CAR-T cells expresses one or more cell-surface marker(s) of a stem memory T cell ($T_{SCM}$) (CAR-$T_{SCM}$). In certain embodiments, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 μmol/kg and 640 μmol/kg, inclusive of the endpoints; palmitic acid at a concentration of between 0.7 μmol/kg and 70 μmol/kg, inclusive of the endpoints; linoleic acid at a concentration of between 0.75 μmol/kg and 75 μmol/kg, inclusive of the endpoints; oleic acid at a concentration of between 0.75 μmol/kg and 75 μmol/kg, inclusive of the endpoints; and a sterol at a concentration of between 0.25 μmol/kg and 25 μmol/kg, inclusive of the endpoints. In certain embodiments, the T-cell expansion composition comprises one or more of octanoic acid at a concentration of about 64 μmol/kg, palmitic acid at a concentration of about 7 μmol/kg, linoleic acid at a concentration of about 7.5 μmol/kg, oleic acid at a concentration of about 7.5 μmol/kg and a sterol at a concentration of about 2.5 μmol/kg. In certain embodiments, the T-cell expansion composition comprises one or more of octanoic acid at a concentration of about 63.75 μmol/kg, palmitic acid at a concentration of about 7.27 μmol/kg, linoleic acid at a concentration of about 7.57 μmol/kg, oleic acid at a concentration of about 7.56 μmol/kg and a sterol at a concentration of about 2.61 μmol/kg. In certain embodiments, the T-cell expansion composition comprises octanoic acid at a concentration of about 63.75 μmol/kg, palmitic acid at a concentration of about 7.27 μmol/kg, linoleic acid at a concentration of about 7.57 μmol/kg, oleic acid at a concentration of 7.56 μmol/kg and a sterol at a concentration of 2.61 μmol/kg. In certain embodiments, at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of expanded CAR-T cells expresses cell-surface marker(s) of a stem memory T cell ($T_{SCM}$) (CAR-$T_{SCM}$). In certain embodiments, the plurality of expanded CAR-T cells may be enriched for CAR-T cells that express cell-surface marker(s) of a stem memory T cell ($T_{SCM}$) (CAR-$T_{SCM}$), and, therefore, following an enrichment step, the method may produce an enriched composition comprising at least 2%, 5%, 10%, 15%, 20%, 25%, 30%, 35%, 40%, 45%, 50%, 60%, 65%, 70%, 75%, 80%, 85%, 90%, 95%, 99% or any percentage in between of CAR-T cells that express cell-surface marker(s) of a stem memory T cell ($T_{SCM}$) (CAR-$T_{SCM}$). In certain embodiments, the cell-surface markers comprise CD62L and CD45RA. In certain embodiments, the cell-surface markers of the CAR-$T_{SCM}$ comprise one or more of CD62L, CD45RA, CD28, CCR7, CD127, CD45RO, CD95, CD95 and IL-2Rβ. In certain embodiments, the cell-surface markers of the CAR-$T_{SCM}$ comprise one or more of CD45RA, CD95, IL-2Rβ, CR7, and CD62L. In certain embodiments, the plurality of expanded CAR-T cells comprises a naïve T-cell (CAR-$T_N$) and the cell-surface markers of the CAR-$T_N$ comprise one or more of CD45RA, CCR7 and CD62L. In certain embodiments, the plurality of expanded CAR-T cells comprises a central memory T-cell (CAR-$T_{CM}$) and the cell-surface markers of the CAR-$T_{CM}$ comprise one or more of CD45RO, CD95, IL-2Rβ, CCR7, and CD62L. In certain embodiments, the plurality of expanded CAR-T cells comprises an effector memory T-cell (CAR-$T_{EM}$) and the cell-surface markers of the CAR-$T_{EM}$ comprise one or more of CD45RO, CD95, and IL-2Rβ. In certain embodiments, the plurality of expanded CAR-T cells comprises an effector T-cell (CAR-$T_{EFF}$) and the cell-surface markers of the CAR-$T_{EFF}$ comprise one or more of CD45RA, CD95, and IL-2Rβ. Additional cell-surface markers are described in Gattinoni et al. (Nat Med. 2011 Sep. 18; 17(10): 1290-7; the contents of which are incorporated herein by reference in their entirety).

The disclosure provides a method of producing a modified stem memory T cell ($T_{SCM}$), comprising: (a) introducing into a primary human T cell a composition comprising a chimeric antigen receptor (CAR) to produce a CAR-T cell and (b) contacting the CAR-T cell and a T-cell activator composition comprising one or more of an anti-human CD3 monospecific tetrameric antibody complex, an anti-human CD28 monospecific tetrameric antibody complex and an activation supplement to produce an activated CAR-T cell, wherein the activated CAR-T cell expresses one or more cell-surface marker(s) of a stem memory T cell ($T_{SCM}$), thereby producing a CAR-expressing stem memory T cell ($T_{SCM}$) (CAR-$T_{SCM}$). The disclosure provides a method of producing a plurality of modified stem memory T cells ($T_{SCM}$), comprising: (a) introducing into a plurality of primary human T cells a composition comprising a chimeric antigen receptor (CAR) to produce a plurality of CAR-T cells and (b) contacting the plurality of CAR-T cells and a T-cell activator composition comprising one or more of an anti-human CD3 monospecific tetrameric antibody complex, an anti-human CD28 monospecific tetrameric antibody complex and an activation supplement to produce a plurality of activated CAR-T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 25% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 50% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 60% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 75% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 80% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 85% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 90% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the method produces a plurality of activated CAR-T cells, wherein at least 95% of the plurality of activated CAR-T cells expresses one or more cell-surface marker(s) of a stem memory T cell ($T_{SCM}$), thereby producing a plurality of activated CAR stem memory T cells ($T_{SCM}$). In certain embodiments, the cell-surface markers comprise CD62L and CD45RA. In certain embodiments, the cell-surface markers of the activated CAR $T_{SCM}$ comprise one or more of CD62L, CD45RA, CD28, CCR7, CD127, CD45RO, CD95, CD95 and IL-2Rβ. In certain embodiments, the cell-surface markers of the activated CAR $T_{SCM}$ comprise one or more of CD45RA, CD95, IL-2Rβ, CR7, and CD62L.

In certain embodiments of the methods of the disclosure, the plurality of expanded CAR-T cells comprises a naïve T-cell (CAR-$T_N$) and the cell-surface markers of the CAR-$T_N$ comprise one or more of CD45RA, CCR7 and CD62L. In certain embodiments, the plurality of expanded CAR-T cells comprises a central memory T-cell (CAR-$T_{CM}$) and the cell-surface markers of the CAR-$T_{CM}$ comprise one or more of CD45RO, CD95, IL-2Rβ, CCR7, and CD62L. In certain embodiments, the plurality of expanded CAR-T cells comprises an effector memory T-cell (CAR-$T_{EM}$) and the cell-surface markers of the CAR-$T_{EM}$ comprise one or more of CD45RO, CD95, and IL-2Rβ. In certain embodiments, the plurality of expanded CAR-T cells comprises an effector T-cell (CAR-$T_{EFF}$) and the cell-surface markers of the CAR-$T_{EFF}$ comprise one or more of CD45RA, CD95, and IL-2Rβ.

In certain embodiments of the methods of the disclosure, a transposon comprises a chimeric antigen receptor (CAR) of the disclosure. The transposon may be a plasmid DNA transposon with a sequence encoding the CAR flanked by two cis-regulatory insulator elements. In certain preferred embodiments, the transposon is a piggyBac transposon. In certain embodiments, a step introducing a composition comprising a chimeric antigen receptor (CAR) of the disclosure may further a composition comprising an mRNA sequence encoding a transposase. In certain preferred embodiments, the transposase is a Super piggyBac™ (SPB) transposase.

In certain embodiments, a transposon of the disclosure may further comprise a selection gene. When a transposon of the disclosure comprises a selection gene, the T-cell expansion composition of the methods of the disclosure may further comprise a selection agent to simultaneously select and expand an activated or modified T cell of the disclosure.

In certain embodiments a CAR of the disclosure may be a CARTyrin. In certain embodiments, the CAR comprises one or more VHH sequence(s). In certain embodiments, the CAR is a VCAR.

In certain embodiments of the methods of producing a modified $T_{SCM}$ of the disclosure, the introducing step may comprise an electroporation or a nucleofection. When the introducing step comprises a nucleofection, the nucleofection may comprise the steps of: (a) contacting a transposon composition, a transposase composition, and a composition comprising a plurality of primary human T cells in a cuvette; (b) applying one or more electrical pulses to the cuvette, and (c) incubating the composition comprising the plurality of primary human T cells in a composition comprising a T-cell expansion composition comprising one or more of human serum albumin, recombinant human insulin, human transferrin, 2-Mercaptoethanol, Iscove's MDM, and an expansion supplement at 37° C. In certain embodiments, the T-cell expansion composition further comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis(2-methylpropyl) ester, palmitic acid, linoleic acid, oleic acid, stearic acid hydrazide, oleamide, a sterol and an alkane. In certain embodiments, the T-cell expansion composition comprises one or more of octanoic acid, palmitic acid, linoleic acid, oleic acid and a sterol (e.g. cholesterol). In certain embodiments, the T-cell expansion composition comprises one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the T-cell expansion composition comprises one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million). In certain embodiments, the T-cell expansion composition comprises one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the T-cell expansion composition comprises octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the T-cell expansion composition comprises one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the T-cell expansion composition comprises one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the T-cell expansion composition comprises one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 µmol/kg. In certain embodiments, the T-cell expansion composition comprises octanoic acid at a concentration of about 63.75 µmol/kg, palmitic acid at a concentration of about 7.27 µmol/kg, linoleic acid at a concentration of about 7.57 µmol/kg, oleic acid at a concentration of 7.56 µmol/kg and a sterol at a concentration of 2.61 µmol/kg. In certain embodiments of the nucleofection, the transposon composition is a 0.5 µg/µl solution comprising nuclease free water and the cuvette comprises 2 µl of the transposon composition to yield 1 µg of transposon. The transposon composition may comprise a piggyBac transposon. The transposon composition may comprise a Sleeping Beauty transposon. In certain embodiments of the nucleofection, the transposase composition comprises 5 µg of transposase. The transposase composition may comprise a hyperactive piggyBac™ or Super piggyBac™ (SPB) transposase. The transposase composition may comprise a hyperactive Sleeping Beauty (SB100X) transposase. In certain embodiments, the transposon may comprise a Helraiser transposon and the transposase composition may comprise a Helitron transposase. In certain embodiments, the transposon may comprise a Tol2 transposon and the transposase composition comprises a Tol2 transposase.

In certain embodiments of the methods of the disclosure, including those embodiments wherein the introducing step comprises a nucleofection or an electroporation, the nucleofection comprises contacting a first transposon composition and a first transposase composition and a composition comprising a plurality of primary human T cells in a cuvette. In certain embodiments of the methods of the disclosure, including those embodiments wherein the introducing step comprises a nucleofection or an electroporation, the nucleofection comprises contacting a first transposon composition, a second transposon composition, a first transposase composition and a composition comprising a plurality of primary human T cells in a cuvette. In certain embodiments of the methods of the disclosure, including those embodiments wherein the introducing step comprises a nucleofection or an electroporation, the nucleofection comprises contacting a first transposon composition, a second transposon composition, a first transposase composition, a second transposase composition and a composition comprising a plurality of primary human T cells in a cuvette. In certain embodiments, the first transposon comprises a sequence encoding an antigen receptor. In certain embodiments, the second transposon comprises a sequence encoding a therapeutic protein. In certain embodiments, the first transposon composition and the second transposon composition are identical. In certain embodiments, the first transposon composition and the second transposon composition are not identical. In certain embodiments, the first transposase mobilizes the first transposon composition and the second transposon composition. In certain embodiments, the first transposase mobilizes the first transposon composition but not the second transposon composition. In certain embodiments, the second transposase mobilizes the second transposon composition but not the first transposon composition. In certain embodiments, the first transposase mobilizes the first transposon composition and the second transposase mobilizes the second transposon composition. In certain embodiments, the first transposon composition or the second transposon composition comprises a sequence encoding an antigen receptor. In certain embodiments, the first transposon composition or the second transposon composition comprises a sequence encoding a therapeutic protein. In certain embodiments, the first transposon composition comprises a sequence encoding an antigen receptor and the second transposon composition comprises a sequence encoding a therapeutic protein. In certain embodiments, the therapeutic protein is a secreted or secretable protein. In certain embodiments of the methods of the disclosure, including those embodiments wherein the introducing step comprises a nucleofection or an electroporation, the nucleofection comprises contacting a transposon composition, a first transposase composition, a second transposase composition and a composition comprising a plurality of primary human T cells in a cuvette. In certain embodiments, the transposon composition comprises a sequence encoding the antigen receptor. In certain embodiments, the transposon composition comprises a sequence encoding the therapeutic protein. In certain embodiments of the methods of the disclosure, including those embodiments wherein the introducing step comprises a nucleofection or an electroporation, the nucleofection further comprises contacting a composition capable of inducing homologous recombination at a specific site in the genome with a composition comprising a plurality of primary human T cells in a cuvette. In certain embodiments, the composition capable of inducing homologous recombination comprises an exogenous donor molecule. In certain embodiments, the exogenous donor molecule comprises a sequence encoding the antigen receptor and the transposon comprises a sequence encoding the therapeutic protein. In certain embodiments, the exogenous donor molecule comprises a sequence encoding the therapeutic protein and the transposon comprises a sequence encoding the antigen receptor. In certain embodiments, the composition comprising the transposon, the composition comprising the transposase and the composition capable of inducing homologous recombination at a specific site in the genome are contacted with the composition comprising a plurality of primary human T cells simultaneously. In certain embodiments, the composition comprising the transposon and the composition comprising the transposase are contacted with the composition comprising a plurality of primary human T cells first, and the composition capable of inducing homologous recombination at a specific site in the genome is contacted with the composition comprising a plurality of primary human T cells second. In certain embodiments, the composition capable of inducing homologous recombination at a specific site in the genome is contacted with the composition comprising a plurality of primary human T cells first and the composition comprising the transposon and the composition comprising the transposase are contacted with the composition comprising a plurality of primary human T cells second. In certain embodiments of the methods of producing a modified $T_{SCM}$ of the disclosure, the composition comprising primary human T cells comprises a buffer that maintains or enhances a level of cell viability and/or a stem-like phenotype of the primary human T cells. In certain embodiments, the buffer maintains or enhances a level of cell viability and/or a stem-like phenotype of the primary human T cells prior to the nucleofection. In certain embodiments, the buffer maintains or enhances a level of cell viability and/or a stem-like phenotype of the primary human T cells during the nucleofection. In certain embodiments, the buffer maintains or enhances a level of cell viability and/or a stem-like phenotype of the primary human T cells following the nucleofection. In certain embodiments, the buffer comprises a P3 primary cell solution (Lonza). In certain embodiments, the buffer comprises one or more of KCl, $MgCl_2$, ClNa, Glucose and $Ca(NO_3)_2$ in any absolute or relative abundance or concentration, and, optionally, the buffer further comprises a supplement selected from the group consisting of HEPES, Tris/HCl, and a phosphate buffer. In certain embodiments, the buffer comprises 5 mM KCl, 15 mM $MgCl_2$, 90 mM ClNa, 10 mM Glucose and 0.4 mM $Ca(NO_3)_2$. In certain embodiments, the buffer comprises 5 mM KCl, 15 mM $MgCl_2$, 90 mM ClNa, 10 mM Glucose and 0.4 mM $Ca(NO_3)_2$ and a supplement comprising 20 mM HEPES and 75 mM Tris/HCl. In certain embodiments, the buffer comprises 5 mM KCl, 15 mM $MgCl_2$, 90 mM ClNa, 10 mM Glucose and 0.4 mM $Ca(NO_3)_2$ and a supplement comprising 40 mM $Na_2HPO_4/NaH_2PO_4$ at pH 7.2. In certain embodiments, the composition comprising primary human T cells comprises 100 µl of the buffer and between $5\times10^6$ and $25\times10^6$ cells.

In certain embodiments of the methods of producing a modified $T_{SCM}$ of the disclosure, the composition comprising primary human T cells is depleted of cells expressing CD14, CD56, and/or CD19. In certain embodiments, the composition comprising primary human T cells comprises 100 µl of the buffer and between $5\times10^6$ and $25\times10^6$ cells.

As used herein, the terms "supplemented T-cell expansion composition" or "T-cell expansion composition" may be used interchangeably with a media comprising one or more of human serum albumin, recombinant human insulin, human transferrin, 2-Mercaptoethanol, Iscove's MDM, and an expansion supplement at 37° C. Alternatively, or in addition, the terms "supplemented T-cell expansion composition" or "T-cell expansion composition" may be used interchangeably with a media comprising one or more of phosphorus, an octanoic fatty acid, a palmitic fatty acid, a linoleic fatty acid and an oleic acid. In certain embodiments, the media comprises an amount of phosphorus that is 10-fold higher than may be found in, for example, Iscove's Modified Dulbecco's Medium ((IMDM); available at ThermoFisher Scientific as Catalog number 12440053).

As used herein, the terms "supplemented T-cell expansion composition" or "T-cell expansion composition" may be used interchangeably with a media comprising one or more of human serum albumin, recombinant human insulin, human transferrin, 2-Mercaptoethanol, Iscove's MDM, and an expansion supplement at 37° C. Alternatively, or in addition, the terms "supplemented T-cell expansion composition" or "T-cell expansion composition" may be used interchangeably with a media comprising one or more of the following elements: boron, sodium, magnesium, phosphorus, potassium, and calcium. In certain embodiments, the terms "supplemented T-cell expansion composition" or "T-cell expansion composition" may be used interchangeably with a media comprising one or more of the following elements present in the corresponding average concentrations: boron at 3.7 mg/L, sodium at 3000 mg/L, magnesium at 18 mg/L, phosphorus at 29 mg/L, potassium at 15 mg/L and calcium at 4 mg/L.

As used herein, the terms "supplemented T-cell expansion composition" or "T-cell expansion composition" may be used interchangeably with a media comprising one or more of human serum albumin, recombinant human insulin, human transferrin, 2-Mercaptoethanol, Iscove's MDM, and an expansion supplement at 37° C. Alternatively, or in addition, the terms "supplemented T-cell expansion composition" or "T-cell expansion composition" may be used interchangeably with a media comprising one or more of the following components: octanoic acid (CAS No. 124-07-2), nicotinamide (CAS No. 98-92-0), 2,4,7,9-tetramethyl-5-decyn-4,7-diol (TMDD) (CAS No. 126-86-3), diisopropyl adipate (DIPA) (CAS No. 6938-94-9), n-butyl-benzenesulfonamide (CAS No. 3622-84-2), 1,2-benzenedicarboxylic acid, bis(2-methylpropyl) ester (CAS No. 84-69-5), palmitic acid (CAS No. 57-10-3), linoleic acid (CAS No. 60-33-3), oleic acid (CAS No. 112-80-1), stearic acid hydrazide (CAS No. 4130-54-5), oleamide (CAS No. 3322-62-1), sterol (e.g., cholesterol) (CAS No. 57-88-5), and alkanes (e.g., nonadecane) (CAS No. 629-92-5). In certain embodiments, the terms "supplemented T-cell expansion composition" or "T-cell expansion composition" may be used interchangeably with a media comprising one or more of the following components: octanoic acid (CAS No. 124-07-2), nicotinamide (CAS No. 98-92-0), 2,4,7,9-tetramethyl-5-decyn-4,7-diol (TMDD) (CAS No. 126-86-3), diisopropyl adipate (DIPA) (CAS No. 6938-94-9), n-butyl-benzenesulfonamide (CAS No. 3622-84-2), 1,2-benzenedicarboxylic acid, bis(2-methylpropyl) ester (CAS No. 84-69-5), palmitic acid (CAS No. 57-10-3), linoleic acid (CAS No. 60-33-3), oleic acid (CAS No. 112-80-1), stearic acid hydrazide (CAS No. 4130-54-5), oleamide (CAS No. 3322-62-1), sterol (e.g., cholesterol) (CAS No. 57-88-5), alkanes (e.g., nonadecane) (CAS No. 629-92-5), and phenol red (CAS No. 143-74-8). In certain embodiments, the terms "supplemented T-cell expansion composition" or "T-cell expansion composition" may be used interchangeably with a media comprising one or more of the following components: octanoic acid (CAS No. 124-07-2), nicotinamide (CAS No. 98-92-0), 2,4,7,9-tetramethyl-5-decyn-4,7-diol (TMDD) (CAS No. 126-86-3), diisopropyl adipate (DIPA) (CAS No. 6938-94-9), n-butylbenzenesulfonamide (CAS No. 3622-84-2), 1,2-benzenedicarboxylic acid, bis(2-methylpropyl) ester (CAS No. 84-69-5), palmitic acid (CAS No. 57-10-3), linoleic acid (CAS No. 60-33-3), oleic acid (CAS No. 112-80-1), stearic acid hydrazide (CAS No. 4130-54-5), oleamide (CAS No. 3322-62-1), phenol red (CAS No. 143-74-8) and lanolin alcohol.

As used herein, the terms "supplemented T-cell expansion composition" or "T-cell expansion composition" may be used interchangeably with a media comprising one or more of human serum albumin, recombinant human insulin, human transferrin, 2-Mercaptoethanol, Iscove's MDM, and an expansion supplement at 37° C. Alternatively, or in addition, the terms "supplemented T-cell expansion composition" or "T-cell expansion composition" may be used interchangeably with a media comprising one or more of the following ions: sodium, ammonium, potassium, magnesium, calcium, chloride, sulfate and phosphate.

As used herein, the terms "supplemented T-cell expansion composition" or "T-cell expansion composition" may be used interchangeably with a media comprising one or more of human serum albumin, recombinant human insulin, human transferrin, 2-Mercaptoethanol, Iscove's MDM, and an expansion supplement at 37° C. Alternatively, or in addition, the terms "supplemented T-cell expansion composition" or "T-cell expansion composition" may be used interchangeably with a media comprising one or more of the following free amino acids: histidine, asparagine, serine, glutamate, arginine, glycine, aspartic acid, glutamic acid, threonine, alanine, proline, cysteine, lysine, tyrosine, methionine, valine, isoleucine, leucine, phenylalanine and tryptophan. In certain embodiments, the terms "supplemented T-cell expansion composition" or "T-cell expansion composition" may be used interchangeably with a media comprising one or more of the following free amino acids in the corresponding average mole percentages: histidine (about 1%), asparagine (about 0.5%), serine (about 1.5%), glutamine (about 67%), arginine (about 1.5%), glycine (about 1.5%), aspartic acid (about 1%), glutamic acid (about 2%), threonine (about 2%), alanine (about 1%), proline (about 1.5%), cysteine (about 1.5%), lysine (about 3%), tyrosine (about 1.5%), methionine (about 1%), valine (about 3.5%), isoleucine (about 3%), leucine (about 3.5%), phenylalanine (about 1.5%) and tryptophan (about 0.5%). In certain embodiments, the terms "supplemented T-cell expansion composition" or "T-cell expansion composition" may be used interchangeably with a media comprising one or more of the following free amino acids in the corresponding average mole percentages: histidine (about 0.78%), asparagine (about 0.4%), serine (about 1.6%), glutamine (about 67.01%), arginine (about 1.67%), glycine (about 1.72%), aspartic acid (about 1.00%), glutamic acid (about 1.93%), threonine (about 2.38%), alanine (about 1.11%), proline (about 1.49%), cysteine (about 1.65%), lysine (about 2.84%), tyrosine (about 1.62%), methionine (about 0.85%), valine (about 3.45%), isoleucine (about 3.14%), leucine (about 3.3%), phenylalanine (about 1.64%) and tryptophan (about 0.37%).

As used herein, the terms "supplemented T-cell expansion composition" or "T-cell expansion composition" may be used interchangeably with a media comprising one or more of octanoic acid, palmitic acid, linoleic acid, oleic acid and a sterol (e.g. cholesterol). In certain embodiments, the terms "supplemented T-cell expansion composition" or "T-cell expansion composition" may be used interchangeably with a media comprising one or more of octanoic acid at a concentration of between 0.9 mg/kg to 90 mg/kg, inclusive of the endpoints; palmitic acid at a concentration of between 0.2 mg/kg to 20 mg/kg, inclusive of the endpoints; linoleic acid at a concentration of between 0.2 mg/kg to 20 mg/kg, inclusive of the endpoints; oleic acid at a concentration of 0.2 mg/kg to 20 mg/kg, inclusive of the endpoints; and a sterol at a concentration of about 0.1 mg/kg to 10 mg/kg, inclusive of the endpoints (wherein mg/kg=parts per million). In certain embodiments, the terms "supplemented T-cell expansion composition" or "T-cell expansion composition" may be used interchangeably with a media comprising one or more of octanoic acid at a concentration of about 9 mg/kg, palmitic acid at a concentration of about 2 mg/kg, linoleic acid at a concentration of about 2 mg/kg, oleic acid at a concentration of about 2 mg/kg, and a sterol at a concentration of about 1 mg/kg (wherein mg/kg=parts per million).). In certain embodiments, the terms "supplemented T-cell expansion composition" or "T-cell expansion composition" may be used interchangeably with a media comprising one or more of octanoic acid at a concentration of 9.19 mg/kg, palmitic acid at a concentration of 1.86 mg/kg, linoleic acid at a concentration of about 2.12 mg/kg, oleic acid at a concentration of about 2.13 mg/kg, and a sterol at a concentration of about 1.01 mg/kg (wherein mg/kg=parts per million). In certain embodiments, the terms "supplemented T-cell expansion composition" or "T-cell expansion composition" may be used interchangeably with a media comprising one or more of octanoic acid at a concentration of 9.19 mg/kg, palmitic acid at a concentration of 1.86 mg/kg, linoleic acid at a concentration of 2.12 mg/kg, oleic acid at a concentration of about 2.13 mg/kg, and a sterol at a concentration of 1.01 mg/kg (wherein mg/kg=parts per million). In certain embodiments, the terms "supplemented T-cell expansion composition" or "T-cell expansion composition" may be used interchangeably with a media comprising one or more of octanoic acid at a concentration of between 6.4 µmol/kg and 640 µmol/kg, inclusive of the endpoints; palmitic acid at a concentration of between 0.7 µmol/kg and 70 µmol/kg, inclusive of the endpoints; linoleic acid at a concentration of between 0.75 µmol/kg and 75 µmol/kg, inclusive of the endpoints; oleic acid at a concentration of between 0.75 µmol/kg and 75 µmol/kg, inclusive of the endpoints; and a sterol at a concentration of between 0.25 µmol/kg and 25 µmol/kg, inclusive of the endpoints. In certain embodiments, the terms "supplemented T-cell expansion composition" or "T-cell expansion composition" may be used interchangeably with a media comprising one or more of octanoic acid at a concentration of about 64 µmol/kg, palmitic acid at a concentration of about 7 µmol/kg, linoleic acid at a concentration of about 7.5 µmol/kg, oleic acid at a concentration of about 7.5 µmol/kg and a sterol at a concentration of about 2.5 µmol/kg. In certain embodiments, the terms "supplemented T-cell expansion composition" or "T-cell expansion composition" may be used interchangeably with a media comprising one or more of octanoic acid at a concentration of about 63.75 µmol/kg, palmitic acid at a concentration of about 7.27 µmol/kg, linoleic acid at a concentration of about 7.57 µmol/kg, oleic acid at a concentration of about 7.56 µmol/kg and a sterol at a concentration of about 2.61 μmol/kg. In certain embodiments, the terms "supplemented T-cell expansion composition" or "T-cell expansion composition" may be used interchangeably with a media comprising one or more of octanoic acid at a concentration of about 63.75 μmol/kg, palmitic acid at a concentration of about 7.27 μmol/kg, linoleic acid at a concentration of about 7.57 μmol/kg, oleic acid at a concentration of 7.56 μmol/kg and a sterol at a concentration of 2.61 μmol/kg.

As used herein, the term "P3 buffer" may be used interchangeably with a buffer comprising one or more of KCl, $MgCl_2$, ClNa, Glucose and $Ca(NO_3)_2$ in any absolute or relative abundance or concentration, and, optionally, the further comprising a supplement selected from the group consisting of HEPES, Tris/HCl, and a phosphate buffer. The term "P3 buffer" may be used interchangeably with a buffer comprising 5 mM KCl, 15 mM $MgCl_2$, 90 mM ClNa, 10 mM Glucose and 0.4 mM $Ca(NO_3)_2$, and, optionally, the further comprising a supplement selected from the group consisting of HEPES, Tris/HCl, and a phosphate buffer. The term "P3 buffer" may be used interchangeably with a buffer comprising 5 mM KCl, 15 mM $MgCl_2$, 90 mM ClNa, 10 mM Glucose and 0.4 mM $Ca(NO_3)_2$ and a supplement comprising 20 mM HEPES and 75 mM Tris/HCl. The term "P3 buffer" may be used interchangeably with a buffer comprising 5 mM KCl, 15 mM $MgCl_2$, 90 mM ClNa, 10 mM Glucose and 0.4 mM $Ca(NO_3)_2$ and a supplement comprising 40 mM $Na_2HPO_4/NaH_2PO_4$ at pH 7.2.

As used herein, the terms "supplemented RPMI-1640 media" or "T-cell conditioned media (TCCM)" may be used interchangeably with a media comprising one or more of water, fetal bovine serum, HEPES, sodium pyruvate, one or more non-essential amino acids, a phenol red indicator, calcium nitrate, magnesium sulfate, potassium chloride, sodium bicarbonate, sodium chloride, sodium phosphate dibasic (anhydrous), L-Alanyl-L-Glutamine, L-Arginine, L-Asparagine (anhydrous), L-Aspartic acid, L-Cysteine 2HCl, L-Glutamic acid, Glycine, L-Histidine, Hydroxy-L-Proline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, D-Biotin, choline chloride, folic acid, Myo-Inositol, niacinamide, p-Aminobenzoic acid, D-Panthothenic acid (hemicalcium), pyridoxine HCl, riboflavin, thiamine HCl, vitamin B12, D-Glucose, Glutathione (reduced), L-Glutamine and 2-Mercaptoethanol in any absolute or relative abundance or concentration. The terms "supplemented RPMI-1640 media" or "T-cell conditioned media (TCCM)" may be used interchangeably with a media comprising water, fetal bovine serum, HEPES, sodium pyruvate, one or more non-essential amino acids, a phenol red indicator, calcium nitrate, magnesium sulfate, potassium chloride, sodium bicarbonate, sodium chloride, sodium phosphate dibasic (anhydrous), L-Alanyl-L-Glutamine, L-Arginine, L-Asparagine (anhydrous), L-Aspartic acid, L-Cysteine 2HCl, L-Glutamic acid, Glycine, L-Histidine, Hydroxy-L-Proline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, D-Biotin, choline chloride, folic acid, Myo-Inositol, niacinamide, p-Aminobenzoic acid, D-Panthothenic acid (hemicalcium), pyridoxine HCl, riboflavin, thiamine HCl, vitamin B12, D-Glucose, Glutathione (reduced), L-Glutamine and 2-Mercaptoethanol in any absolute or relative abundance or concentration.

As used herein, the terms "supplemented AIM-V" or "supplemented AIMV" media may be used interchangeably with a media comprising one or more of water, human serum albumin, streptomycin sulfate, gentamicin, fetal bovine serum, HEPES, sodium pyruvate, one or more non-essential amino acids, a phenol red indicator, calcium nitrate, magnesium sulfate, potassium chloride, sodium bicarbonate, sodium chloride, sodium phosphate dibasic (anhydrous), L-Alanyl-L-Glutamine, L-Arginine, L-Asparagine (anhydrous), L-Aspartic acid, L-Cysteine 2HCl, L-Glutamic acid, Glycine, L-Histidine, Hydroxy-L-Proline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, D-Biotin, choline chloride, folic acid, Myo-Inositol, niacinamide, p-Aminobenzoic acid, D-Panthothenic acid (hemicalcium), pyridoxine HCl, riboflavin, thiamine HCl, vitamin B12, D-Glucose, glutathione (reduced), L-Glutamine and 2-Mercaptoethanol in any absolute or relative abundance or concentration. The terms "supplemented AIM-V" or "supplemented AIMV" media may be used interchangeably with a media comprising water, human serum albumin, streptomycin sulfate, gentamicin, fetal bovine serum, HEPES, sodium pyruvate, one or more non-essential amino acids, a phenol red indicator, calcium nitrate, magnesium sulfate, potassium chloride, sodium bicarbonate, sodium chloride, sodium phosphate dibasic (anhydrous), L-Alanyl-L-Glutamine, L-Arginine, L-Asparagine (anhydrous), L-Aspartic acid, L-Cysteine 2HCl, L-Glutamic acid, Glycine, L-Histidine, Hydroxy-L-Proline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, D-Biotin, choline chloride, folic acid, Myo-Inositol, niacinamide, p-Aminobenzoic acid, D-Panthothenic acid (hemicalcium), pyridoxine HCl, riboflavin, thiamine HCl, vitamin B12, D-Glucose, glutathione (reduced), L-Glutamine and 2-Mercaptoethanol in any absolute or relative abundance or concentration.

As used herein, the term "ImmunoCult™ medium" may be used interchangeably with a medium comprising one or more of water, human serum albumin, recombinant human insulin, human transferrin, 2-Mercaptoethanol, L-Glutamine, phenol red, glycine, L-Alanine, L-Arginine hydrochloride, L-Asparagine, L-Aspartic acid, L-Cysteine 2HCl, L-Glutamic acid, L-Glutamine, L-Histidine hydrochloride H20, L-Isoleucine, L-Leucine, L-Lysine hydrochloride, L-Methionine, L-Phenylalanine, L-Proline, L-Serine, L-Threonine, L-Tryptophan, L-Tyrosine disodium salt, L-Valine, biotin, choline chloride, D-Calcium pantothenate, folic acid, niacinamide, pyridoxal hydrochloride, riboflavin, thiamine hydrochloride, vitamin B12, i-Inositol, calcium chloride (anhydrous), magnesium sulfate (Anhydrous), potassium chloride, potassium nitrate, sodium bicarbonate, sodium chloride, sodium phosphate monobasic, sodium selenite, D-Glucose, HEPES and Sodium pyruvate in any absolute or relative abundance or concentration. The term "ImmunoCult™ medium" may be used interchangeably with a medium comprising water, human serum albumin, recombinant human insulin, human transferrin, 2-Mercaptoethanol, L-Glutamine, phenol red, glycine, L-Alanine, L-Arginine hydrochloride, L-Asparagine, L-Aspartic acid, L-Cysteine 2HCl, L-Glutamic acid, L-Glutamine, L-Histidine hydrochloride H20, L-Isoleucine, L-Leucine, L-Lysine hydrochloride, L-Methionine, L-Phenylalanine, L-Proline, L-Serine, L-Threonine, L-Tryptophan, L-Tyrosine disodium salt, L-Valine, biotin, choline chloride, D-Calcium pantothenate, folic acid, niacinamide, pyridoxal hydrochloride, riboflavin, thiamine hydrochloride, vitamin B12, i-Inositol, calcium chloride (anhydrous), magnesium sulfate (Anhydrous), potassium chloride, potassium nitrate, sodium bicarbonate, sodium chloride, sodium phosphate monobasic, sodium selenite, D-Glucose, HEPES and Sodium pyruvate in any absolute or relative abundance or concentration.

Modified T-cells of the disclosure, including modified $T_{SCM}$ and/or $T_{CM}$ of the disclosure, may be incubated, cultured, grown, stored, or otherwise, combined at any step in the methods of the procedure with a growth medium comprising one or more inhibitors a component of a PI3K pathway. Exemplary inhibitors a component of a PI3K pathway include, but are not limited to, an inhibitor of GSK3β such as TWS119 (also known as GSK 3B inhibitor XII; CAS Number 601514-19-6 having a chemical formula $C_{18}H_{14}N_4O_2$). Exemplary inhibitors a component of a PI3K pathway include, but are not limited to, bb007 (BLUEBIRD-BIO™).

As used herein, the terms "electroporation" and "nucleofection" are meant to describe alternative means to deliver a nucleic acid, transposon, vector or composition of the disclosure to a cell by providing an electric pulse that induces a cell membrane (the cell membrane, nuclear membrane, or both) to become permeable or to become more permeable to the nucleic acid, transposon, vector or composition of the disclosure.

In certain embodiments of the nucleofection, the method is performed one or more cuvette(s) simultaneously. In certain embodiments of the nucleofection, the method is performed in two cuvettes simultaneously. For a process performed on a larger scale for clinical or commercial applications, for example, the nucleofections may be performed in a large-volume cassette with many procedures ongoing simultaneously. In certain embodiments of the nucleofection, the incubating step comprises incubating the composition comprising the plurality of primary human T cells in a pre-warmed T-cell expansion composition. The incubation step may have a period of at least 1, 2, 3, 4, 5, 6, 7, 8, 9, 10, 11, 12, 13, 14, 15, 16, 17, 18, 19, 20, 21, 22, 23, 24 hours, or any number/portion of hours in between. The incubation step may have a period of at least 1, 2, 3, 4, 5, 6 or 7 days or any number/portion of days in between. The incubation step may have a period of at least 1 week. In certain embodiments of the nucleofection, the incubation step has a period of two days. In certain embodiments of the nucleofection, the applying step may comprise applying one or more of the following program(s) EI-115, EI-151, EI-156, EI-158, EG-115, EG-142, EG-151, ES-115, ES-151, EO-151, EO-148, EO-156, EO-210, EO-213, and FI-156. In certain embodiments, the applying step may comprise applying one or more of the following program(s) EI-115, EI-151, EI-156, EI-158, EG-115, EG-142, EG-151, ES-115, ES-151, EO-151, EO-148, EO-156, EO-210, EO-213, and FI-156, or a program that provides the same number of electrical pulses, each pulse having the same duration and intensity, and a substantially similar interpulse duration of time. In certain embodiments, the applying step may be performed using a known electroporation/nucleofection device, including, but not limited to, Lonza Amaxa, MaxCyte technology, BTX PulseAgile, and BioRad GenePulser. In certain embodiments of the nucleofection, the applying step may comprise applying at least one electrical pulse. In certain embodiments of the nucleofection, the applying step may comprise applying at least one electrical pulse sufficient to induce the cell membrane and/or nuclear membrane of a cell to become permeable to a composition of the disclosure.

While the amounts provided herein are exemplary and non-limiting, the relationship between these amounts (e.g. ratios or relative abundances) may be used to modify the methods exemplified herein for larger-scale processes and manufacturing.

In certain embodiments of the methods of producing a modified T cell (e.g. a $T_{SCM}$ and/or $T_{CM}$) of the disclosure, the activation supplement comprises one or more cytokine(s). The one or more cytokine(s) may comprise any cytokine, including but not limited to, lymphokines. Exemplary lymphokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-15 (IL-15), interleukin-21 (IL-21), granulocyte-macrophage colony-stimulating factor (GM-CSF) and interferon-gamma (INFγ). The one or more cytokine(s) may comprise IL-2.

In certain embodiments of the methods of producing a modified T cell (e.g. a $T_{SCM}$ and/or $T_{CM}$) of the disclosure, the expansion supplement comprises one or more cytokine(s). The one or more cytokine(s) may comprise any cytokine, including but not limited to, lymphokines. Exemplary lymphokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-15 (IL-15), interleukin-21 (IL-21), granulocyte-macrophage colony-stimulating factor (GM-CSF) and interferon-gamma (INFγ). The one or more cytokine(s) may comprise IL-2.

In certain embodiments of the methods of producing a modified T cell (e.g. a $T_{SCM}$ and/or $T_{CM}$) of the disclosure, the primary human T cell is a naïve T cell. The naïve T cell may express CD45RA, CCR7 and CD62L. In certain embodiments, the method is applied to a cell population comprising at least 5%, 10%, 15%, 20%, 25%, 30%, 35%, 40%, 45%, 50%, 55%, 60%, 65%, 70%, 75%, 80%, 85%, 90%, 95%, 99%, or any percentage in between of naïve T cells. In certain embodiments, the efficiency of production of modified $T_{SCM}$ and/or $T_{CM}$ of the disclosure may be increased by increasing a proportion or percentage of naïve T cells in a cell population to which the methods of the disclosure are applied.

In certain embodiments of the methods of producing a modified $T_{SCM}$ and/or $T_{CM}$ of the disclosure, the primary human T cell is a memory T cell.

In certain embodiments of the methods of producing a modified $T_{SCM}$ and/or $T_{CM}$ of the disclosure, the primary human T cell expresses one or more of CD62L, CD45RA, CD28, CCR7, CD127, CD45RO, CD95, CD95 and IL-2Rβ.

In certain embodiments of the methods of producing a modified $T_{SCM}$ and/or $T_{CM}$ of the disclosure, the primary human T cell is a naïve T-cell (modified $T_N$) and the modified $T_N$ expresses one or more of CD45RA, CCR7 and CD62L. In certain embodiments of the methods of producing a modified $T_{SCM}$ and/or $T_{CM}$ of the disclosure, the primary human T cell is a modified $T_{SCM}$ a T memory stem cell (modified $T_{SCM}$) and the modified $T_{SCM}$ expresses one or more of CD45RA, CD95, IL-2Rβ, CR7, and CD62L. In certain embodiments of the methods of producing a modified $T_{SCM}$ and/or $T_{CM}$ of the disclosure, the primary human T cell is a central memory T-cell (modified $T_{CM}$) and the modified $T_{CM}$ expresses one or more of CD45RO, CD95, IL-2Rβ, CCR7, and CD62L. In certain embodiments of the methods of producing a modified $T_{SCM}$ and/or $T_{CM}$ of the disclosure, the primary human T cell is an effector memory T-cell (modified $T_{EM}$) and the modified $T_{EM}$ expresses one or more of CD45RO, CD95, and IL-2Rβ. In certain embodiments of the methods of producing a modified $T_{SCM}$ and/or $T_{CM}$ of the disclosure, the primary human T cell is an effector T-cell (modified $T_{EFF}$) and the modified $T_{EFF}$ expresses one or more of CD45RA, CD95, and IL-2Rβ.

In certain embodiments of the methods of producing a modified $T_{SCM}$ and/or $T_{CM}$ of the disclosure, the primary human T cell may express CD4 and/or CD8. In certain embodiments, the primary human T cell may express CD4 and/or CD8 at various ratios. In certain embodiments, the primary human T cell may express CD4 and/or CD8 at various ratios that are not naturally-occurring. In certain embodiments, the primary human T cells that express CD4 and/or CD8 at various ratios, that may be not naturally occurring, are a heterologous cell population.

In certain embodiments of the methods of producing a modified $T_{SCM}$ and/or $T_{CM}$ of the disclosure, the primary human T cell may be isolated, prepared or derived from for example, whole blood, peripheral blood, umbilical cord blood, lymph fluid, lymph node tissue, bone marrow, and cerebral spinal fluid (CSF). The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow. Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

Primary human T cells of the disclosure may comprise pan T cells. As used herein, pan T-cells include all T lymphocytes isolated from a biological sample, without sorting by subtype, activation status, maturation state, or cell-surface marker expression.

In certain embodiments of the methods of the disclosure, the method further comprises introducing into a modified $T_{SCM}$ or $T_{CM}$ cell a composition comprising a genomic editing construct or composition. In certain embodiments, the genomic editing construct comprises a guide RNA and a clustered regularly interspaced short palindromic repeats (CRISPR) associated protein 9 (Cas9) DNA endonuclease. In certain embodiments, the genomic editing construct comprises a DNA binding domain and a type IIS endonuclease. In certain embodiments, the genomic editing construct encodes a fusion protein. In certain embodiments, the genomic editing construct encodes the DNA binding domain and the type IIS endonuclease and wherein the expressed DNA binding domain and the expressed type IIS endonuclease are non-covalently linked. In certain embodiments, including those embodiments wherein the genomic editing construct comprises a DNA binding domain and a type IIS endonuclease, the genomic editing construct comprises a sequence derived from a Cas9 endonuclease. In certain embodiments, including those embodiments wherein the genomic editing construct comprises a DNA binding domain and a type IIS endonuclease, the sequence derived from a Cas9 endonuclease is the DNA binding domain. In certain embodiments, including those embodiments wherein the sequence derived from a Cas9 endonuclease is the DNA binding domain, the sequence derived from a Cas9 endonuclease encodes an inactive Cas9. In certain embodiments, including those embodiments wherein the sequence derived from a Cas9 endonuclease is the DNA binding domain, the sequence derived from a Cas9 endonuclease encodes a truncated Cas9. In certain embodiments, the sequence derived from a Cas9 endonuclease comprises an amino acid substitution of an Alanine (A) for an Aspartic Acid (D) at position 10 (D10A). In certain embodiments, the sequence derived from a Cas9 endonuclease comprises or further comprises an amino acid substitution of an Alanine (A) for a Histidine (H) at position 840 (H840A). In certain embodiments, the sequence derived from a Cas9 endonuclease comprises an inactivated Cas9 (dCas9) (SEQ ID NO: 33). In certain embodiments, the sequence derived from a Cas9 endonuclease comprises an amino acid substitution of an alanine (A) for an Asparagine (N) at position 580 (N580A). In certain embodiments, the sequence derived from a Cas9 endonuclease comprises a truncated and inactivated Cas9 (dSaCas9) (SEQ ID NO: 32). In certain embodiments, including those embodiments wherein the genomic editing construct comprises a DNA binding domain and a type IIS endonuclease, the genomic editing construct comprises a sequence derived from a transcription activator-like effector nuclease (TALEN). In certain embodiments, including those embodiments wherein the genomic editing construct comprises a DNA binding domain and a type IIS endonuclease, the sequence derived from a TALEN is the DNA binding domain. In certain embodiments, the genomic editing construct comprises a TALEN. In certain embodiments, including those embodiments wherein the genomic editing construct comprises a DNA binding domain and a type IIS endonuclease, the genomic editing construct comprises a sequence derived from a zinc-finger nuclease (ZFN). In certain embodiments, including those embodiments wherein the genomic editing construct comprises a DNA binding domain and a type IIS endonuclease, the sequence derived from a ZFN is the DNA binding domain. In certain embodiments, the genomic editing construct comprises a zinc-finger nuclease (ZFN).

The methods of making modified $T_{SCM}$ and/or $T_{CM}$ cells of the disclosure may be optimized to produce a greater number or greater proportion of modified $T_{SCM}$ and/or $T_{CM}$ cells. For example, the population of cells subjected to the methods of the disclosure may be enriched to contain an increased number or greater proportion of naïve T cells. As the number and/or proportion of naïve T cells increases in the population of T cells subjected to the methods of the disclosure, the number and/or proportion of modified $T_{SCM}$ and/or $T_{CM}$ cells of the disclosure produced also increases. Alternatively, or in addition, as the length of time or duration required for a method of disclosure to precede decreases, the number and/or proportion of modified $T_{SCM}$ and/or $T_{CM}$ cells of the disclosure produced by the method increases. The length of time or duration required for a method of disclosure to precede, or the "manufacturing period" may also be referred to as the "out-of-life period" of the T cells subjected to the methods of the disclosure.

In certain embodiments of the methods of making modified T-cells of the disclosure, the primary human T cell expresses one or more of CD62L, CD45RA, CD28, CCR7, CD127, CD45RO, CD95, CD95 and IL-2Rβ. In certain embodiments, the primary human T cell is a naïve T-cell ($T_N$) and the $T_N$ expresses one or more of CD45RA, CCR7 and CD62L. In certain embodiments, the primary human T cell is a T memory stem cell ($T_{SCM}$) and the $T_{SCM}$ expresses one or more of CD45RA, CD95, IL-2Rβ, CR7, and CD62L. In certain embodiments, the primary human T cell is a central memory T-cell ($T_{CM}$) and wherein the $T_{CM}$ expresses one or more of CD45RO, CD95, IL-2Rβ, CCR7, and CD62L. In certain embodiments, the primary human T cell is an effector memory T-cell ($T_{EM}$) and the EM expresses one or more of CD45RO, CD95, and IL-2Rβ. In certain embodiments, the primary human T cell is an effector T-cell ($T_{EFF}$) and the $T_{EFF}$ expresses one or more of CD45RA, CD95, and IL-2Rβ. In certain embodiments, the primary human T cell expresses CD4 and/or CD8.

The disclosure provides a composition comprising a modified $T_{SCM}$ produced a method of the disclosure. The disclosure provides a composition comprising a modified $T_{CM}$ produced a method of the disclosure. The disclosure provides a composition comprising a modified $T_{SCM}$ and a modified $T_{CM}$ produced a method of the disclosure. In certain embodiments of the composition comprising a modified $T_{SCM}$ and a modified $T_{CM}$ produced a method of the disclosure, a plurality of $T_{SCM}$ may comprise at least 1%, 2%, 5%, 10%, 15%, 20%, 25%, 30%, 35%, 40%, 45%, 50%, 55%, 60%, 65%, 70%, 75%, 80%, 85%, 90%, 95%, 97%, 98% or 99% or the composition. In certain embodiments of the composition comprising a modified $T_{SCM}$ and a modified $T_{CM}$ produced a method of the disclosure, a plurality of $T_{CM}$ may comprise at least 1%, 2%, 5%, 10%, 15%, 20%, 25%, 30%, 35%, 40%, 45%, 50%, 55%, 60%, 65%, 70%, 75%, 80%, 85%, 90%, 95%, 97%, 98% or 99% or the composition.

The disclosure provides a use of a composition comprising a modified $T_{SCM}$ and/or $T_{CM}$ produced a method of the disclosure for the manufacture of a medicament to treat a subject in need thereof. In certain embodiments of this use, the modified $T_{SCM}$ and/or $T_{CM}$ is autologous. In certain embodiments of this use, the modified $T_{SCM}$ and/or $T_{CM}$ is allogeneic. In certain embodiments, the antigen receptor is a T-cell receptor. In certain embodiments, the T-cell receptor is naturally-occurring. In certain embodiments, the T-cell receptor is not naturally-occurring. In certain embodiments, and, in particular, in those embodiments wherein the T-cell receptor is not naturally-occurring, the T-cell receptor comprises one or more mutation(s) compared to a wild-type T-cell receptor. In certain embodiments, and, in particular, in those embodiments wherein the T-cell receptor is not naturally-occurring, the T-cell receptor is a recombinant T-cell receptor. In certain embodiments, the antigen receptor is a Chimeric Antigen Receptor (CAR). In certain embodiments, the CAR is a CARTyrin. In certain embodiments, the CAR comprises one or more VHH sequence(s). In certain embodiments, the CAR is a VCAR.

The disclosure provides a method of treating a disease or disorder in a subject in need thereof, comprising administering to the subject a therapeutically effective amount of a composition comprising a modified $T_{SCM}$ and/or $T_{CM}$ produced a method of the disclosure. In certain embodiments of this method, the modified $T_{SCM}$ and/or $T_{CM}$ is autologous. In certain embodiments of this method, the modified $T_{SCM}$ and/or $T_{CM}$ is allogeneic. In certain embodiments, the antigen receptor is a T-cell receptor. In certain embodiments, the T-cell receptor is naturally-occurring. In certain embodiments, the T-cell receptor is not naturally-occurring. In certain embodiments, and, in particular, in those embodiments wherein the T-cell receptor is not naturally-occurring, the T-cell receptor comprises one or more mutation(s) compared to a wild-type T-cell receptor. In certain embodiments, and, in particular, in those embodiments wherein the T-cell receptor is not naturally-occurring, the T-cell receptor is a recombinant T-cell receptor. In certain embodiments, the antigen receptor is a Chimeric Antigen Receptor (CAR). In certain embodiments, the CAR is a CARTyrin. In certain embodiments, the CAR comprises one or more VHH sequence(s). In certain embodiments, the CAR is a VCAR. In certain embodiments of this method, the disease or disorder is cancer and the antigen receptor specifically targets a cancer antigen. In certain embodiments of this method, the disease or disorder is an infectious disease or disorder and the antigen receptor specifically targets a viral, bacterial, yeast or microbial antigen. In certain embodiments, the disease or disorder is a disease or disorder caused by a lack of an activity or an insufficient amount of a secretory protein. In certain embodiments, the disease or disorder is a disease or disorder treated by a replacement of an activity of a therapeutic protein or by an increase in an amount of the therapeutic protein. In certain embodiments, the therapeutic protein is a secreted protein. In certain embodiments, the secretory protein is lacking an activity or a sufficient amount within a local area of a body. In certain embodiments, the local area of a body is accessible by a native T-cell or a modified T-cell. In certain embodiments, the modified T-cell is produced in vivo, ex vivo, in vitro or in situ.

BRIEF DESCRIPTION OF THE DRAWINGS

FIG. 6C is a table depicting the percent of transformed T cells resulting from transposition with WT versus hyperactive piggyBac transposase. T cells contacted with the hyperactive piggyBac transposase (the Super piggyBac transposase) were transformed at a rate 4-fold greater than WT transposase.

In FIGS. 10A and 10B, the x-axis, in order from left to right, in the first and second columns shows Forward Scatter (FSC), units from 0 to 250 thousand (abbreviated "k"), in increments of 50 k. The x axis of the third column from the left shows CD8 expression, with markings reading from 0 to $10^5$ incrementing by powers of 10. The final right hand column shows CD62L expression, with markings reading from 0 to $10^5$ incrementing by powers of 10. In FIGS. 10A and 10B, the y-axis, in the first column, shows Side Scatter (SSC), in units from 0 to 250 k in increments of 50 k. The y-axis in the second column from the left shows expression of the cell viability marker 7 aminoactinomycin D (7AAD), from 0 to $10^5$ incrementing by powers of 10. The y-axis of the third column from the left shows the expression of the marker CD4, from 0 to $10^5$ incrementing by powers of 10. The y-axis in the right hand column show expression of the marker CD45RA, from 0 to $10^5$ incrementing by powers of 10.

FIGS. 14A-E are a series of plasmid maps for site-specific integration into the AAVS1 site using either HR or MMEJ and corresponding sequences. Donor plasmids for testing stable integration into the genome of human pan T cells via A) site-specific (AAVS1) homologous recombination (HR), B) site-specific (AAVS1) microhomology-mediated end-joining (MMEJ) recombination and C) TTAA-specific piggyBac™ transposition. For HR and MMEJ donor plasmids, GFP-2A-DHFR gene expression cassettes were flanked by CRISPR/Cas9 targeting sites and homology arms for AAVS1 site integration; for piggyBac™ donor plasmid, GFP-2A-DHFR gene expression cassette is flanked by piggyBac™ transposon elements. The homology arms for the HR and MMEJ plasmids are 500 bp and 25 bp, respectively. Panels D and E depict SEQ ID NOs 41 and 42 respectively.

DETAILED DESCRIPTION

Figure 1:
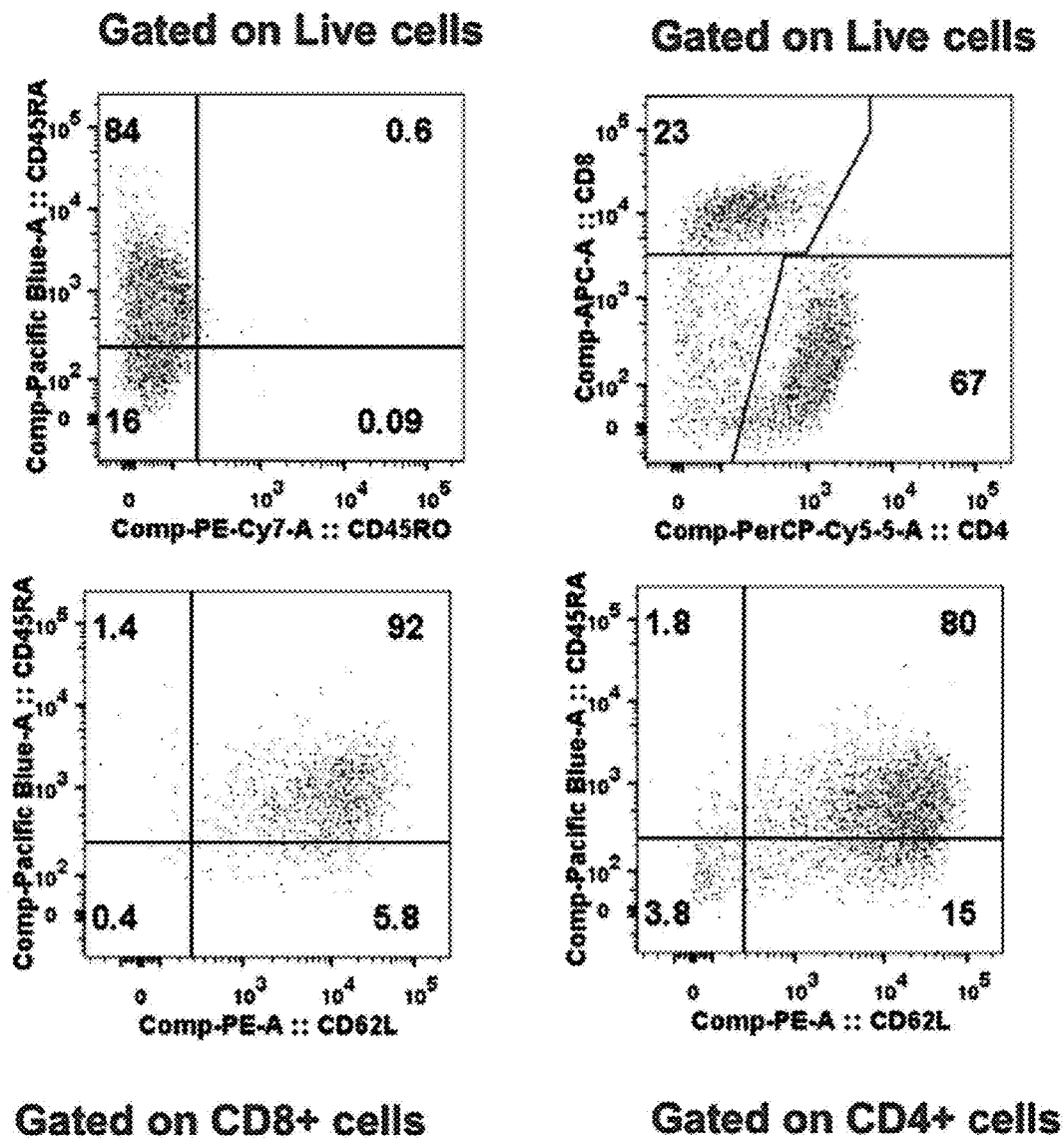
FIG. 1 is a series of plots depicting the emergence of the CAR-$T_{SCM}$ phenotype at Day 11 of the method of Example 1. Cells were nucleofected with a surrogate CARTyrin plasmid. CAR-$T_{SCM}$ cells express CD62L and CD45RA as shown in the bottom two plots.
Figure 2:
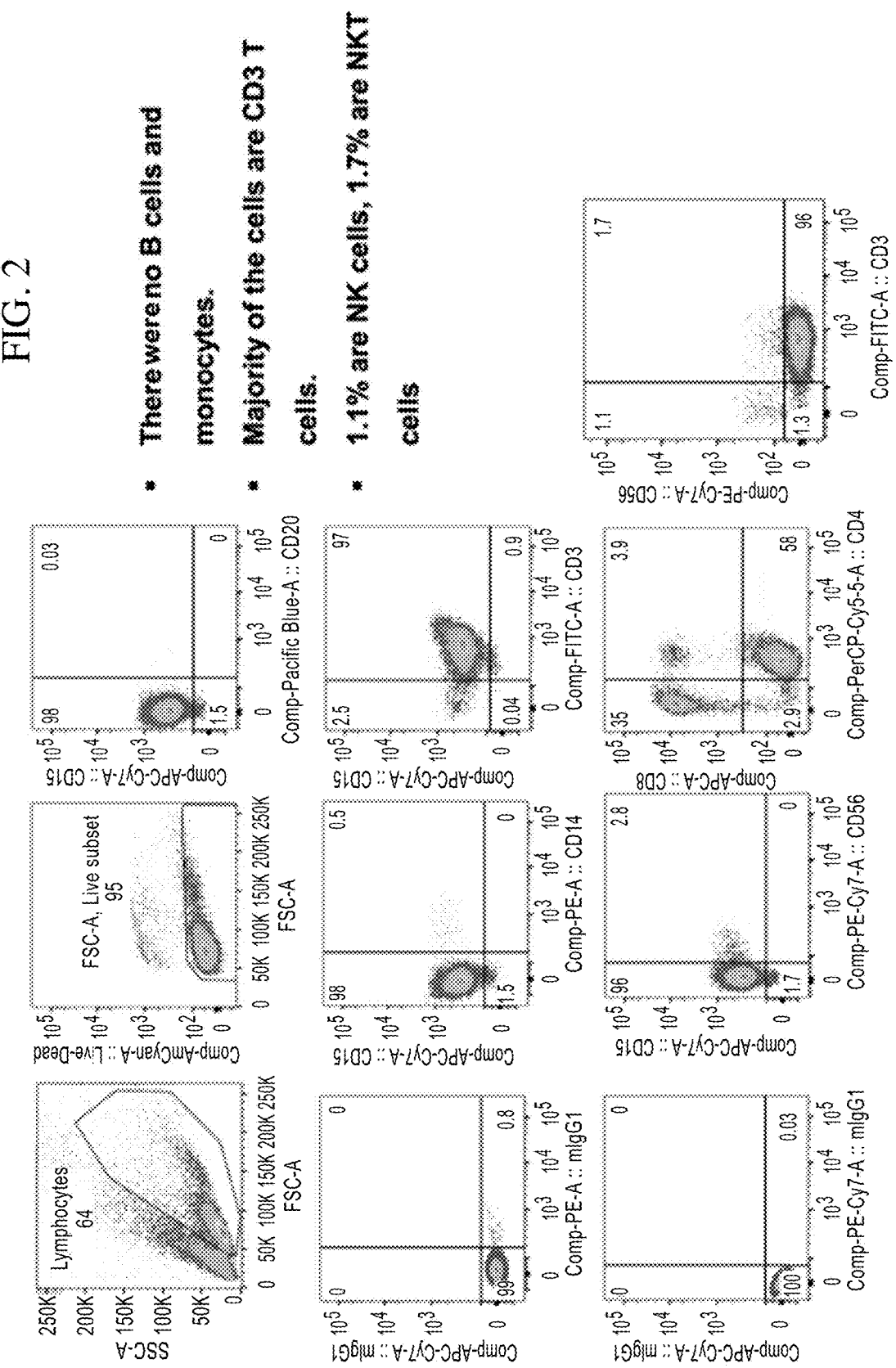
FIG. 2 is a series of plots depicting the purity of the CAR-$T_{SCM}$ produced by the method of Example 1 at day 19. The population of CAR-$T_{SCM}$ cells produced by the method described in Example 1 at day 19 contained no B cells or lymphocytes. The majority of the cells are CD3+ T-cells. Only 1.1% are Natural Killer cells and 1.7% are Natural Killer T-cells.
Figure 3:
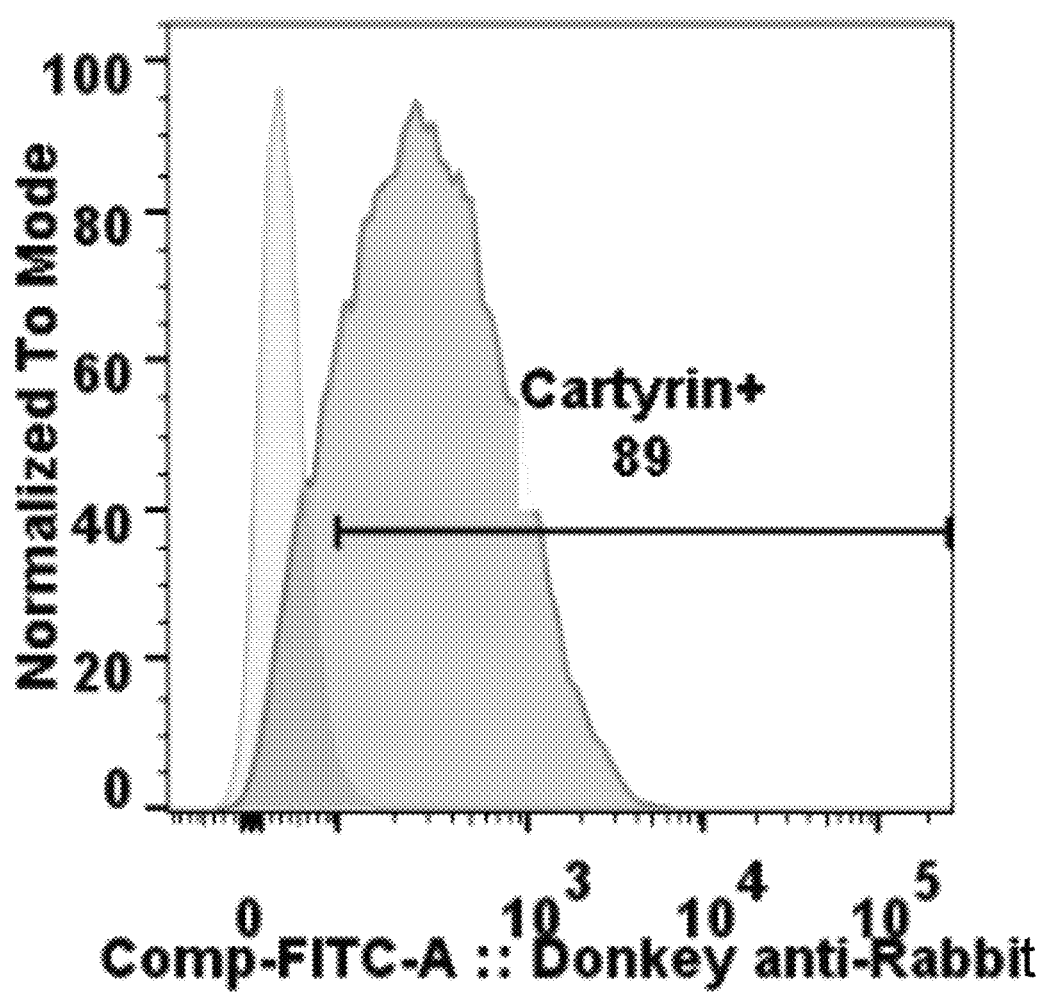
FIG. 3 is a plot showing that at Day 11 of the method described in Example 1, the majority of the T-cells produced express the CARTyrin.
Figure 4:
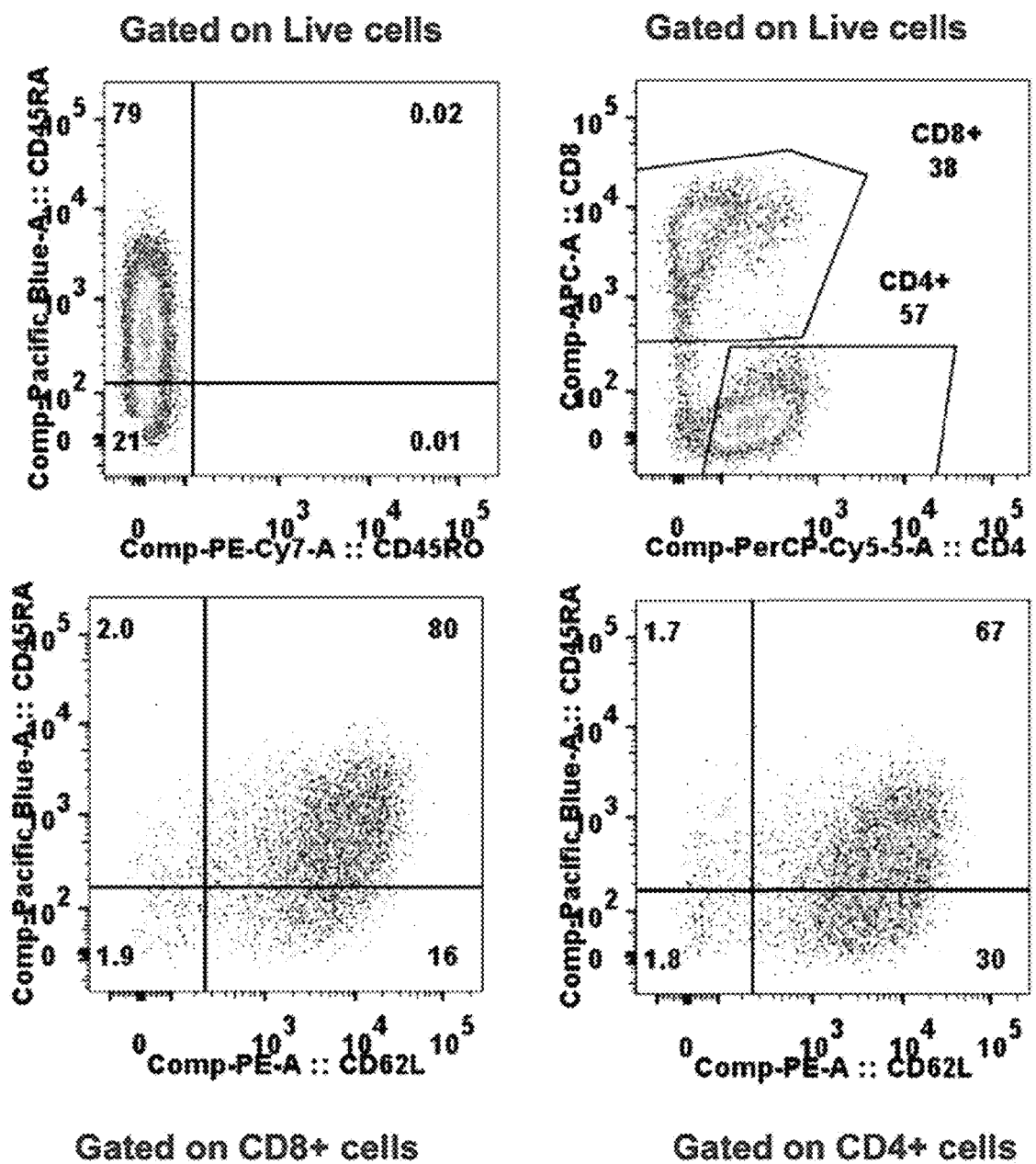
FIG. 4 is a series of plots depicting an enrichment of the CAR-$T_{SCM}$ phenotype at Day 19 of the method described in Example 1. Cells were nucleofected with a surrogate CAR-Tyrin plasmid. CAR-$T_{SCM}$ cells express CD62L and CD45RA as shown in the bottom two plots.
Figure 5:
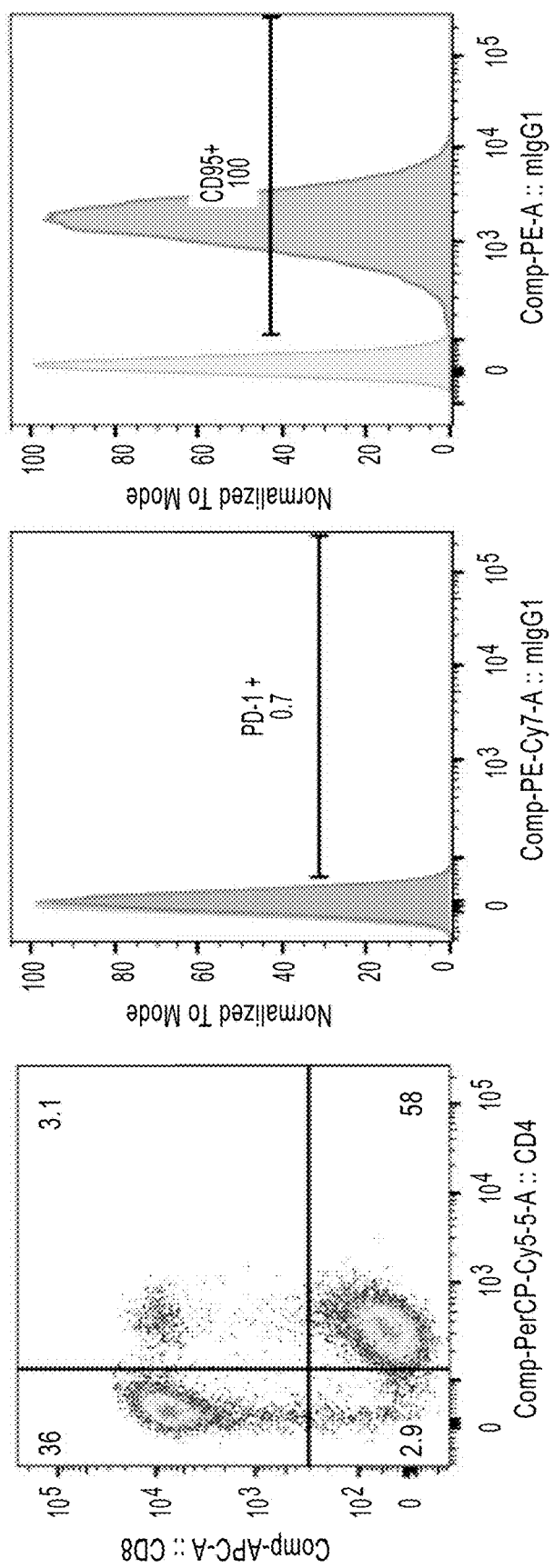
FIG. 5 is a series of plots depicting the absence of T-cell exhaustion at Day 19 of the method described in Example 1. At Day 19, the cell population produced by this method does not express PD1, which is a marker for T cell activation and exhaustion. These cells expressing the CARTyrin have almost successfully reached a resting state post-manufacture. They do not exhibit signs of antigen-independent (tonic) signaling which would otherwise drive higher levels of PD1 expression. Tonic signaling is hypothesized to be caused by some CAR molecules that lead to early exhaustion and reduced efficacy of a CAR T-cell therapy.
Figure 6A:
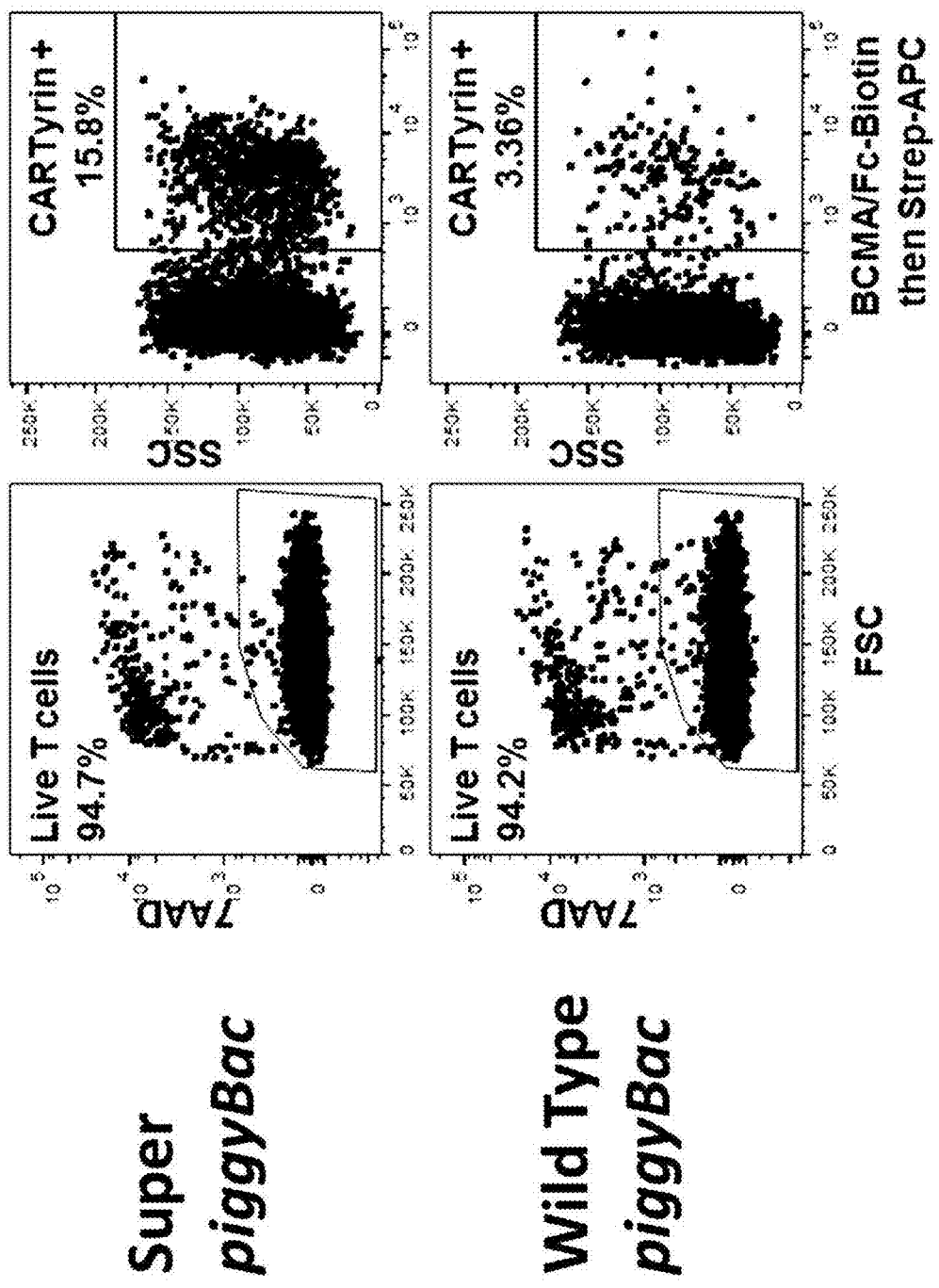
FIG. 6A is a series of plots depicting T cells transposed with a plasmid containing a sequence encoding a transposon comprising a sequence encoding an inducible caspase polypeptide (a safety switch, "iC9"), a CARTyrin (anti-BCMA), and a selectable marker. Left-hand plots depict live T cells exposed to transposase in the absence of the plasmid. Right-hand plots depict live T cells exposed to transposase in the presence of the plasmid. Cells were exposed to either a hyperactive transposase (the "Super piggyBac") or a wild type piggyBac transposase.
Figure 6B:
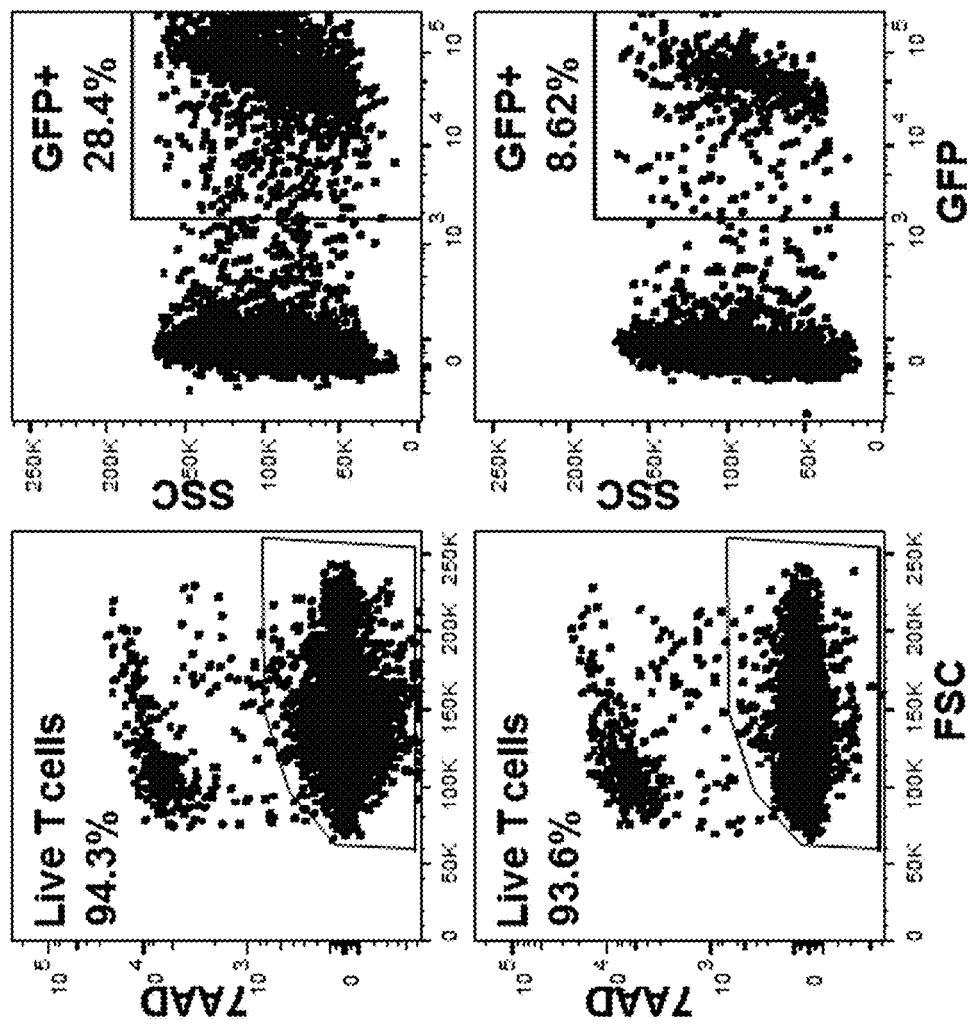
FIG. 6B is a series of plots depicting T cells transposed with a plasmid containing a sequence encoding a green fluorescent protein (GFP). Left-hand plots depict live T cells exposed to transposase in the absence of the plasmid. Right-hand plots depict live T cells exposed to transposase in the presence of the plasmid. Cells were exposed to either a hyperactive transposase (the "Super piggyBac") or a wild type piggyBac transposase.
Figure 6D:
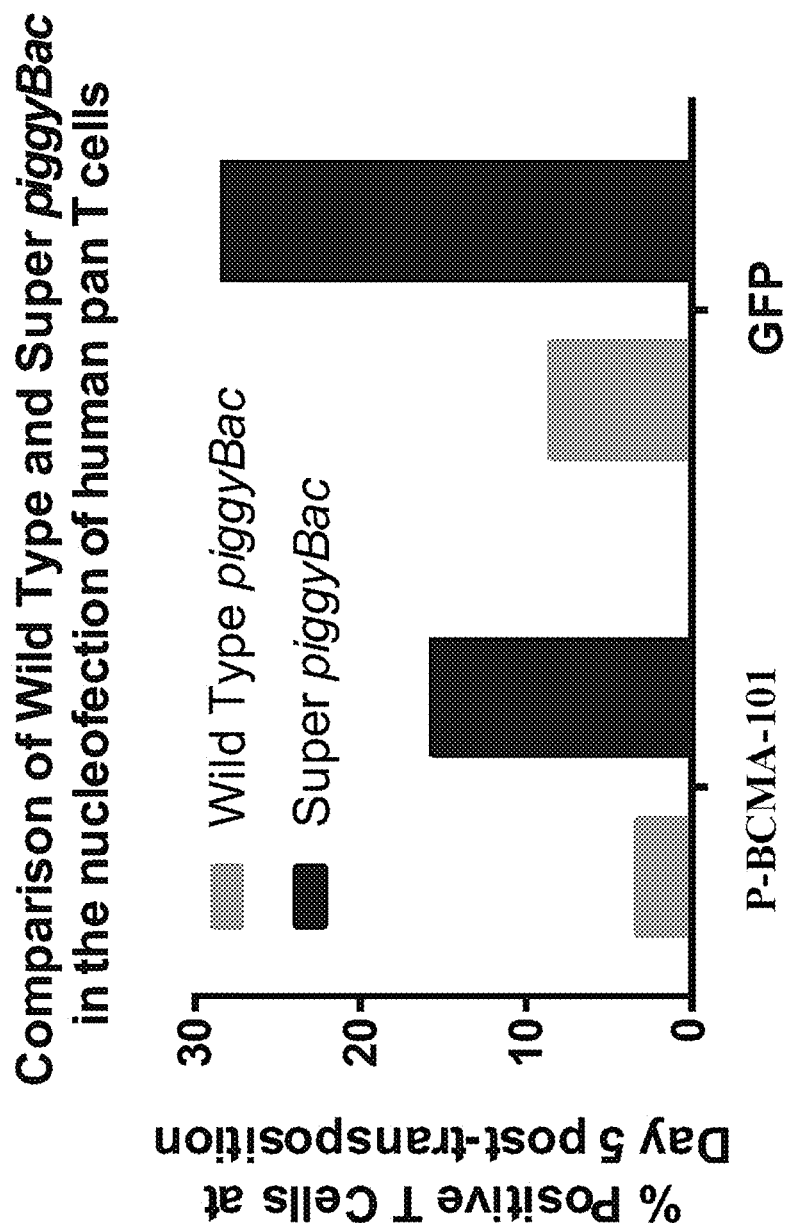
FIG. 6D is a graph depicting the percent of transformed T cells resulting from transposition with WT versus hyperactive piggyBac transposase 5 days after nucleofection. T cells contacted with the hyperactive piggyBac transposase (the Super piggyBac transposase) were transformed at a rate far greater than WT transposase.
Figure 7:
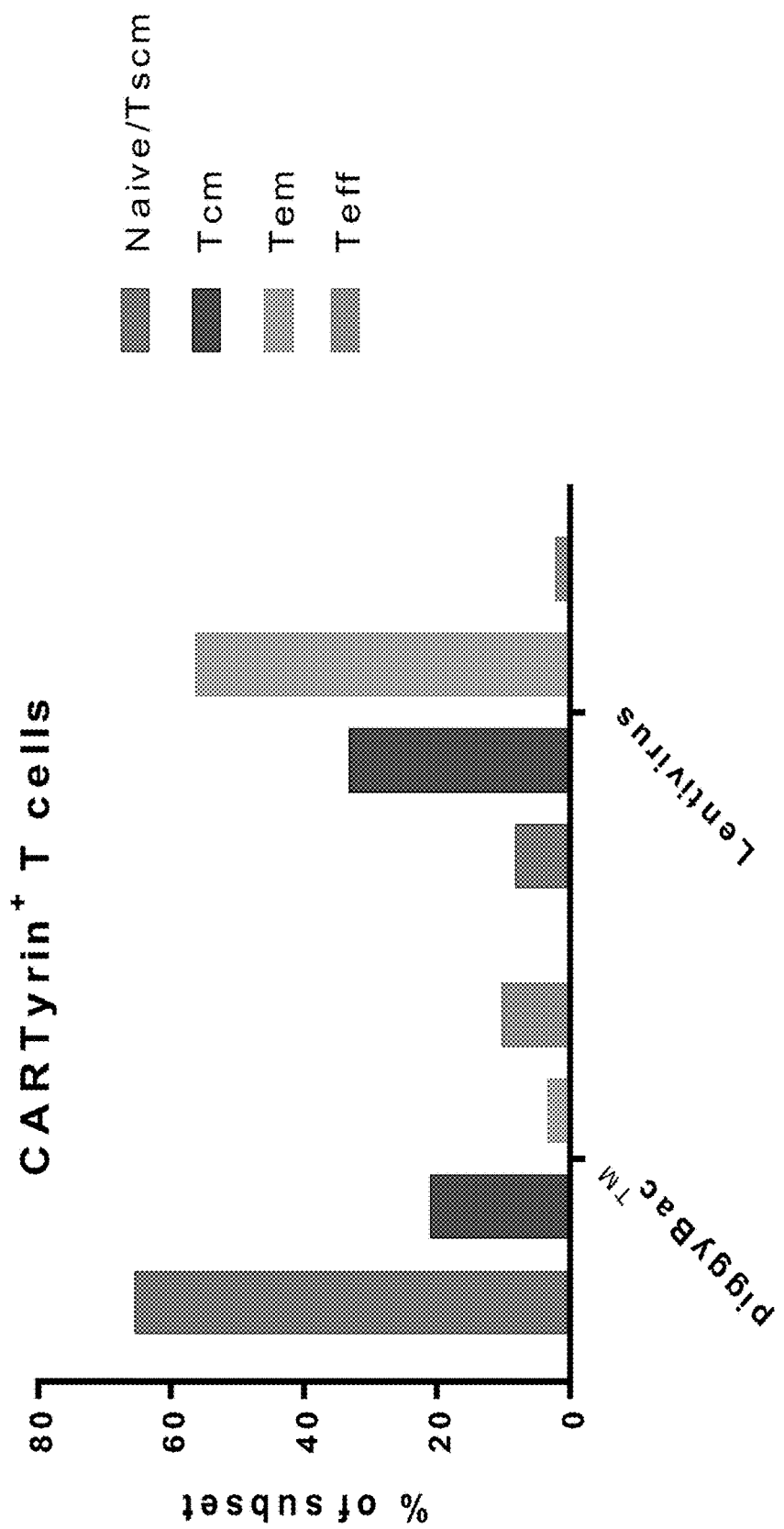
FIG. 7 is a graph showing a phenotypic difference between piggyBac™- and lentivirus-produced CAR+ T cells. CAR+ T cells were produced using either piggyBac transposition or lentivirus transduction. Human pan T cells were transposed with piggyBac encoding CAR, stimulated with anti-CD3/CD28 beads at day 2 post-transposition, expanded, and examined on day 19 post-transposition. For production using lentivirus, pan T cells were stimulated with aCD3/CD28 beads, transduced with lentivirus encoding CAR (MOI 5), expanded, and examined on day 18 post-stimulation. Then, each population of CAR+ T cells was characterized based on their expression of the standard memory markers CD62L, CD45RA and CD95. The percentage of each CAR+ T cell subset was defined as naïve (CD62L+CD45RA+), $T_{CM}$ (CD62L+CD45RA−), Tem (CD62L−CD45RA−) and Teff (CD62L−CD45RA+). All CAR+ T cells were CD95+.
Figure 8A:
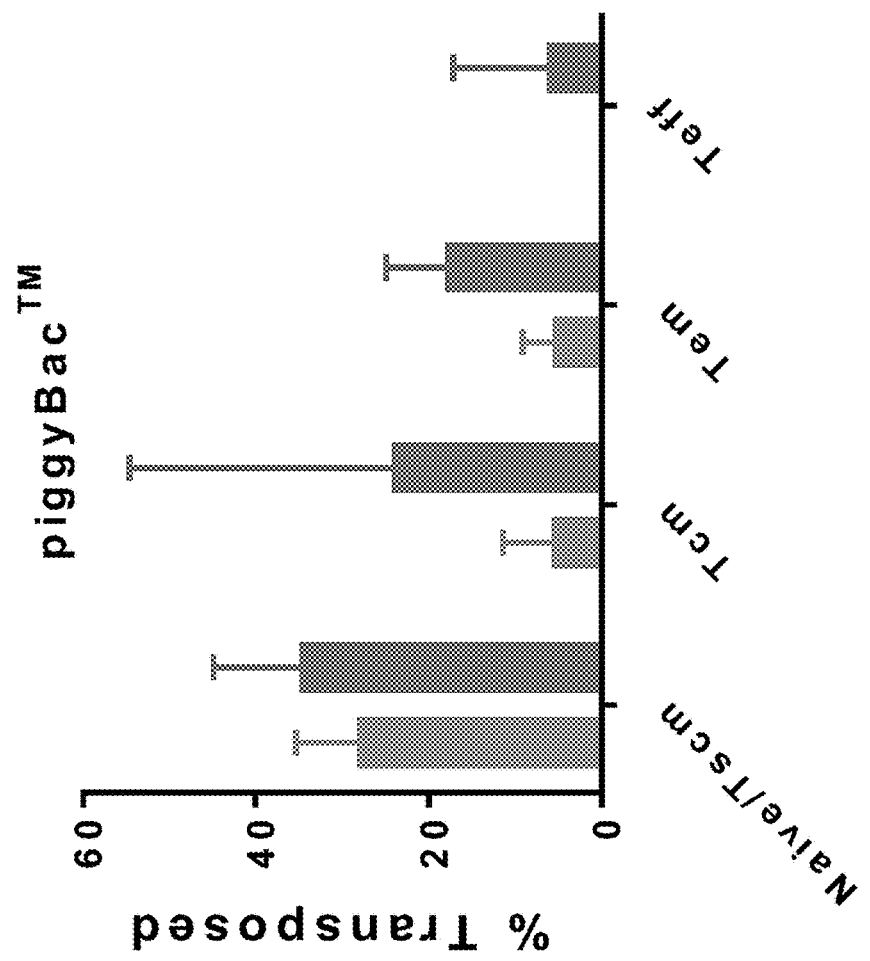
FIGS. 8A-B is a pair of graphs showing that piggyBac™ preferentially transposes naïve T cells. Human pan T cells were sorted (using a BD FACSAria II flow cytometer) into naïve (CD62L+CD45RA+), $T_{CM}$ (CD62L+CD45RA−), Tem (CD62L−CD45RA−), and Teff (CD62L−CD45RA+) subsets. The sorted subsets were each either transposed with piggyBac-GFP or transduced with lentivirus-GFP. For the former, each sorted subset was transposed with PiggyBac-GFP, stimulated with anti-CD3/CD28 beads at day 2 post-transposition, expanded, and examined on day 19 post-transposition. For the latter, the sorted subsets were stimulated with aCD3/CD28 beads, transduced with lentivirus encoding GFP (MOI 5), expanded, and examined on day 19 post-stimulation. n=3 donors.
Figure 8B:
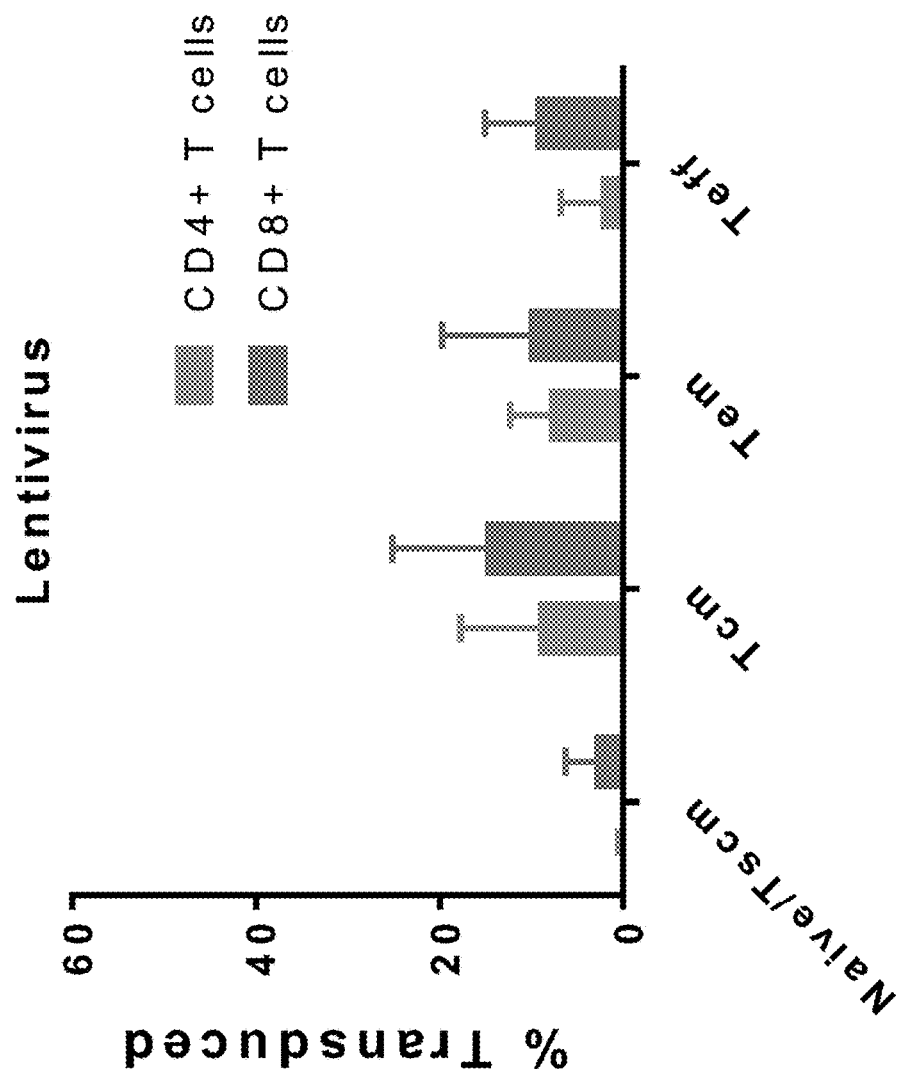
Figure 9:
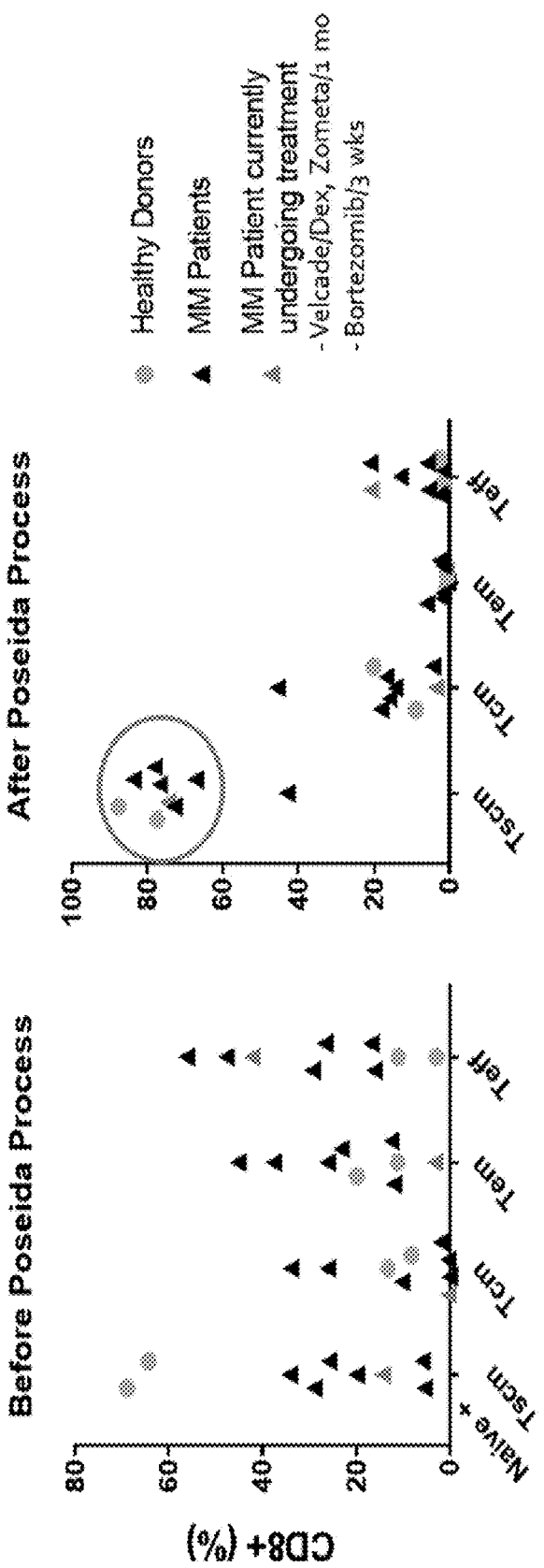
FIG. 9 is a pair of graphs showing that the piggyBac™ manufacturing process yields high levels of $T_{SCM}$ in samples from multiple myeloma (MM) patients even when naïve T cells are rare. T cells from MM patients (triangles) and healthy donors (circles) were characterized for memory marker expression by flow cytometry before (left) and after (right) the Poseida manufacturing process. Expression of CD45RA and CD62L was assessed by FACS and plots are shown for the MM patients and a healthy donor. It is known that T cells from MM patients generally have lower frequencies of naïve and $T_{SCM}$ cells, but higher frequencies of Teff, unlike those from healthy normal donors which are the opposite. Regardless of the input frequency of naïve and $T_{SCM}$ from different MM patients, production of P-BCMA-101 using the Poseida manufacturing process resulted in a product that exhibited a high level of CD8+$T_{SCM}$ (E). This was also true for a MM patient who was actively receiving treatment (red triangle).

The disclosure provides a method for producing human chimeric antigen receptor (CAR) expressing-T cells using the piggyBac™ Transposon System under conditions that preserve or induce stem-cell memory T cells ($T_{SCM}$) with potent CAR activity (referred to herein as a CAR-$T_{SCM}$. Compositions comprising CAR-$T_{SCM}$ produced using the methods of the disclosure comprise >60% CAR-$T_{SCM}$ and exhibit a distinct functional profile that is consistent with this T cell subset. Other T cell subsets found in the compositions of the disclosure include, but are not limited to, central memory CAR-T cells (CAR-$T_{CM}$), effector memory CAR-T cells (CAR-$T_{EM}$), effector CAR-T cells (CAR-$T_E$), and terminally-differentiated effector CAR-T cells (CAR-$T_{TE}$). A linear pathway of differentiation may be responsible for generating these cells: Naïve T cells ($T_N$)>$T_{SCM}$>$T_{CM}$>$T_{EM}$>$T_E$>$T_{TE}$, whereby $T_N$ is the parent precursor cell that directly gives rise to $T_{SCM}$, which then, in turn, directly gives rise to $T_{CM}$, etc. Compositions comprising CAR-$T_{SCM}$, CARTyrin-$T_{SCM}$ and/or VCAR-$T_{SCM}$ of the disclosure may comprise one or more of each parental CAR-T cell subset with CAR-$T_{SCM}$ being the most abundant (e.g. $T_{SCM}$>$T_{CM}$>$T_{EM}$>$T_E$>$T_{TE}$). While, the absolute quantities/abundances and relative proportions of each parental T cell subset may vary among samples of patient blood and naturally-occurring cell populations, and naturally-occurring cell populations may have a high abundance and/or proportion of $T_{SCM}$, compositions of the disclosure comprising non-naturally occurring CAR-$T_{SCM}$ are more potent and efficacious in treating patients against diseases and cancers.

Immunotherapy using chimeric-antigen receptor (CAR)-T cells is emerging as an exciting therapeutic approach for cancer therapies. Autologous CAR-modified T cells targeting a tumor-associated antigen (Ag) can result in robust tumor killing, in some cases resulting in complete remission of CD19+ hematological malignancies. Unlike traditional biologics and chemotherapeutics, CAR-T cells possess the capacity to rapidly reproduce upon Ag recognition, thereby potentially obviating the need for repeat treatments. To achieve this, CAR-T cells must not only drive tumor destruction initially, but must also persist in the patient as a stable population of viable memory T cells to prevent potential cancer relapses. Thus, intensive efforts have been focused on the development of CAR molecules that do not cause T cell exhaustion through Ag-independent (tonic) signaling, as well as of a CAR-T product containing early memory cells, especially stem cell memory ($T_{SCM}$). A stem cell-like CAR-T would exhibit the greatest capacity for self-renewal and multipotent capacity to derive central memory ($T_{CM}$), effector memory ($T_{EM}$) and effector T cells (TE), thereby producing better tumor eradication and long-term CAR-T engraftment.

CAR-$T_{SCM}$ of the disclosure may comprise a Centyrin-based CAR, referred to as a CARTyrin (and hence, the cell may be referred to as a CARTyrin-$T_{SCM}$). Centyrins are alternative scaffold molecules based on human consensus tenascin FN3 domain, are smaller than scFv molecules, and can be selected for monomeric properties that favor stability and decrease the likelihood of tonic signaling in CAR molecules. CARTyrins of the disclosure may be introduced to T cells using a plasmid DNA transposon encoding the CARTyrin that is flanked by two cis-regulatory insulator elements to help stabilize CARTyrin expression by blocking improper gene activation or silencing.

CAR-$T_{SCM}$ of the disclosure may comprise a VHH-based CAR, referred to as a VCAR (and hence, the cell may be referred to as a VCAR-$T_{SCM}$). VCARs of the disclosure may be introduced to T cells using a plasmid DNA transposon encoding the VHH that is flanked by two cis-regulatory insulator elements to help stabilize VHH expression by blocking improper gene activation or silencing.

In certain embodiments of the methods of the disclosure, the piggyBac™ (PB) Transposon System may be used for stable integration of antigen-specific (including cancer antigen-specific) CARTyrin or VCAR into resting pan T cells, whereby the transposon was co-delivered along with an mRNA transposase enzyme (although the transposon and transposase would be comprised in separate compositions until they were introduced into a cell), called Super piggyBac™ (SPB), in a single electroporation reaction. Delivery of piggyBac™ transposon into untouched, resting primary human pan T cells resulted in 20-30% of cells with stable integration and expression of PB-delivered genes. Unexpectedly, a majority of these modified CARTyrin-expressing T cells were positive for expression of CD62L and CD45RA, markers commonly associated with stem memory T-cells ($T_{SCM}$ cells). To confirm that this phenotype was retained upon CAR-T cell stimulation and expansion, the modified CARTyrin-expressing T cells positive for expression of CD62L and CD45RA were activated via stimulation of CD3 and CD28. As a result of stimulation of CD3 and CD28, >60% of CARTyrin+ T cells exhibited a stem-cell memory phenotype. Furthermore, these cells, which expressed a CARTyrin specific for a cancer antigen, were fully capable of expressing potent anti-tumor effector function.

To determine whether or not the PB system directly contributed to enhancing the expression of stem-like markers, the phenotype of CAR-T cells generated either by PB transposition or lentiviral (LV) transduction was compared. To do this, a new vector was constructed by subcloning the CARTyrin transgene into a common LV construct for production of virus. Following introduction of the CARTyrin to untouched resting T cells either by PB-transposition or LV-transduction, the CARTyrin+ cells were expanded and then allowed to return to a resting state. A variety of phenotypic and functional characteristics were measured including kinetic analysis of memory and exhaustion-associated markers, secondary proliferation in response to homeostatic cytokine or tumor-associated Ag, cytokine production, and lytic capability in response to target tumor cells. Unlike the PB-transposed CARTyrin+ T cells, the LV-transduced CARTyrin+ T cells did not exhibit an augmented memory phenotype. In addition, PB-transposed cells exhibited a comparable or greater capability for secondary proliferation and killing of target tumor cells. Together, these data demonstrate that CAR-T cells produced by PB transposition are predominantly $T_{SCM}$ cells, a highly desirable product phenotype in the CAR-T field. Furthermore, these CARTyrin+ T cells exhibit strong anti-tumor activity and may give rise to cells that persist longer in vivo due to the use of a Centyrin-based CAR, which may be less prone to tonic signaling and functional exhaustion.

Chimeric Antigen Receptors

The disclosure provides a chimeric antigen receptor (CAR) comprising: (a) an ectodomain comprising an antigen recognition region, wherein the antigen recognition region comprises one or more sequences that each specifically bind an antigen; (b) a transmembrane domain, and (c) an endodomain comprising at least one costimulatory domain. In certain embodiments, the antigen recognition region may comprise two sequences that each specifically bind an antigen to produce a bi-specific or tandem CAR. In certain embodiments, the antigen recognition region may comprise three sequences that each specifically bind an antigen to produce a tri-specific CAR. In certain embodiments, the ectodomain may further comprise a signal peptide. Alternatively, or in addition, in certain embodiments, the ectodomain may further comprise a hinge between the antigen recognition region and the transmembrane domain. Sequences that each specifically bind an antigen may include, but not limited to, a single chain antibody (e.g. a scFv), a sequence comprising one or more fragments of an antibody (e.g. a VHH, referred to in the context of a CAR as a VCAR), an antibody mimic, and a Centyrin (referred to in the context of a CAR as a CARTyrin).

In certain embodiments of the CARs of the disclosure, the signal peptide may comprise a sequence encoding a human CD2, CD3δ, CD3ε, CD3γ, CD3ζ, CD4, CD8α, CD19, CD28, 4-1BB or GM-CSFR signal peptide. In certain embodiments of the CARs of the disclosure, the signal peptide may comprise a sequence encoding a human CD8a signal peptide. The human CD8a signal peptide may comprise an amino acid sequence comprising MALPVTALLL- PLALLLHAARP (SEQ ID NO: 8). The human CD8a signal peptide may comprise an amino acid sequence comprising MALPVTALLLPLALLLHAARP (SEQ ID NO: 8) or a sequence having at least 70%, 80%, 90%, 95%, or 99% identity to the an amino acid sequence comprising MALPVTALLLPLALLLHAARP (SEQ ID NO: 8). The human CD8a signal peptide may be encoded by a nucleic acid sequence comprising atggcactgccagtcaccgccctgctgctgctctggctctgctgctgcacgcagctagacca (SEQ ID NO: 9).

In certain embodiments of the CARs of the disclosure, the transmembrane domain may comprise a sequence encoding a human CD2, CD3δ, CD3ε, CD3γ, CD3ζ, CD4, CD8α, CD19, CD28, 4-1BB or GM-CSFR transmembrane domain. In certain embodiments of the CARs of the disclosure, the transmembrane domain may comprise a sequence encoding a human CD8a transmembrane domain. The CD8a transmembrane domain may comprise an amino acid sequence comprising IYIWAPLAGTCGVLLLSLVITLYC (SEQ ID NO: 10) or a sequence having at least 70%, 80%, 90%, 95%, or 99% identity to the amino acid sequence comprising IYIWAPLAGTCGVLLLSLVITLYC (SEQ ID NO: 10). The CD8a transmembrane domain may be encoded by the nucleic acid sequence comprising atctacatttgggcaccactggccgggacctgtggagtgctgctgctgagcctggtcatcacactgtactgc (SEQ ID NO: 11).

In certain embodiments of the CARs of the disclosure, the endodomain may comprise a human CD3ζ endodomain.

In certain embodiments of the CARs of the disclosure, the at least one costimulatory domain may comprise a human 4-1BB, CD28, CD40, ICOS, MyD88, OX-40 intracellular segment, or any combination thereof. In certain embodiments of the CARs of the disclosure, the at least one costimulatory domain may comprise a CD28 and/or a 4-1BB costimulatory domain. The CD28 costimulatory domain may comprise an amino acid sequence comprising RVKFSRSADAPAYKQGQNQLYNELNLGRREEYDVLDKRRGRDPEMGGKPRRKNPQEGL YNELQKDKMAEAYSEIGMKGERRRGKGHDGLYQGLSTATKDTYDAL HMQALPPR (SEQ ID NO: 12) or a sequence having at least 70%, 80%, 90%, 95%, or 99% identity to the amino acid sequence comprising RVKFSRSADAPAYKQGQNQLYNELNLGRREEYDVLDKRRGRDPEMGGKPRRKNPQEGL YNELQKDKMAEAYSEIGMKGERRRGKGHDGLYQGLSTATKDTYDALHMQALPPR (SEQ ID NO: 12). The CD28 costimulatory domain may be encoded by the nucleic acid sequence comprising cgcgtgaagtttagtcgatcagcagatgccccagcttacaaacagggacagaaccagctgtataacgagctgaatctgggccgccgagag gaatatgacgtgctggataagcggagaggacgcgaccccgaaatgggaggcaagcccaggcgcaaaaaccctcaggaaggcctgtat aacgagctgcagaaggacaaaatggcagaagcctattctgagatcggcatgaaggggagcgacggagaggcaaagggcacgatgg gctgtaccagggactgagcaccgccacaaaggacacctatgatgctctgcatatgcaggcactgcctccaagg (SEQ ID NO: 13). The 4-1BB costimulatory domain may comprise an amino acid sequence comprising KRGRKKLLYIFKQPFMRPVQTTQEEDGCSCRFPEEEEGGCEL (SEQ ID NO: 14) or a sequence having at least 70%, 80%, 90%, 95%, or 99% identity to the amino acid sequence comprising KRGRKKLLYIFKQPFMRPVQTTQEEDGCSCRFPEEEEGGCEL (SEQ ID NO: 14). The 4-1BB costimulatory domain may be encoded by the nucleic acid sequence comprising aagagaggcaggaagaaactgctgtatattttcaaacagccatcatgcgccccgtgcagactacccaggaggaagacgggtgctcctgt cgattccctgaggaagaggaaggcgggtgtgagctg (SEQ ID NO: 15). The 4-1BB costimulatory domain may be located between the transmembrane domain and the CD28 costimulatory domain.

In certain embodiments of the CARs of the disclosure, the hinge may comprise a sequence derived from a human CD8α, IgG4, and/or CD4 sequence. In certain embodiments of the CARs of the disclosure, the hinge may comprise a sequence derived from a human CD8a sequence. The hinge may comprise a human CD8a amino acid sequence comprising TTTPAPRPPTPAPTIASQPLSLRPEACRPAAGGAVHTRGLDFACD (SEQ ID NO: 16) or a sequence having at least 70%, 80%, 90%, 95%, or 99% identity to the amino acid sequence comprising TTTPAPRPPTPAPTIASQPLSLRPEACRPAAGGAVHTRGLDFACD (SEQ ID NO: 16). The human CD8a hinge amino acid sequence may be encoded by the nucleic acid sequence comprising actaccacaccagcacctagaccaccaactccagctccaaccatcgcgagtcagcccctgagtctgagacctgaggcctgcaggccagc tgcaggaggagctgtgcacaccaggggcctggacttcgcctgcgac (SEQ ID NO: 17).

The disclosure provides a composition comprising the CAR of the disclosure and at least one pharmaceutically acceptable carrier.

The disclosure provides a transposon comprising the CAR of the disclosure. Transposons of the disclosure be episomally maintained or integrated into the genome of the recombinant/modified cell. The transposon may be part of a two component piggyBac system that utilizes a transposon and transposase for enhanced non-viral gene transfer.

Transposons of the disclosure may comprise a selection gene for identification, enrichment and/or isolation of cells that express the transposon. Exemplary selection genes encode any gene product (e.g. transcript, protein, enzyme) essential for cell viability and survival. Exemplary selection genes encode any gene product (e.g. transcript, protein, enzyme) essential for conferring resistance to a drug challenge against which the cell is sensitive (or which could be lethal to the cell) in the absence of the gene product encoded by the selection gene. Exemplary selection genes encode any gene product (e.g. transcript, protein, enzyme) essential for viability and/or survival in a cell media lacking one or more nutrients essential for cell viability and/or survival in the absence of the selection gene. Exemplary selection genes include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), and NKX2.2 (encoding NK2 Homeobox 2).

Transposons of the disclosure may comprise at least one self-cleaving peptide(s) located, for example, between one or more of a sequence that specifically binds an antigen and a selection gene of the disclosure. The at least one self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaaggggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, 95%, or 99% identity to the amino acid sequence comprising GSGQCTNYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTLNFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNFSLLKQAGDVEENPGP (SEQ ID NO: 26).

Transposons of the disclosure may comprise a first and a second self-cleaving peptide, the first self-cleaving peptide located, for example, upstream of one or more of a sequence that specifically binds an antigen of the disclosure the second self-cleaving peptide located, for example, downstream of the one or more of a sequence that specifically binds an antigen of the disclosure. The first and/or the second self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaaggggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, or 99% identity to the amino acid sequence comprising GSGQCTNYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTLNFDLLKLAGDVESNPGP (SEQ ID NO: 023). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNFSLLKQAGDVEENPGP (SEQ ID NO: 26).

The disclosure provides a composition comprising the transposon the disclosure. In certain embodiments, a method introducing the composition may further comprise a composition comprising a plasmid comprising a sequence encoding a transposase enzyme. The sequence encoding a transposase enzyme may be an mRNA sequence.

Transposons of the disclosure may comprise piggyBac transposons. Transposase enzymes of the disclosure may include piggyBac transposases or compatible enzymes.

The disclosure provides a vector comprising the CAR of the disclosure. In certain embodiments, the vector is a viral vector. The vector may be a recombinant vector.

Viral vectors of the disclosure may comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV). Exemplary adeno-associated viruses and recombinant adeno-associated viruses of the disclosure comprise two or more inverted terminal repeat (ITR) sequences located in cis next to one or more of a sequence that specifically binds an antigen. Exemplary adeno-associated viruses and recombinant adeno-associated viruses of the disclosure include, but are not limited to all serotypes (e.g. AAV1, AAV2, AAV3, AAV4, AAV5, AAV6, AAV7, AAV8, and AAV9). Exemplary adeno-associated viruses and recombinant adeno-associated viruses of the disclosure include, but are not limited to, self-complementary AAV (scAAV) and AAV hybrids containing the genome of one serotype and the capsid of another serotype (e.g. AAV2/5, AAV-DJ and AAV-DJ8). Exemplary adeno-associated viruses and recombinant adeno-associated viruses of the disclosure include, but are not limited to, rAAV-LK03.

Viral vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Viral vectors of the disclosure may comprise at least one self-cleaving peptide. In some embodiments, the vector may comprise at least one self-cleaving peptide and wherein a self-cleaving peptide is located between a CAR and a selection gene. In some embodiments, the vector may comprise at least one self-cleaving peptide and wherein a first self-cleaving peptide is located upstream of a CAR and a second self-cleaving peptide is located downstream of a CAR. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaagggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, 95%, or 99% identity to the amino acid sequence comprising GSGQCTNYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTLNFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNFSLLKQAGDVEENPGP (SEQ ID NO: 26).

The disclosure provides a vector comprising the CAR of the disclosure. In certain embodiments, the vector is an mRNA vector. The vector may be a recombinant mRNA vector. T cells of the disclosure may be expanded prior to contacting the T-cell and the mRNA vector comprising the CAR of the disclosure. The T cell comprising the mRNA vector, the modified T cell, may then be administered to a subject.

The disclosure provides a vector comprising the CAR of the disclosure. In certain embodiments, the vector is a nanoparticle. Exemplary nanoparticle vectors of the disclosure include, but are not limited to, nucleic acids (e.g. RNA, DNA, synthetic nucleotides, modified nucleotides or any combination thereof), amino acids (L-amino acids, D-amino acids, synthetic amino acids, modified amino acids, or any combination thereof), polymers (e.g. polymerosomes), micelles, lipids (e.g. liposomes), organic molecules (e.g. carbon atoms, sheets, fibers, tubes), inorganic molecules (e.g. calcium phosphate or gold) or any combination thereof. A nanoparticle vector may be passively or actively transported across a cell membrane.

Nanoparticle vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Nanoparticle vectors of the disclosure may comprise at least one self-cleaving peptide. In some embodiments, the nanoparticle vector may comprise at least one self-cleaving peptide and wherein a self-cleaving peptide is located between a CAR and the nanoparticle. In some embodiments, the nanoparticle vector may comprise at least one self-cleaving peptide and wherein a first self-cleaving peptide is located upstream of a CAR and a second self-cleaving peptide is located downstream of a CAR. In some embodiments, the nanoparticle vector may comprise at least one self-cleaving peptide and wherein a first self-cleaving peptide is located between a CAR and the nanoparticle and a second self-cleaving peptide is located downstream of the CAR. In some embodiments, the nanoparticle vector may comprise at least one self-cleaving peptide and wherein a first self-cleaving peptide is located between a CAR and the nanoparticle and a second self-cleaving peptide is located downstream of the CAR, for example, between the CAR and a selection gene. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaagggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGD-VESNPGP (SEQ ID NO: 21). A GSG-E2A peptide may comprise an amino acid sequence comprising GSGQCT-NYALLKLAGDVESNPGP (SEQ ID NO: 22) or a sequence having at least 70%, 80%, 90%, 95%, or 99% identity to the amino acid sequence comprising GSGQCT-NYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTL-NFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNF-SLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNF-SLLKQAGDVEENPGP (SEQ ID NO: 26).

The disclosure provides a composition comprising a vector of the disclosure.

CARTyrins

The disclosure provides a chimeric antigen receptor (CAR) comprising: (a) an ectodomain comprising an antigen recognition region, wherein the antigen recognition region comprises at least one Centyrin; (b) a transmembrane domain, and (c) an endodomain comprising at least one costimulatory domain. As used throughout the disclosure, a CAR comprising a Centyrin is referred to as a CARTyrin. In certain embodiments, the antigen recognition region may comprise two Centyrins to produce a bi-specific or tandem CAR. In certain embodiments, the antigen recognition region may comprise three Centyrins to produce a tri-specific CAR. In certain embodiments, the ectodomain may further comprise a signal peptide. Alternatively, or in addition, in certain embodiments, the ectodomain may further comprise a hinge between the antigen recognition region and the transmembrane domain.

The disclosure provides a chimeric antigen receptor (CAR) comprising: (a) an ectodomain comprising an antigen recognition region, wherein the antigen recognition region comprises at least one protein scaffold or antibody mimetic; (b) a transmembrane domain, and (c) an endodomain comprising at least one costimulatory domain. In certain embodiments, the antigen recognition region may comprise two scaffold proteins or antibody mimetics to produce a bi-specific or tandem CAR. In certain embodiments, the antigen recognition region may comprise three protein scaffolds or antibody mimetics to produce a tri-specific CAR. In certain embodiments, the ectodomain may further comprise a signal peptide. Alternatively, or in addition, in certain embodiments, the ectodomain may further comprise a hinge between the antigen recognition region and the transmembrane domain.

In certain embodiments of the CARs of the disclosure, the signal peptide may comprise a sequence encoding a human CD2, CD3δ, CD3ε, CD3γ, CD3ζ, CD4, CD8α, CD19, CD28, 4-1BB or GM-CSFR signal peptide. In certain embodiments of the CARs of the disclosure, the signal peptide may comprise a sequence encoding a human CD8a signal peptide. The human CD8a signal peptide may comprise an amino acid sequence comprising MALPVTALLL-PLALLLHAARP (SEQ ID NO: 8). The human CD8a signal peptide may comprise an amino acid sequence comprising MALPVTALLLPLALLLHAARP (SEQ ID NO: 8) or a sequence having at least 70%, 80%, 90%, 95%, or 99% identity to the an amino acid sequence comprising MALPVTALLLPLALLLHAARP (SEQ ID NO: 8). The human CD8a signal peptide may be encoded by a nucleic acid sequence comprising atggcactgccagtcaccgccctgctgctgc-ctctggctctgctgctgcacgcagctagacca (SEQ ID NO: 9).

In certain embodiments of the CARs of the disclosure, the transmembrane domain may comprise a sequence encoding a human CD2, CD3δ, CD3ε, CD3γ, CD3ζ, CD4, CD8α, CD19, CD28, 4-1BB or GM-CSFR transmembrane domain. In certain embodiments of the CARs of the disclosure, the transmembrane domain may comprise a sequence encoding a human CD8a transmembrane domain. The CD8a transmembrane domain may comprise an amino acid sequence comprising IYIWAPLAGTCGVLLLSLVITLYC (SEQ ID NO: 10) or a sequence having at least 70%, 80%, 90%, 95%, or 99% identity to the amino acid sequence comprising IYIWAPLAGTCGVLLLSLVITLYC (SEQ ID NO: 10). The CD8a transmembrane domain may be encoded by the nucleic acid sequence comprising atctacatttgggcaccactggc-cgggacctgtggagtgctgctgctgagcctggtcatcacactgtactgc (SEQ ID NO: 11).

In certain embodiments of the CARs of the disclosure, the endodomain may comprise a human CD3ζ endodomain.

In certain embodiments of the CARs of the disclosure, the at least one costimulatory domain may comprise a human 4-1BB, CD28, CD40, ICOS, MyD88, OX-40 intracellular segment, or any combination thereof. In certain embodiments of the CARs of the disclosure, the at least one costimulatory domain may comprise a CD28 and/or a 4-1BB costimulatory domain. The CD28 costimulatory domain may comprise an amino acid sequence comprising RVKF-SRSADAPAYKQGQNQLYNELNLGRREEYDVLD-KRRGRDPEMGGKPRRKNPQEGL YNELQKDKMAE-AYSEIGMKGERRRGKGHDGLYQGLSTATKDTYDAL HMQALPPR (SEQ ID NO: 12) or a sequence having at least 70%, 80%, 90%, 95%, or 99% identity to the amino acid sequence comprising RVKFSRSADAPAYKQGQNQLY-NELNLGRREEYDVLDKRRGRDPEMGGKPRRKN-PQEGL YNELQKDKMAEAYSEIGMKGERRRGKGH-DGLYQGLSTATKDTYDALHMQALPPR (SEQ ID NO: 12). The CD28 costimulatory domain may be encoded by the nucleic acid sequence comprising cgcgtgaagtttagtcgatca-gcagatgccccagcttacaaacagggacagaaccagctgtataacgagct-gaatctgggccgccgagag gaatatgacgtgctggataagcggagaggacgc-gacccccgaaatggggaggcaagcccaggcgcaaaaaccctcaggaaggcctgtat aacgagctgcagaaggacaaaatggcagaagcctattctgagatcggcat-gaaggggggagcgacggagaggcaaagggcacgatgg gctgtaccagggact-gagcaccgccacaaaggacacctatgatgctctgcatatgcaggcactgcctc-caagg (SEQ ID NO: 13). The 4-1BB costimulatory domain may comprise an amino acid sequence comprising KRGRK-KLLYIFKQPFMRPVQTTQEEDGCSCRFPEEEEGGCEL (SEQ ID NO: 14) or a sequence having at least 70%, 80%, 90%, 95%, or 99% identity to the amino acid sequence comprising KRGRKKLLYIFKQPFMRPVQTTQEEDGC-SCRFPEEEEGGCEL (SEQ ID NO: 14). The 4-1BB costimulatory domain may be encoded by the nucleic acid sequence comprising aagagaggcaggaagaaactgctgtat-attttcaaacagccatcatgcgcccccgtgcagactacccaggaggaagacgggt-gctcctgt cgattccctgaggaagaggaaggcgggtgtgagctg (SEQ ID NO: 15). The 4-1BB costimulatory domain may be located between the transmembrane domain and the CD28 costimulatory domain.

In certain embodiments of the CARs of the disclosure, the hinge may comprise a sequence derived from a human CD8α, IgG4, and/or CD4 sequence. In certain embodiments of the CARs of the disclosure, the hinge may comprise a sequence derived from a human CD8a sequence. The hinge may comprise a human CD8a amino acid sequence comprising TTTPAPRPPTPAPTIASQPLSLRPEACR-PAAGGAVHTRGLDFACD (SEQ ID NO: 16) or a sequence having at least 70%, 80%, 90%, 95%, or 99% identity to the amino acid sequence comprising TTTPAPRPPTPAPTIA-SQPLSLRPEACRPAAGGAVHTRGLDFACD (SEQ ID NO: 16). The human CD8a hinge amino acid sequence may be encoded by the nucleic acid sequence comprising actaccacaccagcacctagaccaccaactccagctccaaccatcgcgagtcagcccctgagtctgagacctgaggcctgcaggccagc tgcaggaggagctgtgcacaccaggggcctggacttcgcctgcgac (SEQ ID NO: 17).

Centyrins of the disclosure may comprise a protein scaffold, wherein the scaffold is capable of specifically binding an antigen. Centyrins of the disclosure may comprise a protein scaffold comprising a consensus sequence of at least one fibronectin type III (FN3) domain, wherein the scaffold is capable of specifically binding an antigen. The at least one fibronectin type III (FN3) domain may be derived from a human protein. The human protein may be Tenascin-C. The consensus sequence may comprise LPAPKNLVVSEVTED-SLRLSWTAPDAAFDSFLIQYQESEKVGEAINLTVPG-SERSYDLTG LKPGTEYTVSIYGVKGGHRSNPL-SAEFTT (SEQ ID NO: 1) or MLPAPKNLVVSEVTEDSLRLSWTAPDAAFDSFLIQY-QESEKVGEAINLTVPGSERSYDLT GLKPGTEYTVSI-YGVKGGHRSNPLSAEFTT (SEQ ID NO: 2). The consensus sequence may encoded by a nucleic acid sequence comprising atgctgcctgcaccaaagaacctggtggtgtctcatgtgacagaggatagtgccagactgtcatggactgctcccgacgcagccttcgata gtttatcatcgtgtaccgggagaacatcgaaaccggcgaggccattgtcctgacagtgccagggtccgaacgctcttatgacctgacagat ctgaagcccggaactgagtactatgtgcagatcgccggcgtcaaaggaggcaatatcagatccctctgtccgcaatcttcaccaca (SEQ ID NO: 3). The consensus sequence may be modified at one or more positions within (a) a A-B loop comprising or consisting of the amino acid residues TEDS (SEQ ID NO: 43) at positions 13-16 of the consensus sequence; (b) a B-C loop comprising or consisting of the amino acid residues TAPDAAF (SEQ ID NO: 44) at positions 22-28 of the consensus sequence; (c) a C-D loop comprising or consisting of the amino acid residues SEKVGE (SEQ ID NO: 45) at positions 38-43 of the consensus sequence; (d) a D-E loop comprising or consisting of the amino acid residues GSER (SEQ ID NO: 46) at positions 51-54 of the consensus sequence; (e) a E-F loop comprising or consisting of the amino acid residues GLKPG (SEQ ID NO: 47) at positions 60-64 of the consensus sequence; (f) a F-G loop comprising or consisting of the amino acid residues KGGHRSN (SEQ ID NO: 48) at positions 75-81 of the consensus sequence; or (g) any combination of (a)-(f). Centyrins of the disclosure may comprise a consensus sequence of at least 5 fibronectin type III (FN3) domains, at least 10 fibronectin type III (FN3) domains or at least 15 fibronectin type III (FN3) domains. The scaffold may bind an antigen with at least one affinity selected from a $K_D$ of less than or equal to $10^{-9}$M, less than or equal to $10^{-10}$ M, less than or equal to $10^{-11}$ M, less than or equal to $10^{-12}$M, less than or equal to $10^{-13}$M, less than or equal to $10^{-14}$M, and less than or equal to $10^{-15}$M. The $K_D$ may be determined by surface plasmon resonance.

The disclosure provides a composition comprising the CAR of the disclosure and at least one pharmaceutically acceptable carrier.

The disclosure provides a transposon comprising the CAR of the disclosure. Transposons of the disclosure be episomally maintained or integrated into the genome of the recombinant/modified cell. The transposon may be part of a two component piggyBac system that utilizes a transposon and transposase for enhanced non-viral gene transfer.

Transposons of the disclosure may comprise a selection gene for identification, enrichment and/or isolation of cells that express the transposon. Exemplary selection genes encode any gene product (e.g. transcript, protein, enzyme) essential for cell viability and survival. Exemplary selection genes encode any gene product (e.g. transcript, protein, enzyme) essential for conferring resistance to a drug challenge against which the cell is sensitive (or which could be lethal to the cell) in the absence of the gene product encoded by the selection gene. Exemplary selection genes encode any gene product (e.g. transcript, protein, enzyme) essential for viability and/or survival in a cell media lacking one or more nutrients essential for cell viability and/or survival in the absence of the selection gene. Exemplary selection genes include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), and NKX2.2 (encoding NK2 Homeobox 2).

Transposons of the disclosure may comprise at least one self-cleaving peptide(s) located, for example, between on or more of a protein scaffold, Centyrin or CARTyrin of the disclosure and a selection gene of the disclosure. The at least one self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEEN-PGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaaggggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCT-NYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, 95%, or 99% identity to the amino acid sequence comprising GSGQCT-NYALLKLAGDVESNPGP (SEQ ID NO: 22). An F2A peptide may comprise an amino acid sequence comprising VKQTLNFDLLKLAGDVESNPGP (SEQ NO: 23) or a sequence having at least 70%, 80%, 90%, 95%, or 99% identity to the amino acid sequence comprising VKQTL-NFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNF-SLLKQAGDVEENPGP (SEQ ID NO: 26).

Transposons of the disclosure may comprise a first and a second self-cleaving peptide, the first self-cleaving peptide located, for example, upstream of one or more of a protein scaffold, Centyrin or CARTyrin of the disclosure the second self-cleaving peptide located, for example, downstream of the one or more of a protein scaffold, Centyrin or CARTyrin of the disclosure. The first and/or the second self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRG-SLLTCGDVEENPGP (SEQ ID NO: 19). A GSG-T2A peptide may comprise a nucleic acid sequence comprising ggatctggagagggaagggggaagcctgctgacctgtggagacgtggag-gaaaacccaggacca (SEQ ID NO: 20). An E2A peptide may comprise an amino acid sequence comprising QCT-NYALLKLAGDVESNPGP (SEQ ID NO: 21) or a sequence having at least 70%, 80%, 90%, 95%, or 99% identity to the amino acid sequence comprising QCTNYALLKLAGD-VESNPGP (SEQ ID NO:21). A GSG-E2A peptide may comprise an amino acid sequence comprising GSGQCT-NYALLKLAGDVESNPGP (SEQ ID NO: 22) or a sequence having at least 70%, 80%, 90%, 95%, or 99% identity to the amino acid sequence comprising GSGQCT-NYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTL-NFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNF-SLLKQAGDVEENPGP (SEQ ID NO: 26).

The disclosure provides a composition comprising the transposon the disclosure. In certain embodiments, a method introducing the composition may further comprise a composition comprising a plasmid comprising a sequence encoding a transposase enzyme. The sequence encoding a transposase enzyme may be an mRNA sequence.

Transposons of the disclosure may comprise piggyBac transposons. Transposase enzymes of the disclosure may include piggyBac transposases or compatible enzymes.

The disclosure provides a vector comprising the CAR of the disclosure. In certain embodiments, the vector is a viral vector. The vector may be a recombinant vector.

Viral vectors of the disclosure may comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV). Exemplary adeno-associated viruses and recombinant adeno-associated viruses of the disclosure comprise two or more inverted terminal repeat (ITR) sequences located in cis next to a sequence encoding a protein scaffold, Centyrin or CARTyrin of the disclosure. Exemplary adeno-associated viruses and recombinant adeno-associated viruses of the disclosure include, but are not limited to all serotypes (e.g. AAV1, AAV2, AAV3, AAV4, AAV5, AAV6, AAV7, AAV8, and AAV9). Exemplary adeno-associated viruses and recombinant adeno-associated viruses of the disclosure include, but are not limited to, self-complementary AAV (scAAV) and AAV hybrids containing the genome of one serotype and the capsid of another serotype (e.g. AAV2/5, AAV-DJ and AAV-DJ8). Exemplary adeno-associated viruses and recombinant adeno-associated viruses of the disclosure include, but are not limited to, rAAV-LK03.

Viral vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Viral vectors of the disclosure may comprise at least one self-cleaving peptide. In some embodiments, the vector may comprise at least one self-cleaving peptide and wherein a self-cleaving peptide is located between a CAR and a selection gene. In some embodiments, the vector may comprise at least one self-cleaving peptide and wherein a first self-cleaving peptide is located upstream of a CAR and a second self-cleaving peptide is located downstream of a CAR. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGD- VEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaaggggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, 95%, or 99% identity to the amino acid sequence comprising GSGQCTNYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTLNFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNFSLLKQAGDVEENPGP (SEQ ID NO: 26).

The disclosure provides a vector comprising the CAR of the disclosure. In certain embodiments, the vector is an mRNA vector. The vector may be a recombinant mRNA vector. T cells of the disclosure may be expanded prior to contacting the T-cell and the mRNA vector comprising the CAR of the disclosure. The T cell comprising the mRNA vector, the modified T cell, may then be administered to a subject.

The disclosure provides a vector comprising the CAR of the disclosure. In certain embodiments, the vector is a nanoparticle. Exemplary nanoparticle vectors of the disclosure include, but are not limited to, nucleic acids (e.g. RNA, DNA, synthetic nucleotides, modified nucleotides or any combination thereof), amino acids (L-amino acids, D-amino acids, synthetic amino acids, modified amino acids, or any combination thereof), polymers (e.g. polymerosomes), micelles, lipids (e.g. liposomes), organic molecules (e.g. carbon atoms, sheets, fibers, tubes), inorganic molecules (e.g. calcium phosphate or gold) or any combination thereof. A nanoparticle vector may be passively or actively transported across a cell membrane.

Nanoparticle vectors of the disclosure may comprise a selection gene. The selection gene may encode a gene product essential for cell viability and survival. The selection gene may encode a gene product essential for cell viability and survival when challenged by selective cell culture conditions. Selective cell culture conditions may comprise a compound harmful to cell viability or survival and wherein the gene product confers resistance to the compound. Exemplary selection genes of the disclosure may include, but are not limited to, neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2) or any combination thereof.

Nanoparticle vectors of the disclosure may comprise at least one self-cleaving peptide. In some embodiments, the nanoparticle vector may comprise at least one self-cleaving peptide and wherein a self-cleaving peptide is located between a CAR and the nanoparticle. In some embodiments, the nanoparticle vector may comprise at least one self-cleaving peptide and wherein a first self-cleaving peptide is located upstream of a CAR and a second self-cleaving peptide is located downstream of a CAR. In some embodiments, the nanoparticle vector may comprise at least one self-cleaving peptide and wherein a first self-cleaving peptide is located between a CAR and the nanoparticle and a second self-cleaving peptide is located downstream of the CAR. In some embodiments, the nanoparticle vector may comprise at least one self-cleaving peptide and wherein a first self-cleaving peptide is located between a CAR and the nanoparticle and a second self-cleaving peptide is located downstream of the CAR, for example, between the CAR and a selection gene. The self-cleaving peptide may comprise, for example, a T2A peptide, GSG-T2A peptide, an E2A peptide, a GSG-E2A peptide, an F2A peptide, a GSG-F2A peptide, a P2A peptide, or a GSG-P2A peptide. A T2A peptide may comprise an amino acid sequence comprising EGRGSLLTCGDVEENPGP (SEQ ID NO: 18) or a sequence having at least 70%, 80%, 90%, 95%, or 99% identity to the amino acid sequence comprising EGRGSLLTCGDVEENPGP (SEQ ID NO: 18). A GSG-T2A peptide may comprise an amino acid sequence comprising GSGEGRGSLLTCGDVEENPGP (SEQ ID NO: 19) or a sequence having at least 70%, 80%, 90%, 95%, or 99% identity to the amino acid sequence comprising GSGEGRGSLLTCGDVEENPGP (SEQ ID NO: 19). A GSG-T2A peptide may comprise a nucleic acid sequence comprising ggatctggagagggaaggggaagcctgctgacctgtggagacgtggaggaaaacccaggacca (SEQ ID NO: 20). An E2A peptide may comprise an amino acid sequence comprising QCTNYALLKLAGDVESNPGP (SEQ ID NO: 21) or a sequence having at least 70%, 80%, 90%, 95%, or 99% identity to the amino acid sequence comprising QCTNYALLKLAGDVESNPGP (SEQ ID NO: 21). A GSG-E2A peptide may comprise an amino acid sequence comprising GSGQCTNYALLKLAGDVESNPGP (SEQ ID NO: 22) or a sequence having at least 70%, 80%, 90%, 95%, or 99% identity to the amino acid sequence comprising GSGQCTNYALLKLAGDVESNPGP (SEQ ID NO: 22). An F2A peptide may comprise an amino acid sequence comprising VKQTLNFDLLKLAGDVESNPGP (SEQ ID NO: 23) or a sequence having at least 70%, 80%, 90%, 95%, or 99% identity to the amino acid sequence comprising VKQTLNFDLLKLAGDVESNPGP (SEQ ID NO: 23). A GSG-F2A peptide may comprise an amino acid sequence comprising GSGVKQTLNFDLLKLAGDVESNPGP (SEQ ID NO: 24) or a sequence having at least 70%, 80%, 90%, 95%, or 99% identity to the amino acid sequence comprising GSGVKQTLNFDLLKLAGDVESNPGP (SEQ ID NO: 24). A P2A peptide may comprise an amino acid sequence comprising ATNFSLLKQAGDVEENPGP (SEQ ID NO: 25) or a sequence having at least 70%, 80%, 90%, 95%, or 99% identity to the amino acid sequence comprising ATNFSLLKQAGDVEENPGP (SEQ ID NO: 25). A GSG-P2A peptide may comprise an amino acid sequence comprising GSGATNFSLLKQAGDVEENPGP (SEQ ID NO: 26) or a sequence having at least 70%, 80%, 90%, 95%, or 99% identity to the amino acid sequence comprising GSGATNFSLLKQAGDVEENPGP (SEQ ID NO: 26).

The disclosure provides a composition comprising a vector of the disclosure.

Scaffold Proteins

A Centyrin is one example of a protein scaffold of the disclosure. An antigen recognition region of a CAR of the disclosure may comprise at least one protein scaffold.

Protein scaffolds of the disclosure may be derived from a fibronectin type III (FN3) repeat protein, encoding or complementary nucleic acids, vectors, host cells, compositions, combinations, formulations, devices, and methods of making and using them. In a preferred embodiment, the protein scaffold is comprised of a consensus sequence of multiple FN3 domains from human Tenascin-C (hereinafter "Tenascin"). In a further preferred embodiment, the protein scaffold of the present invention is a consensus sequence of 15 FN3 domains. The protein scaffolds of the disclosure can be designed to bind various molecules, for example, a cellular target protein. In a preferred embodiment, the protein scaffolds of the disclosure can be designed to bind an epitope of a wild type and/or variant form of an antigen.

Protein scaffolds of the disclosure may include additional molecules or moieties, for example, the Fc region of an antibody, albumin binding domain, or other moiety influencing half-life. In further embodiments, the protein scaffolds of the disclosure may be bound to a nucleic acid molecule that may encode the protein scaffold.

The disclosure provides at least one method for expressing at least one protein scaffold based on a consensus sequence of multiple FN3 domains, in a host cell, comprising culturing a host cell as described herein under conditions wherein at least one protein scaffold is expressed in detectable and/or recoverable amounts.

The disclosure provides at least one composition comprising (a) a protein scaffold based on a consensus sequence of multiple FN3 domains and/or encoding nucleic acid as described herein; and (b) a suitable and/or pharmaceutically acceptable carrier or diluent.

The disclosure provides a method of generating libraries of a protein scaffold based on a fibronectin type III (FN3) repeat protein, preferably, a consensus sequence of multiple FN3 domains and, more preferably, a consensus sequence of multiple FN3 domains from human Tenascin. The library is formed by making successive generations of scaffolds by altering (by mutation) the amino acids or the number of amino acids in the molecules in particular positions in portions of the scaffold, e.g., loop regions. Libraries can be generated by altering the amino acid composition of a single loop or the simultaneous alteration of multiple loops or additional positions of the scaffold molecule. The loops that are altered can be lengthened or shortened accordingly. Such libraries can be generated to include all possible amino acids at each position, or a designed subset of amino acids. The library members can be used for screening by display, such as in vitro or CIS display (DNA, RNA, ribosome display, etc.), yeast, bacterial, and phage display.

Protein scaffolds of the disclosure provide enhanced biophysical properties, such as stability under reducing conditions and solubility at high concentrations; they may be expressed and folded in prokaryotic systems, such as *E. coli*, in eukaryotic systems, such as yeast, and in in vitro transcription/translation systems, such as the rabbit reticulocyte lysate system.

The disclosure provides an isolated, recombinant and/or synthetic protein scaffold based on a consensus sequence of fibronectin type III (FN3) repeat protein, including, without limitation, mammalian-derived scaffold, as well as compositions and encoding nucleic acid molecules comprising at least one polynucleotide encoding protein scaffold based on the consensus FN3 sequence. The disclosure further includes, but is not limited to, methods of making and using such nucleic acids and protein scaffolds, including diagnostic and therapeutic compositions, methods and devices.

The protein scaffolds of the disclosure offer advantages over conventional therapeutics, such as ability to administer locally, orally, or cross the blood-brain barrier, ability to express in *E. Coli* allowing for increased expression of protein as a function of resources versus mammalian cell expression ability to be engineered into bispecific or tandem molecules that bind to multiple targets or multiple epitopes of the same target, ability to be conjugated to drugs, polymers, and probes, ability to be formulated to high concentrations, and the ability of such molecules to effectively penetrate diseased tissues and tumors.

Moreover, the protein scaffolds possess many of the properties of antibodies in relation to their fold that mimics the variable region of an antibody. This orientation enables the FN3 loops to be exposed similar to antibody complementarity determining regions (CDRs). They should be able to bind to cellular targets and the loops can be altered, e.g., affinity matured, to improve certain binding or related properties.

Three of the six loops of the protein scaffold of the disclosure correspond topologically to the complementarity determining regions (CDRs 1-3), i.e., antigen-binding regions, of an antibody, while the remaining three loops are surface exposed in a manner similar to antibody CDRs. These loops span at or about residues 13-16, 22-28, 38-43, 51-54, 60-64, and 75-81 of SEQ ID NO: 1. Preferably, the loop regions at or about residues 22-28, 51-54, and 75-81 are altered for binding specificity and affinity. One or more of these loop regions are randomized with other loop regions and/or other strands maintaining their sequence as backbone portions to populate a library and potent binders can be selected from the library having high affinity for a particular protein target. One or more of the loop regions can interact with a target protein similar to an antibody CDR interaction with the protein.

Scaffolds of the disclosure may comprise a single chain antibody (e.g. a scFv). Single chain antibodies of the disclosure may comprise three light chain and three heavy chain CDRs of an antibody. In certain embodiments, the single chain antibodies of the disclosure comprise three light chain and three heavy chain CDRs of an antibody, wherein the complementarity-determining regions (CDRs) of the single chain antibody are human sequences. The disclosure provides a chimeric antigen receptor (CAR) comprising: (a) an ectodomain comprising an antigen recognition region, wherein the antigen recognition region comprises at least one single chain antibody (e.g. a scFv); (b) a transmembrane domain, and (c) an endodomain comprising at least one costimulatory domain. In certain embodiments, the antigen recognition region may comprise two single chain antibodies (e.g. two scFvs) to produce a bi-specific or tandem CAR. In certain embodiments, the antigen recognition region may comprise three single chain antibodies (e.g. three scFvs) to produce a tri-specific CAR. In certain embodiments, the ectodomain may further comprise a signal peptide. Alternatively, or in addition, in certain embodiments, the ectodomain may further comprise a hinge between the antigen recognition region and the transmembrane domain.

Scaffolds of the disclosure may comprise a sequence comprising one or more fragments of an antibody (e.g. a VHH). Sequence comprising one or more fragments of an antibody of the disclosure may comprise two heavy chain variable regions of an antibody. In certain embodiments, the sequence comprises two heavy chain variable regions of an antibody, wherein the complementarity-determining regions (CDRs) of the VHH are human sequences. Scaffolds of the disclosure may comprise a sequence comprising one or more fragments of an antibody (e.g. a VHH). The disclosure provides a chimeric antigen receptor (CAR) comprising: (a) an ectodomain comprising an antigen recognition region, wherein the antigen recognition region comprises at least one a sequence comprising one or more fragments of an antibody (e.g. a VHH); (b) a transmembrane domain, and (c) an endodomain comprising at least one costimulatory domain. In certain embodiments, the antigen recognition region may comprise two sequences comprising one or more fragments of an antibody (e.g. two VHHs) to produce a bi-specific or tandem CAR. In certain embodiments, the antigen recognition region may comprise three sequences comprising one or more fragments of an antibody (e.g. three VHHs) to produce a tri-specific CAR. In certain embodiments, the ectodomain may further comprise a signal peptide. Alternatively, or in addition, in certain embodiments, the ectodomain may further comprise a hinge between the antigen recognition region and the transmembrane domain.

Scaffolds of the disclosure may comprise an antibody mimetic.

The term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Antibody mimetics may provide superior properties over antibodies including, but not limited to, superior solubility, tissue penetration, stability towards heat and enzymes (e.g. resistance to enzymatic degradation), and lower production costs. Exemplary antibody mimetics include, but are not limited to, an affibody, an afflilin, an affimer, an affitin, an alphabody, an anticalin, and avimer (also known as avidity multimer), a DARPin (Designed Ankyrin Repeat Protein), a Fynomer, a Kunitz domain peptide, and a monobody.

Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

Affilin molecules of the disclosure comprise a protein scaffold produced by modification of exposed amino acids of, for example, either gamma-B crystallin or ubiquitin. Affilin molecules functionally mimic an antibody's affinity to antigen, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target sequence or antigen.

Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

Affitin molecules of the disclosure comprise an artificial protein scaffold, the structure of which may be derived, for example, from a DNA binding protein (e.g. the DNA binding protein Sac7d). Affitins of the disclosure selectively bind a target sequence, which may be the entirety or part of an antigen. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In certain embodiments of the disclosure, an affitin molecule may be used as a specific inhibitor of an enzyme. Affitin molecules of the disclosure may include heat-resistant proteins or derivatives thereof.

Alphabody molecules of the disclosure may also be referred to as Cell-Penetrating Alphabodies (CPAB). Alphabody molecules of the disclosure comprise small proteins (typically of less than 10 kDa) that bind to a variety of target sequences (including antigens). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In preferred embodiments, anticalin molecules of the disclosure comprise a barrel structure comprising eight antiparallel beta-strands pairwise connected by loops and an attached alpha helix.

Avimer molecules of the disclosure comprise an artificial protein that specifically binds to a target sequence (which may also be an antigen). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

DARPins (Designed Ankyrin Repeat Proteins) of the disclosure comprise genetically-engineered, recombinant, or chimeric proteins having high specificity and high affinity for a target sequence. In certain embodiments, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

Fynomers of the disclosure comprise small binding proteins (about 7 kDa) derived from the human Fyn SH3 domain and engineered to bind to target sequences and molecules with equal affinity and equal specificity as an antibody.

Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

Monobodies of the disclosure are small proteins (comprising about 94 amino acids and having a mass of about 10 kDa) comparable in size to a single chain antibody. These genetically engineered proteins specifically bind target sequences including antigens. Monobodies of the disclosure may specifically target one or more distinct proteins or target sequences. In preferred embodiments, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof, contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Multispecific monobodies may be optimized by modifying the loops BC and FG. Monobodies of the disclosure may comprise an adnectin.

Production and Generation of Scaffold Proteins

At least one scaffold protein of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino acids from a scaffold protein can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, scaffold proteins can be engineered with retention of high affinity for the antigen and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate scaffold protein to bind its antigen. In this way, residues can be selected and combined from the parent and reference sequences so that the desired characteristic, such as affinity for the target antigen(s), is achieved. Alternatively, or in addition to, the above procedures, other suitable methods of engineering can be used.

piggyBac Transposon System

The methods of the disclosure produce a modified $T_{SCM}$ of the disclosure regardless of the method used for introducing an antigen receptor into a primary human T cell of the disclosure. The methods of the disclosure produce a modified $T_{SCM}$ of the disclosure with greater efficacy and/or a greater abundance, proportion, yield of modified $-T_{SCM}$ of the disclosure when the antigen receptor or the therapeutic protein of the disclosure is introduced to the primary human T cell using the piggyBac transposon system. A piggyBac transposon system of the disclosure may comprise a piggyBac transposon comprising an antigen receptor of the disclosure. Preferably, the primary human T cell contacts a piggyBac transposon comprising an antigen receptor of the disclosure and a transposase of the disclosure simultaneously (or in very close temporal proximity, e.g. the primary human T cell, the transposon and the transposase are contained in the same container (such as a cuvette) prior to introduction of the transposon and transposase into the cell—however they would not be permitted to interact in the absence of the cell. Preferably, the primary human T cell contacts a piggyBac transposon comprising an antigen receptor of the disclosure and a Super piggyBac™ (SPB) transposase of the disclosure simultaneously prior to introduction of the transposon and transposase into the cell. In certain preferred embodiments, the Super piggyBac™ (SPB) transposase is an mRNA sequence encoding the Super piggyBac™ (SPB) transposase.

Additional disclosure regarding piggyBac transposons and Super piggyBac™ (SPB) transposases may be found in International Patent Publication WO 2010/099296, U.S. Pat. Nos. 8,399,643, 9,546,382, 6,218,185, 6,551,825, 6,962,810, and 7,105,343, the contents of which are each herein incorporated by reference in their entireties.

The disclosure provides methods of introducing a polynucleotide construct comprising a DNA sequence into a host cell. Preferably, the introducing steps are mediated by the piggyBac transposon system.

In certain embodiments of the methods of the disclosure, the transposon is a plasmid DNA transposon with a sequence encoding the antigen receptor or the therapeutic protein flanked by two cis-regulatory insulator elements. In certain embodiments, the transposon is a piggyBac transposon. In certain embodiments, and, in particular, those embodiments wherein the transposon is a piggyBac transposon, the transposase is a piggyBac™ or a Super piggyBac™ (SPB) transposase. In certain embodiments, and, in particular, those embodiments wherein the transposase is a Super piggyBac™ (SPB) transposase, the sequence encoding the transposase is an mRNA sequence.

In certain embodiments of the methods of the disclosure, the transposase enzyme is a piggyBac™ (PB) transposase enzyme. The piggyBac (PB) transposase enzyme may comprise or consist of an amino acid sequence at least 75%, 80%, 85%, 90%, 95%, 99% or any percentage in between identical to:

In certain embodiments, the transposase enzyme is a piggyBac™ (PB) transposase enzyme that comprises or consists of an amino acid sequence having an amino acid substitution at two or more of positions 30, 165, 282, or 538 of the sequence of SEQ ID NO: 4. In certain embodiments, the transposase enzyme is a piggyBac™ (PB) transposase enzyme that comprises or consists of an amino acid sequence having an amino acid substitution at three or more of positions 30, 165, 282, or 538 of the sequence of SEQ ID NO: 4. In certain embodiments, the transposase enzyme is a piggyBac™ (PB) transposase enzyme that comprises or consists of an amino acid sequence having an amino acid substitution at each of the following positions 30, 165, 282, and 538 of the sequence of SEQ ID NO: 4. In certain embodiments, the amino acid substitution at position 30 of the sequence of SEQ ID NO: 4 is a substitution of a valine (V) for an isoleucine (I). In certain embodiments, the amino acid substitution at position 165 of the sequence of SEQ ID NO: 4 is a substitution of a serine (S) for a glycine (G). In certain embodiments, the amino acid substitution at position 282 of the sequence of SEQ ID NO: 4 is a substitution of a

```
                                                                    (SEQ ID NO: 4)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a piggyBac™ (PB) transposase enzyme that comprises or consists of an amino acid sequence having an amino acid substitution at one or more of positions 30, 165, 282, or 538 of the sequence:

valine (V) for a methionine (M). In certain embodiments, the amino acid substitution at position 538 of the sequence of SEQ ID NO: 4 is a substitution of a lysine (K) for an asparagine (N).

```
                                                                    (SEQ ID NO: 4)
  1 MGSSLDDEHI LSALLQSDDE LVGEDSDSEI SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTGATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RMYIPNKPSK YGIKILMMCD

301 SGYKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPNEV

541 PGTSDDSTEE PVMKKRTYCT YCPSKIRRKA NASCKKCKKV ICREHNIDMC QSCF.
```

In certain embodiments of the methods of the disclosure, the transposase enzyme is a Super piggyBac™ (SPB) transposase enzyme. In certain embodiments, the Super piggyBac™ (SPB) transposase enzymes of the disclosure may comprise or consist of the amino acid sequence of the sequence of SEQ ID NO: 4 wherein the amino acid substitution at position 30 is a substitution of a valine (V) for an isoleucine (I), the amino acid substitution at position 165 is a substitution of a serine (S) for a glycine (G), the amino acid substitution at position 282 is a substitution of a valine (V) for a methionine (M), and the amino acid substitution at position 538 is a substitution of a lysine (K) for an asparagine (N). In certain embodiments, the Super piggyBac™ (SPB) transposase enzyme may comprise or consist of an amino acid sequence at least 75%, 80%, 85%, 90%, 95%, 99% or any percentage in between identical to:

amino acid substitution at position 119 of SEQ ID NO: 4 or SEQ ID NO: 5 is a substitution of a proline (P) for an arginine (R). In certain embodiments, the amino acid substitution at position 125 of SEQ ID NO: 4 or SEQ ID NO: 5 is a substitution of an alanine (A) a cysteine (C). In certain embodiments, the amino acid substitution at position 125 of SEQ ID NO: 4 or SEQ ID NO: 5 is a substitution of a leucine (L) for a cysteine (C). In certain embodiments, the amino acid substitution at position 177 of SEQ ID NO: 4 or SEQ ID NO: 5 is a substitution of a lysine (K) for a tyrosine (Y). In certain embodiments, the amino acid substitution at position 177 of SEQ ID NO: 4 or SEQ ID NO: 5 is a substitution of a histidine (H) for a tyrosine (Y). In certain embodiments, the amino acid substitution at position 180 of SEQ ID NO: 4 or SEQ ID NO: 5 is a substitution of a leucine (L) for a phenylalanine (F). In certain embodiments, the

```
                                                                    (SEQ ID NO: 5)
  1 MGSSLDDEHI LSALLQSDDE LVGEDSDSEV SDHVSEDDVQ SDTEEAFIDE VHEVQPTSSG

61 SEILDEQNVI EQPGSSLASN RILTLPQRTI RGKNKHCWST SKSTRRSRVS ALNIVRSQRG

121 PTRMCRNIYD PLLCFKLFFT DEIISEIVKW TNAEISLKRR ESMTSATFRD TNEDEIYAFF

181 GILVMTAVRK DNHMSTDDLF DRSLSMVYVS VMSRDRFDFL IRCLRMDDKS IRPTLRENDV

241 FTPVRKIWDL FIHQCIQNYT PGAHLTIDEQ LLGFRGRCPF RVYIPNKPSK YGIKILMMCD

301 SGTKYMINGM PYLGRGTQTN GVPLGEYYVK ELSKPVHGSC RNITCDNWFT SIPLAKNLLQ

361 EPYKLTIVGT VRSNKREIPE VLKNSRSRPV GTSMFCFDGP LTLVSYKPKP AKMVYLLSSC

421 DEDASINEST GKPQMVMYYN QTKGGVDTLD QMCSVMTCSR KTNRWPMALL YGMINIACIN

481 SFIIYSHNVS SKGEKVQSRK KFMRNLYMSL TSSFMRKRLE APTLKRYLRD NISNILPKEV

541 PGTSDDSTEE PVMKKRTYCT YCPSKIRRKA NASCKKCKKV ICREHNIDMC QSCF.
```

In certain embodiments of the methods of the disclosure, including those embodiments wherein the transposase comprises the above-described mutations at positions 30, 165, 282 and/or 538, the piggyBac™ or Super piggyBac™ transposase enzyme may further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 4 or SEQ ID NO: 5. In certain embodiments, including those embodiments wherein the transposase comprises the above-described mutations at positions 30, 165, 282 and/or 538, the piggyBac™ or Super piggyBac™ transposase enzyme may further comprise an amino acid substitution at one or more of positions 46, 119, 125, 177, 180, 185, 187, 200, 207, 209, 226, 235, 240, 241, 243, 296, 298, 311, 315, 319, 327, 328, 340, 421, 436, 456, 470, 485, 503, 552 and 570. In certain embodiments, the amino acid substitution at position 3 of SEQ ID NO: 4 or SEQ ID NO: 5 is a substitution of an asparagine (N) for a serine (S). In certain embodiments, the amino acid substitution at position 46 of SEQ ID NO: 4 or SEQ ID NO: 5 is a substitution of a serine (S) for an alanine (A). In certain embodiments, the amino acid substitution at position 46 of SEQ ID NO: 4 or SEQ ID NO: 5 is a substitution of a threonine (T) for an alanine (A). In certain embodiments, the amino acid substitution at position 82 of SEQ ID NO: 4 or SEQ ID NO: 5 is a substitution of a tryptophan (W) for an isoleucine (I). In certain embodiments, the amino acid substitution at position 103 of SEQ ID NO: 4 or SEQ ID NO: 5 is a substitution of a proline (P) for a serine (S). In certain embodiments, the amino acid substitution at position 180 of SEQ ID NO: 4 or SEQ ID NO: 5 is a substitution of an isoleucine (I) for a phenylalanine (F). In certain embodiments, the amino acid substitution at position 180 of SEQ ID NO: 4 or SEQ ID NO: 5 is a substitution of a valine (V) for a phenylalanine (F). In certain embodiments, the amino acid substitution at position 185 of SEQ ID NO: 4 or SEQ ID NO: 5 is a substitution of a leucine (L) for a methionine (M). In certain embodiments, the amino acid substitution at position 187 of SEQ ID NO: 4 or SEQ ID NO: 5 is a substitution of a glycine (G) for an alanine (A). In certain embodiments, the amino acid substitution at position 200 of SEQ ID NO: 4 or SEQ ID NO: 5 is a substitution of a tryptophan (W) for a phenylalanine (F), In certain embodiments, the amino acid substitution at position 207 of SEQ ID NO: 4 or SEQ ID NO: 5 is a substitution of a proline (P) for a valine (V). In certain embodiments, the amino acid substitution at position 209 of SEQ ID NO: 4 or SEQ ID NO: 5 is a substitution of a phenylalanine (F) for a valine (V). In certain embodiments, the amino acid substitution at position 226 of SEQ ID NO: 4 or SEQ ID NO: 5 is a substitution of a phenylalanine (F) for a methionine (M). In certain embodiments, the amino acid substitution at position 235 of SEQ ID NO: 4 or SEQ ID NO: 5 is a substitution of an arginine (R) for a leucine (L). In certain embodiments, the amino acid substitution at position 240 of SEQ ID NO: 4 or SEQ ID NO: 5 is a substitution of a lysine (K) for a valine (V). In certain embodiments, the amino acid substitution at position 241 of SEQ ID NO: 4 or SEQ ID NO: 5 is a substitution of a leucine (L) for a phenylalanine (F). In certain embodiments, the amino acid substitution at position 243 of SEQ ID NO: 4 or SEQ ID NO: 5 is a substitution of a lysine (K) for a proline (P). In certain embodiments, the amino acid substitution at position 258 of SEQ ID NO: 4 or SEQ ID NO: 5 is a substitution of a serine (S) for an asparagine (N). In certain embodiments, the amino acid substitution at position 296 of SEQ ID NO: 4 or SEQ ID NO: 5 is a substitution of a tryptophan (W) for a leucine (L). In certain embodiments, the amino acid substitution at position 296 of SEQ ID NO: 4 or SEQ ID NO: 5 is a substitution of a tyrosine (Y) for a leucine (L). In certain embodiments, the amino acid substitution at position 296 of SEQ ID NO: 4 or SEQ ID NO: 5 is a substitution of a phenylalanine (F) for a leucine (L). In certain embodiments, the amino acid substitution at position 298 of SEQ ID NO: 4 or SEQ ID NO: 5 is a substitution of a leucine (L) for a methionine (M). In certain embodiments, the amino acid substitution at position 298 of SEQ ID NO: 4 or SEQ ID NO: 5 is a substitution of an alanine (A) for a methionine (M). In certain embodiments, the amino acid substitution at position 298 of SEQ ID NO: 4 or SEQ ID NO: 5 is a substitution of a valine (V) for a methionine (M). In certain embodiments, the amino acid substitution at position 311 of SEQ ID NO: 4 or SEQ ID NO: 5 is a substitution of an isoleucine (I) for a proline (P). In certain embodiments, the amino acid substitution at position 311 of SEQ ID NO: 4 or SEQ ID NO: 5 is a substitution of a valine for a proline (P). In certain embodiments, the amino acid substitution at position 315 of SEQ ID NO: 4 or SEQ ID NO: 5 is a substitution of a lysine (K) for an arginine (R), In certain embodiments, the amino acid substitution at position 319 of SEQ ID NO: 4 or SEQ ID NO: 5 is a substitution of a glycine (G) for a threonine (T). In certain embodiments, the amino acid substitution at position 327 of SEQ ID NO: 4 or SEQ ID NO: 5 is a substitution of an arginine (R) for a tyrosine (Y). In certain embodiments, the amino acid substitution at position 328 of SEQ ID NO: 4 or SEQ ID NO: 5 is a substitution of a valine (V) for a tyrosine (Y). In certain embodiments, the amino acid substitution at position 340 of SEQ ID NO: 4 or SEQ ID NO: 5 is a substitution of a glycine (G) for a cysteine (C). In certain embodiments, the amino acid substitution at position 340 of SEQ ID NO: 4 or SEQ ID NO: 5 is a substitution of a leucine (L) for a cysteine (C). In certain embodiments, the amino acid substitution at position 421 of SEQ ID NO: 4 or SEQ ID NO: 5 is a substitution of a histidine (H) for the aspartic acid (D). In certain embodiments, the amino acid substitution at position 436 of SEQ ID NO: 4 or SEQ ID NO: 5 is a substitution of an isoleucine (I) for a valine (V). In certain embodiments, the amino acid substitution at position 456 of SEQ ID NO: 4 or SEQ ID NO: 5 is a substitution of a tyrosine (Y) for a methionine (M). In certain embodiments, the amino acid substitution at position 470 of SEQ ID NO: 4 or SEQ ID NO: 5 is a substitution of a phenylalanine (F) for a leucine (L). In certain embodiments, the amino acid substitution at position 485 of SEQ ID NO: 4 or SEQ ID NO: 5 is a substitution of a lysine (K) for a serine (S). In certain embodiments, the amino acid substitution at position 503 of SEQ ID NO: 4 or SEQ ID NO: 5 is a substitution of a leucine (L) for a methionine (M). In certain embodiments, the amino acid substitution at position 503 of SEQ ID NO: 4 or SEQ ID NO: 5 is a substitution of an isoleucine (I) for a methionine (M). In certain embodiments, the amino acid substitution at position 552 of SEQ ID NO: 4 or SEQ ID NO: 5 is a substitution of a lysine (K) for a valine (V). In certain embodiments, the amino acid substitution at position 570 of SEQ ID NO: 4 or SEQ ID NO: 5 is a substitution of a threonine (T) for an alanine (A). In certain embodiments, the amino acid substitution at position 591 of SEQ ID NO: 4 or SEQ ID NO: 5 is a substitution of a proline (P) for a glutamine (Q). In certain embodiments, the amino acid substitution at position 591 of SEQ ID NO: 4 or SEQ ID NO: 5 is a substitution of an arginine (R) for a glutamine (Q).

In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at one or more of positions 103, 194, 372, 375, 450, 509 and 570 of the sequence of SEQ ID NO: 4 or SEQ ID NO: 5. In certain embodiments of the methods of the disclosure, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at two, three, four, five, six or more of positions 103, 194, 372, 375, 450, 509 and 570 of the sequence of SEQ ID NO: 4 or SEQ ID NO: 5. In certain embodiments, including those embodiments wherein the transposase comprises the above-described mutations at positions 30, 165, 282 and/or 538, the piggyBac™ transposase enzyme may comprise or the Super piggyBac™ transposase enzyme may further comprise an amino acid substitution at positions 103, 194, 372, 375, 450, 509 and 570 of the sequence of SEQ ID NO: 4 or SEQ ID NO: 5. In certain embodiments, the amino acid substitution at position 103 of SEQ ID NO: 4 or SEQ ID NO: 5 is a substitution of a proline (P) for a serine (S). In certain embodiments, the amino acid substitution at position 194 of SEQ ID NO: 4 or SEQ ID NO: 5 is a substitution of a valine (V) for a methionine (M). In certain embodiments, the amino acid substitution at position 372 of SEQ ID NO: 4 or SEQ ID NO: 5 is a substitution of an alanine (A) for an arginine (R). In certain embodiments, the amino acid substitution at position 375 of SEQ ID NO: 4 or SEQ ID NO: 5 is a substitution of an alanine (A) for a lysine (K). In certain embodiments, the amino acid substitution at position 450 of SEQ ID NO: 4 or SEQ ID NO: 5 is a substitution of an asparagine (N) for an aspartic acid (D). In certain embodiments, the amino acid substitution at position 509 of SEQ ID NO: 4 or SEQ ID NO: 5 is a substitution of a glycine (G) for a serine (S). In certain embodiments, the amino acid substitution at position 570 of SEQ ID NO: 4 or SEQ ID NO: 5 is a substitution of a serine (S) for an asparagine (N). In certain embodiments, the piggyBac™ transposase enzyme may comprise a substitution of a valine (V) for a methionine (M) at position 194 of SEQ ID NO: 4. In certain embodiments, including those embodiments wherein the piggyBac™ transposase enzyme may comprise a substitution of a valine (V) for a methionine (M) at position 194 of SEQ ID NO: 4, the piggyBac™ transposase enzyme may further comprise an amino acid substitution at positions 372, 375 and 450 of the sequence of SEQ ID NO: 4 or SEQ ID NO: 5. In certain embodiments, the piggyBac™ transposase enzyme may comprise a substitution of a valine (V) for a methionine (M) at position 194 of SEQ ID NO: 4, a substitution of an alanine (A) for an arginine (R) at position 372 of SEQ ID NO: 4, and a substitution of an alanine (A) for a lysine (K) at position 375 of SEQ ID NO: 4. In certain embodiments, the piggyBac™ transposase enzyme may comprise a substitution of a valine (V) for a methionine (M) at position 194 of SEQ ID NO: 4, a substitution of an alanine (A) for an arginine (R) at position 372 of SEQ ID NO: 4, a substitution of an alanine (A) for a lysine (K) at position 375 of SEQ ID NO: 4 and a substitution of an asparagine (N) for an aspartic acid (D) at position 450 of SEQ ID NO: 4.

By "introducing" is intended presenting to the plant the polynucleotide construct in such a manner that the construct gains access to the interior of the host cell. The methods of the invention do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

As used throughout the disclosure, the term "endogenous" refers to nucleic acid or protein sequence naturally associated with a target gene or a host cell into which it is introduced.

By "stable transformation" is intended that the polynucleotide construct introduced into a plant integrates into the genome of the host and is capable of being inherited by progeny thereof.

By "transient transformation" is intended that a polynucleotide construct introduced into the host does not integrate into the genome of the host.

In preferred embodiments, the piggyBac transposon system is used to introduce exogenous sequences into a primary human T cell by stable transformation to generate a modified $T_{SCM}$ or $T_{CM}$.

Additional Transposon Systems

In certain embodiments of the methods of the disclosure, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X).

The disclosure provides a method of producing a modified stem memory T-cell ($T_{SCM}$) or a modified central memory T-cell ($T_{CM}$), comprising introducing into a primary human T cell (a) a transposon composition comprising a transposon comprising an antigen receptor or a therapeutic protein and (b) a transposase composition comprising a transposase or a sequence encoding the transposase; to produce a modified T cell, wherein the modified T cell expresses one or more cell-surface marker(s) of a modified stem memory T-cell ($T_{SCM}$) or a modified central memory T-cell ($T_{CM}$), thereby producing a modified stem memory T-cell ($T_{SCM}$) or a modified central memory T-cell ($T_{CM}$). The disclosure provides a method of producing a plurality of modified stem memory T-cells ($T_{SCM}$) or a plurality of modified central memory T-cells ($T_{CM}$), comprising introducing into a plurality of primary human T cells (a) a transposon composition comprising a transposon comprising an antigen receptor and (b) a transposase composition comprising a transposase or a sequence encoding the transposase; to produce a plurality of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells expresses one or more cell-surface marker(s) of a stem memory T-cell ($T_{SCM}$) or a central memory T-cell ($T_{CM}$), thereby producing a plurality of modified stem memory T-cells ($T_{SCM}$) or a plurality of modified central memory T-cells ($T_{CM}$).

In certain embodiments of the methods of the disclosure, the transposon is a Sleeping Beauty transposon. In certain embodiments, and, in particular, those embodiments wherein the transposon is a Sleeping Beauty transposon, the transposase is a Sleeping Beauty transposase or a hyperactive Sleeping Beauty transposase (SB100X).

In certain embodiments of the methods of the disclosure, the Sleeping Beauty transposase enzyme comprises an amino acid sequence at least 75%, 80%, 85%, 90%, 95%, 99% or any percentage in between identical to:

```
                                                                (SEQ ID NO: 6)
  1 MGKSKEISQD LRKKIVDLHK SGSSLGAISK RLKVPRSSVQ TIVRKYKHHG TTQPSYRSGR

61 RRYLSPRDER TLVRKVQINP RTTAKDLVKM LEETGTKVSI STVKRVLYRH NLKGRSARKK

121 PLLQNRHKKA RLRFATAHGD KDRTFWRNVL WSDETKIELF GHNDHRYVWR KKGEACKPKN

181 TIPTVKHGGG SIMLWGCFAA GGTGALHKID GIMRKENYVD ILKQHLKTSV RKLKLGRKWV

241 FQMDNDPKHT SKVVAKWLKD NKVKVLEWPS QSPDLNPIEN LWAELKKRVR ARRPTNLTQL

301 HQLCQEEWAK IHPTYCGKLV EGYPKRLTQV KQFKGNATKY.
```

In certain embodiments of the methods of the disclosure, the hyperactive Sleeping Beauty (SB100X) transposase enzyme comprises an amino acid sequence at least 75%, 80%, 85%, 90%, 95%, 99% or any percentage in between identical to:

```
                                                                (SEQ ID NO: 7)
  1 MGKSKEISQD LRKRIVDLHK SGSSLGAISK RLAVPRSSVQ TIVRKYKHHG TTQPSYRSGR

61 RRYLSPRDER TLVRKVQINP RTTAKDLVKM LEETGTKVSI STVKRVLYRH NLKGHSARKK

121 PLLQNRHKKA RLRFATAHGD KDRTFWRNVL WSDETKIELF GHNDHRYVWR KKGEACKPKN

181 TIPTVKHGGG SIMLWGCFAA GGTGALHKID GIMDAVQYVD ILKQHLKTSV RKLKLGRKWV

241 FQHDNDPKHT SKVVAKWLKD NKVKVLEWPS QSPDLNPIEN LWAELKKRVR ARRPTNLTQL

301 HQLCQEEWAK IHPNYCGKLV EGYPKRLTQV KQFKGNATKY.
```

In certain embodiments of the methods of the disclosure, the transposase is a Helitron transposase. Helitron transposases mobilize the Helraiser transposon, an ancient element from the bat genome that was active about 30 to 36 million years ago. An exemplary Helraiser transposon of the disclosure includes Helibat1, which comprises a nucleic acid sequence comprising:

(SEQ ID NO: 27)

```
   1 TCCTATATAA TAAAAGAGAA ACATGCAAAT TGACCATCCC TCCGCTACGC TCAAGCCACG
  61 CCCACCAGCC AATCAGAAGT GACTATGCAA ATTAACCCAA CAAAGATGGC AGTTAAATTT
 121 GCATACGCAG GTGTCAAGCG CCCCAGGAGG CAACGGCGGC CGCGGGCTCC CAGGACCTTC
 181 GCTGGCCCCG GGAGGCGAGG CCGGCCGCGC CTAGCCACAC CCGCGGGCTC CCGGGACCTT
 241 CGCCAGCAGA GAGCAGAGCG GGAGAGCGGG CGGAGAGCGG GAGGTTTGGA GGACTTGGCA
 301 GAGCAGGAGG CCGCTGGACA TAGAGCAGAG CGAGAGAGAG GGTGGCTTGG AGGGCGTGGC
 361 TCCCTCTGTC ACCCCAGCTT CCTCATCACA GCTGTGGAAA CTGACAGCAG GGAGGAGGAA
 421 GTCCCACCCC CACAGAATCA GCCAGAATCA GCCGTTGGTC AGACAGCTCT CAGCGGCCTG
 481 ACAGCCAGGA CTCTCATTCA CCTGCATCTC AGACCGTGAC AGTAGAGAGG TGGGACTATG
 541 TCTAAAGAAC AACTGTTGAT ACAACGTAGC TCTGCAGCCG AAAGATGCCG GCGTTATCGA
 601 CAGAAAATGT CTGCAGAGCA ACGTGCGTCT GATCTTGAAA GAAGGCGGCG CCTGCAACAG
 661 AATGTATCTG AAGAGCAGCT ACTGGAAAAA CGTCGCTCTG AAGCCGAAAA ACAGCGGCGT
 721 CATCGACAGA AAATGTCTAA AGACCAACGT GCCTTTGAAG TTGAAAGAAG GCGGTGGCGA
 781 CGACAGAATA TGTCTAGAGA ACAGTCATCA ACAAGTACTA CCAATACCGG TAGGAACTGC
 841 CTTCTCAGCA AAAATGGAGT ACATGAGGAT GCAATTCTCG AACATAGTTG TGGTGGAATG
 901 ACTGTTCGAT GTGAATTTTG CCTATCACTA AATTTCTCTG ATGAAAAACC ATCCGATGGG
 961 AAATTTACTC GATGTTGTAG CAAAGGGAAA GTCTGTCCAA ATGATATACA TTTTCCAGAT
1021 TACCCGGCAT ATTTAAAAAG ATTAATGACA AACGAAGATT CTGACAGTAA AAATTTCATG
1081 GAAAATATTC GTTCCATAAA TAGTTCTTTT GCTTTTGCTT CCATGGGTGC AAATATTGCA
1141 TCGCCATCAG GATATGGGCC ATACTGTTTT AGAATACACG GACAAGTTTA TCACCGTACT
1201 GGAACTTTAC ATCCTTCGGA TGGTGTTTCT CGGAAGTTTG CTCAACTCTA TATTTTGGAT
1261 ACAGCCGAAG CTACAAGTAA AAGATTAGCA ATGCCAGAAA ACCAGGGCTG CTCAGAAAGA
1321 CTCATGATCA ACATCAACAA CCTCATGCAT GAAATAAATG AATTAACAAA ATCGTACAAG
1381 ATGCTACATG AGGTAGAAAA GGAAGCCCAA TCTGAAGCAG CAGCAAAAGG TATTGCTCCC
1441 ACAGAAGTAA CAATGGCGAT TAAATACGAT CGTAACAGTG ACCCAGGTAG ATATAATTCT
1501 CCCCGTGTAA CCGAGGTTGC TGTCATATTC AGAAACGAAG ATGGAGAACC TCCTTTTGAA
1561 AGGGACTTGC TCATTCATTG TAAACCAGAT CCCAATAATC CAAATGCCAC TAAAATGAAA
1621 CAAATCAGTA TCCTGTTTCC TACATTAGAT GCAATGACAT ATCCTATTCT TTTTCCACAT
1681 GGTGAAAAAG GCTGGGGAAC AGATATTGCA TTAAGACTCA GAGACAACAG TGTAATCGAC
1741 AATAATACTA GACAAAATGT AAGGACACGA GTCACACAAA TGCAGTATTA TGGATTTCAT
1801 CTCTCTGTGC GGGACACGTT CAATCCTATT TTAAATGCAG GAAAATTAAC TCAACAGTTT
1861 ATTGTGGATT CATATTCAAA AATGGAGGCC AATCGGATAA ATTTCATCAA AGCAAACCAA
1921 TCTAAGTTGA GAGTTGAAAA ATATAGTGGT TTGATGGATT ATCTCAAATC TAGATCTGAA
1981 AATGACAATG TGCCGATTGG TAAAATGATA ATACTTCCAT CATCTTTTGA GGGTAGTCCC
2041 AGAAATATGC AGCAGCGATA TCAGGATGCT ATGGCAATTG TAACGAAGTA TGGCAAGCCC
2101 GATTTATTCA TAACCATGAC ATGCAACCCC AAATGGGCAG ATATTACAAA CAATTTACAA
2161 CGCTGGCAAA AAGTTGAAAA CAGACCTGAC TTGGTAGCCA GAGTTTTTAA TATTAAGCTG
2221 AATGCTCTTT TAAATGATAT ATGTAAATTC CATTTATTTG GCAAAGTAAT AGCTAAAATT
```

-continued

```
2281 CATGTCATTG AATTTCAGAA ACGCGGACTG CCTCACGCTC ACATATTATT GATATTAGAT

2341 AGTGAGTCCA AATTACGTTC AGAAGATGAC ATTGACCGTA TAGTTAAGGC AGAAATTCCA
2401 GATGAAGACC AGTGTCCTCG ACTTTTTCAA ATTGTAAAAT CAAATATGGT ACATGGACCA

2461 TGTGGAATAC AAAATCCAAA TAGTCCATGT ATGGAAAATG AAAATGTTC AAAGGGATAT

2521 CCAAAAGAAT TTCAAAATGC GACCATTGGA AATATTGATG GATATCCCAA ATACAAACGA

2581 AGATCTGGTA GCACCATGTC TATTGGAAAT AAAGTTGTCG ATAACACTTG GATTGTCCCT

2641 TATAACCCGT ATTTGTGCCT TAAATATAAC TGTCATATAA ATGTTGAAGT CTGTGCATCA

2701 ATTAAAAGTG TCAAATATTT ATTTAAATAC ATCTATAAAG GGCACGATTG TGCAAATATT

2761 CAAATTTCTG AAAAAAATAT TATCAATCAT GACGAAGTAC AGGACTTCAT TGACTCCAGG

2821 TATGTGAGCG CTCCTGAGGC TGTTTGGAGA CTTTTTGCAA TGCGAATGCA TGACCAATCT

2881 CATGCAATCA CAAGATTAGC TATTCATTTG CCAAATGATC AGAATTTGTA TTTTCATACC

2941 GATGATTTTG CTGAAGTTTT AGATAGGGCT AAAAGGCATA ACTCGACTTT GATGGCTTGG

3001 TTCTTATTGA ATAGAGAAGA TTCTGATGCA CGTAATTATT ATTATTGGGA GATTCCACAG

3061 CATTATGTGT TTAATAATTC TTTGTGGACA AAACGCCGAA AGGGTGGGAA TAAAGTATTA

3121 GGTAGACTGT TCACTGTGAG CTTTAGAGAA CCAGAACGAT ATTACCTTAG ACTTTTGCTT

3181 CTGCATGTAA AAGGTGCGAT AAGTTTTGAG GATCTGCGAA CTGTAGGAGG TGTAACTTAT

3241 GATACATTTC ATGAAGCTGC TAAACACCGA GGATTATTAC TTGATGACAC TATCTGGAAA

3301 GATACGATTG ACGATGCAAT CATCCTTAAT ATGCCCAAAC AACTACGGCA ACTTTTTGCA

3361 TATATATGTG TGTTTGGATG TCCTTCTGCT GCAGACAAAT TATGGGATGA GAATAAATCT

3421 CATTTTATTG AAGATTTCTG TTGGAAATTA CACCGAAGAG AAGGTGCCTG TGTGAACTGT

3481 GAAATGCATG CCCTTAACGA AATTCAGGAG GTATTCACAT TGCATGGAAT GAAATGTTCA

3541 CATTTCAAAC TTCCGGACTA TCCTTTATTA ATGAATGCAA ATACATGTGA TCAATTGTAC

3601 GAGCAACAAC AGGCAGAGGT TTTGATAAAT TCTCTGAATG ATGAACAGTT GGCAGCCTTT

3661 CAGACTATAA CTTCAGCCAT CGAAGATCAA ACTGTACACC CCAAATGCTT TTTCTTGGAT

3721 GGTCCAGGTG GTAGTGGAAA ACATATCTG TATAAAGTTT TAACACATTA TATTAGAGGT

3781 CGTGGTGGTA CTGTTTTACC CACAGCATCT ACAGGAATTG CTGCAAATTT ACTTCTTGGT

3841 GGAAGAACCT TCATTCCCA ATATAAATTA CCAATTCCAT TAAATGAAAC TTCAATTTCT

3901 AGACTCGATA TAAAGAGTGA AGTTGCTAAA ACCATTAAAA AGGCCCAACT TCTCATTATT

3961 GATGAATGCA CCATGGCATC CAGTCATGCT ATAAACGCCA TAGATAGATT ACTAAGAGAA

4021 ATTATGAATT TGAATGTTGC ATTTGGTGGG AAAGTTCTCC TTCTCGGAGG GGATTTTCGA

4081 CAATGTCTCA GTATTGTACC ACATGCTATG CGATCGGCCA TAGTACAAAC GAGTTTAAAG

4141 TACTGTAATG TTTGGGGATG TTTCAGAAAG TTGTCTCTTA AACAAATAT GAGATCAGAG

4201 GATTCTGCTT ATAGTGAATG GTTAGTAAAA CTTGGAGATG GCAAACTTGA TAGCAGTTTT

4261 CATTTAGGAA TGGATATTAT TGAAATCCCC CATGAAATGA TTTGTAACGG ATCTATTATT

4321 GAAGCTACCT TTGGAAATAG TATATCTATA GATAATATTA AAATATATC TAAACGTGCA

4381 ATTCTTTGTC CAAAAAATGA GCATGTTCAA AAATTAAATG AAGAAATTTT GGATATACTT

4441 GATGGAGATT TCACACATA TTTGAGTGAT GATTCCATTG ATTCAACAGA TGATGCTGAA

4501 AAGGAAAATT TTCCCATCGA ATTTCTTAAT AGTATTACTC CTTCGGGAAT GCCGTGTCAT

4561 AAATTAAAAT TGAAAGTGGG TGCAATCATC ATGCTATTGA GAAATCTTAA TAGTAAATGG

4621 GGTCTTTGTA ATGGTACTAG ATTTATTATC AAAAGATTAC GACCTAACAT TATCGAAGCT

4681 GAAGTATTAA CAGGATCTGC AGAGGGAGAG GTTGTTCTGA TTCCAAGAAT TGATTTGTCC
```

-continued

4741 CCATCTGACA CTGGCCTCCC ATTTAAATTA ATTCGAAGAC AGTTTCCCGT GATGCCAGCA

```
-continued
4801 TTTGCGATGA CTATTAATAA ATCACAAGGA CAAACTCTAG ACAGAGTAGG AATATTCCTA

4861 CCTGAACCCG TTTTCGCACA TGGTCAGTTA TATGTTGCTT TCTCTCGAGT TCGAAGAGCA

4921 TGTGACGTTA AAGTTAAAGT TGTAAATACT TCATCACAAG GGAAATTAGT CAAGCACTCT

4981 GAAAGTGTTT TTACTCTTAA TGTGGTATAC AGGGAGATAT TAGAATAAGT TTAATCACTT

5041 TATCAGTCAT TGTTTGCATC AATGTTGTTT TTATATCATG TTTTTGTTGT TTTTATATCA

5101 TGTCTTTGTT GTTGTTATAT CATGTTGTTA TTGTTTATTT ATTAATAAAT TTATGTATTA

5161 TTTTCATATA CATTTTACTC ATTTCCTTTC ATCTCTCACA CTTCTATTAT AGAGAAAGGG

5221 CAAATAGCAA TATTAAAATA TTTCCTCTAA TTAATTCCCT TTCAATGTGC ACGAATTTCG

5281 TGCACCGGGC CACTAG.
```

Unlike other transposases, the Helitron transposase does not contain an RNase-H like catalytic domain, but instead comprises a RepHel motif made up of a replication initiator domain (Rep) and a DNA helicase domain. The Rep domain is a nuclease domain of the HUH superfamily of nucleases.

An exemplary Helitron transposase of the disclosure comprises an amino acid sequence comprising:

In Helitron transpositions, a hairpin close to the 3' end of the transposon functions as a terminator. However, this hairpin can be bypassed by the transposase, resulting in the transduction of flanking sequences. In addition, Helraiser transposition generates covalently closed circular intermediates. Furthermore, Helitron transpositions can lack target site duplications. In the Helraiser sequence, the transposase

```
                                                                    (SEQ ID NO: 28)
   1 MSKEQLLIQR SSAAERCRRY RQKMSAEQRA SDLERRRRLQ QNVSEEQLLE KRRSEAEKQR

61 RHRQKMSKDQ RAFEVERRRW RRQNMSREQS STSTTNTGRN CLLSKNGVHE DAILEHSCGG

121 MTVRCEFCLS LNFSDEKPSD GKFTRCCSKG KVCPNDIHFP DYPAYLKRLM TNEDSDSKNF

181 MENIRSINSS FAFASMGANI ASPSGYGPYC FRIHGQVYHR TGTLHPSDGV SRKFAQLYIL

241 DTAEATSKRL AMPENQGCSE RLMININNLM HEINELTKSY KMLHEVEKEA QSEAAAKGIA

301 PTEVTMAIKY DRNSDPGRYN SPRVTEVAVI FRNEDGEPPF ERDLLIHCKP DPNNPNATKM

361 KQISILFPTL DAMTYPILFP HGEKGWGTDI ALRLRDNSVI DNNTRQNVRT RVTQMQYYGF

421 HLSVRDTFNP ILNAGKLTQQ FIVDSYSKME ANRINFIKAN QSKLRVEKYS GLMDYLKSRS

481 ENDNVPIGKM IILPSSFEGS PRNMQQRYQD AMAIVTKYGK PDLFITMTCN PKWADITNNL

541 QRWQKVENRP DLVARVFNIK LNALLNDICK FHLFGKVIAK IHVIEFQKRG LPHAHILLIL

601 DSESKLRSED DIDRIVKAEI PDEDQCPRLF QIVKSNMVHG PCGIQNPNSP CMENGKCSKG

661 YPKEFQNATI GNIDGYPKYK RRSGSTMSIG NKVVDNTWIV PYNPYLCLKY NCHINVEVCA

721 SIKSVKYLFK YIYKGHDCAN IQISEKNIIN HDEVQDFIDS RYVSAPEAVW RLFAMRMHDQ

781 SHAITRLAIH LPNDQNLYFH TDDFAEVLDR AKRHNSTLMA WFLLNREDSD ARNYYYWEIP

841 QHYVFNNSLW TKRRKGGNKV LGRLFTVSFR EPERYYLRLL LLHVKGAISF EDLRTVGGVT

901 YDTFHEAAKH RGLLLDDTIW KDTIDDAIIL NMPKQLRQLF AYICVFGCPS AADKLWDENK

961 SHFIEDFCWK LHRREGACVN CEMHALNEIQ EVFTLHGMKC SHFKLPDYPL LMNANTCDQL

1021 YEQQQAEVLI NSLNDEQLAA FQTITSAIED QTVHPKCFFL DGPGGSGKTY LYKVLTHYIR

1081 GRGGTVLPTA STGIAANLLL GGRTFHSQYK LPIPLNETSI SRLDIKSEVA KTIKKAQLLI

1141 IDECTMASSH AINAIDRLLR EIMNLNVAFG GKVLLLGGDF RQCLSIVPHA MRSAIVQTSL

1201 KYCNVWGCFR KLSLKTNMRS EDSAYSEWLV KLGDGKLDSS FHLGMDIIEI PHEMICNGSI

1261 IEATFGNSIS IDNIKNISKR AILCPKNEHV QKLNEEILDI LDGDFHTYLS DDSIDSTDDA

1321 EKENFPIEFL NSITPSGMPC HKLKLKVGAI IMLLRNLNSK WGLCNGTRFI IKRLRPNIIE

1381 AEVLTGSAEG EVVLIPRIDL SPSDTGLPFK LIRRQFPVMP AFAMTINKSQ GQTLDRVGIF

1441 LPEPVFAHGQ LYVAFSRVRR ACDVKVKVVN TSSQGKLVKH SESVFTLNVV YREILE.
``` is flanked by left and right terminal sequences termed LTS and RTS. These sequences terminate with a conserved 5'-TC/CTAG-3' motif. A 19 bp palindromic sequence with the potential to form the hairpin termination structure is located 11 nucleotides upstream of the RTS and consists of the sequence

```
                                              (SEQ ID NO: 29)
       GTGCACGAATTTCGTGCACCGGGCCACTAG.
```

In certain embodiments of the methods of the disclosure, the transposase is a Tol2 transposase. Tol2 transposons may be isolated or derived from the genome of the medaka fish, and may be similar to transposons of the hAT family. Exemplary Tol2 transposons of the disclosure are encoded by a sequence comprising about 4.7 kilobases and contain a gene encoding the Tol2 transposase, which contains four exons. An exemplary Tol2 transposase of the disclosure comprises an amino acid sequence comprising the following:

```
                                                              (SEQ ID NO: 30)
      1 MEEVCDSSAA ASSTVQNQPQ DQEHPWPYLR EFFSLSGVNK DSFKMKCVLC LPLNKEISAF

61 KSSPSNLRKH IERMHPNYLK NYSKLTAQKR KIGTSTHASS SKQLKVDSVF PVKHVSPVTV

121 NKAILRYIIQ GLHPFSTVDL PSFKELISTL QPGISVITRP TLRSKIAEAA LIMKQKVTAA

181 MSEVEWIATT TDCWTARRKS FIGVTAHWIN PGSLERHSAA LACKRLMGSH TFEVLASAMN

241 DIHSEYEIRD KVVCTTTDSG SNFMKAFRVF GVENNDIETE ARRCESDDTD SEGCGEGSDG

301 VEFQDASRVL DQDDGFEFQL PKHQKCACHL LNLVSSVDAQ KALSNEHYKK LYRSVFGKCQ

361 ALWNKSSRSA LAAEAVESES RLQLLRPNQT RWNSTFMAVD RILQICKEAG EGALRNICTS

421 LEVPMFNPAE MLFLTEWANT MRPVAKVLDI LQAETNTQLG WLLPSVHQLS LKLQRLHHSL

481 RYCDPLVDAL QQGIQTRFKH MFEDPEIIAA AILLPKFRTS WTNDETIIKR GMDYIRVHLE

541 PLDHKKELAN SSSDDEDFFA SLKPTTHEAS KELDGYLACV SDTRESLLTF PAICSLSIKT

601 NTPLPASAAC ERLFSTAGLL FSPKRARLDT NNFENQLLLK LNLRFYNFE.
```

An exemplary Tol2 transposon of the disclosure, including inverted repeats, subterminal sequences and the Tol2 transposase, is encoded by a nucleic acid sequence comprising the following:

```
                                                              (SEQ ID NO: 31)
       1 CAGAGGTGTA AAGTACTTGA GTAATTTTAC TTGATTACTG TACTTAAGTA TTATTTTTGG

61 GGATTTTTAC TTTACTTGAG TACAATTAAA AATCAATACT TTTACTTTTA CTTAATTACA

121 TTTTTTTAGA AAAAAAAGTA CTTTTTACTC CTTACAATTT TATTTACAGT CAAAAAGTAC

181 TTATTTTTTG GAGATCACTT CATTCTATTT TCCCTTGCTA TTACCAAACC AATTGAATTG

241 CGCTGATGCC CAGTTTAATT TAAATGTTAT TTATTCTGCC TATGAAAATC GTTTTCACAT

301 TATATGAAAT TGGTCAGACA TGTTCATTGG TCCTTTGGAA GTGACGTCAT GTCACATCTA

361 TTACCACAAT GCACAGCACC TTGACCTGGA AATTAGGGAA ATTATAACAG TCAATCAGTG

421 GAAGAAAATG GAGGAAGTAT GTGATTCATC AGCAGCTGCG AGCAGCACAG TCCAAAATCA

481 GCCACAGGAT CAAGAGCACC CGTGGCCGTA TCTTCGCGAA TTCTTTTCTT TAAGTGGTGT

541 AAATAAAGAT TCATTCAAGA TGAAATGTGT CCTCTGTCTC CCGCTTAATA AAGAAATATC

601 GGCCTTCAAA AGTTCGCCAT CAAACCTAAG GAAGCATATT GAGGTAAGTA CATTAAGTAT

661 TTTGTTTTAC TGATAGTTTT TTTTTTTTTT TTTTTTTTTT TTTTGGGTG TGCATGTTTT

721 GACGTTGATG GCGCGCCTTT TATATGTGTA GTAGGCCTAT TTTCACTAAT GCATGCGATT

781 GACAATATAA GGCTCACGTA ATAAAATGCT AAAATGCATT TGTAATTGGT AACGTTAGGT

841 CCACGGGAAA TTTGGCGCCT ATTGCAGCTT TGAATAATCA TTATCATTCC GTGCTCTCAT

901 TGTGTTTGAA TTCATGCAAA ACACAAGAAA ACCAAGCGAG AAATTTTTTT CCAAACATGT

961 TGTATTGTCA AAACGGTAAC ACTTTACAAT GAGGTTGATT AGTTCATGTA TTAACTAACA
    1021 TTAAATAACC ATGAGCAATA CATTTGTTAC TGTATCTGTT AATCTTTGTT AACGTTAGTT
```

```
1081 AATAGAAATA CAGATGTTCA TTGTTTGTTC ATGTTAGTTC ACAGTGCATT AACTAATGTT
1141 AACAAGATAT AAAGTATTAG TAAATGTTGA AATTAACATG TATACGTGCA GTTCATTATT
1201 AGTTCATGTT AACTAATGTA GTTAACTAAC GAACCTTATT GTAAAAGTGT TACCATCAAA
1261 ACTAATGTAA TGAAATCAAT TCACCCTGTC ATGTCAGCCT TACAGTCCTG TGTTTTTGTC
1321 AATATAATCA GAAATAAAAT TAATGTTTGA TTGTCACTAA ATGCTACTGT ATTTCTAAAA
1381 TCAACAAGTA TTTAACATTA TAAAGTGTGC AATTGGCTGC AAATGTCAGT TTTATTAAAG
1441 GGTTAGTTCA CCCAAAAATG AAAATAATGT CATTAATGAC TCGCCCTCAT GTCGTTCCAA
1501 GCCCGTAAGA CCTCCGTTCA TCTTCAGAAC ACAGTTTAAG ATATTTTAGA TTTAGTCCGA
1561 GAGCTTTCTG TGCCTCCATT GAGAATGTAT GTACGGTATA CTGTCCATGT CCAGAAAGGT
1621 AATAAAAACA TCAAAGTAGT CCATGTGACA TCAGTGGGTT AGTTAGAATT TTTTGAAGCA
1681 TCGAATACAT TTTGGTCCAA AAATAACAAA ACCTACGACT TTATTCGGCA TTGTATTCTC
1741 TTCCGGGTCT GTTGTCAATC CGCGTTCACG ACTTCGCAGT GACGCTACAA TGCTGAATAA
1801 AGTCGTAGGT TTTGTTATTT TTGGACCAAA ATGTATTTTC GATGCTTCAA ATAATTCTAC
1861 CTAACCCACT GATGTCACAT GGACTACTTT GATGTTTTTA TTACCTTTCT GGACATGGAC
1921 AGTATACCGT ACATACATTT TCAGTGGAGG GACAGAAAGC TCTCGGACTA AATCTAAAAT
1981 ATCTTAAACT GTGTTCCGAA GATGAACGGA GGTGTTACGG GCTTGGAACG ACATGAGGGT
2041 GAGTCATTAA TGACATCTTT TCATTTTTGG GTGAACTAAC CCTTTAATGC TGTAATCAGA
2101 GAGTGTATGT GTAATTGTTA CATTTATTGC ATACAATATA AATATTTATT TGTTGTTTTT
2161 ACAGAGAATG CACCCAAATT ACCTCAAAAA CTACTCTAAA TTGACAGCAC AGAAGAGAAA
2221 GATCGGGACC TCCACCCATG CTTCCAGCAG TAAGCAACTG AAAGTTGACT CAGTTTTCCC
2281 AGTCAAACAT GTGTCTCCAG TCACTGTGAA CAAAGCTATA TTAAGGTACA TCATTCAAGG
2341 ACTTCATCCT TTCAGCACTG TTGATCTGCC ATCATTTAAA GAGCTGATTA GTACACTGCA
2401 GCCTGGCATT TCTGTCATTA CAAGGCCTAC TTTACGCTCC AAGATAGCTG AAGCTGCTCT
2461 GATCATGAAA CAGAAAGTGA CTGCTGCCAT GAGTGAAGTT GAATGGATTG CAACCACAAC
2521 GGATTGTTGG ACTGCACGTA GAAAGTCATT CATTGGTGTA ACTGCTCACT GGATCAACCC
2581 TGGAAGTCTT GAAAGACATT CCGCTGCACT TGCCTGCAAA AGATTAATGG GCTCTCATAC
2641 TTTTGAGGTA CTGGCCAGTG CCATGAATGA TATCCACTCA GAGTATGAAA TACGTGACAA
2701 GGTTGTTTGC ACAACCACAG ACAGTGGTTC CAACTTTATG AAGGCTTTCA GAGTTTTTGG
2761 TGTGGAAAAC AATGTATATCG AGACTGAGGC AAGAAGGTGT GAAAGTGATG ACACTGATTC
2821 TGAAGGCTGT GGTGAGGGAA GTGATGGTGT GGAATTCCAA GATGCCTCAC GAGTCCTGGA
2881 CCAAGACGAT GGCTTCGAAT TCCAGCTACC AAAACATCAA AAGTGTGCCT GTCACTTACT
2941 TAACCTAGTC TCAAGCGTTG ATGCCCAAAA AGCTCTCTCA AATGAACACT ACAAGAAACT
3001 CTACAGATCT GTCTTTGGCA AATGCCAAGC TTTATGGAAT AAAAGCAGCC GATCGGCTCT
3061 AGCAGCTGAA GCTGTTGAAT CAGAAAGCCG GCTTCAGCTT TTAAGGCCAA ACCAAACGCG
3121 GTGGAATTCA ACTTTTATGG CTGTTGACAG AATTCTTCAA ATTTGCAAAG AAGCAGGAGA
3181 AGGCGCACTT CGGAATATAT GCACCTCTCT TGAGGTTCCA ATGTAAGTGT TTTTCCCCTC
3241 TATCGATGTA AACAAATGTG GGTTGTTTTT GTTTAATACT CTTTGATTAT GCTGATTTCT
3301 CCTGTAGGTT TAATCCAGCA GAAATGCTGT TCTTGACAGA GTGGGCCAAC ACAATGCGTC
3361 CAGTTGCAAA AGTACTCGAC ATCTTGCAAG CGGAAACGAA TACACAGCTG GGGTGGCTGC
3421 TGCCTAGTGT CCATCAGTTA AGCTTGAAAC TTCAGCGACT CCACCATTCT CTCAGGTACT
3481 GTGACCCACT TGTGGATGCC CTACAACAAG GAATCCAAAC ACGATTCAAG CATATGTTTG
```

-continued

```
3541 AAGATCCTGA GATCATAGCA GCTGCCATCC TTCTCCCTAA ATTTCGGACC TCTTGGACAA

3601 ATGATGAAAC CATCATAAAA CGAGGTAAAT GAATGCAAGC AACATACACT TGACGAATTC

3661 TAATCTGGGC AACCTTTGAG CCATACCAAA ATTATTCTTT TATTTATTTA TTTTTGCACT

3721 TTTTAGGAAT GTTATATCCC ATCTTTGGCT GTGATCTCAA TATGAATATT GATGTAAAGT

3781 ATTCTTGCAG CAGGTTGTAG TTATCCCTCA GTGTTTCTTG AAACCAAACT CATATGTATC

3841 ATATGTGGTT TGGAAATGCA GTTAGATTTT ATGCTAAAAT AAGGGATTTG CATGATTTTA

3901 GATGTAGATG ACTGCACGTA AATGTAGTTA ATGACAAAAT CCATAAAATT TGTTCCCAGT

3961 CAGAAGCCCC TCAACCAAAC TTTTCTTTGT GTCTGCTCAC TGTGCTTGTA GGCATGGACT

4021 ACATCAGAGT GCATCTGGAG CCTTTGGACC ACAAGAAGGA ATTGGCCAAC AGTTCATCTG

4081 ATGATGAAGA TTTTTTCGCT TCTTTGAAAC CGACAACACA TGAAGCCAGC AAAGAGTTGG

4141 ATGGATATCT GGCCTGTGTT TCAGACACCA GGGAGTCTCT GCTCACGTTT CCTGCTATTT

4201 GCAGCCTCTC TATCAAGACT AATACACCTC TTCCCGCATC GGCTGCCTGT GAGAGGCTTT

4261 TCAGCACTGC AGGATTGCTT TTCAGCCCCA AAAGAGCTAG GCTTGACACT AACAATTTTG

4321 AGAATCAGCT TCTACTGAAG TTAAATCTGA GGTTTTACAA CTTTGAGTAG CGTGTACTGG

4381 CATTAGATTG TCTGTCTTAT AGTTTGATAA TTAAATACAA ACAGTTCTAA AGCAGGATAA

4441 AACCTTGTAT GCATTTCATT TAATGTTTTT TGAGATTAAA AGCTTAAACA AGAATCTCTA

4501 GTTTTCTTTC TTGCTTTTAC TTTTACTTCC TTAATACTCA AGTACAATTT TAATGGAGTA

4561 CTTTTTTACT TTTACTCAAG TAAGATTCTA GCCAGATACT TTTACTTTTA ATTGAGTAAA

4621 ATTTTCCCTA AGTACTTGTA CTTTCACTTG AGTAAAATTT TTGAGTACTT TTTACACCTC

4681 TG.
```

Homologous Recombination

In certain embodiments of the methods of the disclosure, a modified CAR-$T_{SCM}$ or CAR-$T_{CM}$ of the disclosure is produced by introducing an antigen receptor into a primary human T cell of the disclosure by homologous recombination. In certain embodiments of the disclosure, the homologous recombination is induced by a single or double strand break induced by a genomic editing composition or construct of the disclosure. Homologous recombination methods of the disclosure comprise contacting a genomic editing composition or construct of the disclosure to a genomic sequence to induce at least one break in the sequence and to provide an entry point in the genomic sequence for an exogenous donor sequence composition. Donor sequence compositions of the disclosure are integrated into the genomic sequence at the induced entry point by the cell's native DNA repair machinery.

In certain embodiments of the methods of the disclosure, homologous recombination introduces a sequence encoding an antigen receptor and/or a donor sequence composition of the disclosure into a "genomic safe harbor" site. In certain embodiments, a mammalian genomic sequence comprises the genomic safe harbor site. In certain embodiments, a primate genomic sequence comprises the genomic safe harbor site. In certain embodiments, a human genomic sequence comprises the genomic safe harbor site.

Genomic safe harbor sites are able to accommodate the integration of new genetic material in a manner that ensures that the newly inserted genetic elements function reliably (for example, are expressed at a therapeutically effective level of expression) and do not cause deleterious alterations to the host genome that cause a risk to the host organism. Potential genomic safe harbors include, but are not limited to, intronic sequences of the human albumin gene, the adeno-associated virus site 1 (AAVS1), a naturally occurring site of integration of AAV virus on chromosome 19, the site of the chemokine (C-C motif) receptor 5 (CCR5) gene and the site of the human ortholog of the mouse Rosa26 locus.

In certain embodiments of the methods of the disclosure, homologous recombination introduces a sequence encoding an antigen receptor and/or a donor sequence composition of the disclosure into a sequence encoding one or more components of an endogenous T-cell receptor or a major histocompatibility complex (MHC). In certain embodiments, inducing homologous recombination within a genomic sequence encoding the endogenous T-cell receptor or the MHC disrupts the endogenous gene, and optionally, replaces part of the coding sequence of the endogenous gene with a donor sequence composition of the disclosure. In certain embodiments, inducing homologous recombination within a genomic sequence encoding the endogenous T-cell receptor or the MHC disrupts the endogenous gene, and optionally, replaces the entire coding sequence of the endogenous gene with a donor sequence composition of the disclosure. In certain embodiments of the methods of the disclosure, introduction of a sequence encoding an antigen receptor or a donor sequence composition of the disclosure by homologous recombination operably links the antigen receptor to an endogenous T cell promoter. In certain embodiments of the methods of the disclosure, introduction of a sequence encoding an antigen receptor or a donor sequence composition of the disclosure by homologous recombination operably links the antigen receptor or the therapeutic protein to a transcriptional or translational regulatory element. In certain embodiments of the methods of the disclosure, introduction of a sequence encoding an antigen receptor or a donor sequence composition of the disclosure by homologous recombination operably links the antigen receptor or the therapeutic protein to a transcriptional regulatory element. In certain embodiments, the transcriptional regulatory element comprises an endogenous T cell 5' UTR.

In certain embodiments of the introduction step comprising a homologous recombination, a genomic editing composition contacts a genomic sequence of at least one primary T cell of the plurality of T cells. In certain embodiments of the introduction step comprising a homologous recombination, a genomic editing composition contacts a genomic sequence of a portion of primary T cells of the plurality of T cells. In certain embodiments, the portion of primary T cells is at least 1%, 2%, 5%, 7%, 10%, 15%, 20%, 25%, 30%, 35%, 40%, 45%, 50%, 55%, 60%, 65%, 70%, 75%, 80%, 85%, 90%, 95%, 97%, 99% or any percentage in between of the total number of primary T cells in the plurality of T cells. In certain embodiments of the introduction step comprising a homologous recombination, a genomic editing composition contacts a genomic sequence of each primary T cell of the plurality of T cells. In certain embodiments of the introduction step comprising a homologous recombination, a genomic editing composition induces a single strand break. In certain embodiments of the introduction step comprising a homologous recombination, a genomic editing composition induces a double strand break. In certain embodiments of the introduction step comprising a homologous recombination, the introduction step further comprises a donor sequence composition. In certain embodiments, the donor sequence composition comprises a sequence encoding the antigen receptor. In certain embodiments, the donor sequence composition comprises a sequence encoding the antigen receptor, a 5' genomic sequence and a 3' genomic sequence, wherein the 5' genomic sequence is homologous or identical to a genomic sequence of the primary T cell that is 5' to the break point induced by the genomic editing composition and the 3' genomic sequence is homologous or identical to a genomic sequence of the primary T cell that is 3' to the break point induced by the genomic editing composition. In certain embodiments, the 5' genomic sequence and/or the 3' genomic sequence comprises at least 50 bp, 100 bp, at least 200 bp, at least 300 bp, at least 400 bp, at least 500 bp, at least 600 bp, at least 700 bp, at least 800 bp, at least 900 bp, at least 1000 bp, at least 1100 bp, at least 1200 bp, at least 1300 bp, at least 1400, or at least 1500 bp, at least 1600 bp, at least 1700 bp, at least 1800 bp, at least 1900 bp, at least 2000 bp in length or any length of base pairs (bp) in between, inclusive of the end points. In certain embodiments of the introduction step comprising a homologous recombination, the genomic editing composition and donor sequence composition are contacted with the genomic sequence simultaneously or sequentially. In certain embodiments of the introduction step comprising a homologous recombination, the genomic editing composition and donor sequence composition are contacted with the genomic sequence sequentially, and the genomic editing composition is provided first. In certain embodiments of the introduction step comprising a homologous recombination, the genomic editing composition comprises a sequence encoding a DNA binding domain and a sequence encoding a nuclease domain. In certain embodiments of the introduction step comprising a homologous recombination, the genomic editing composition comprises a DNA binding domain and a nuclease domain. In certain embodiments of the genomic editing composition, the DNA binding domain comprises a guide RNA (gRNA). In certain embodiments of the genomic editing composition, the DNA binding domain comprises a DNA-binding domain of a TALEN. In certain embodiments of the genomic editing composition, the DNA binding domain comprises a DNA-binding domain of a ZFN. In certain embodiments of the genomic editing composition, the nuclease domain comprises a Cas9 nuclease or a sequence thereof. In certain embodiments of the genomic editing composition, the nuclease domain comprises an inactive Cas9 (SEQ ID NO: 33, comprising a substitution of a Alanine (A) for Aspartic Acid (D) at position 10 (D10A) and a substitution of Alanine (A) for Histidine (H) at position 840 (H840A)). In certain embodiments of the genomic editing composition, the nuclease domain comprises a short and inactive Cas9 (SEQ ID NO: 32, comprising a substitution of an Alanine (A) for an Aspartic Acid (D) at position 10 (D10A) and a substitution of an Alanine (A) for an Asparagine (N) at position 540 (N540A)). In certain embodiments of the genomic editing composition, the nuclease domain comprises or further comprises a type IIS endonuclease. In certain embodiments of the genomic editing composition, the type IIS endonuclease comprises AciI, MnlI, AlwI, BbvI, BccI, BceAI, BsmAI, BsmFI, BspCNI, BsrI, BtsCI, HgaI, HphI, HpyAV, MboII, MyII, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the type IIS endonuclease comprises Clo051. In certain embodiments of the genomic editing composition, the nuclease domain comprises or further comprises a TALEN or a nuclease domain thereof. In certain embodiments of the genomic editing composition, the nuclease domain comprises or further comprises a ZFN or a nuclease domain thereof. In certain embodiments of the introduction step comprising a homologous recombination, the genomic editing composition induces a break in a genomic sequence and the donor sequence composition is inserted using the endogenous DNA repair mechanisms of the primary T cell. In certain embodiments of the introduction step comprising a homologous recombination, the insertion of the donor sequence composition eliminates a DNA binding site of the genomic editing composition, thereby preventing further activity of the genomic editing composition.

In certain embodiments of the methods of homologous recombination of the disclosure, the nuclease domain of a genomic editing composition or construct is capable of introducing a break at a defined location in a genomic sequence of the primary human T cell, and, furthermore, may comprise, consist essentially of or consist of, a homodimer or a heterodimer. In certain embodiments, the nuclease is an endonuclease. Effector molecules, including those effector molecules comprising a homodimer or a heterodimer, may comprise, consist essentially of or consist of, a Cas9, a Cas9 nuclease domain or a fragment thereof. In certain embodiments, the Cas9 is a catalytically inactive or "inactivated" Cas9 (dCas9). In certain embodiments, the Cas9 is a catalytically inactive or "inactivated" nuclease domain of Cas9. In certain embodiments, the dCas9 is encoded by a shorter sequence that is derived from a full length, catalytically inactivated, Cas9, referred to herein as a "small" dCas9 or dSaCas9.

In certain embodiments, the inactivated, small, Cas9 (dSaCas9) operatively-linked to an active nuclease. In certain embodiments, the disclosure provides a fusion protein comprising, consisting essentially of or consisting of a DNA binding domain and molecule nuclease, wherein the nuclease comprises a small, inactivated Cas9 (dSaCas9). In certain embodiments, the dSaCas9 of the disclosure comprises the mutations D10A and N580A (underlined and bolded) which inactivate the catalytic site. In certain embodiments, the dSaCas9 of the disclosure comprises the amino acid sequence of:

(SEQ ID NO: 32)
```
   1 MKRNYILGLA IGITSVGYGI IDYETRDVID AGVRLFKEAN VENNEGRRSK RGARRLKRRR
  61 RHRIQRVKKL LFDYNLLTDH SELSGINPYE ARVKGLSQKL SEEEFSAALL HLAKRRGVHN
 121 VNEVEEDTGN ELSTKEQISR NSKALEEKYV AELQLERLKK DGEVRGSINR FKTSDYVKEA
 181 KQLLKVQKAY HQLDQSFIDT YIDLLETRRT YYEGPGEGSP FGWKDIKEWY EMLMGHCTYF
 241 PEELRSVKYA YNADLYNALN DLNNLVITRD ENEKLEYYEK FQIIENVFKQ KKKPTLKQIA
 301 KEILVNEEDI KGYRVTSTGK PEFTNLKVYH DIKDITARKE IIENAELLDQ IAKILTIYQS
 361 SEDIQEELTN LNSELTQEEI EQISNLKGYT GTHNLSLKAI NLILDELWHT NDNQIAIFNR
 421 LKLVPKKVDL SQQKEIPTTL VDDFILSPVV KRSFIQSIKV INAIIKKYGL PNDIIIELAR
 481 EKNSKDAQKM INEMQKRNRQ TNERIEEIIR TTGKENAKYL IEKIKLHDMQ EGKCLYSLEA
 541 IPLEDLLNNP FNYEVDHIIP RSVSFDNSFN NKVLVKQEEA SKKGNRTPFQ YLSSSDSKIS
 601 YETFKKHILN LAKGKGRISK TKKEYLLEER DINRFSVQKD FINRNLVDTR YATRGLMNLL
 661 RSYFRVNNLD VKVKSINGGF TSFLRRKWKF KKERNKGYKH HAEDALIIAN ADFIFKEWKK
 721 LDKAKKVMEN QMFEEKQAES MPEIETEQEY KEIFITPHQI KHIKDFKDYK YSHRVDKKPN
 781 RELINDTLYS TRKDDKGNTL IVNNLNGLYD KDNDKLKKLI NKSPEKLLMY HHDPQTYQKL
 841 KLIMEQYGDE KNPLYKYYEE TGNYLTKYSK KDNGPVIKKI KYYGNKLNAH LDITDDYPNS
 901 RNKVVKLSLK PYRFDVYLDN GVYKFVTVKN LDVIKKENYY EVNSKCYEEA KKLKKISNQA
 961 EFIASFYNND LIKINGELYR VIGVNNDLLN RIEVNMIDIT YREYLENMND KRPPRIIKTI
1021 ASKTQSIKKY STDILGNLYE VKSKKHPQII KKG.
```

In certain embodiments, the dCas9 of the disclosure comprises a dCas9 isolated or derived from *Staphyloccocus pyogenes*. In certain embodiments, the dCas9 comprises a dCas9 with substitutions at positions 10 and 840 of the amino acid sequence of the dCas9 which inactivate the catalytic site. In certain embodiments, these substitutions are D10A and H840A. In certain embodiments, the amino acid sequence of the dCas9 comprises the sequence of:

(SEQ ID NO: 33)
```
  1 XDKKYSIGLA IGTNSVGWAV ITDEYKVPSK KFKVLGNTDR HSIKKNLIGA LLFDSGETAE
 61 ATRLKRTARR RYTRRKNRIC YLQEIFSNEM AKVDDSFFHR LEESFLVEED KKHERHPIFG
121 NIVDEVAYHE KYPTIYHLRK KLVDSTDKAD LRLIYLALAH MIKFRGHFLI EGDLNPDNSD
181 VDKLFIQLVQ TYNQLFEENP INASGVDAKA ILSARLSKSR RLENLIAQLP GEKKNGLFGN
241 LIALSLGLTP NFKSNFDLAE DAKLQLSKDT YDDDLDNLLA QIGDQYADLF LAAKNLSDAI
301 LLSDILRVNT EITKAPLSAS MIKRYDEHHQ DLTLLKALVR QQLPEKYKEI FFDQSKNGYA
361 GYIDGGASQE EFYKFIKPIL EKMDGTEELL VKLNREDLLR KQRTFDNGSI PHQIHLGELH
421 AILRRQEDFY PFLKDNREKI EKILTFRIPY YVGPLARGNS RFAWMTRKSE ETITPWNFEE
481 VVDKGASAQS FIERMTNFDK NLPNEKVLPK HSLLYEYFTV YNELTKVKYV TEGMRKPAFL
541 SGEQKKAIVD LLFKTNRKVT VKQLKEDYFK KIECFDSVEI SGVEDRFNAS LGTYHDLLKI
601 IKDKDFLDNE ENEDILEDIV LTLTLFEDRE MIEERLKTYA HLFDDKVMKQ LKRRRYTGWG
661 RLSRKLINGI RDKQSGKTIL DFLKSDGFAN RNFMQLIHDD SLTFKEDIQK AQVSGQGDSL
721 HEHIANLAGS PAIKKGILQT VKVVDELVKV MGRHKPENIV IEMARENQTT QKGQKNSRER
781 MKRIEEGIKE LGSQILKEHP VENTQLQNEK LYLYYLQNGR DMYVDQELDI NRLSDYDVDA
```

```
 841 IVPQSFLKDD SIDNKVLTRS DKNRGKSDNV PSEEVVKKMK NYWRQLLNAK LITQRKFDNL

901 TKAERGGLSE LDKAGFIKRQ LVETRQITKH VAQILDSRMN TKYDENDKLI REVKVITLKS

961 KLVSDFRKDF QFYKVREINN YHHAHDAYLN AVVGTALIKK YPKLESEFVY GDYKVYDVRK

1021 MIAKSEQEIG KATAKYFFYS NIMNFFKTEI TLANGEIRKR PLIETNGETG EIVWDKGRDF

1081 ATVRKVLSMP QVNIVKKTEV QTGGFSKESI LPKRNSDKLI ARKKDWDPKK YGGFDSPTVA

1141 YSVLVVAKVE KGKSKKLKSV KELLGITIME RSSFEKNPID FLEAKGYKEV KKDLIIKLPK

1201 YSLFELENGR KRMLASAGEL QKGNELALPS KYVNFLYLAS HYEKLKGSPE DNEQKQLFVE

1261 QHKHYLDEII EQISEFSKRV ILADANLDKV LSAYNKHRDK PIREQAENII HLFTLTNLGA

1321 PAAFKYFDTT IDRKRYTSTK EVLDATLIHQ SITGLYETRI DLSQLGGD.
```

In certain embodiments of the disclosure, the nuclease domain may comprise, consist essentially of or consist of a dCas9 or a dSaCas9 and a type IIS endonuclease. In certain embodiments of the disclosure, the nuclease domain may comprise, consist essentially of or consist of a dSaCas9 and a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments of the disclosure, the nuclease domain may comprise, consist essentially of or consist of a dSaCas9 and Clo051. An exemplary Clo051 nuclease domain may comprise, consist essentially of or consist of, the amino acid sequence of:

(SEQ ID NO: 34)
EGIKSNISLLKDELRGQISHISHEYLSLIDLAFDSKQNRLFEMKVLELLV

NEYGFKGRHLGGSRKPDGIVYSTTLEDNFGIIVDTKAYSEGYSLPISQAD

EMERYVRENSNRDEEVNPNKWWENFSEEVKKYYFVFISGSFKGKFEEQLR

RLSMTTGVNGSAVNVVNLLLGAEKIRSGEMTIEELERAMFNNSEFILKY.

An exemplary dCas9-Clo051 nuclease domain may comprise, consist essentially of or consist of, the amino acid sequence of (Clo051 sequence underlined, linker bold italics, dCas9 sequence in italics):

(SEQ ID NO: 40)
MAPKKKRKV<u>EGIKSNISLLKDELRGQISHISHEYLSLIDLAFDSKQNRLF

EMKVLELLVNEYGFKGRHLGGSRKPDGIVYSTTLEDNFGIIVDTKAYSEG

YSLPISQADEMERYVRENSNRDEEVNPNKWWENFSEEVKKYYFVFISGSF

KGKFEEQLRRLSMTTGVNGSAVNVVNLLLGAEKIRSGEMTIEELERAMFN

NSEFILKY</u>*GGGGS**DKKYSIGLAIGTNSVGWAVITDEYKVPSKKFKVLGN*

*TDRHSIKKNLIGALLFDSGETAEATRLKRTARRRYTRRKNRICYLQEIFS*

*NEMAKVDDSFFHRLEESFLVEEDKKHERHPIFGNIVDEVAYHEKYPTIYH*

*LRKKLVDSTDKADLRLIYLALAHMIKFRGHFLIEGDLNPDNSDVDKLFIQ*

*LVQTYNQLFEENPINASGVDAKAILSARLSKSRRLENLIAQLPGEKKNGL*

*FGNLIALSLGLTPNFKSNFDLAEDAKLQLSKDTYDDDLDNLLAQIGDQYA*

*DLFLAAKNLSDAILLSDILRVNTEITKAPLSASMIKRYDEHHQDLTLLKA*

*LVRQQLPEKYKEIFFDQSKNGYAGYIDGGASQEEFYKFIKPILEKMDGTE*

*ELLVKLNREDLLRKQRTFDNGSIPHQIHLGELHAILRRQEDFYPFLKDNR*

*EKIEKILTFRIPYYVGPLARGNSRFAWMTRKSEETITPWNFEEVVDKGAS*

*AQSFIERMTNFDKNLPNEKVLPKHSLLYEYFTVYNELTKVKYVTEGMRKP*

*AFLSGEQKKAIVDLLFKTNRKVTVKQLKEDYFKKIECFDSVEISGVEDRF*

*NASLGTYHDLLKIIKDKDFLDNEENEDILEDIVLTLTLFEDREMIEERLK*

*TYAHLFDDKVMKQLKRRRYTGWGRLSRKLINGIRDKQSGKTILDFLKSDG*

*FANRNFMQLIHDDSLTFKEDIQKAQVSGQGDSLHEHIANLAGSPAIKKGI*

*LQTVKVVDELVKVMGRHKPENIVIEMARENQTTQKGQKNSRERMKRIEEG*

*IKELGSQILKEHPVENTQLQNEKLYLYYLQNGRDMYVDQELDINRLSDYD*

*VDAIVPQSFLKDDSIDNKVLTRSDKNRGKSDNVPSEEVVKKMKNYWRQLL*

*NAKLITQRKFDNLTKAERGGLSELDKAGFIKRQLVETRQITKHVAQILDS*

*RMNTKYDENDKLIREVKVITLKSKLVSDFRKDFQFYKVREINNYHHAHDA*

*YLNAVVGTALIKKYPKLESEFVYGDYKVYDVRKMIAKSEQEIGKATAKYF*

*FYSNIMNFFKTEITLANGEIRKRPLIETNGETGEIVWDKGRDFATVRKVL*

*SMPQVNIVKKTEVQTGGFSKESILPKRNSDKLIARKKDWDPKKYGGFDSP*

*TVAYSVLVVAKVEKGKSKKLKSVKELLGITIMERSSFEKNPIDFLEAKGY*

*KEVKKDLIIKLPKYSLFELENGRKRMLASAGELQKGNELALPSKYVNFLY*

*LASHYEKLKGSPEDNEQKQLFVEQHKHYLDEIIEQISEFSKRVILADANL*

*DKVLSAYNKHRDKPIREQAENIIHLFTLTNLGAPAAFKYFDTTIDRKRYT*

*STKEVLDATLIHQSITGLYETRIDLSQLGGD*<b>GSPKKKRKVSS</b>.

In certain embodiments, the nuclease capable of introducing a break at a defined location in the genomic DNA of the primary human T cell may comprise, consist essentially of or consist of, a homodimer or a heterodimer. Nuclease domains of the genomic editing compositions or constructs of the disclosure may comprise, consist essentially of or consist of a nuclease domain isolated, derived or recombined from a transcription-activator-like effector nuclease (TALEN). TALENs are transcription factors with programmable DNA binding domains that provide a means to create designer proteins that bind to pre-determined DNA sequences or individual nucleic acids. Modular DNA binding domains have been identified in transcriptional activator-like (TAL) proteins, or, more specifically, transcriptional activator-like effector nucleases (TALENs), thereby allowing for the de novo creation of synthetic transcription factors that bind to DNA sequences of interest and, if desirable, also allowing a second domain present on the protein or polypeptide to perform an activity related to DNA. TAL proteins have been derived from the organisms *Xanthomonas* and *Ralstonia*.

In certain embodiments of the disclosure, the nuclease domain of the genomic editing composition or construct may comprise, consist essentially of or consist of a nuclease domain isolated, derived or recombined from a TALEN and a type IIS endonuclease. In certain embodiments of the disclosure, the type IIS endonuclease may comprise, consist essentially of or consist of AciI, MnlI, AlwI, BbvI, BccI, BceAI, BsmAI, BsmFI, BspCNI, BsrI, BtsCI, HgaI, HphI, HpyAV, MboII, MyII, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments of the disclosure, the type IIS endonuclease may comprise, consist essentially of or consist of Clo051 (SEQ ID NO: 34).

In certain embodiments of the disclosure, the nuclease domain of the genomic editing composition or construct may comprise, consist essentially of or consist of a nuclease domain isolated, derived or recombined from a zinc finger nuclease (ZFN) and a type IIS endonuclease. In certain embodiments of the disclosure, the type IIS endonuclease may comprise, consist essentially of or consist of AciI, MnlI, AlwI, BbvI, BccI, BceAI, BsmAI, BsmFI, BspCNI, BsrI, BtsCI, HgaI, HphI, HpyAV, MboII, MyII, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments of the disclosure, the type IIS endonuclease may comprise, consist essentially of or consist of Clo051 (SEQ ID NO: 34).

In certain embodiments of the genomic editing compositions or constructs of the disclosure, the DNA binding domain and the nuclease domain may be covalently linked. For example, a fusion protein may comprise the DNA binding domain and the nuclease domain. In certain embodiments of the genomic editing compositions or constructs of the disclosure, the DNA binding domain and the nuclease domain may be operably linked through a non-covalent linkage.

Secreted Proteins from Modified T Cells

In certain embodiments of the composition and methods of the disclosure, modified T-cells express therapeutic proteins. Therapeutic proteins of the disclosure include secreted proteins. Preferably, in a therapeutic context, the therapeutic protein is a human protein, including a secreted human protein. When expressed or secreted by CAR-T cells of the disclosure, the combination comprising the CAR-T cell and the therapeutic protein secreted therefrom may be considered a monotherapy. However, the CAR-T cells of the disclosure may be administered as a combination therapy with a second agent. A database of human secreted proteins that may be expressed or secreted by modified T-cell of the disclosure can be found at proteinatlas.org/search/protein_class:Predicted%20secreted%20proteins, the contents of which are incorporated herein by reference. Exemplary human secreted proteins are provided, but are not limited to the human secreted proteins, in Table 1.

TABLE 1

Exemplary Human Secreted Proteins

| Gene | Ensembl ID | Gene description |
|---|---|---|
| A1BG | ENSG00000121410 | Alpha-1-B glycoprotein |
| A2M | ENSG00000175899 | Alpha-2-macroglobulin |
| A2ML1 | ENSG00000166535 | Alpha-2-macroglobulin-like 1 |
| A4GNT | ENSG00000118017 | Alpha-1,4-N-acetylglucosaminyltransferase |
| AADACL2 | ENSG00000197953 | Arylacetamide deacetylase-like 2 |
| AANAT | ENSG00000129673 | Aralkylamine N-acetyltransferase |
| ABCG1 | ENSG00000160179 | ATP-binding cassette, sub-family G (WHITE), member 1 |
| ABHD1 | ENSG00000143994 | Abhydrolase domain containing 1 |
| ABHD10 | ENSG00000144827 | Abhydrolase domain containing 10 |
| ABHD14A | ENSG00000248487 | Abhydrolase domain containing 14A |
| ABHD15 | ENSG00000168792 | Abhydrolase domain containing 15 |
| ABI3BP | ENSG00000154175 | ABI family, member 3 (NESH) binding protein |
| AC008641.1 | ENSG00000279109 | |
| AC009133.22 | ENSG00000277669 | |
| AC009491.2 | ENSG00000279664 | |
| AC011513.3 | ENSG00000267881 | |
| AC136352.5 | ENSG00000277666 | |
| AC145212.4 | ENSG00000277400 | MaFF-interacting protein |
| AC233755.1 | ENSG00000275063 | |
| ACACB | ENSG00000076555 | Acetyl-CoA carboxylase beta |
| ACAN | ENSG00000157766 | Aggrecan |
| ACE | ENSG00000159640 | Angiotensin I converting enzyme |
| ACHE | ENSG00000087085 | Acetylcholinesterase (Yt blood group) |
| ACP2 | ENSG00000134575 | Acid phosphatase 2, lysosomal |
| ACP5 | ENSG00000102575 | Acid phosphatase 5, tartrate resistant |
| ACP6 | ENSG00000162836 | Acid phosphatase 6, lysophosphatidic |
| ACPP | ENSG00000014257 | Acid phosphatase, prostate |
| ACR | ENSG00000100312 | Acrosin |
| ACRBP | ENSG00000111644 | Acrosin binding protein |
| ACRV1 | ENSG00000134940 | Acrosomal vesicle protein 1 |
| ACSF2 | ENSG00000167107 | Acyl-CoA synthetase family member 2 |
| ACTL10 | ENSG00000182584 | Actin-like 10 |
| ACVR1 | ENSG00000115170 | Activin A receptor, type I |
| ACVR1C | ENSG00000123612 | Activin A receptor, type IC |
| ACVRL1 | ENSG00000139567 | Activin A receptor type II-like 1 |

TABLE 1-continued

Exemplary Human Secreted Proteins

| Gene | Ensembl ID | Gene description |
|---|---|---|
| ACYP1 | ENSG00000119640 | Acylphosphatase 1, erythrocyte (common) type |
| ACYP2 | ENSG00000170634 | Acylphosphatase 2, muscle type |
| ADAM10 | ENSG00000137845 | ADAM metallopeptidase domain 10 |
| ADAM12 | ENSG00000148848 | ADAM metallopeptidase domain 12 |
| ADAM15 | ENSG00000143537 | ADAM metallopeptidase domain 15 |
| ADAM17 | ENSG00000151694 | ADAM metallopeptidase domain 17 |
| ADAM18 | ENSG00000168619 | ADAM metallopeptidase domain 18 |
| ADAM22 | ENSG00000008277 | ADAM metallopeptidase domain 22 |
| ADAM28 | ENSG00000042980 | ADAM metallopeptidase domain 28 |
| ADAM29 | ENSG00000168594 | ADAM metallopeptidase domain 29 |
| ADAM32 | ENSG00000197140 | ADAM metallopeptidase domain 32 |
| ADAM33 | ENSG00000149451 | ADAM metallopeptidase domain 33 |
| ADAM7 | ENSG00000069206 | ADAM metallopeptidase domain 7 |
| ADAM8 | ENSG00000151651 | ADAM metallopeptidase domain 8 |
| ADAM9 | ENSG00000168615 | ADAM metallopeptidase domain 9 |
| ADAMDEC1 | ENSG00000134028 | ADAM-like, decysin 1 |
| ADAMTS1 | ENSG00000154734 | ADAM metallopeptidase with thrombospondin type 1 motif, 1 |
| ADAMTS10 | ENSG00000142303 | ADAM metallopeptidase with thrombospondin type 1 motif, 10 |
| ADAMTS12 | ENSG00000151388 | ADAM metallopeptidase with thrombospondin type 1 motif, 12 |
| ADAMTS13 | ENSG00000160323 | ADAM metallopeptidase with thrombospondin type 1 motif, 13 |
| ADAMTS14 | ENSG00000138316 | ADAM metallopeptidase with thrombospondin type 1 motif, 14 |
| ADAMTS15 | ENSG00000166106 | ADAM metallopeptidase with thrombospondin type 1 motif, 15 |
| ADAMTS16 | ENSG00000145536 | ADAM metallopeptidase with thrombospondin type 1 motif, 16 |
| ADAMTS17 | ENSG00000140470 | ADAM metallopeptidase with thrombospondin type 1 motif, 17 |
| ADAMTS18 | ENSG00000140873 | ADAM metallopeptidase with thrombospondin type 1 motif, 18 |
| ADAMTS19 | ENSG00000145808 | ADAM metallopeptidase with thrombospondin type 1 motif, 19 |
| ADAMTS2 | ENSG00000087116 | ADAM metallopeptidase with thrombospondin type 1 motif, 2 |
| ADAMTS20 | ENSG00000173157 | ADAM metallopeptidase with thrombospondin type 1 motif, 20 |
| ADAMTS3 | ENSG00000156140 | ADAM metallopeptidase with thrombospondin type 1 motif, 3 |
| ADAMTS5 | ENSG00000154736 | ADAM metallopeptidase with thrombospondin type 1 motif, 5 |
| ADAMTS6 | ENSG00000049192 | ADAM metallopeptidase with thrombospondin type 1 motif, 6 |
| ADAMTS7 | ENSG00000136378 | ADAM metallopeptidase with thrombospondin type 1 motif, 7 |
| ADAMTS8 | ENSG00000134917 | ADAM metallopeptidase with thrombospondin type 1 motif, 8 |
| ADAMTS9 | ENSG00000163638 | ADAM metallopeptidase with thrombospondin type 1 motif, 9 |
| ADAMTSL1 | ENSG00000178031 | ADAMTS-like 1 |
| ADAMTSL2 | ENSG00000197859 | ADAMTS-like 2 |
| ADAMTSL3 | ENSG00000156218 | ADAMTS-like 3 |
| ADAMTSL4 | ENSG00000143382 | ADAMTS-like 4 |
| ADAMTSL5 | ENSG00000185761 | ADAMTS-like 5 |
| ADCK1 | ENSG00000063761 | AarF domain containing kinase 1 |
| ADCYAP1 | ENSG00000141433 | Adenylate cyclase activating polypeptide 1 (pituitary) |
| ADCYAP1R1 | ENSG00000078549 | Adenylate cyclase activating polypeptide 1 (pituitary) receptor type I |
| ADGRA3 | ENSG00000152990 | Adhesion G protein-coupled receptor A3 |
| ADGRB2 | ENSG00000121753 | Adhesion G protein-coupled receptor B2 |
| ADGRD1 | ENSG00000111452 | Adhesion G protein-coupled receptor D1 |
| ADGRE3 | ENSG00000131355 | Adhesion G protein-coupled receptor E3 |
| ADGRE5 | ENSG00000123146 | Adhesion G protein-coupled receptor E5 |
| ADGRF1 | ENSG00000153292 | Adhesion G protein-coupled receptor F1 |
| ADGRG1 | ENSG00000205336 | Adhesion G protein-coupled receptor G1 |
| ADGRG5 | ENSG00000159618 | Adhesion G protein-coupled receptor G5 |
| ADGRG6 | ENSG00000112414 | Adhesion G protein-coupled receptor G6 |
| ADGRV1 | ENSG00000164199 | Adhesion G protein-coupled receptor V1 |
| ADI1 | ENSG00000182551 | Acireductone dioxygenase 1 |
| ADIG | ENSG00000182035 | Adipogenin |
| ADIPOQ | ENSG00000181092 | Adiponectin, C1Q and collagen domain containing |
| ADM | ENSG00000148926 | Adrenomedullin |
| ADM2 | ENSG00000128165 | Adrenomedullin 2 |
| ADM5 | ENSG00000224420 | Adrenomedullin 5 (putative) |
| ADPGK | ENSG00000159322 | ADP-dependent glucokinase |
| ADPRHL2 | ENSG00000116863 | ADP-ribosylhydrolase like 2 |
| AEBP1 | ENSG00000106624 | AE binding protein 1 |
| AFM | ENSG00000079557 | Afamin |
| AFP | ENSG00000081051 | Alpha-fetoprotein |
| AGA | ENSG00000038002 | Aspartylglucosaminidase |
| AGER | ENSG00000204305 | Advanced glycosylation end product-specific receptor |
| AGK | ENSG00000006530 | Acylglycerol kinase |
| AGPS | ENSG00000018510 | Alkylglycerone phosphate synthase |
| AGR2 | ENSG00000106541 | Anterior gradient 2, protein disulphide isomerase family member |
| AGR3 | ENSG00000173467 | Anterior gradient 3, protein disulphide isomerase family member |
| AGRN | ENSG00000188157 | Agrin |
| AGRP | ENSG00000159723 | Agouti related neuropeptide |
| AGT | ENSG00000135744 | Angiotensinogen (serpin peptidase inhibitor, clade A, member 8) |

TABLE 1-continued

Exemplary Human Secreted Proteins

| Gene | Ensembl ID | Gene description |
|---|---|---|
| AGTPBP1 | ENSG00000135049 | ATP/GTP binding protein 1 |
| AGTRAP | ENSG00000177674 | Angiotensin II receptor-associated protein |
| AHCYL2 | ENSG00000158467 | Adenosylhomocysteinase-like 2 |
| AHSG | ENSG00000145192 | Alpha-2-HS-glycoprotein |
| AIG1 | ENSG00000146416 | Androgen-induced 1 |
| AK4 | ENSG00000162433 | Adenylate kinase 4 |
| AKAP10 | ENSG00000108599 | A kinase (PRKA) anchor protein 10 |
| AKR1C1 | ENSG00000187134 | Aldo-keto reductase family 1, member C1 |
| AL356289.1 | ENSG00000279096 | |
| AL589743.1 | ENSG00000279508 | |
| ALAS2 | ENSG00000158578 | 5'-aminolevulinate synthase 2 |
| ALB | ENSG00000163631 | Albumin |
| ALDH9A1 | ENSG00000143149 | Aldehyde dehydrogenase 9 family, member A1 |
| ALDOA | ENSG00000149925 | Aldolase A, fructose-bisphosphate |
| ALG1 | ENSG00000033011 | ALG1, chitobiosyldiphosphodolichol beta-mannosyltransferase |
| ALG5 | ENSG00000120697 | ALG5, dolichyl-phosphate beta-glucosyltransferase |
| ALG9 | ENSG00000086848 | ALG9, alpha-1,2-mannosyltransferase |
| ALKBH1 | ENSG00000100601 | AlkB homolog 1, histone H2A dioxygenase |
| ALKBH5 | ENSG00000091542 | AlkB homolog 5, RNA demethylase |
| ALPI | ENSG00000163295 | Alkaline phosphatase, intestinal |
| ALPL | ENSG00000162551 | Alkaline phosphatase, liver/bone/kidney |
| ALPP | ENSG00000163283 | Alkaline phosphatase, placental |
| ALPPL2 | ENSG00000163286 | Alkaline phosphatase, placental-like 2 |
| AMBN | ENSG00000178522 | Ameloblastin (enamel matrix protein) |
| AMBP | ENSG00000106927 | Alpha-1-microglobulin/bikunin precursor |
| AMELX | ENSG00000125363 | Amelogenin, X-linked |
| AMELY | ENSG00000099721 | Amelogenin, Y-linked |
| AMH | ENSG00000104899 | Anti-Mullerian hormone |
| AMICA1 | ENSG00000160593 | Adhesion molecule, interacts with CXADR antigen 1 |
| AMPD1 | ENSG00000116748 | Adenosine monophosphate deaminase 1 |
| AMTN | ENSG00000187689 | Amelotin |
| AMY1A | ENSG00000237763 | Amylase, alpha 1A (salivary) |
| AMY1B | ENSG00000174876 | Amylase, alpha 1B (salivary) |
| AMY1C | ENSG00000187733 | Amylase, alpha 1C (salivary) |
| AMY2A | ENSG00000243480 | Amylase, alpha 2A (pancreatic) |
| AMY2B | ENSG00000240038 | Amylase, alpha 2B (pancreatic) |
| ANG | ENSG00000214274 | Angiogenin, ribonuclease, RNase A family, 5 |
| ANGEL1 | ENSG00000013523 | Angel homolog 1 (*Drosophila*) |
| ANGPT1 | ENSG00000154188 | Angiopoietin 1 |
| ANGPT2 | ENSG00000091879 | Angiopoietin 2 |
| ANGPT4 | ENSG00000101280 | Angiopoietin 4 |
| ANGPTL1 | ENSG00000116194 | Angiopoietin-like 1 |
| ANGPTL2 | ENSG00000136859 | Angiopoietin-like 2 |
| ANGPTL3 | ENSG00000132855 | Angiopoietin-like 3 |
| ANGPTL4 | ENSG00000167772 | Angiopoietin-like 4 |
| ANGPTL5 | ENSG00000187151 | Angiopoietin-like 5 |
| ANGPTL6 | ENSG00000130812 | Angiopoietin-like 6 |
| ANGPTL7 | ENSG00000171819 | Angiopoietin-like 7 |
| ANK1 | ENSG00000029534 | Ankyrin 1, erythrocytic |
| ANKDD1A | ENSG00000166839 | Ankyrin repeat and death domain containing 1A |
| ANKRD54 | ENSG00000100124 | Ankyrin repeat domain 54 |
| ANKRD60 | ENSG00000124227 | Ankyrin repeat domain 60 |
| ANO7 | ENSG00000146205 | Anoctamin 7 |
| ANOS1 | ENSG00000011201 | Anosmin 1 |
| ANTXR1 | ENSG00000169604 | Anthrax toxin receptor 1 |
| AOAH | ENSG00000136250 | Acyloxyacyl hydrolase (neutrophil) |
| AOC1 | ENSG00000002726 | Amine oxidase, copper containing 1 |
| AOC2 | ENSG00000131480 | Amine oxidase, copper containing 2 (retina-specific) |
| AOC3 | ENSG00000131471 | Amine oxidase, copper containing 3 |
| AP000721.4 | ENSG00000256100 | |
| AP000866.1 | ENSG00000279342 | |
| APBB1 | ENSG00000166313 | Amyloid beta (A4) precursor protein-binding, family B, member 1 (Fe65) |
| APCDD1 | ENSG00000154856 | Adenomatosis polyposis coli down-regulated 1 |
| APCS | ENSG00000132703 | Amyloid P component, serum |
| APELA | ENSG00000248329 | Apelin receptor early endogenous ligand |
| APLN | ENSG00000171388 | Apelin |
| APLP2 | ENSG00000084234 | Amyloid beta (A4) precursor-like protein 2 |
| APOA1 | ENSG00000118137 | Apolipoprotein A-I |
| APOA1BP | ENSG00000163382 | Apolipoprotein A-I binding protein |
| APOA2 | ENSG00000158874 | Apolipoprotein A-II |
| APOA4 | ENSG00000110244 | Apolipoprotein A-IV |
| APOA5 | ENSG00000110243 | Apolipoprotein A-V |
| APOB | ENSG00000084674 | Apolipoprotein B |
| APOC1 | ENSG00000130208 | Apolipoprotein C-I |
| APOC2 | ENSG00000234906 | Apolipoprotein C-II |

TABLE 1-continued

Exemplary Human Secreted Proteins

| Gene | Ensembl ID | Gene description |
|---|---|---|
| APOC3 | ENSG00000110245 | Apolipoprotein C-III |
| APOC4 | ENSG00000267467 | Apolipoprotein C-IV |
| APOC4-APOC2 | ENSG00000224916 | APOC4-APOC2 readthrough (NMD candidate) |
| APOD | ENSG00000189058 | Apolipoprotein D |
| APOE | ENSG00000130203 | Apolipoprotein E |
| APOF | ENSG00000175336 | Apolipoprotein F |
| APOH | ENSG00000091583 | Apolipoprotein H (beta-2-glycoprotein I) |
| APOL1 | ENSG00000100342 | Apolipoprotein L, 1 |
| APOL3 | ENSG00000128284 | Apolipoprotein L, 3 |
| APOM | ENSG00000204444 | Apolipoprotein M |
| APOOL | ENSG00000155008 | Apolipoprotein O-like |
| ARCN1 | ENSG00000095139 | Archain 1 |
| ARFIP2 | ENSG00000132254 | ADP-ribosylation factor interacting protein 2 |
| ARHGAP36 | ENSG00000147256 | Rho GTPase activating protein 36 |
| ARHGAP6 | ENSG00000047648 | Rho GTPase activating protein 6 |
| ARHGEF4 | ENSG00000136002 | Rho guanine nucleotide exchange factor (GEF) 4 |
| ARL16 | ENSG00000214087 | ADP-ribosylation factor-like 16 |
| ARMC5 | ENSG00000140691 | Armadillo repeat containing 5 |
| ARNTL | ENSG00000133794 | Aryl hydrocarbon receptor nuclear translocator-like |
| ARSA | ENSG00000100299 | Arylsulfatase A |
| ARSB | ENSG00000113273 | Arylsulfatase B |
| ARSE | ENSG00000157399 | Arylsulfatase E (chondrodysplasia punctata 1) |
| ARSG | ENSG00000141337 | Arylsulfatase G |
| ARSI | ENSG00000183876 | Arylsulfatase family, member I |
| ARSK | ENSG00000164291 | Arylsulfatase family, member K |
| ART3 | ENSG00000156219 | ADP-ribosyltransferase 3 |
| ART4 | ENSG00000111339 | ADP-ribosyltransferase 4 (Dombrock blood group) |
| ART5 | ENSG00000167311 | ADP-ribosyltransferase 5 |
| ARTN | ENSG00000117407 | Artemin |
| ASAH1 | ENSG00000104763 | N-acylsphingosine amidohydrolase (acid ceramidase) 1 |
| ASAH2 | ENSG00000188611 | N-acylsphingosine amidohydrolase (non-lysosomal ceramidase) 2 |
| ASCL1 | ENSG00000139352 | Achaete-scute family bHLH transcription factor 1 |
| ASIP | ENSG00000101440 | Agouti signaling protein |
| ASPN | ENSG00000106819 | Asporin |
| ASTL | ENSG00000188886 | Astacin-like metallo-endopeptidase (M12 family) |
| ATAD5 | ENSG00000176208 | ATPase family, AAA domain containing 5 |
| ATAT1 | ENSG00000137343 | Alpha tubulin acetyltransferase 1 |
| ATG2A | ENSG00000110046 | Autophagy related 2A |
| ATG5 | ENSG00000057663 | Autophagy related 5 |
| ATMIN | ENSG00000166454 | ATM interactor |
| ATP13A1 | ENSG00000105726 | ATPase type 13A1 |
| ATP5F1 | ENSG00000116459 | ATP synthase, H+ transporting, mitochondrial Fo complex, subunit B1 |
| ATP6AP1 | ENSG00000071553 | ATPase, H+ transporting, lysosomal accessory protein 1 |
| ATP6AP2 | ENSG00000182220 | ATPase, H+ transporting, lysosomal accessory protein 2 |
| ATPAF1 | ENSG00000123472 | ATP synthase mitochondrial F1 complex assembly factor 1 |
| AUH | ENSG00000148090 | AU RNA binding protein/enoyl-CoA hydratase |
| AVP | ENSG00000101200 | Arginine vasopressin |
| AXIN2 | ENSG00000168646 | Axin 2 |
| AZGP1 | ENSG00000160862 | Alpha-2-glycoprotein 1, zinc-binding |
| AZU1 | ENSG00000172232 | Azurocidin 1 |
| B2M | ENSG00000166710 | Beta-2-microglobulin |
| B3GALNT1 | ENSG00000169255 | Beta-1,3-N-acetylgalactosaminyltransferase 1 (globoside blood group) |
| B3GALNT2 | ENSG00000162885 | Beta-1,3-N-acetylgalactosaminyltransferase 2 |
| B3GALT1 | ENSG00000172318 | UDP-Gal:betaGlcNAc beta 1,3-galactosyltransferase, polypeptide 1 |
| B3GALT4 | ENSG00000235863 | UDP-Gal:betaGlcNAc beta 1,3-galactosyltransferase, polypeptide 4 |
| B3GALT5 | ENSG00000183778 | UDP-Gal:betaGlcNAc beta 1,3-galactosyltransferase, polypeptide 5 |
| B3GALT6 | ENSG00000176022 | UDP-Gal:betaGal beta 1,3-galactosyltransferase polypeptide 6 |
| B3GAT3 | ENSG00000149541 | Beta-1,3-glucuronyltransferase 3 |
| B3GLCT | ENSG00000187676 | Beta 3-glucosyltransferase |
| B3GNT3 | ENSG00000179913 | UDP-GlcNAc:betaGal beta-1,3-N-acetylglucosaminyltransferase 3 |
| B3GNT4 | ENSG00000176383 | UDP-GlcNAc:betaGal beta-1,3-N-acetylglucosaminyltransferase 4 |
| B3GNT6 | ENSG00000198488 | UDP-GlcNAc:betaGal beta-1,3-N-acetylglucosaminyltransferase 6 |
| B3GNT7 | ENSG00000156966 | UDP-GlcNAc:betaGal beta-1,3-N-acetylglucosaminyltransferase 7 |
| B3GNT8 | ENSG00000177191 | UDP-GlcNAc:betaGal beta-1,3-N-acetylglucosaminyltransferase 8 |
| B3GNT9 | ENSG00000237172 | UDP-GlcNAc:betaGal beta-1,3-N-acetylglucosaminyltransferase 9 |

TABLE 1-continued

Exemplary Human Secreted Proteins

| Gene | Ensembl ID | Gene description |
|---|---|---|
| B4GALNT1 | ENSG00000135454 | Beta-1,4-N-acetyl-galactosaminyl transferase 1 |
| B4GALNT3 | ENSG00000139044 | Beta-1,4-N-acetyl-galactosaminyl transferase 3 |
| B4GALNT4 | ENSG00000182272 | Beta-1,4-N-acetyl-galactosaminyl transferase 4 |
| B4GALT4 | ENSG00000121578 | UDP-Gal:betaGlcNAc beta 1,4-galactosyltransferase, polypeptide 4 |
| B4GALT5 | ENSG00000158470 | UDP-Gal:betaGlcNAc beta 1,4-galactosyltransferase, polypeptide 5 |
| B4GALT6 | ENSG00000118276 | UDP-Gal:betaGlcNAc beta 1,4-galactosyltransferase, polypeptide 6 |
| B4GAT1 | ENSG00000174684 | Beta-1,4-glucuronyltransferase 1 |
| B9D1 | ENSG00000108641 | B9 protein domain 1 |
| BACE2 | ENSG00000182240 | Beta-site APP-cleaving enzyme 2 |
| BAGE5 | ENSG00000279973 | B melanoma antigen family, member 5 |
| BCAM | ENSG00000187244 | Basal cell adhesion molecule (Lutheran blood group) |
| BCAN | ENSG00000132692 | Brevican |
| BCAP29 | ENSG00000075790 | B-cell receptor-associated protein 29 |
| BCAR1 | ENSG00000050820 | Breast cancer anti-estrogen resistance 1 |
| BCHE | ENSG00000114200 | Butyrylcholinesterase |
| BCKDHB | ENSG00000083123 | Branched chain keto acid dehydrogenase E1, beta polypeptide |
| BDNF | ENSG00000176697 | Brain-derived neurotrophic factor |
| BGLAP | ENSG00000242252 | Bone gamma-carboxyglutamate (gla) protein |
| BGN | ENSG00000182492 | Biglycan |
| BLVRB | ENSG00000090013 | Biliverdin reductase B |
| BMP1 | ENSG00000168487 | Bone morphogenetic protein 1 |
| BMP10 | ENSG00000163217 | Bone morphogenetic protein 10 |
| BMP15 | ENSG00000130385 | Bone morphogenetic protein 15 |
| BMP2 | ENSG00000125845 | Bone morphogenetic protein 2 |
| BMP3 | ENSG00000152785 | Bone morphogenetic protein 3 |
| BMP4 | ENSG00000125378 | Bone morphogenetic protein 4 |
| BMP6 | ENSG00000153162 | Bone morphogenetic protein 6 |
| BMP7 | ENSG00000101144 | Bone morphogenetic protein 7 |
| BMP8A | ENSG00000183682 | Bone morphogenetic protein 8a |
| BMP8B | ENSG00000116985 | Bone morphogenetic protein 8b |
| BMPER | ENSG00000164619 | BMP binding endothelial regulator |
| BNC1 | ENSG00000169594 | Basonuclin 1 |
| BOC | ENSG00000144857 | BOC cell adhesion associated, oncogene regulated |
| BOD1 | ENSG00000145919 | Biorientation of chromosomes in cell division 1 |
| BOLA1 | ENSG00000178096 | BolA family member 1 |
| BPI | ENSG00000101425 | Bactericidal/permeability-increasing protein |
| BPIFA1 | ENSG00000198183 | BPI fold containing family A, member 1 |
| BPIFA2 | ENSG00000131050 | BPI fold containing family A, member 2 |
| BPIFA3 | ENSG00000131059 | BPI fold containing family A, member 3 |
| BPIFB1 | ENSG00000125999 | BPI fold containing family B, member 1 |
| BPIFB2 | ENSG00000078898 | BPI fold containing family B, member 2 |
| BPIFB3 | ENSG00000186190 | BPI fold containing family B, member 3 |
| BPIFB4 | ENSG00000186191 | BPI fold containing family B, member 4 |
| BPIFB6 | ENSG00000167104 | BPI fold containing family B, member 6 |
| BPIFC | ENSG00000184459 | BPI fold containing family C |
| BRF1 | ENSG00000185024 | BRF1, RNA polymerase III transcription initiation factor 90 kDa subunit |
| BRINP1 | ENSG00000078725 | Bone morphogenetic protein/retinoic acid inducible neural-specific 1 |
| BRINP2 | ENSG00000198797 | Bone morphogenetic protein/retinoic acid inducible neural-specific 2 |
| BRINP3 | ENSG00000162670 | Bone morphogenetic protein/retinoic acid inducible neural-specific 3 |
| BSG | ENSG00000172270 | Basigin (Ok blood group) |
| BSPH1 | ENSG00000188334 | Binder of sperm protein homolog 1 |
| BST1 | ENSG00000109743 | Bone marrow stromal cell antigen 1 |
| BTBD17 | ENSG00000204347 | BTB (POZ) domain containing 17 |
| BTD | ENSG00000169814 | Biotinidase |
| BTN2A2 | ENSG00000124508 | Butyrophilin, subfamily 2, member A2 |
| BTN3A1 | ENSG00000026950 | Butyrophilin, subfamily 3, member A1 |
| BTN3A2 | ENSG00000186470 | Butyrophilin, subfamily 3, member A2 |
| BTN3A3 | ENSG00000111801 | Butyrophilin, subfamily 3, member A3 |
| C10orf10 | ENSG00000165507 | Chromosome 10 open reading frame 10 |
| C10orf99 | ENSG00000188373 | Chromosome 10 open reading frame 99 |
| C11orf1 | ENSG00000137720 | Chromosome 11 open reading frame 1 |
| C11orf24 | ENSG00000171067 | Chromosome 11 open reading frame 24 |
| C11orf45 | ENSG00000174370 | Chromosome 11 open reading frame 45 |
| C11orf94 | ENSG00000234776 | Chromosome 11 open reading frame 94 |
| C12orf10 | ENSG00000139637 | Chromosome 12 open reading frame 10 |
| C12orf49 | ENSG00000111412 | Chromosome 12 open reading frame 49 |
| C12orf73 | ENSG00000204954 | Chromosome 12 open reading frame 73 |
| C12orf76 | ENSG00000174456 | Chromosome 12 open reading frame 76 |
| C14orf80 | ENSG00000185347 | Chromosome 14 open reading frame 80 |

TABLE 1-continued

Exemplary Human Secreted Proteins

| Gene | Ensembl ID | Gene description |
| --- | --- | --- |
| C14orf93 | ENSG00000100802 | Chromosome 14 open reading frame 93 |
| C16orf89 | ENSG00000153446 | Chromosome 16 open reading frame 89 |
| C16orf90 | ENSG00000215131 | Chromosome 16 open reading frame 90 |
| C17orf67 | ENSG00000214226 | Chromosome 17 open reading frame 67 |
| C17orf75 | ENSG00000108666 | Chromosome 17 open reading frame 75 |
| C17orf99 | ENSG00000187997 | Chromosome 17 open reading frame 99 |
| C18orf54 | ENSG00000166845 | Chromosome 18 open reading frame 54 |
| C19orf47 | ENSG00000160392 | Chromosome 19 open reading frame 47 |
| C19orf70 | ENSG00000174917 | Chromosome 19 open reading frame 70 |
| C19orf80 | ENSG00000130173 | Chromosome 19 open reading frame 80 |
| C1GALT1 | ENSG00000106392 | Core 1 synthase, glycoprotein-N-acetylgalactosamine 3-beta-galactosyltransferase 1 |
| C1orf127 | ENSG00000175262 | Chromosome 1 open reading frame 127 |
| C1orf159 | ENSG00000131591 | Chromosome 1 open reading frame 159 |
| C1orf198 | ENSG00000119280 | Chromosome 1 open reading frame 198 |
| C1orf234 | ENSG00000227868 | Chromosome 1 open reading frame 234 |
| C1orf54 | ENSG00000118292 | Chromosome 1 open reading frame 54 |
| C1orf56 | ENSG00000143443 | Chromosome 1 open reading frame 56 |
| C1QA | ENSG00000173372 | Complement component 1, q subcomponent, A chain |
| C1QB | ENSG00000173369 | Complement component 1, q subcomponent, B chain |
| C1QC | ENSG00000159189 | Complement component 1, q subcomponent, C chain |
| C1QL1 | ENSG00000131094 | Complement component 1, q subcomponent-like 1 |
| C1QL2 | ENSG00000144119 | Complement component 1, q subcomponent-like 2 |
| C1QL3 | ENSG00000165985 | Complement component 1, q subcomponent-like 3 |
| C1QL4 | ENSG00000186897 | Complement component 1, q subcomponent-like 4 |
| C1QTNF1 | ENSG00000173918 | C1q and tumor necrosis factor related protein 1 |
| C1QTNF2 | ENSG00000145861 | C1q and tumor necrosis factor related protein 2 |
| C1QTNF3 | ENSG00000082196 | C1q and tumor necrosis factor related protein 3 |
| C1QTNF4 | ENSG00000172247 | C1q and tumor necrosis factor related protein 4 |
| C1QTNF5 | ENSG00000223953 | C1q and tumor necrosis factor related protein 5 |
| C1QTNF7 | ENSG00000163145 | C1q and tumor necrosis factor related protein 7 |
| C1QTNF8 | ENSG00000184471 | C1q and tumor necrosis factor related protein 8 |
| C1QTNF9 | ENSG00000240654 | C1q and tumor necrosis factor related protein 9 |
| C1QTNF9B | ENSG00000205863 | C1q and tumor necrosis factor related protein 9B |
| C1R | ENSG00000159403 | Complement component 1, r subcomponent |
| C1RL | ENSG00000139178 | Complement component 1, r subcomponent-like |
| C1S | ENSG00000182326 | Complement component 1, s subcomponent |
| C2 | ENSG00000166278 | Complement component 2 |
| C21orf33 | ENSG00000160221 | Chromosome 21 open reading frame 33 |
| C21orf62 | ENSG00000205929 | Chromosome 21 open reading frame 62 |
| C22orf15 | ENSG00000169314 | Chromosome 22 open reading frame 15 |
| C22orf46 | ENSG00000184208 | Chromosome 22 open reading frame 46 |
| C2CD2 | ENSG00000157617 | C2 calcium-dependent domain containing 2 |
| C2orf40 | ENSG00000119147 | Chromosome 2 open reading frame 40 |
| C2orf66 | ENSG00000187944 | Chromosome 2 open reading frame 66 |
| C2orf69 | ENSG00000178074 | Chromosome 2 open reading frame 69 |
| C2orf78 | ENSG00000187833 | Chromosome 2 open reading frame 78 |
| C3 | ENSG00000125730 | Complement component 3 |
| C3orf33 | ENSG00000174928 | Chromosome 3 open reading frame 33 |
| C3orf58 | ENSG00000181744 | Chromosome 3 open reading frame 58 |
| C4A | ENSG00000244731 | Complement component 4A (Rodgers blood group) |
| C4B | ENSG00000224389 | Complement component 4B (Chido blood group) |
| C4BPA | ENSG00000123838 | Complement component 4 binding protein, alpha |
| C4BPB | ENSG00000123843 | Complement component 4 binding protein, beta |
| C4orf26 | ENSG00000174792 | Chromosome 4 open reading frame 26 |
| C4orf48 | ENSG00000243449 | Chromosome 4 open reading frame 48 |
| C5 | ENSG00000106804 | Complement component 5 |
| C5orf46 | ENSG00000178776 | Chromosome 5 open reading frame 46 |
| C6 | ENSG00000039537 | Complement component 6 |
| C6orf120 | ENSG00000185127 | Chromosome 6 open reading frame 120 |
| C6orf15 | ENSG00000204542 | Chromosome 6 open reading frame 15 |
| C6orf25 | ENSG00000204420 | Chromosome 6 open reading frame 25 |
| C6orf58 | ENSG00000184530 | Chromosome 6 open reading frame 58 |
| C7 | ENSG00000112936 | Complement component 7 |
| C7orf57 | ENSG00000164746 | Chromosome 7 open reading frame 57 |
| C7orf73 | ENSG00000243317 | Chromosome 7 open reading frame 73 |
| C8A | ENSG00000157131 | Complement component 8, alpha polypeptide |
| C8B | ENSG00000021852 | Complement component 8, beta polypeptide |
| C8G | ENSG00000176919 | Complement component 8, gamma polypeptide |
| C9 | ENSG00000113600 | Complement component 9 |
| C9orf47 | ENSG00000186354 | Chromosome 9 open reading frame 47 |
| CA10 | ENSG00000154975 | Carbonic anhydrase X |
| CA11 | ENSG00000063180 | Carbonic anhydrase XI |
| CA6 | ENSG00000131686 | Carbonic anhydrase VI |
| CA9 | ENSG00000107159 | Carbonic anhydrase IX |
| CABLES1 | ENSG00000134508 | Cdk5 and Abl enzyme substrate 1 |

TABLE 1-continued

| Gene | Ensembl ID | Gene description |
|---|---|---|
| CABP1 | ENSG00000157782 | Calcium binding protein 1 |
| CACNA2D1 | ENSG00000153956 | Calcium channel, voltage-dependent, alpha 2/delta subunit 1 |
| CACNA2D4 | ENSG00000151062 | Calcium channel, voltage-dependent, alpha 2/delta subunit 4 |
| CADM3 | ENSG00000162706 | Cell adhesion molecule 3 |
| CALCA | ENSG00000110680 | Calcitonin-related polypeptide alpha |
| CALCB | ENSG00000175868 | Calcitonin-related polypeptide beta |
| CALCR | ENSG00000004948 | Calcitonin receptor |
| CALCRL | ENSG00000064989 | Calcitonin receptor-like |
| CALR | ENSG00000179218 | Calreticulin |
| CALR3 | ENSG00000269058 | Calreticulin 3 |
| CALU | ENSG00000128595 | Calumenin |
| CAMK2D | ENSG00000145349 | Calcium/calmodulin-dependent protein kinase II delta |
| CAMP | ENSG00000164047 | Cathelicidin antimicrobial peptide |
| CANX | ENSG00000127022 | Calnexin |
| CARKD | ENSG00000213995 | Carbohydrate kinase domain containing |
| CARM1 | ENSG00000142453 | Coactivator-associated arginine methyltransferase 1 |
| CARNS1 | ENSG00000172508 | Carnosine synthase 1 |
| CARTPT | ENSG00000164326 | CART prepropeptide |
| CASQ1 | ENSG00000143318 | Calsequestrin 1 (fast-twitch, skeletal muscle) |
| CASQ2 | ENSG00000118729 | Calsequestrin 2 (cardiac muscle) |
| CATSPERG | ENSG00000099338 | Catsper channel auxiliary subunit gamma |
| CBLN1 | ENSG00000102924 | Cerebellin 1 precursor |
| CBLN2 | ENSG00000141668 | Cerebellin 2 precursor |
| CBLN3 | ENSG00000139899 | Cerebellin 3 precursor |
| CBLN4 | ENSG00000054803 | Cerebellin 4 precursor |
| CCBE1 | ENSG00000183287 | Collagen and calcium binding EGF domains 1 |
| CCDC108 | ENSG00000181378 | Coiled-coil domain containing 108 |
| CCDC112 | ENSG00000164221 | Coiled-coil domain containing 112 |
| CCDC129 | ENSG00000180347 | Coiled-coil domain containing 129 |
| CCDC134 | ENSG00000100147 | Coiled-coil domain containing 134 |
| CCDC149 | ENSG00000181982 | Coiled-coil domain containing 149 |
| CCDC3 | ENSG00000151468 | Coiled-coil domain containing 3 |
| CCDC80 | ENSG00000091986 | Coiled-coil domain containing 80 |
| CCDC85A | ENSG00000055813 | Coiled-coil domain containing 85A |
| CCDC88B | ENSG00000168071 | Coiled-coil domain containing 88B |
| CCER2 | ENSG00000262484 | Coiled-coil glutamate-rich protein 2 |
| CCK | ENSG00000187094 | Cholecystokinin |
| CCL1 | ENSG00000108702 | Chemokine (C-C motif) ligand 1 |
| CCL11 | ENSG00000172156 | Chemokine (C-C motif) ligand 11 |
| CCL13 | ENSG00000181374 | Chemokine (C-C motif) ligand 13 |
| CCL14 | ENSG00000276409 | Chemokine (C-C motif) ligand 14 |
| CCL15 | ENSG00000275718 | Chemokine (C-C motif) ligand 15 |
| CCL16 | ENSG00000275152 | Chemokine (C-C motif) ligand 16 |
| CCL17 | ENSG00000102970 | Chemokine (C-C motif) ligand 17 |
| CCL18 | ENSG00000275385 | Chemokine (C-C motif) ligand 18 (pulmonary and activation-regulated) |
| CCL19 | ENSG00000172724 | Chemokine (C-C motif) ligand 19 |
| CCL2 | ENSG00000108691 | Chemokine (C-C motif) ligand 2 |
| CCL20 | ENSG00000115009 | Chemokine (C-C motif) ligand 20 |
| CCL21 | ENSG00000137077 | Chemokine (C-C motif) ligand 21 |
| CCL22 | ENSG00000102962 | Chemokine (C-C motif) ligand 22 |
| CCL23 | ENSG00000274736 | Chemokine (C-C motif) ligand 23 |
| CCL24 | ENSG00000106178 | Chemokine (C-C motif) ligand 24 |
| CCL25 | ENSG00000131142 | Chemokine (C-C motif) ligand 25 |
| CCL26 | ENSG00000006606 | Chemokine (C-C motif) ligand 26 |
| CCL27 | ENSG00000213927 | Chemokine (C-C motif) ligand 27 |
| CCL28 | ENSG00000151882 | Chemokine (C-C motif) ligand 28 |
| CCL3 | ENSG00000277632 | Chemokine (C-C motif) ligand 3 |
| CCL3L3 | ENSG00000276085 | Chemokine (C-C motif) ligand 3-like 3 |
| CCL4 | ENSG00000275302 | Chemokine (C-C motif) ligand 4 |
| CCL4L2 | ENSG00000276070 | Chemokine (C-C motif) ligand 4-like 2 |
| CCL5 | ENSG00000271503 | Chemokine (C-C motif) ligand 5 |
| CCL7 | ENSG00000108688 | Chemokine (C-C motif) ligand 7 |
| CCL8 | ENSG00000108700 | Chemokine (C-C motif) ligand 8 |
| CCNB1IP1 | ENSG00000100814 | Cyclin B1 interacting protein 1, E3 ubiquitin protein ligase |
| CCNL1 | ENSG00000163660 | Cyclin L1 |
| CCNL2 | ENSG00000221978 | Cyclin L2 |
| CD14 | ENSG00000170458 | CD14 molecule |
| CD160 | ENSG00000117281 | CD160 molecule |
| CD164 | ENSG00000135535 | CD164 molecule, sialomucin |
| CD177 | ENSG00000204936 | CD177 molecule |
| CD1E | ENSG00000158488 | CD1e molecule |
| CD2 | ENSG00000116824 | CD2 molecule |
| CD200 | ENSG00000091972 | CD200 molecule |
| CD200R1 | ENSG00000163606 | CD200 receptor 1 |
| CD22 | ENSG00000012124 | CD22 molecule |

TABLE 1-continued

Exemplary Human Secreted Proteins

| Gene | Ensembl ID | Gene description |
|---|---|---|
| CD226 | ENSG00000150637 | CD226 molecule |
| CD24 | ENSG00000272398 | CD24 molecule |
| CD276 | ENSG00000103855 | CD276 molecule |
| CD300A | ENSG00000167851 | CD300a molecule |
| CD300LB | ENSG00000178789 | CD300 molecule-like family member b |
| CD300LF | ENSG00000186074 | CD300 molecule-like family member f |
| CD300LG | ENSG00000161649 | CD300 molecule-like family member g |
| CD3D | ENSG00000167286 | CD3d molecule, delta (CD3-TCR complex) |
| CD4 | ENSG00000010610 | CD4 molecule |
| CD40 | ENSG00000101017 | CD40 molecule, TNF receptor superfamily member 5 |
| CD44 | ENSG00000026508 | CD44 molecule (Indian blood group) |
| CD48 | ENSG00000117091 | CD48 molecule |
| CD5 | ENSG00000110448 | CD5 molecule |
| CD55 | ENSG00000196352 | CD55 molecule, decay accelerating factor for complement (Cromer blood group) |
| CD59 | ENSG00000085063 | CD59 molecule, complement regulatory protein |
| CD5L | ENSG00000073754 | CD5 molecule-like |
| CD6 | ENSG00000013725 | CD6 molecule |
| CD68 | ENSG00000129226 | CD68 molecule |
| CD7 | ENSG00000173762 | CD7 molecule |
| CD79A | ENSG00000105369 | CD79a molecule, immunoglobulin-associated alpha |
| CD80 | ENSG00000121594 | CD80 molecule |
| CD86 | ENSG00000114013 | CD86 molecule |
| CD8A | ENSG00000153563 | CD8a molecule |
| CD8B | ENSG00000172116 | CD8b molecule |
| CD99 | ENSG00000002586 | CD99 molecule |
| CDC23 | ENSG00000094880 | Cell division cycle 23 |
| CDC40 | ENSG00000168438 | Cell division cycle 40 |
| CDC45 | ENSG00000093009 | Cell division cycle 45 |
| CDCP1 | ENSG00000163814 | CUB domain containing protein 1 |
| CDCP2 | ENSG00000157211 | CUB domain containing protein 2 |
| CDH1 | ENSG00000039068 | Cadherin 1, type 1 |
| CDH11 | ENSG00000140937 | Cadherin 11, type 2, OB-cadherin (osteoblast) |
| CDH13 | ENSG00000140945 | Cadherin 13 |
| CDH17 | ENSG00000079112 | Cadherin 17, LI cadherin (liver-intestine) |
| CDH18 | ENSG00000145526 | Cadherin 18, type 2 |
| CDH19 | ENSG00000071991 | Cadherin 19, type 2 |
| CDH23 | ENSG00000107736 | Cadherin-related 23 |
| CDH5 | ENSG00000179776 | Cadherin 5, type 2 (vascular endothelium) |
| CDHR1 | ENSG00000148600 | Cadherin-related family member 1 |
| CDHR4 | ENSG00000187492 | Cadherin-related family member 4 |
| CDHR5 | ENSG00000099834 | Cadherin-related family member 5 |
| CDKN2A | ENSG00000147889 | Cyclin-dependent kinase inhibitor 2A |
| CDNF | ENSG00000185267 | Cerebral dopamine neurotrophic factor |
| CDON | ENSG00000064309 | Cell adhesion associated, oncogene regulated |
| CDSN | ENSG00000204539 | Corneodesmosin |
| CEACAM16 | ENSG00000213892 | Carcinoembryonic antigen-related cell adhesion molecule 16 |
| CEACAM18 | ENSG00000213822 | Carcinoembryonic antigen-related cell adhesion molecule 18 |
| CEACAM19 | ENSG00000186567 | Carcinoembryonic antigen-related cell adhesion molecule 19 |
| CEACAM5 | ENSG00000105388 | Carcinoembryonic antigen-related cell adhesion molecule 5 |
| CEACAM7 | ENSG00000007306 | Carcinoembryonic antigen-related cell adhesion molecule 7 |
| CEACAM8 | ENSG00000124469 | Carcinoembryonic antigen-related cell adhesion molecule 8 |
| CECR1 | ENSG00000093072 | Cat eye syndrome chromosome region, candidate 1 |
| CECR5 | ENSG00000069998 | Cat eye syndrome chromosome region, candidate 5 |
| CEL | ENSG00000170835 | Carboxyl ester lipase |
| CELA2A | ENSG00000142615 | Chymotrypsin-like elastase family, member 2A |
| CELA2B | ENSG00000215704 | Chymotrypsin-like elastase family, member 2B |
| CELA3A | ENSG00000142789 | Chymotrypsin-like elastase family, member 3A |
| CELA3B | ENSG00000219073 | Chymotrypsin-like elastase family, member 3B |
| CEMIP | ENSG00000103888 | Cell migration inducing protein, hyaluronan binding |
| CEP89 | ENSG00000121289 | Centrosomal protein 89 kDa |
| CER1 | ENSG00000147869 | Cerberus 1, DAN family BMP antagonist |
| CERCAM | ENSG00000167123 | Cerebral endothelial cell adhesion molecule |
| CERS1 | ENSG00000223802 | Ceramide synthase 1 |
| CES1 | ENSG00000198848 | Carboxylesterase 1 |
| CES3 | ENSG00000172828 | Carboxylesterase 3 |
| CES4A | ENSG00000172824 | Carboxylesterase 4A |
| CES5A | ENSG00000159398 | Carboxylesterase 5A |
| CETP | ENSG00000087237 | Cholesteryl ester transfer protein, plasma |
| CFB | ENSG00000243649 | Complement factor B |
| CFC1 | ENSG00000136698 | Cripto, FRL-1, cryptic family 1 |
| CFC1B | ENSG00000152093 | Cripto, FRL-1, cryptic family 1B |
| CFD | ENSG00000197766 | Complement factor D (adipsin) |
| CFDP1 | ENSG00000153774 | Craniofacial development protein 1 |
| CFH | ENSG00000000971 | Complement factor H |
| CFHR1 | ENSG00000244414 | Complement factor H-related 1 |

TABLE 1-continued

Exemplary Human Secreted Proteins

| Gene | Ensembl ID | Gene description |
|---|---|---|
| CFHR2 | ENSG00000080910 | Complement factor H-related 2 |
| CFHR3 | ENSG00000116785 | Complement factor H-related 3 |
| CFHR4 | ENSG00000134365 | Complement factor H-related 4 |
| CFHR5 | ENSG00000134389 | Complement factor H-related 5 |
| CFI | ENSG00000205403 | Complement factor I |
| CFP | ENSG00000126759 | Complement factor properdin |
| CGA | ENSG00000135346 | Glycoprotein hormones, alpha polypeptide |
| CGB | ENSG00000104827 | Chorionic gonadotropin, beta polypeptide |
| CGB1 | ENSG00000267631 | Chorionic gonadotropin, beta polypeptide 1 |
| CGB2 | ENSG00000104818 | Chorionic gonadotropin, beta polypeptide 2 |
| CGB5 | ENSG00000189052 | Chorionic gonadotropin, beta polypeptide 5 |
| CGB7 | ENSG00000196337 | Chorionic gonadotropin, beta polypeptide 7 |
| CGB8 | ENSG00000213030 | Chorionic gonadotropin, beta polypeptide 8 |
| CGREF1 | ENSG00000138028 | Cell growth regulator with EF-hand domain 1 |
| CH507-9B2.3 | ENSG00000280071 | |
| CHAD | ENSG00000136457 | Chondroadherin |
| CHADL | ENSG00000100399 | Chondroadherin-like |
| CHEK2 | ENSG00000183765 | Checkpoint kinase 2 |
| CHGA | ENSG00000100604 | Chromogranin A |
| CHGB | ENSG00000089199 | Chromogranin B |
| CHI3L1 | ENSG00000133048 | Chitinase 3-like 1 (cartilage glycoprotein-39) |
| CHI3L2 | ENSG00000064886 | Chitinase 3-like 2 |
| CHIA | ENSG00000134216 | Chitinase, acidic |
| CHID1 | ENSG00000177830 | Chitinase domain containing 1 |
| CHIT1 | ENSG00000133063 | Chitinase 1 (chitotriosidase) |
| CHL1 | ENSG00000134121 | Cell adhesion molecule L1-like |
| CHN1 | ENSG00000128656 | Chimerin 1 |
| CHPF | ENSG00000123989 | Chondroitin polymerizing factor |
| CHPF2 | ENSG00000033100 | Chondroitin polymerizing factor 2 |
| CHRD | ENSG00000090539 | Chordin |
| CHRDL1 | ENSG00000101938 | Chordin-like 1 |
| CHRDL2 | ENSG00000054938 | Chordin-like 2 |
| CHRNA2 | ENSG00000120903 | Cholinergic receptor, nicotinic, alpha 2 (neuronal) |
| CHRNA5 | ENSG00000169684 | Cholinergic receptor, nicotinic, alpha 5 (neuronal) |
| CHRNB1 | ENSG00000170175 | Cholinergic receptor, nicotinic, beta 1 (muscle) |
| CHRND | ENSG00000135902 | Cholinergic receptor, nicotinic, delta (muscle) |
| CHST1 | ENSG00000175264 | Carbohydrate (keratan sulfate Gal-6) sulfotransferase 1 |
| CHST10 | ENSG00000115526 | Carbohydrate sulfotransferase 10 |
| CHST11 | ENSG00000171310 | Carbohydrate (chondroitin 4) sulfotransferase 11 |
| CHST13 | ENSG00000180767 | Carbohydrate (chondroitin 4) sulfotransferase 13 |
| CHST4 | ENSG00000140835 | Carbohydrate (N-acetylglucosamine 6-O) sulfotransferase 4 |
| CHST5 | ENSG00000135702 | Carbohydrate (N-acetylglucosamine 6-O) sulfotransferase 5 |
| CHST6 | ENSG00000183196 | Carbohydrate (N-acetylglucosamine 6-O) sulfotransferase 6 |
| CHST7 | ENSG00000147119 | Carbohydrate (N-acetylglucosamine 6-O) sulfotransferase 7 |
| CHST8 | ENSG00000124302 | Carbohydrate (N-acetylgalactosamine 4-0) sulfotransferase 8 |
| CHSY1 | ENSG00000131873 | Chondroitin sulfate synthase 1 |
| CHSY3 | ENSG00000198108 | Chondroitin sulfate synthase 3 |
| CHTF8 | ENSG00000168802 | Chromosome transmission fidelity factor 8 |
| CILP | ENSG00000138615 | Cartilage intermediate layer protein, nucleotide pyrophosphohydrolase |
| CILP2 | ENSG00000160161 | Cartilage intermediate layer protein 2 |
| CIRH1A | ENSG00000141076 | Cirrhosis, autosomal recessive 1A (cirhin) |
| CKLF | ENSG00000217555 | Chemokine-like factor |
| CKMT1A | ENSG00000223572 | Creatine kinase, mitochondrial 1A |
| CKMT1B | ENSG00000237289 | Creatine kinase, mitochondrial 1B |
| CLCA1 | ENSG00000016490 | Chloride channel accessory 1 |
| CLCF1 | ENSG00000175505 | Cardiotrophin-like cytokine factor 1 |
| CLDN15 | ENSG00000106404 | Claudin 15 |
| CLDN7 | ENSG00000181885 | Claudin 7 |
| CLDND1 | ENSG00000080822 | Claudin domain containing 1 |
| CLEC11A | ENSG00000105472 | C-type lectin domain family 11, member A |
| CLEC16A | ENSG00000038532 | C-type lectin domain family 16, member A |
| CLEC18A | ENSG00000157322 | C-type lectin domain family 18, member A |
| CLEC18B | ENSG00000140839 | C-type lectin domain family 18, member B |
| CLEC18C | ENSG00000157335 | C-type lectin domain family 18, member C |
| CLEC19A | ENSG00000261210 | C-type lectin domain family 19, member A |
| CLEC2B | ENSG00000110852 | C-type lectin domain family 2, member B |
| CLEC3A | ENSG00000166509 | C-type lectin domain family 3, member A |
| CLEC3B | ENSG00000163815 | C-type lectin domain family 3, member B |
| CLGN | ENSG00000153132 | Calmegin |
| CLN5 | ENSG00000102805 | Ceroid-lipofuscinosis, neuronal 5 |
| CLPS | ENSG00000137392 | Colipase, pancreatic |
| CLPSL1 | ENSG00000204140 | Colipase-like 1 |
| CLPSL2 | ENSG00000196748 | Colipase-like 2 |
| CLPX | ENSG00000166855 | Caseinolytic mitochondrial matrix peptidase chaperone subunit |
| CLSTN3 | ENSG00000139182 | Calsyntenin 3 |

TABLE 1-continued

Exemplary Human Secreted Proteins

| Gene | Ensembl ID | Gene description |
| --- | --- | --- |
| CLU | ENSG00000120885 | Clusterin |
| CLUL1 | ENSG00000079101 | Clusterin-like 1 (retinal) |
| CMA1 | ENSG00000092009 | Chymase 1, mast cell |
| CMPK1 | ENSG00000162368 | Cytidine monophosphate (UMP-CMP) kinase 1, cytosolic |
| CNBD1 | ENSG00000176571 | Cyclic nucleotide binding domain containing 1 |
| CNDP1 | ENSG00000150656 | Carnosine dipeptidase 1 (metallopeptidase M20 family) |
| CNPY2 | ENSG00000257727 | Canopy FGF signaling regulator 2 |
| CNPY3 | ENSG00000137161 | Canopy FGF signaling regulator 3 |
| CNPY4 | ENSG00000166997 | Canopy FGF signaling regulator 4 |
| CNTFR | ENSG00000122756 | Ciliary neurotrophic factor receptor |
| CNTN1 | ENSG00000018236 | Contactin 1 |
| CNTN2 | ENSG00000184144 | Contactin 2 (axonal) |
| CNTN3 | ENSG00000113805 | Contactin 3 (plasmacytoma associated) |
| CNTN4 | ENSG00000144619 | Contactin 4 |
| CNTN5 | ENSG00000149972 | Contactin 5 |
| CNTNAP2 | ENSG00000174469 | Contactin associated protein-like 2 |
| CNTNAP3 | ENSG00000106714 | Contactin associated protein-like 3 |
| CNTNAP3B | ENSG00000154529 | Contactin associated protein-like 3B |
| COASY | ENSG00000068120 | CoA synthase |
| COCH | ENSG00000100473 | Cochlin |
| COG3 | ENSG00000136152 | Component of oligomeric golgi complex 3 |
| COL10A1 | ENSG00000123500 | Collagen, type X, alpha 1 |
| COL11A1 | ENSG00000060718 | Collagen, type XI, alpha 1 |
| COL11A2 | ENSG00000204248 | Collagen, type XI, alpha 2 |
| COL12A1 | ENSG00000111799 | Collagen, type XII, alpha 1 |
| COL14A1 | ENSG00000187955 | Collagen, type XIV, alpha 1 |
| COL15A1 | ENSG00000204291 | Collagen, type XV, alpha 1 |
| COL16A1 | ENSG00000084636 | Collagen, type XVI, alpha 1 |
| COL18A1 | ENSG00000182871 | Collagen, type XVIII, alpha 1 |
| COL19A1 | ENSG00000082293 | Collagen, type XIX, alpha 1 |
| COL1A1 | ENSG00000108821 | Collagen, type I, alpha 1 |
| COL1A2 | ENSG00000164692 | Collagen, type I, alpha 2 |
| COL20A1 | ENSG00000101203 | Collagen, type XX, alpha 1 |
| COL21A1 | ENSG00000124749 | Collagen, type XXI, alpha 1 |
| COL22A1 | ENSG00000169436 | Collagen, type XXII, alpha 1 |
| COL24A1 | ENSG00000171502 | Collagen, type XXIV, alpha 1 |
| COL26A1 | ENSG00000160963 | Collagen, type XXVI, alpha 1 |
| COL27A1 | ENSG00000196739 | Collagen, type XXVII, alpha 1 |
| COL28A1 | ENSG00000215018 | Collagen, type XXVIII, alpha 1 |
| COL2A1 | ENSG00000139219 | Collagen, type II, alpha 1 |
| COL3A1 | ENSG00000168542 | Collagen, type III, alpha 1 |
| COL4A1 | ENSG00000187498 | Collagen, type IV, alpha 1 |
| COL4A2 | ENSG00000134871 | Collagen, type IV, alpha 2 |
| COL4A3 | ENSG00000169031 | Collagen, type IV, alpha 3 (Goodpasture antigen) |
| COL4A4 | ENSG00000081052 | Collagen, type IV, alpha 4 |
| COL4A5 | ENSG00000188153 | Collagen, type IV, alpha 5 |
| COL4A6 | ENSG00000197565 | Collagen, type IV, alpha 6 |
| COL5A1 | ENSG00000130635 | Collagen, type V, alpha 1 |
| COL5A2 | ENSG00000204262 | Collagen, type V, alpha 2 |
| COL5A3 | ENSG00000080573 | Collagen, type V, alpha 3 |
| COL6A1 | ENSG00000142156 | Collagen, type VI, alpha 1 |
| COL6A2 | ENSG00000142173 | Collagen, type VI, alpha 2 |
| COL6A3 | ENSG00000163359 | Collagen, type VI, alpha 3 |
| COL6A5 | ENSG00000172752 | Collagen, type VI, alpha 5 |
| COL6A6 | ENSG00000206384 | Collagen, type VI, alpha 6 |
| COL7A1 | ENSG00000114270 | Collagen, type VII, alpha 1 |
| COL8A1 | ENSG00000144810 | Collagen, type VIII, alpha 1 |
| COL8A2 | ENSG00000171812 | Collagen, type VIII, alpha 2 |
| COL9A1 | ENSG00000112280 | Collagen, type IX, alpha 1 |
| COL9A2 | ENSG00000049089 | Collagen, type IX, alpha 2 |
| COL9A3 | ENSG00000092758 | Collagen, type IX, alpha 3 |
| COLEC10 | ENSG00000184374 | Collectin sub-family member 10 (C-type lectin) |
| COLEC11 | ENSG00000118004 | Collectin sub-family member 11 |
| COLGALT1 | ENSG00000130309 | Collagen beta(1-O)galactosyltransferase 1 |
| COLGALT2 | ENSG00000198756 | Collagen beta(1-O)galactosyltransferase 2 |
| COLQ | ENSG00000206561 | Collagen-like tail subunit (single strand of homotrimer) of asymmetric acetylcholinesterase |
| COMP | ENSG00000105664 | Cartilage oligomeric matrix protein |
| COPS6 | ENSG00000168090 | COP9 signalosome subunit 6 |
| COQ6 | ENSG00000119723 | Coenzyme Q6 monooxygenase |
| CORT | ENSG00000241563 | Cortistatin |
| CP | ENSG00000047457 | Ceruloplasmin (ferroxidase) |
| CPA1 | ENSG00000091704 | Carboxypeptidase A1 (pancreatic) |
| CPA2 | ENSG00000158516 | Carboxypeptidase A2 (pancreatic) |
| CPA3 | ENSG00000163751 | Carboxypeptidase A3 (mast cell) |
| CPA4 | ENSG00000128510 | Carboxypeptidase A4 |

TABLE 1-continued

Exemplary Human Secreted Proteins

| Gene | Ensembl ID | Gene description |
|---|---|---|
| CPA6 | ENSG00000165078 | Carboxypeptidase A6 |
| CPAMD8 | ENSG00000160111 | C3 and PZP-like, alpha-2-macroglobulin domain containing 8 |
| CPB1 | ENSG00000153002 | Carboxypeptidase B1 (tissue) |
| CPB2 | ENSG00000080618 | Carboxypeptidase B2 (plasma) |
| CPE | ENSG00000109472 | Carboxypeptidase E |
| CPM | ENSG00000135678 | Carboxypeptidase M |
| CPN1 | ENSG00000120054 | Carboxypeptidase N, polypeptide 1 |
| CPN2 | ENSG00000178772 | Carboxypeptidase N, polypeptide 2 |
| CPO | ENSG00000144410 | Carboxypeptidase O |
| CPQ | ENSG00000104324 | Carboxypeptidase Q |
| CPVL | ENSG00000106066 | Carboxypeptidase, vitellogenic-like |
| CPXM1 | ENSG00000088882 | Carboxypeptidase X (M14 family), member 1 |
| CPXM2 | ENSG00000121898 | Carboxypeptidase X (M14 family), member 2 |
| CPZ | ENSG00000109625 | Carboxypeptidase Z |
| CR1L | ENSG00000197721 | Complement component (3b/4b) receptor 1-like |
| CRB2 | ENSG00000148204 | Crumbs family member 2 |
| CREG1 | ENSG00000143162 | Cellular repressor of E1A-stimulated genes 1 |
| CREG2 | ENSG00000175874 | Cellular repressor of E1A-stimulated genes 2 |
| CRELD1 | ENSG00000163703 | Cysteine-rich with EGF-like domains 1 |
| CRELD2 | ENSG00000184164 | Cysteine-rich with EGF-like domains 2 |
| CRH | ENSG00000147571 | Corticotropin releasing hormone |
| CRHBP | ENSG00000145708 | Corticotropin releasing hormone binding protein |
| CRHR1 | ENSG00000120088 | Corticotropin releasing hormone receptor 1 |
| CRHR2 | ENSG00000106113 | Corticotropin releasing hormone receptor 2 |
| CRISP1 | ENSG00000124812 | Cysteine-rich secretory protein 1 |
| CRISP2 | ENSG00000124490 | Cysteine-rich secretory protein 2 |
| CRISP3 | ENSG00000096006 | Cysteine-rich secretory protein 3 |
| CRISPLD2 | ENSG00000103196 | Cysteine-rich secretory protein LCCL domain containing 2 |
| CRLF1 | ENSG00000006016 | Cytokine receptor-like factor 1 |
| CRP | ENSG00000132693 | C-reactive protein, pentraxin-related |
| CRTAC1 | ENSG00000095713 | Cartilage acidic protein 1 |
| CRTAP | ENSG00000170275 | Cartilage associated protein |
| CRY2 | ENSG00000121671 | Cryptochrome circadian clock 2 |
| CSAD | ENSG00000139631 | Cysteine sulfinic acid decarboxylase |
| CSF1 | ENSG00000184371 | Colony stimulating factor 1 (macrophage) |
| CSF1R | ENSG00000182578 | Colony stimulating factor 1 receptor |
| CSF2 | ENSG00000164400 | Colony stimulating factor 2 (granulocyte-macrophage) |
| CSF2RA | ENSG00000198223 | Colony stimulating factor 2 receptor, alpha, low-affinity (granulocyte-macrophage) |
| CSF3 | ENSG00000108342 | Colony stimulating factor 3 (granulocyte) |
| CSGALNACT1 | ENSG00000147408 | Chondroitin sulfate N-acetylgalactosaminyltransferase 1 |
| CSH1 | ENSG00000136488 | Chorionic somatomammotropin hormone 1 (placental lactogen) |
| CSH2 | ENSG00000213218 | Chorionic somatomammotropin hormone 2 |
| CSHL1 | ENSG00000204414 | Chorionic somatomammotropin hormone-like 1 |
| CSN1S1 | ENSG00000126545 | Casein alpha s1 |
| CSN2 | ENSG00000135222 | Casein beta |
| CSN3 | ENSG00000171209 | Casein kappa |
| CST1 | ENSG00000170373 | Cystatin SN |
| CST11 | ENSG00000125831 | Cystatin 11 |
| CST2 | ENSG00000170369 | Cystatin SA |
| CST3 | ENSG00000101439 | Cystatin C |
| CST4 | ENSG00000101441 | Cystatin S |
| CST5 | ENSG00000170367 | Cystatin D |
| CST6 | ENSG00000175315 | Cystatin E/M |
| CST7 | ENSG00000077984 | Cystatin F (leukocystatin) |
| CST8 | ENSG00000125815 | Cystatin 8 (cystatin-related epididymal specific) |
| CST9 | ENSG00000173335 | Cystatin 9 (testatin) |
| CST9L | ENSG00000101435 | Cystatin 9-like |
| CSTL1 | ENSG00000125823 | Cystatin-like 1 |
| CT55 | ENSG00000169551 | Cancer/testis antigen 55 |
| CTB-60B18.6 | ENSG00000267335 | |
| CTBS | ENSG00000117151 | Chitobiase, di-N-acetyl- |
| CTD-2313N18.7 | ENSG00000225802 | |
| CTD-2370N5.3 | ENSG00000265118 | |
| CTGF | ENSG00000118523 | Connective tissue growth factor |
| CTHRC1 | ENSG00000164932 | Collagen triple helix repeat containing 1 |
| CTLA4 | ENSG00000163599 | Cytotoxic T-lymphocyte-associated protein 4 |
| CTNS | ENSG00000040531 | Cystinosin, lysosomal cystine transporter |
| CTRB1 | ENSG00000168925 | Chymotrypsinogen B1 |
| CTRB2 | ENSG00000168928 | Chymotrypsinogen B2 |
| CTRC | ENSG00000162438 | Chymotrypsin C (caldecrin) |
| CTRL | ENSG00000141086 | Chymotrypsin-like |
| CTSA | ENSG00000064601 | Cathepsin A |
| CTSB | ENSG00000164733 | Cathepsin B |
| CTSC | ENSG00000109861 | Cathepsin C |
| CTSD | ENSG00000117984 | Cathepsin D |

TABLE 1-continued

Exemplary Human Secreted Proteins

| Gene | Ensembl ID | Gene description |
| --- | --- | --- |
| CTSE | ENSG00000196188 | Cathepsin E |
| CTSF | ENSG00000174080 | Cathepsin F |
| CTSG | ENSG00000100448 | Cathepsin G |
| CTSH | ENSG00000103811 | Cathepsin H |
| CTSK | ENSG00000143387 | Cathepsin K |
| CTSL | ENSG00000135047 | Cathepsin L |
| CTSO | ENSG00000256043 | Cathepsin O |
| CTSS | ENSG00000163131 | Cathepsin S |
| CTSV | ENSG00000136943 | Cathepsin V |
| CTSW | ENSG00000172543 | Cathepsin W |
| CTSZ | ENSG00000101160 | Cathepsin Z |
| CUBN | ENSG00000107611 | Cubilin (intrinsic factor-cobalamin receptor) |
| CUTA | ENSG00000112514 | CutA divalent cation tolerance homolog (*E. coli*) |
| CX3CL1 | ENSG00000006210 | Chemokine (C—X3—C motif) ligand 1 |
| CXADR | ENSG00000154639 | Coxsackie virus and adenovirus receptor |
| CXCL1 | ENSG00000163739 | Chemokine (C—X—C motif) ligand 1 (melanoma growth stimulating activity, alpha) |
| CXCL10 | ENSG00000169245 | Chemokine (C—X—C motif) ligand 10 |
| CXCL11 | ENSG00000169248 | Chemokine (C—X—C motif) ligand 11 |
| CXCL12 | ENSG00000107562 | Chemokine (C—X—C motif) ligand 12 |
| CXCL13 | ENSG00000156234 | Chemokine (C—X—C motif) ligand 13 |
| CXCL14 | ENSG00000145824 | Chemokine (C—X—C motif) ligand 14 |
| CXCL17 | ENSG00000189377 | Chemokine (C—X—C motif) ligand 17 |
| CXCL2 | ENSG00000081041 | Chemokine (C—X—C motif) ligand 2 |
| CXCL3 | ENSG00000163734 | Chemokine (C—X—C motif) ligand 3 |
| CXCL5 | ENSG00000163735 | Chemokine (C—X—C motif) ligand 5 |
| CXCL6 | ENSG00000124875 | Chemokine (C—X—C motif) ligand 6 |
| CXCL8 | ENSG00000169429 | Chemokine (C—X—C motif) ligand 8 |
| CXCL9 | ENSG00000138755 | Chemokine (C—X—C motif) ligand 9 |
| CXorf36 | ENSG00000147113 | Chromosome X open reading frame 36 |
| CYB5D2 | ENSG00000167740 | Cytochrome b5 domain containing 2 |
| CYHR1 | ENSG00000187954 | Cysteine/histidine-rich 1 |
| CYP17A1 | ENSG00000148795 | Cytochrome P450, family 17, subfamily A, polypeptide 1 |
| CYP20A1 | ENSG00000119004 | Cytochrome P450, family 20, subfamily A, polypeptide 1 |
| CYP21A2 | ENSG00000231852 | Cytochrome P450, family 21, subfamily A, polypeptide 2 |
| CYP26B1 | ENSG00000003137 | Cytochrome P450, family 26, subfamily B, polypeptide 1 |
| CYP2A6 | ENSG00000255974 | Cytochrome P450, family 2, subfamily A, polypeptide 6 |
| CYP2A7 | ENSG00000198077 | Cytochrome P450, family 2, subfamily A, polypeptide 7 |
| CYP2B6 | ENSG00000197408 | Cytochrome P450, family 2, subfamily B, polypeptide 6 |
| CYP2C18 | ENSG00000108242 | Cytochrome P450, family 2, subfamily C, polypeptide 18 |
| CYP2C19 | ENSG00000165841 | Cytochrome P450, family 2, subfamily C, polypeptide 19 |
| CYP2C8 | ENSG00000138115 | Cytochrome P450, family 2, subfamily C, polypeptide 8 |
| CYP2C9 | ENSG00000138109 | Cytochrome P450, family 2, subfamily C, polypeptide 9 |
| CYP2E1 | ENSG00000130649 | Cytochrome P450, family 2, subfamily E, polypeptide 1 |
| CYP2F1 | ENSG00000197446 | Cytochrome P450, family 2, subfamily F, polypeptide 1 |
| CYP2J2 | ENSG00000134716 | Cytochrome P450, family 2, subfamily J, polypeptide 2 |
| CYP2R1 | ENSG00000186104 | Cytochrome P450, family 2, subfamily R, polypeptide 1 |
| CYP2S1 | ENSG00000167600 | Cytochrome P450, family 2, subfamily S, polypeptide 1 |
| CYP2W1 | ENSG00000073067 | Cytochrome P450, family 2, subfamily W, polypeptide 1 |
| CYP46A1 | ENSG00000036530 | Cytochrome P450, family 46, subfamily A, polypeptide 1 |
| CYP4F11 | ENSG00000171903 | Cytochrome P450, family 4, subfamily F, polypeptide 11 |
| CYP4F2 | ENSG00000186115 | Cytochrome P450, family 4, subfamily F, polypeptide 2 |
| CYR61 | ENSG00000142871 | Cysteine-rich, angiogenic inducer, 61 |
| CYTL1 | ENSG00000170891 | Cytokine-like 1 |
| D2HGDH | ENSG00000180902 | D-2-hydroxyglutarate dehydrogenase |
| DAG1 | ENSG00000173402 | Dystroglycan 1 (dystrophin-associated glycoprotein 1) |
| DAND5 | ENSG00000179284 | DAN domain family member 5, BMP antagonist |
| DAO | ENSG00000110887 | D-amino-acid oxidase |
| DAZAP2 | ENSG00000183283 | DAZ associated protein 2 |
| DBH | ENSG00000123454 | Dopamine beta-hydroxylase (dopamine beta-monooxygenase) |
| DBNL | ENSG00000136279 | Drebrin-like |
| DCD | ENSG00000161634 | Dermcidin |
| DCN | ENSG00000011465 | Decorin |
| DDIAS | ENSG00000165490 | DNA damage-induced apoptosis suppressor |
| DDOST | ENSG00000244038 | Dolichyl-diphosphooligosaccharide--protein glycosyltransferase subunit (non-catalytic) |
| DDR1 | ENSG00000204580 | Discoidin domain receptor tyrosine kinase 1 |
| DDR2 | ENSG00000162733 | Discoidin domain receptor tyrosine kinase 2 |
| DDT | ENSG00000099977 | D-dopachrome tautomerase |
| DDX17 | ENSG00000100201 | DEAD (Asp-Glu-Ala-Asp) box helicase 17 |
| DDX20 | ENSG00000064703 | DEAD (Asp-Glu-Ala-Asp) box polypeptide 20 |
| DDX25 | ENSG00000109832 | DEAD (Asp-Glu-Ala-Asp) box helicase 25 |
| DDX28 | ENSG00000182810 | DEAD (Asp-Glu-Ala-Asp) box polypeptide 28 |
| DEAF1 | ENSG00000177030 | DEAF1 transcription factor |
| DEF8 | ENSG00000140995 | Differentially expressed in FDCP 8 homolog (mouse) |
| DEFA1 | ENSG00000206047 | Defensin, alpha 1 |

TABLE 1-continued

Exemplary Human Secreted Proteins

| Gene | Ensembl ID | Gene description |
|---|---|---|
| DEFA1B | ENSG00000240247 | Defensin, alpha 1B |
| DEFA3 | ENSG00000239839 | Defensin, alpha 3, neutrophil-specific |
| DEFA4 | ENSG00000164821 | Defensin, alpha 4, corticostatin |
| DEFA5 | ENSG00000164816 | Defensin, alpha 5, Paneth cell-specific |
| DEFA6 | ENSG00000164822 | Defensin, alpha 6, Paneth cell-specific |
| DEFB1 | ENSG00000164825 | Defensin, beta 1 |
| DEFB103A | ENSG00000176797 | Defensin, beta 103A |
| DEFB103B | ENSG00000177243 | Defensin, beta 103B |
| DEFB104A | ENSG00000176782 | Defensin, beta 104A |
| DEFB104B | ENSG00000177023 | Defensin, beta 104B |
| DEFB105A | ENSG00000186562 | Defensin, beta 105A |
| DEFB105B | ENSG00000186599 | Defensin, beta 105B |
| DEFB106A | ENSG00000186579 | Defensin, beta 106A |
| DEFB106B | ENSG00000187082 | Defensin, beta 106B |
| DEFB107A | ENSG00000186572 | Defensin, beta 107A |
| DEFB107B | ENSG00000198129 | Defensin, beta 107B |
| DEFB108B | ENSG00000184276 | Defensin, beta 108B |
| DEFB110 | ENSG00000203970 | Defensin, beta 110 |
| DEFB113 | ENSG00000214642 | Defensin, beta 113 |
| DEFB114 | ENSG00000177684 | Defensin, beta 114 |
| DEFB115 | ENSG00000215547 | Defensin, beta 115 |
| DEFB116 | ENSG00000215545 | Defensin, beta 116 |
| DEFB118 | ENSG00000131068 | Defensin, beta 118 |
| DEFB119 | ENSG00000180483 | Defensin, beta 119 |
| DEFB121 | ENSG00000204548 | Defensin, beta 121 |
| DEFB123 | ENSG00000180424 | Defensin, beta 123 |
| DEFB124 | ENSG00000180383 | Defensin, beta 124 |
| DEFB125 | ENSG00000178591 | Defensin, beta 125 |
| DEFB126 | ENSG00000125788 | Defensin, beta 126 |
| DEFB127 | ENSG00000088782 | Defensin, beta 127 |
| DEFB128 | ENSG00000185982 | Defensin, beta 128 |
| DEFB129 | ENSG00000125903 | Defensin, beta 129 |
| DEFB130 | ENSG00000232948 | Defensin, beta 130 |
| DEFB131 | ENSG00000186146 | Defensin, beta 131 |
| DEFB132 | ENSG00000186458 | Defensin, beta 132 |
| DEFB133 | ENSG00000214643 | Defensin, beta 133 |
| DEFB134 | ENSG00000205882 | Defensin, beta 134 |
| DEFB135 | ENSG00000205883 | Defensin, beta 135 |
| DEFB136 | ENSG00000205884 | Defensin, beta 136 |
| DEFB4A | ENSG00000171711 | Defensin, beta 4A |
| DEFB4B | ENSG00000177257 | Defensin, beta 4B |
| DFNA5 | ENSG00000105928 | Deafness, autosomal dominant 5 |
| DFNB31 | ENSG00000095397 | Deafness, autosomal recessive 31 |
| DGCR2 | ENSG00000070413 | DiGeorge syndrome critical region gene 2 |
| DHH | ENSG00000139549 | Desert hedgehog |
| DHRS4 | ENSG00000157326 | Dehydrogenase/reductase (SDR family) member 4 |
| DHRS4L2 | ENSG00000187630 | Dehydrogenase/reductase (SDR family) member 4 like 2 |
| DHRS7 | ENSG00000100612 | Dehydrogenase/reductase (SDR family) member 7 |
| DHRS7C | ENSG00000184544 | Dehydrogenase/reductase (SDR family) member 7C |
| DHRS9 | ENSG00000073737 | Dehydrogenase/reductase (SDR family) member 9 |
| DHRSX | ENSG00000169084 | Dehydrogenase/reductase (SDR family) X-linked |
| DHX29 | ENSG00000067248 | DEAH (Asp-Glu-Ala-His) box polypeptide 29 |
| DHX30 | ENSG00000132153 | DEAH (Asp-Glu-Ala-His) box helicase 30 |
| DHX8 | ENSG00000067596 | DEAH (Asp-Glu-Ala-His) box polypeptide 8 |
| DIO2 | ENSG00000211448 | Deiodinase, iodothyronine, type II |
| DIXDC1 | ENSG00000150764 | DIX domain containing 1 |
| DKK1 | ENSG00000107984 | Dickkopf WNT signaling pathway inhibitor 1 |
| DKK2 | ENSG00000155011 | Dickkopf WNT signaling pathway inhibitor 2 |
| DKK3 | ENSG00000050165 | Dickkopf WNT signaling pathway inhibitor 3 |
| DKK4 | ENSG00000104371 | Dickkopf WNT signaling pathway inhibitor 4 |
| DKKL1 | ENSG00000104901 | Dickkopf-like 1 |
| DLG4 | ENSG00000132535 | Discs, large homolog 4 (*Drosophila*) |
| DLK1 | ENSG00000185559 | Delta-like 1 homolog (*Drosophila*) |
| DLL1 | ENSG00000198719 | Delta-like 1 (*Drosophila*) |
| DLL3 | ENSG00000090932 | Delta-like 3 (*Drosophila*) |
| DMBT1 | ENSG00000187908 | Deleted in malignant brain tumors 1 |
| DMKN | ENSG00000161249 | Dermokine |
| DMP1 | ENSG00000152592 | Dentin matrix acidic phosphoprotein 1 |
| DMRTA2 | ENSG00000142700 | DMRT-like family A2 |
| DNAAF5 | ENSG00000164818 | Dynein, axonemal, assembly factor 5 |
| DNAH14 | ENSG00000185842 | Dynein, axonemal, heavy chain 14 |
| DNAJB11 | ENSG00000090520 | DnaJ (Hsp40) homolog, subfamily B, member 11 |
| DNAJB9 | ENSG00000128590 | DnaJ (Hsp40) homolog, subfamily B, member 9 |
| DNAJC25-GNG10 | ENSG00000244115 | DNAJC25-GNG10 readthrough |
| DNAJC3 | ENSG00000102580 | DnaJ (Hsp40) homolog, subfamily C, member 3 |
| DNASE1 | ENSG00000213918 | Deoxyribonuclease I |

TABLE 1-continued

Exemplary Human Secreted Proteins

| Gene | Ensembl ID | Gene description |
|---|---|---|
| DNASE1L1 | ENSG00000013563 | Deoxyribonuclease I-like 1 |
| DNASE1L2 | ENSG00000167968 | Deoxyribonuclease I-like 2 |
| DNASE1L3 | ENSG00000163687 | Deoxyribonuclease I-like 3 |
| DNASE2 | ENSG00000105612 | Deoxyribonuclease II, lysosomal |
| DNASE2B | ENSG00000137976 | Deoxyribonuclease II beta |
| DPEP1 | ENSG00000015413 | Dipeptidase 1 (renal) |
| DPEP2 | ENSG00000167261 | Dipeptidase 2 |
| DPEP3 | ENSG00000141096 | Dipeptidase 3 |
| DPF3 | ENSG00000205683 | D4, zinc and double PHD fingers, family 3 |
| DPP4 | ENSG00000197635 | Dipeptidyl-peptidase 4 |
| DPP7 | ENSG00000176978 | Dipeptidyl-peptidase 7 |
| DPT | ENSG00000143196 | Dermatopontin |
| DRAXIN | ENSG00000162490 | Dorsal inhibitory axon guidance protein |
| DSE | ENSG00000111817 | Dermatan sulfate epimerase |
| DSG2 | ENSG00000046604 | Desmoglein 2 |
| DSPP | ENSG00000152591 | Dentin sialophosphoprotein |
| DST | ENSG00000151914 | Dystonin |
| DUOX1 | ENSG00000137857 | Dual oxidase 1 |
| DYNLT3 | ENSG00000165169 | Dynein, light chain, Tctex-type 3 |
| E2F5 | ENSG00000133740 | E2F transcription factor 5, p130-binding |
| EBAG9 | ENSG00000147654 | Estrogen receptor binding site associated, antigen, 9 |
| EBI3 | ENSG00000105246 | Epstein-Barr virus induced 3 |
| ECHDC1 | ENSG00000093144 | Ethylmalonyl-CoA decarboxylase 1 |
| ECM1 | ENSG00000143369 | Extracellular matrix protein 1 |
| ECM2 | ENSG00000106823 | Extracellular matrix protein 2, female organ and adipocyte specific |
| ECSIT | ENSG00000130159 | ECSIT signalling integrator |
| EDDM3A | ENSG00000181562 | Epididymal protein 3A |
| EDDM3B | ENSG00000181552 | Epididymal protein 3B |
| EDEM2 | ENSG00000088298 | ER degradation enhancer, mannosidase alpha-like 2 |
| EDEM3 | ENSG00000116406 | ER degradation enhancer, mannosidase alpha-like 3 |
| EDIL3 | ENSG00000164176 | EGF-like repeats and discoidin I-like domains 3 |
| EDN1 | ENSG00000078401 | Endothelin 1 |
| EDN2 | ENSG00000127129 | Endothelin 2 |
| EDN3 | ENSG00000124205 | Endothelin 3 |
| EDNRB | ENSG00000136160 | Endothelin receptor type B |
| EFEMP1 | ENSG00000115380 | EGF containing fibulin-like extracellular matrix protein 1 |
| EFEMP2 | ENSG00000172638 | EGF containing fibulin-like extracellular matrix protein 2 |
| EFNA1 | ENSG00000169242 | Ephrin-A1 |
| EFNA2 | ENSG00000099617 | Ephrin-A2 |
| EFNA4 | ENSG00000243364 | Ephrin-A4 |
| EGFL6 | ENSG00000198759 | EGF-like-domain, multiple 6 |
| EGFL7 | ENSG00000172889 | EGF-like-domain, multiple 7 |
| EGFL8 | ENSG00000241404 | EGF-like-domain, multiple 8 |
| EGFLAM | ENSG00000164318 | EGF-like, fibronectin type III and laminin G domains |
| EGFR | ENSG00000146648 | Epidermal growth factor receptor |
| EHBP1 | ENSG00000115504 | EH domain binding protein 1 |
| EHF | ENSG00000135373 | Ets homologous factor |
| EHMT1 | ENSG00000181090 | Euchromatic histone-lysine N-methyltransferase 1 |
| EHMT2 | ENSG00000204371 | Euchromatic histone-lysine N-methyltransferase 2 |
| EIF2AK1 | ENSG00000086232 | Eukaryotic translation initiation factor 2-alpha kinase 1 |
| ELANE | ENSG00000197561 | Elastase, neutrophil expressed |
| ELN | ENSG00000049540 | Elastin |
| ELP2 | ENSG00000134759 | Elongator acetyltransferase complex subunit 2 |
| ELSPBP1 | ENSG00000169393 | Epididymal sperm binding protein 1 |
| EMC1 | ENSG00000127463 | ER membrane protein complex subunit 1 |
| EMC10 | ENSG00000161671 | ER membrane protein complex subunit 10 |
| EMC9 | ENSG00000100908 | ER membrane protein complex subunit 9 |
| EMCN | ENSG00000164035 | Endomucin |
| EMID1 | ENSG00000186998 | EMI domain containing 1 |
| EMILIN1 | ENSG00000138080 | Elastin microfibril interfacer 1 |
| EMILIN2 | ENSG00000132205 | Elastin microfibril interfacer 2 |
| EMILIN3 | ENSG00000183798 | Elastin microfibril interfacer 3 |
| ENAM | ENSG00000132464 | Enamelin |
| ENDOG | ENSG00000167136 | Endonuclease G |
| ENDOU | ENSG00000111405 | Endonuclease, polyU-specific |
| ENHO | ENSG00000168913 | Energy homeostasis associated |
| ENO4 | ENSG00000188316 | Enolase family member 4 |
| ENPP6 | ENSG00000164303 | Ectonucleotide pyrophosphatase/phosphodiesterase 6 |
| ENPP7 | ENSG00000182156 | Ectonucleotide pyrophosphatase/phosphodiesterase 7 |
| ENTPD5 | ENSG00000187097 | Ectonucleoside triphosphate diphosphohydrolase 5 |
| ENTPD8 | ENSG00000188833 | Ectonucleoside triphosphate diphosphohydrolase 8 |
| EOGT | ENSG00000163378 | EGF domain-specific O-linked N-acetylglucosamine (GlcNAc) transferase |
| EPCAM | ENSG00000119888 | Epithelial cell adhesion molecule |
| EPDR1 | ENSG00000086289 | Ependymin related 1 |

TABLE 1-continued

Exemplary Human Secreted Proteins

| Gene | Ensembl ID | Gene description |
|---|---|---|
| EPGN | ENSG00000182585 | Epithelial mitogen |
| EPHA10 | ENSG00000183317 | EPH receptor A10 |
| EPHA3 | ENSG00000044524 | EPH receptor A3 |
| EPHA4 | ENSG00000116106 | EPH receptor A4 |
| EPHA7 | ENSG00000135333 | EPH receptor A7 |
| EPHA8 | ENSG00000070886 | EPH receptor A8 |
| EPHB2 | ENSG00000133216 | EPH receptor B2 |
| EPHB4 | ENSG00000196411 | EPH receptor B4 |
| EPHX3 | ENSG00000105131 | Epoxide hydrolase 3 |
| EPO | ENSG00000130427 | Erythropoietin |
| EPPIN | ENSG00000101448 | Epididymal peptidase inhibitor |
| EPPIN-WFDC6 | ENSG00000249139 | EPPIN-WFDC6 readthrough |
| EPS15 | ENSG00000085832 | Epidermal growth factor receptor pathway substrate 15 |
| EPS8L1 | ENSG00000131037 | EPS8-like 1 |
| EPX | ENSG00000121053 | Eosinophil peroxidase |
| EPYC | ENSG00000083782 | Epiphycan |
| EQTN | ENSG00000120160 | Equatorin, sperm acrosome associated |
| ERAP1 | ENSG00000164307 | Endoplasmic reticulum aminopeptidase 1 |
| ERAP2 | ENSG00000164308 | Endoplasmic reticulum aminopeptidase 2 |
| ERBB3 | ENSG00000065361 | Erb-b2 receptor tyrosine kinase 3 |
| ERLIN1 | ENSG00000107566 | ER lipid raft associated 1 |
| ERLIN2 | ENSG00000147475 | ER lipid raft associated 2 |
| ERN1 | ENSG00000178607 | Endoplasmic reticulum to nucleus signaling 1 |
| ERN2 | ENSG00000134398 | Endoplasmic reticulum to nucleus signaling 2 |
| ERO1A | ENSG00000197930 | Endoplasmic reticulum oxidoreductase alpha |
| ERO1B | ENSG00000086619 | Endoplasmic reticulum oxidoreductase beta |
| ERP27 | ENSG00000139055 | Endoplasmic reticulum protein 27 |
| ERP29 | ENSG00000089248 | Endoplasmic reticulum protein 29 |
| ERP44 | ENSG00000023318 | Endoplasmic reticulum protein 44 |
| ERV3-1 | ENSG00000213462 | Endogenous retrovirus group 3, member 1 |
| ESM1 | ENSG00000164283 | Endothelial cell-specific molecule 1 |
| ESRP1 | ENSG00000104413 | Epithelial splicing regulatory protein 1 |
| EXOG | ENSG00000157036 | Endo/exonuclease (5'-3'), endonuclease G-like |
| EXTL1 | ENSG00000158008 | Exostosin-like glycosyltransferase 1 |
| EXTL2 | ENSG00000162694 | Exostosin-like glycosyltransferase 2 |
| F10 | ENSG00000126218 | Coagulation factor X |
| F11 | ENSG00000088926 | Coagulation factor XI |
| F12 | ENSG00000131187 | Coagulation factor XII (Hageman factor) |
| F13B | ENSG00000143278 | Coagulation factor XIII, B polypeptide |
| F2 | ENSG00000180210 | Coagulation factor II (thrombin) |
| F2R | ENSG00000181104 | Coagulation factor II (thrombin) receptor |
| F2RL3 | ENSG00000127533 | Coagulation factor II (thrombin) receptor-like 3 |
| F5 | ENSG00000198734 | Coagulation factor V (proaccelerin, labile factor) |
| F7 | ENSG00000057593 | Coagulation factor VII (serum prothrombin conversion accelerator) |
| F8 | ENSG00000185010 | Coagulation factor VIII, procoagulant component |
| F9 | ENSG00000101981 | Coagulation factor IX |
| FABP6 | ENSG00000170231 | Fatty acid binding protein 6, ileal |
| FAM107B | ENSG00000065809 | Family with sequence similarity 107, member B |
| FAM131A | ENSG00000175182 | Family with sequence similarity 131, member A |
| FAM132A | ENSG00000184163 | Family with sequence similarity 132, member A |
| FAM132B | ENSG00000178752 | Family with sequence similarity 132, member B |
| FAM150A | ENSG00000196711 | Family with sequence similarity 150, member A |
| FAM150B | ENSG00000189292 | Family with sequence similarity 150, member B |
| FAM171A1 | ENSG00000148468 | Family with sequence similarity 171, member A1 |
| FAM171B | ENSG00000144369 | Family with sequence similarity 171, member B |
| FAM172A | ENSG00000113391 | Family with sequence similarity 172, member A |
| FAM175A | ENSG00000163322 | Family with sequence similarity 175, member A |
| FAM177A1 | ENSG00000151327 | Family with sequence similarity 177, member A1 |
| FAM179B | ENSG00000198718 | Family with sequence similarity 179, member B |
| FAM180A | ENSG00000189320 | Family with sequence similarity 180, member A |
| FAM189A1 | ENSG00000104059 | Family with sequence similarity 189, member A1 |
| FAM198A | ENSG00000144649 | Family with sequence similarity 198, member A |
| FAM19A1 | ENSG00000183662 | Family with sequence similarity 19 (chemokine (C-C motif)-like), member A1 |
| FAM19A2 | ENSG00000198673 | Family with sequence similarity 19 (chemokine (C-C motif)-like), member A2 |
| FAM19A3 | ENSG00000184599 | Family with sequence similarity 19 (chemokine (C-C motif)-like), member A3 |
| FAM19A4 | ENSG00000163377 | Family with sequence similarity 19 (chemokine (C-C motif)-like), member A4 |
| FAM19A5 | ENSG00000219438 | Family with sequence similarity 19 (chemokine (C-C motif)-like), member A5 |
| FAM20A | ENSG00000108950 | Family with sequence similarity 20, member A |
| FAM20C | ENSG00000177706 | Family with sequence similarity 20, member C |
| FAM213A | ENSG00000122378 | Family with sequence similarity 213, member A |

TABLE 1-continued

Exemplary Human Secreted Proteins

| Gene | Ensembl ID | Gene description |
|---|---|---|
| FAM26D | ENSG00000164451 | Family with sequence similarity 26, member D |
| FAM46B | ENSG00000158246 | Family with sequence similarity 46, member B |
| FAM57A | ENSG00000167695 | Family with sequence similarity 57, member A |
| FAM78A | ENSG00000126882 | Family with sequence similarity 78, member A |
| FAM96A | ENSG00000166797 | Family with sequence similarity 96, member A |
| FAM9B | ENSG00000177138 | Family with sequence similarity 9, member B |
| FAP | ENSG00000078098 | Fibroblast activation protein, alpha |
| FAS | ENSG00000026103 | Fas cell surface death receptor |
| FAT1 | ENSG00000083857 | FAT atypical cadherin 1 |
| FBLN1 | ENSG00000077942 | Fibulin 1 |
| FBLN2 | ENSG00000163520 | Fibulin 2 |
| FBLN5 | ENSG00000140092 | Fibulin 5 |
| FBLN7 | ENSG00000144152 | Fibulin 7 |
| FBN1 | ENSG00000166147 | Fibrillin 1 |
| FBN2 | ENSG00000138829 | Fibrillin 2 |
| FBN3 | ENSG00000142449 | Fibrillin 3 |
| FBXW7 | ENSG00000109670 | F-box and WD repeat domain containing 7, E3 ubiquitin protein ligase |
| FCAR | ENSG00000186431 | Fc fragment of IgA receptor |
| FCGBP | ENSG00000275395 | Fc fragment of IgG binding protein |
| FCGR1B | ENSG00000198019 | Fc fragment of IgG, high affinity Ib, receptor (CD64) |
| FCGR3A | ENSG00000203747 | Fc fragment of IgG, low affinity IIIa, receptor (CD16a) |
| FCGRT | ENSG00000104870 | Fc fragment of IgG, receptor, transporter, alpha |
| FCMR | ENSG00000162894 | Fc fragment of IgM receptor |
| FCN1 | ENSG00000085265 | Ficolin (collagen/fibrinogen domain containing) 1 |
| FCN2 | ENSG00000160339 | Ficolin (collagen/fibrinogen domain containing lectin) 2 |
| FCN3 | ENSG00000142748 | Ficolin (collagen/fibrinogen domain containing) 3 |
| FCRL1 | ENSG00000163534 | Fc receptor-like 1 |
| FCRL3 | ENSG00000160856 | Fc receptor-like 3 |
| FCRL5 | ENSG00000143297 | Fc receptor-like 5 |
| FCRLA | ENSG00000132185 | Fc receptor-like A |
| FCRLB | ENSG00000162746 | Fc receptor-like B |
| FDCSP | ENSG00000181617 | Follicular dendritic cell secreted protein |
| FETUB | ENSG00000090512 | Fetuin B |
| FGA | ENSG00000171560 | Fibrinogen alpha chain |
| FGB | ENSG00000171564 | Fibrinogen beta chain |
| FGF10 | ENSG00000070193 | Fibroblast growth factor 10 |
| FGF17 | ENSG00000158815 | Fibroblast growth factor 17 |
| FGF18 | ENSG00000156427 | Fibroblast growth factor 18 |
| FGF19 | ENSG00000162344 | Fibroblast growth factor 19 |
| FGF21 | ENSG00000105550 | Fibroblast growth factor 21 |
| FGF22 | ENSG00000070388 | Fibroblast growth factor 22 |
| FGF23 | ENSG00000118972 | Fibroblast growth factor 23 |
| FGF3 | ENSG00000186895 | Fibroblast growth factor 3 |
| FGF4 | ENSG00000075388 | Fibroblast growth factor 4 |
| FGF5 | ENSG00000138675 | Fibroblast growth factor 5 |
| FGF7 | ENSG00000140285 | Fibroblast growth factor 7 |
| FGF8 | ENSG00000107831 | Fibroblast growth factor 8 (androgen-induced) |
| FGFBP1 | ENSG00000137440 | Fibroblast growth factor binding protein 1 |
| FGFBP2 | ENSG00000137441 | Fibroblast growth factor binding protein 2 |
| FGFBP3 | ENSG00000174721 | Fibroblast growth factor binding protein 3 |
| FGFR1 | ENSG00000077782 | Fibroblast growth factor receptor 1 |
| FGFR2 | ENSG00000066468 | Fibroblast growth factor receptor 2 |
| FGFR3 | ENSG00000068078 | Fibroblast growth factor receptor 3 |
| FGFR4 | ENSG00000160867 | Fibroblast growth factor receptor 4 |
| FGFRL1 | ENSG00000127418 | Fibroblast growth factor receptor-like 1 |
| FGG | ENSG00000171557 | Fibrinogen gamma chain |
| FGL1 | ENSG00000104760 | Fibrinogen-like 1 |
| FGL2 | ENSG00000127951 | Fibrinogen-like 2 |
| FHL1 | ENSG00000022267 | Four and a half LIM domains 1 |
| FHOD3 | ENSG00000134775 | Formin homology 2 domain containing 3 |
| FIBIN | ENSG00000176971 | Fin bud initiation factor homolog (zebrafish) |
| FICD | ENSG00000198855 | FIC domain containing |
| FIGF | ENSG00000165197 | C-fos induced growth factor (vascular endothelial growth factor D) |
| FJX1 | ENSG00000179431 | Four jointed box 1 |
| FKBP10 | ENSG00000141756 | FK506 binding protein 10, 65 kDa |
| FKBP11 | ENSG00000134285 | FK506 binding protein 11, 19 kDa |
| FKBP14 | ENSG00000106080 | FK506 binding protein 14, 22 kDa |
| FKBP2 | ENSG00000173486 | FK506 binding protein 2, 13 kDa |
| FKBP7 | ENSG00000079150 | FK506 binding protein 7 |
| FKBP9 | ENSG00000122642 | FK506 binding protein 9, 63 kDa |
| FLT1 | ENSG00000102755 | Fms-related tyrosine kinase 1 |
| FLT4 | ENSG00000037280 | Fms-related tyrosine kinase 4 |
| FMO1 | ENSG00000010932 | Flavin containing monooxygenase 1 |
| FMO2 | ENSG00000094963 | Flavin containing monooxygenase 2 (non-functional) |

TABLE 1-continued

Exemplary Human Secreted Proteins

| Gene | Ensembl ID | Gene description |
|---|---|---|
| FMO3 | ENSG00000007933 | Flavin containing monooxygenase 3 |
| FMO5 | ENSG00000131781 | Flavin containing monooxygenase 5 |
| FMOD | ENSG00000122176 | Fibromodulin |
| FN1 | ENSG00000115414 | Fibronectin 1 |
| FNDC1 | ENSG00000164694 | Fibronectin type III domain containing 1 |
| FNDC7 | ENSG00000143107 | Fibronectin type III domain containing 7 |
| FOCAD | ENSG00000188352 | Focadhesin |
| FOLR2 | ENSG00000165457 | Folate receptor 2 (fetal) |
| FOLR3 | ENSG00000110203 | Folate receptor 3 (gamma) |
| FOXRED2 | ENSG00000100350 | FAD-dependent oxidoreductase domain containing 2 |
| FP325331.1 | ENSG00000278881 | Uncharacterized protein UNQ6126/PRO20091 |
| FPGS | ENSG00000136877 | Folylpolyglutamate synthase |
| FRAS1 | ENSG00000138759 | Fraser extracellular matrix complex subunit 1 |
| FREM1 | ENSG00000164946 | FRAS1 related extracellular matrix 1 |
| FREM3 | ENSG00000183090 | FRAS1 related extracellular matrix 3 |
| FRMPD2 | ENSG00000170324 | FERM and PDZ domain containing 2 |
| FRZB | ENSG00000162998 | Frizzled-related protein |
| FSHB | ENSG00000131808 | Follicle stimulating hormone, beta polypeptide |
| FSHR | ENSG00000170820 | Follicle stimulating hormone receptor |
| FST | ENSG00000134363 | Follistatin |
| FSTL1 | ENSG00000163430 | Follistatin-like 1 |
| FSTL3 | ENSG00000070404 | Follistatin-like 3 (secreted glycoprotein) |
| FSTL4 | ENSG00000053108 | Follistatin-like 4 |
| FSTL5 | ENSG00000168843 | Follistatin-like 5 |
| FTCDNL1 | ENSG00000226124 | Formiminotransferase cyclodeaminase N-terminal like |
| FUCA1 | ENSG00000179163 | Fucosidase, alpha-L-1, tissue |
| FUCA2 | ENSG00000001036 | Fucosidase, alpha-L-2, plasma |
| FURIN | ENSG00000140564 | Furin (paired basic amino acid cleaving enzyme) |
| FUT10 | ENSG00000172728 | Fucosyltransferase 10 (alpha (1,3) fucosyltransferase) |
| FUT11 | ENSG00000196968 | Fucosyltransferase 11 (alpha (1,3) fucosyltransferase) |
| FXN | ENSG00000165060 | Frataxin |
| FXR1 | ENSG00000114416 | Fragile X mental retardation, autosomal homolog 1 |
| FXYD3 | ENSG00000089356 | FXYD domain containing ion transport regulator 3 |
| GABBR1 | ENSG00000204681 | Gamma-aminobutyric acid (GABA) B receptor, 1 |
| GABRA1 | ENSG00000022355 | Gamma-aminobutyric acid (GABA) A receptor, alpha 1 |
| GABRA2 | ENSG00000151834 | Gamma-aminobutyric acid (GABA) A receptor, alpha 2 |
| GABRA5 | ENSG00000186297 | Gamma-aminobutyric acid (GABA) A receptor, alpha 5 |
| GABRG3 | ENSG00000182256 | Gamma-aminobutyric acid (GABA) A receptor, gamma 3 |
| GABRP | ENSG00000094755 | Gamma-aminobutyric acid (GABA) A receptor, pi |
| GAL | ENSG00000069482 | Galanin/GMAP prepropeptide |
| GAL3ST1 | ENSG00000128242 | Galactose-3-O-sulfotransferase 1 |
| GAL3ST2 | ENSG00000154252 | Galactose-3-O-sulfotransferase 2 |
| GAL3ST3 | ENSG00000175229 | Galactose-3-O-sulfotransferase 3 |
| GALC | ENSG00000054983 | Galactosylceramidase |
| GALNS | ENSG00000141012 | Galactosamine (N-acetyl)-6-sulfatase |
| GALNT10 | ENSG00000164574 | Polypeptide N-acetylgalactosaminyltransferase 10 |
| GALNT12 | ENSG00000119514 | Polypeptide N-acetylgalactosaminyltransferase 12 |
| GALNT15 | ENSG00000131386 | Polypeptide N-acetylgalactosaminyltransferase 15 |
| GALNT2 | ENSG00000143641 | Polypeptide N-acetylgalactosaminyltransferase 2 |
| GALNT6 | ENSG00000139629 | Polypeptide N-acetylgalactosaminyltransferase 6 |
| GALNT8 | ENSG00000130035 | Polypeptide N-acetylgalactosaminyltransferase 8 |
| GALNTL6 | ENSG00000174473 | Polypeptide N-acetylgalactosaminyltransferase-like 6 |
| GALP | ENSG00000197487 | Galanin-like peptide |
| GANAB | ENSG00000089597 | Glucosidase, alpha; neutral AB |
| GARS | ENSG00000106105 | Glycyl-tRNA synthetase |
| GAS1 | ENSG00000180447 | Growth arrest-specific 1 |
| GAS6 | ENSG00000183087 | Growth arrest-specific 6 |
| GAST | ENSG00000184502 | Gastrin |
| GBA | ENSG00000177628 | Glucosidase, beta, acid |
| GBGT1 | ENSG00000148288 | Globoside alpha-1,3-N-acetylgalactosaminyltransferase 1 |
| GC | ENSG00000145321 | Group-specific component (vitamin D binding protein) |
| GCG | ENSG00000115263 | Glucagon |
| GCGR | ENSG00000215644 | Glucagon receptor |
| GCNT7 | ENSG00000124091 | Glucosaminyl (N-acetyl) transferase family member 7 |
| GCSH | ENSG00000140905 | Glycine cleavage system protein H (aminomethyl carrier) |
| GDF1 | ENSG00000130283 | Growth differentiation factor 1 |
| GDF10 | ENSG00000266524 | Growth differentiation factor 10 |
| GDF11 | ENSG00000135414 | Growth differentiation factor 11 |
| GDF15 | ENSG00000130513 | Growth differentiation factor 15 |
| GDF2 | ENSG00000263761 | Growth differentiation factor 2 |
| GDF3 | ENSG00000184344 | Growth differentiation factor 3 |
| GDF5 | ENSG00000125965 | Growth differentiation factor 5 |
| GDF6 | ENSG00000156466 | Growth differentiation factor 6 |
| GDF7 | ENSG00000143869 | Growth differentiation factor 7 |
| GDF9 | ENSG00000164404 | Growth differentiation factor 9 |
| GDNF | ENSG00000168621 | Glial cell derived neurotrophic factor |

TABLE 1-continued

Exemplary Human Secreted Proteins

| Gene | Ensembl ID | Gene description |
|---|---|---|
| GFOD2 | ENSG00000141098 | Glucose-fructose oxidoreductase domain containing 2 |
| GFPT2 | ENSG00000131459 | Glutamine-fructose-6-phosphate transaminase 2 |
| GFRA2 | ENSG00000168546 | GDNF family receptor alpha 2 |
| GFRA4 | ENSG00000125861 | GDNF family receptor alpha 4 |
| GGA2 | ENSG00000103365 | Golgi-associated, gamma adaptin ear containing, ARF binding protein 2 |
| GGH | ENSG00000137563 | Gamma-glutamyl hydrolase (conjugase, folylpolygammaglutamyl hydrolase) |
| GGT1 | ENSG00000100031 | Gamma-glutamyltransferase 1 |
| GGT5 | ENSG00000099998 | Gamma-glutamyltransferase 5 |
| GH1 | ENSG00000259384 | Growth hormone 1 |
| GH2 | ENSG00000136487 | Growth hormone 2 |
| GHDC | ENSG00000167925 | GH3 domain containing |
| GHRH | ENSG00000118702 | Growth hormone releasing hormone |
| GHRHR | ENSG00000106128 | Growth hormone releasing hormone receptor |
| GHRL | ENSG00000157017 | Ghrelin/obestatin prepropeptide |
| GIF | ENSG00000134812 | Gastric intrinsic factor (vitamin B synthesis) |
| GIP | ENSG00000159224 | Gastric inhibitory polypeptide |
| GKN1 | ENSG00000169605 | Gastrokine 1 |
| GKN2 | ENSG00000183607 | Gastrokine 2 |
| GLA | ENSG00000102393 | Galactosidase, alpha |
| GLB1 | ENSG00000170266 | Galactosidase, beta 1 |
| GLB1L | ENSG00000163521 | Galactosidase, beta 1-like |
| GLB1L2 | ENSG00000149328 | Galactosidase, beta 1-like 2 |
| GLCE | ENSG00000138604 | Glucuronic acid epimerase |
| GLG1 | ENSG00000090863 | Golgi glycoprotein 1 |
| GLIPR1 | ENSG00000139278 | GLI pathogenesis-related 1 |
| GLIPR1L1 | ENSG00000173401 | GLI pathogenesis-related 1 like 1 |
| GLIS3 | ENSG00000107249 | GLIS family zinc finger 3 |
| GLMP | ENSG00000198715 | Glycosylated lysosomal membrane protein |
| GLRB | ENSG00000109738 | Glycine receptor, beta |
| GLS | ENSG00000115419 | Glutaminase |
| GLT6D1 | ENSG00000204007 | Glycosyltransferase 6 domain containing 1 |
| GLTPD2 | ENSG00000182327 | Glycolipid transfer protein domain containing 2 |
| GLUD1 | ENSG00000148672 | Glutamate dehydrogenase 1 |
| GM2A | ENSG00000196743 | GM2 ganglioside activator |
| GML | ENSG00000104499 | Glycosylphosphatidylinositol anchored molecule like |
| GNAS | ENSG00000087460 | GNAS complex locus |
| GNLY | ENSG00000115523 | Granulysin |
| GNPTG | ENSG00000090581 | N-acetylglucosamine-1-phosphate transferase, gamma subunit |
| GNRH1 | ENSG00000147437 | Gonadotropin-releasing hormone 1 (luteinizing-releasing hormone) |
| GNRH2 | ENSG00000125787 | Gonadotropin-releasing hormone 2 |
| GNS | ENSG00000135677 | Glucosamine (N-acetyl)-6-sulfatase |
| GOLM1 | ENSG00000135052 | Golgi membrane protein 1 |
| GORAB | ENSG00000120370 | Golgin, RAB6-interacting |
| GOT2 | ENSG00000125166 | Glutamic-oxaloacetic transaminase 2, mitochondrial |
| GP2 | ENSG00000169347 | Glycoprotein 2 (zymogen granule membrane) |
| GP6 | ENSG00000088053 | Glycoprotein VI (platelet) |
| GPC2 | ENSG00000213420 | Glypican 2 |
| GPC5 | ENSG00000179399 | Glypican 5 |
| GPC6 | ENSG00000183098 | Glypican 6 |
| GPD2 | ENSG00000115159 | Glycerol-3-phosphate dehydrogenase 2 (mitochondrial) |
| GPER1 | ENSG00000164850 | G protein-coupled estrogen receptor 1 |
| GPHA2 | ENSG00000149735 | Glycoprotein hormone alpha 2 |
| GPHB5 | ENSG00000179600 | Glycoprotein hormone beta 5 |
| GPIHBP1 | ENSG00000277494 | Glycosylphosphatidylinositol anchored high density lipoprotein binding protein 1 |
| GPLD1 | ENSG00000112293 | Glycosylphosphatidylinositol specific phospholipase D1 |
| GPNMB | ENSG00000136235 | Glycoprotein (transmembrane) nmb |
| GPR162 | ENSG00000250510 | G protein-coupled receptor 162 |
| GPX3 | ENSG00000211445 | Glutathione peroxidase 3 |
| GPX4 | ENSG00000167468 | Glutathione peroxidase 4 |
| GPX5 | ENSG00000224586 | Glutathione peroxidase 5 |
| GPX6 | ENSG00000198704 | Glutathione peroxidase 6 |
| GPX7 | ENSG00000116157 | Glutathione peroxidase 7 |
| GREM1 | ENSG00000166923 | Gremlin 1, DAN family BMP antagonist |
| GREM2 | ENSG00000180875 | Gremlin 2, DAN family BMP antagonist |
| GRHL3 | ENSG00000158055 | Grainyhead-like transcription factor 3 |
| GRIA2 | ENSG00000120251 | Glutamate receptor, ionotropic, AMPA 2 |
| GRIA3 | ENSG00000125675 | Glutamate receptor, ionotropic, AMPA 3 |
| GRIA4 | ENSG00000152578 | Glutamate receptor, ionotropic, AMPA 4 |
| GRIK2 | ENSG00000164418 | Glutamate receptor, ionotropic, kainate 2 |
| GRIN2B | ENSG00000273079 | Glutamate receptor, ionotropic, N-methyl D-aspartate 2B |
| GRM2 | ENSG00000164082 | Glutamate receptor, metabotropic 2 |
| GRM3 | ENSG00000198822 | Glutamate receptor, metabotropic 3 |

TABLE 1-continued

Exemplary Human Secreted Proteins

| Gene | Ensembl ID | Gene description |
|---|---|---|
| GRM5 | ENSG00000168959 | Glutamate receptor, metabotropic 5 |
| GRN | ENSG00000030582 | Granulin |
| GRP | ENSG00000134443 | Gastrin-releasing peptide |
| GSG1 | ENSG00000111305 | Germ cell associated 1 |
| GSN | ENSG00000148180 | Gelsolin |
| GTDC1 | ENSG00000121964 | Glycosyltransferase-like domain containing 1 |
| GTPBP10 | ENSG00000105793 | GTP-binding protein 10 (putative) |
| GUCA2A | ENSG00000197273 | Guanylate cyclase activator 2A (guanylin) |
| GUCA2B | ENSG00000044012 | Guanylate cyclase activator 2B (uroguanylin) |
| GUSB | ENSG00000169919 | Glucuronidase, beta |
| GVQW1 | ENSG00000241043 | GVQW motif containing 1 |
| GXYLT1 | ENSG00000151233 | Glucoside xylosyltransferase 1 |
| GXYLT2 | ENSG00000172986 | Glucoside xylosyltransferase 2 |
| GYLTL1B | ENSG00000165905 | Glycosyltransferase-like 1B |
| GYPB | ENSG00000250361 | Glycophorin B (MNS blood group) |
| GZMA | ENSG00000145649 | Granzyme A (granzyme 1, cytotoxic T-lymphocyte-associated serine esterase 3) |
| GZMB | ENSG00000100453 | Granzyme B (granzyme 2, cytotoxic T-lymphocyte-associated serine esterase 1) |
| GZMH | ENSG00000100450 | Granzyme H (cathepsin G-like 2, protein h-CCPX) |
| GZMK | ENSG00000113088 | Granzyme K (granzyme 3; tryptase II) |
| GZMM | ENSG00000197540 | Granzyme M (lymphocyte met-ase 1) |
| H6PD | ENSG00000049239 | Hexose-6-phosphate dehydrogenase (glucose 1-dehydrogenase) |
| HABP2 | ENSG00000148702 | Hyaluronan binding protein 2 |
| HADHB | ENSG00000138029 | Hydroxyacyl-CoA dehydrogenase/3-ketoacyl-CoA thiolase/enoyl-CoA hydratase (trifunctional protein), beta subunit |
| HAMP | ENSG00000105697 | Hepcidin antimicrobial peptide |
| HAPLN1 | ENSG00000145681 | Hyaluronan and proteoglycan link protein 1 |
| HAPLN2 | ENSG00000132702 | Hyaluronan and proteoglycan link protein 2 |
| HAPLN3 | ENSG00000140511 | Hyaluronan and proteoglycan link protein 3 |
| HAPLN4 | ENSG00000187664 | Hyaluronan and proteoglycan link protein 4 |
| HARS2 | ENSG00000112855 | Histidyl-tRNA synthetase 2, mitochondrial |
| HAVCR1 | ENSG00000113249 | Hepatitis A virus cellular receptor 1 |
| HCCS | ENSG00000004961 | Holocytochrome c synthase |
| HCRT | ENSG00000161610 | Hypocretin (orexin) neuropeptide precursor |
| HEATR5A | ENSG00000129493 | HEAT repeat containing 5A |
| HEPH | ENSG00000089472 | Hephaestin |
| HEXA | ENSG00000213614 | Hexosaminidase A (alpha polypeptide) |
| HEXB | ENSG00000049860 | Hexosaminidase B (beta polypeptide) |
| HFE2 | ENSG00000168509 | Hemochromatosis type 2 (juvenile) |
| HGF | ENSG00000019991 | Hepatocyte growth factor (hepapoietin A; scatter factor) |
| HGFAC | ENSG00000109758 | HGF activator |
| HHIP | ENSG00000164161 | Hedgehog interacting protein |
| HHIPL1 | ENSG00000182218 | HHIP-like 1 |
| HHIPL2 | ENSG00000143512 | HHIP-like 2 |
| HHLA1 | ENSG00000132297 | HERV-H LTR-associating 1 |
| HHLA2 | ENSG00000114455 | HERV-H LTR-associating 2 |
| HIBADH | ENSG00000106049 | 3-hydroxyisobutyrate dehydrogenase |
| HINT2 | ENSG00000137133 | Histidine triad nucleotide binding protein 2 |
| HLA-A | ENSG00000206503 | Major histocompatibility complex, class I, A |
| HLA-C | ENSG00000204525 | Major histocompatibility complex, class I, C |
| HLA-DOA | ENSG00000204252 | Major histocompatibility complex, class II, DO alpha |
| HLA-DPA1 | ENSG00000231389 | Major histocompatibility complex, class II, DP alpha 1 |
| HLA-DQA1 | ENSG00000196735 | Major histocompatibility complex, class II, DQ alpha 1 |
| HLA-DQB1 | ENSG00000179344 | Major histocompatibility complex, class II, DQ beta 1 |
| HLA-DQB2 | ENSG00000232629 | Major histocompatibility complex, class II, DQ beta 2 |
| HMCN1 | ENSG00000143341 | Hemicentin 1 |
| HMCN2 | ENSG00000148357 | Hemicentin 2 |
| HMGCL | ENSG00000117305 | 3-hydroxymethyl-3-methylglutaryl-CoA lyase |
| HMHA1 | ENSG00000180448 | Histocompatibility (minor) HA-1 |
| HMSD | ENSG00000221887 | Histocompatibility (minor) serpin domain containing |
| HP | ENSG00000257017 | Haptoglobin |
| HPR | ENSG00000261701 | Haptoglobin-related protein |
| HPSE | ENSG00000173083 | Heparanase |
| HPSE2 | ENSG00000172987 | Heparanase 2 (inactive) |
| HPX | ENSG00000110169 | Hemopexin |
| HRC | ENSG00000130528 | Histidine rich calcium binding protein |
| HRG | ENSG00000113905 | Histidine-rich glycoprotein |
| HRSP12 | ENSG00000132541 | Heat-responsive protein 12 |
| HS2ST1 | ENSG00000153936 | Heparan sulfate 2-O-sulfotransferase 1 |
| HS3ST1 | ENSG00000002587 | Heparan sulfate (glucosamine) 3-O-sulfotransferase 1 |
| HS6ST1 | ENSG00000136720 | Heparan sulfate 6-O-sulfotransferase 1 |
| HS6ST3 | ENSG00000185352 | Heparan sulfate 6-O-sulfotransferase 3 |
| HSD11B1L | ENSG00000167733 | Hydroxysteroid (11-beta) dehydrogenase 1-like |
| HSD17B11 | ENSG00000198189 | Hydroxysteroid (17-beta) dehydrogenase 11 |

TABLE 1-continued

Exemplary Human Secreted Proteins

| Gene | Ensembl ID | Gene description |
| --- | --- | --- |
| HSD17B7 | ENSG00000132196 | Hydroxysteroid (17-beta) dehydrogenase 7 |
| HSP90B1 | ENSG00000166598 | Heat shock protein 90 kDa beta (Grp94), member 1 |
| HSPA13 | ENSG00000155304 | Heat shock protein 70 kDa family, member 13 |
| HSPA5 | ENSG00000044574 | Heat shock 70 kDa protein 5 (glucose-regulated protein, 78 kDa) |
| HSPG2 | ENSG00000142798 | Heparan sulfate proteoglycan 2 |
| HTATIP2 | ENSG00000109854 | HIV-1 Tat interactive protein 2, 30 kDa |
| HTN1 | ENSG00000126550 | Histatin 1 |
| HTN3 | ENSG00000205649 | Histatin 3 |
| HTRA1 | ENSG00000166033 | HtrA serine peptidase 1 |
| HTRA3 | ENSG00000170801 | HtrA serine peptidase 3 |
| HTRA4 | ENSG00000169495 | HtrA serine peptidase 4 |
| HYAL1 | ENSG00000114378 | Hyaluronoglucosaminidase 1 |
| HYAL2 | ENSG00000068001 | Hyaluronoglucosaminidase 2 |
| HYAL3 | ENSG00000186792 | Hyaluronoglucosaminidase 3 |
| HYOU1 | ENSG00000149428 | Hypoxia up-regulated 1 |
| IAPP | ENSG00000121351 | Islet amyloid polypeptide |
| IBSP | ENSG00000029559 | Integrin-binding sialoprotein |
| ICAM1 | ENSG00000090339 | Intercellular adhesion molecule 1 |
| ICAM2 | ENSG00000108622 | Intercellular adhesion molecule 2 |
| ICAM4 | ENSG00000105371 | Intercellular adhesion molecule 4 (Landsteiner-Wiener blood group) |
| ID1 | ENSG00000125968 | Inhibitor of DNA binding 1, dominant negative helix-loop-helix protein |
| IDE | ENSG00000119912 | Insulin-degrading enzyme |
| IDNK | ENSG00000148057 | IdnK, gluconokinase homolog (E. coli) |
| IDS | ENSG00000010404 | Iduronate 2-sulfatase |
| IDUA | ENSG00000127415 | Iduronidase, alpha-L- |
| IFI27L2 | ENSG00000119632 | Interferon, alpha-inducible protein 27-like 2 |
| IFI30 | ENSG00000216490 | Interferon, gamma-inducible protein 30 |
| IFNA1 | ENSG00000197919 | Interferon, alpha 1 |
| IFNA10 | ENSG00000186803 | Interferon, alpha 10 |
| IFNA13 | ENSG00000233816 | Interferon, alpha 13 |
| IFNA14 | ENSG00000228083 | Interferon, alpha 14 |
| IFNA16 | ENSG00000147885 | Interferon, alpha 16 |
| IFNA17 | ENSG00000234829 | Interferon, alpha 17 |
| IFNA2 | ENSG00000188379 | Interferon, alpha 2 |
| IFNA21 | ENSG00000137080 | Interferon, alpha 21 |
| IFNA4 | ENSG00000236637 | Interferon, alpha 4 |
| IFNA5 | ENSG00000147873 | Interferon, alpha 5 |
| IFNA6 | ENSG00000120235 | Interferon, alpha 6 |
| IFNA7 | ENSG00000214042 | Interferon, alpha 7 |
| IFNA8 | ENSG00000120242 | Interferon, alpha 8 |
| IFNAR1 | ENSG00000142166 | Interferon (alpha, beta and omega) receptor 1 |
| IFNB1 | ENSG00000171855 | Interferon, beta 1, fibroblast |
| IFNE | ENSG00000184995 | Interferon, epsilon |
| IFNG | ENSG00000111537 | Interferon, gamma |
| IFNGR1 | ENSG00000027697 | Interferon gamma receptor 1 |
| IFNL1 | ENSG00000182393 | Interferon, lambda 1 |
| IFNL2 | ENSG00000183709 | Interferon, lambda 2 |
| IFNL3 | ENSG00000197110 | Interferon, lambda 3 |
| IFNLR1 | ENSG00000185436 | Interferon, lambda receptor 1 |
| IFNW1 | ENSG00000177047 | Interferon, omega 1 |
| IGF1 | ENSG00000017427 | Insulin-like growth factor 1 (somatomedin C) |
| IGF2 | ENSG00000167244 | Insulin-like growth factor 2 |
| IGFALS | ENSG00000099769 | Insulin-like growth factor binding protein, acid labile subunit |
| IGFBP1 | ENSG00000146678 | Insulin-like growth factor binding protein 1 |
| IGFBP2 | ENSG00000115457 | Insulin-like growth factor binding protein 2, 36 kDa |
| IGFBP3 | ENSG00000146674 | Insulin-like growth factor binding protein 3 |
| IGFBP4 | ENSG00000141753 | Insulin-like growth factor binding protein 4 |
| IGFBP5 | ENSG00000115461 | Insulin-like growth factor binding protein 5 |
| IGFBP6 | ENSG00000167779 | Insulin-like growth factor binding protein 6 |
| IGFBP7 | ENSG00000163453 | Insulin-like growth factor binding protein 7 |
| IGFBPL1 | ENSG00000137142 | Insulin-like growth factor binding protein-like 1 |
| IGFL1 | ENSG00000188293 | IGF-like family member 1 |
| IGFL2 | ENSG00000204866 | IGF-like family member 2 |
| IGFL3 | ENSG00000188624 | IGF-like family member 3 |
| IGFLR1 | ENSG00000126246 | IGF-like family receptor 1 |
| IGIP | ENSG00000182700 | IgA-inducing protein |
| IGLON5 | ENSG00000142549 | IgLON family member 5 |
| IGSF1 | ENSG00000147255 | Immunoglobulin superfamily, member 1 |
| IGSF10 | ENSG00000152580 | Immunoglobulin superfamily, member 10 |
| IGSF11 | ENSG00000144847 | Immunoglobulin superfamily, member 11 |
| IGSF21 | ENSG00000117154 | Immunoglobin superfamily, member 21 |
| IGSF8 | ENSG00000162729 | Immunoglobulin superfamily, member 8 |
| IGSF9 | ENSG00000085552 | Immunoglobulin superfamily, member 9 |
| IHH | ENSG00000163501 | Indian hedgehog |

TABLE 1-continued

Exemplary Human Secreted Proteins

| Gene | Ensembl ID | Gene description |
|---|---|---|
| IL10 | ENSG00000136634 | Interleukin 10 |
| IL11 | ENSG00000095752 | Interleukin 11 |
| IL11RA | ENSG00000137070 | Interleukin 11 receptor, alpha |
| IL12B | ENSG00000113302 | Interleukin 12B |
| IL12RB1 | ENSG00000096996 | Interleukin 12 receptor, beta 1 |
| IL12RB2 | ENSG00000081985 | Interleukin 12 receptor, beta 2 |
| IL13 | ENSG00000169194 | Interleukin 13 |
| IL13RA1 | ENSG00000131724 | Interleukin 13 receptor, alpha 1 |
| IL15RA | ENSG00000134470 | Interleukin 15 receptor, alpha |
| IL17A | ENSG00000112115 | Interleukin 17A |
| IL17B | ENSG00000127743 | Interleukin 17B |
| IL17C | ENSG00000124391 | Interleukin 17C |
| IL17D | ENSG00000172458 | Interleukin 17D |
| IL17F | ENSG00000112116 | Interleukin 17F |
| IL17RA | ENSG00000177663 | Interleukin 17 receptor A |
| IL17RC | ENSG00000163702 | Interleukin 17 receptor C |
| IL17RE | ENSG00000163701 | Interleukin 17 receptor E |
| IL18BP | ENSG00000137496 | Interleukin 18 binding protein |
| IL18R1 | ENSG00000115604 | Interleukin 18 receptor 1 |
| IL18RAP | ENSG00000115607 | Interleukin 18 receptor accessory protein |
| IL19 | ENSG00000142224 | Interleukin 19 |
| IL1R1 | ENSG00000115594 | Interleukin 1 receptor, type I |
| IL1R2 | ENSG00000115590 | Interleukin 1 receptor, type II |
| IL1RAP | ENSG00000196083 | Interleukin 1 receptor accessory protein |
| IL1RL1 | ENSG00000115602 | Interleukin 1 receptor-like 1 |
| IL1RL2 | ENSG00000115598 | Interleukin 1 receptor-like 2 |
| IL1RN | ENSG00000136689 | Interleukin 1 receptor antagonist |
| IL2 | ENSG00000109471 | Interleukin 2 |
| IL20 | ENSG00000162891 | Interleukin 20 |
| IL20RA | ENSG00000016402 | Interleukin 20 receptor, alpha |
| IL21 | ENSG00000138684 | Interleukin 21 |
| IL22 | ENSG00000127318 | Interleukin 22 |
| IL22RA2 | ENSG00000164485 | Interleukin 22 receptor, alpha 2 |
| IL23A | ENSG00000110944 | Interleukin 23, alpha subunit p19 |
| IL24 | ENSG00000162892 | Interleukin 24 |
| IL25 | ENSG00000166090 | Interleukin 25 |
| IL26 | ENSG00000111536 | Interleukin 26 |
| IL27 | ENSG00000197272 | Interleukin 27 |
| IL2RB | ENSG00000100385 | Interleukin 2 receptor, beta |
| IL3 | ENSG00000164399 | Interleukin 3 |
| IL31 | ENSG00000204671 | Interleukin 31 |
| IL31RA | ENSG00000164509 | Interleukin 31 receptor A |
| IL32 | ENSG00000008517 | Interleukin 32 |
| IL34 | ENSG00000157368 | Interleukin 34 |
| IL3RA | ENSG00000185291 | Interleukin 3 receptor, alpha (low affinity) |
| IL4 | ENSG00000113520 | Interleukin 4 |
| IL4I1 | ENSG00000104951 | Interleukin 4 induced 1 |
| IL4R | ENSG00000077238 | Interleukin 4 receptor |
| IL5 | ENSG00000113525 | Interleukin 5 |
| IL5RA | ENSG00000091181 | Interleukin 5 receptor, alpha |
| IL6 | ENSG00000136244 | Interleukin 6 |
| IL6R | ENSG00000160712 | Interleukin 6 receptor |
| IL6ST | ENSG00000134352 | Interleukin 6 signal transducer |
| IL7 | ENSG00000104432 | Interleukin 7 |
| IL7R | ENSG00000168685 | Interleukin 7 receptor |
| IL9 | ENSG00000145839 | Interleukin 9 |
| ILDR1 | ENSG00000145103 | Immunoglobulin-like domain containing receptor 1 |
| ILDR2 | ENSG00000143195 | Immunoglobulin-like domain containing receptor 2 |
| IMP4 | ENSG00000136718 | IMP4, U3 small nucleolar ribonucleoprotein |
| IMPG1 | ENSG00000112706 | Interphotoreceptor matrix proteoglycan 1 |
| INHA | ENSG00000123999 | Inhibin, alpha |
| INHBA | ENSG00000122641 | Inhibin, beta A |
| INHBB | ENSG00000163083 | Inhibin, beta B |
| INHBC | ENSG00000175189 | Inhibin, beta C |
| INHBE | ENSG00000139269 | Inhibin, beta E |
| INPP5A | ENSG00000068383 | Inositol polyphosphate-5-phosphatase A |
| INS | ENSG00000254647 | Insulin |
| INS-IGF2 | ENSG00000129965 | INS-IGF2 readthrough |
| INSL3 | ENSG00000248099 | Insulin-like 3 (Leydig cell) |
| INSL4 | ENSG00000120211 | Insulin-like 4 (placenta) |
| INSL5 | ENSG00000172410 | Insulin-like 5 |
| INSL6 | ENSG00000120210 | Insulin-like 6 |
| INTS3 | ENSG00000143624 | Integrator complex subunit 3 |
| IPO11 | ENSG00000086200 | Importin 11 |
| IPO9 | ENSG00000198700 | Importin 9 |
| IQCF6 | ENSG00000214686 | IQ motif containing F6 |

TABLE 1-continued

Exemplary Human Secreted Proteins

| Gene | Ensembl ID | Gene description |
|---|---|---|
| IRAK3 | ENSG00000090376 | Interleukin-1 receptor-associated kinase 3 |
| IRS4 | ENSG00000133124 | Insulin receptor substrate 4 |
| ISLR | ENSG00000129009 | Immunoglobulin superfamily containing leucine-rich repeat |
| ISLR2 | ENSG00000167178 | Immunoglobulin superfamily containing leucine-rich repeat 2 |
| ISM1 | ENSG00000101230 | Isthmin 1, angiogenesis inhibitor |
| ISM2 | ENSG00000100593 | Isthmin 2 |
| ITGA4 | ENSG00000115232 | Integrin, alpha 4 (antigen CD49D, alpha 4 subunit of VLA-4 receptor) |
| ITGA9 | ENSG00000144668 | Integrin, alpha 9 |
| ITGAL | ENSG00000005844 | Integrin, alpha L (antigen CD11A (p180), lymphocyte function-associated antigen 1; alpha polypeptide) |
| ITGAX | ENSG00000140678 | Integrin, alpha X (complement component 3 receptor 4 subunit) |
| ITGB1 | ENSG00000150093 | Integrin, beta 1 (fibronectin receptor, beta polypeptide, antigen CD29 includes MDF2, MSK12) |
| ITGB2 | ENSG00000160255 | Integrin, beta 2 (complement component 3 receptor 3 and 4 subunit) |
| ITGB3 | ENSG00000259207 | Integrin, beta 3 (platelet glycoprotein IIIa, antigen CD61) |
| ITGB7 | ENSG00000139626 | Integrin, beta 7 |
| ITGBL1 | ENSG00000198542 | Integrin, beta-like 1 (with EGF-like repeat domains) |
| ITIH1 | ENSG00000055957 | Inter-alpha-trypsin inhibitor heavy chain 1 |
| ITIH2 | ENSG00000151655 | Inter-alpha-trypsin inhibitor heavy chain 2 |
| ITIH3 | ENSG00000162267 | Inter-alpha-trypsin inhibitor heavy chain 3 |
| ITIH4 | ENSG00000055955 | Inter-alpha-trypsin inhibitor heavy chain family, member 4 |
| ITIH5 | ENSG00000123243 | Inter-alpha-trypsin inhibitor heavy chain family, member 5 |
| ITIH6 | ENSG00000102313 | Inter-alpha-trypsin inhibitor heavy chain family, member 6 |
| ITLN1 | ENSG00000179914 | Intelectin 1 (galactofuranose binding) |
| ITLN2 | ENSG00000158764 | Intelectin 2 |
| IZUMO1R | ENSG00000183560 | IZUMO1 receptor, JUNO |
| IZUMO4 | ENSG00000099840 | IZUMO family member 4 |
| JCHAIN | ENSG00000132465 | Joining chain of multimeric IgA and IgM |
| JMJD8 | ENSG00000161999 | Jumonji domain containing 8 |
| JSRP1 | ENSG00000167476 | Junctional sarcoplasmic reticulum protein 1 |
| KANSL2 | ENSG00000139620 | KAT8 regulatory NSL complex subunit 2 |
| KAZALD1 | ENSG00000107821 | Kazal-type serine peptidase inhibitor domain 1 |
| KCNIP3 | ENSG00000115041 | Kv channel interacting protein 3, calsenilin |
| KCNK7 | ENSG00000173338 | Potassium channel, two pore domain subfamily K, member 7 |
| KCNN4 | ENSG00000104783 | Potassium channel, calcium activated intermediate/small conductance subfamily N alpha, member 4 |
| KCNU1 | ENSG00000215262 | Potassium channel, subfamily U, member 1 |
| KCP | ENSG00000135253 | Kielin/chordin-like protein |
| KDELC1 | ENSG00000134901 | KDEL (Lys-Asp-Glu-Leu) containing 1 |
| KDELC2 | ENSG00000178202 | KDEL (Lys-Asp-Glu-Leu) containing 2 |
| KDM1A | ENSG00000004487 | Lysine (K)-specific demethylase 1A |
| KDM3B | ENSG00000120733 | Lysine (K)-specific demethylase 3B |
| KDM6A | ENSG00000147050 | Lysine (K)-specific demethylase 6A |
| KDM7A | ENSG00000006459 | Lysine (K)-specific demethylase 7A |
| KDSR | ENSG00000119537 | 3-ketodihydrosphingosine reductase |
| KERA | ENSG00000139330 | Keratocan |
| KIAA0100 | ENSG00000007202 | KIAA0100 |
| KIAA0319 | ENSG00000137261 | KIAA0319 |
| KIAA1324 | ENSG00000116299 | KIAA1324 |
| KIFC2 | ENSG00000167702 | Kinesin family member C2 |
| KIR2DL4 | ENSG00000189013 | Killer cell immunoglobulin-like receptor, two domains, long cytoplasmic tail, 4 |
| KIR3DX1 | ENSG00000104970 | Killer cell immunoglobulin-like receptor, three domains, X1 |
| KIRREL2 | ENSG00000126259 | Kin of IRRE like 2 (*Drosophila*) |
| KISS1 | ENSG00000170498 | KiSS-1 metastasis-suppressor |
| KLHL11 | ENSG00000178502 | Kelch-like family member 11 |
| KLHL22 | ENSG00000099910 | Kelch-like family member 22 |
| KLK1 | ENSG00000167748 | Kallikrein 1 |
| KLK10 | ENSG00000129451 | Kallikrein-related peptidase 10 |
| KLK11 | ENSG00000167757 | Kallikrein-related peptidase 11 |
| KLK12 | ENSG00000186474 | Kallikrein-related peptidase 12 |
| KLK13 | ENSG00000167759 | Kallikrein-related peptidase 13 |
| KLK14 | ENSG00000129437 | Kallikrein-related peptidase 14 |
| KLK15 | ENSG00000174562 | Kallikrein-related peptidase 15 |
| KLK2 | ENSG00000167751 | Kallikrein-related peptidase 2 |
| KLK3 | ENSG00000142515 | Kallikrein-related peptidase 3 |
| KLK4 | ENSG00000167749 | Kallikrein-related peptidase 4 |
| KLK5 | ENSG00000167754 | Kallikrein-related peptidase 5 |
| KLK6 | ENSG00000167755 | Kallikrein-related peptidase 6 |
| KLK7 | ENSG00000169035 | Kallikrein-related peptidase 7 |
| KLK8 | ENSG00000129455 | Kallikrein-related peptidase 8 |
| KLK9 | ENSG00000213022 | Kallikrein-related peptidase 9 |
| KLKB1 | ENSG00000164344 | Kallikrein B, plasma (Fletcher factor) 1 |
| KNDC1 | ENSG00000171798 | Kinase non-catalytic C-lobe domain (KIND) containing 1 |

TABLE 1-continued

Exemplary Human Secreted Proteins

| Gene | Ensembl ID | Gene description |
|---|---|---|
| KNG1 | ENSG00000113889 | Kininogen 1 |
| KRBA2 | ENSG00000184619 | KRAB-A domain containing 2 |
| KREMEN2 | ENSG00000131650 | Kringle containing transmembrane protein 2 |
| KRTDAP | ENSG00000188508 | Keratinocyte differentiation-associated protein |
| L1CAM | ENSG00000198910 | L1 cell adhesion molecule |
| L3MBTL2 | ENSG00000100395 | L(3)mbt-like 2 (*Drosophila*) |
| LA16c-380H5.3 | ENSG00000270168 | |
| LACE1 | ENSG00000135537 | Lactation elevated 1 |
| LACRT | ENSG00000135413 | Lacritin |
| LACTB | ENSG00000103642 | Lactamase, beta |
| LAG3 | ENSG00000089692 | Lymphocyte-activation gene 3 |
| LAIR2 | ENSG00000167618 | Leukocyte-associated immunoglobulin-like receptor 2 |
| LALBA | ENSG00000167531 | Lactalbumin, alpha- |
| LAMA1 | ENSG00000101680 | Laminin, alpha 1 |
| LAMA2 | ENSG00000196569 | Laminin, alpha 2 |
| LAMA3 | ENSG00000053747 | Laminin, alpha 3 |
| LAMA4 | ENSG00000112769 | Laminin, alpha 4 |
| LAMA5 | ENSG00000130702 | Laminin, alpha 5 |
| LAMB1 | ENSG00000091136 | Laminin, beta 1 |
| LAMB2 | ENSG00000172037 | Laminin, beta 2 (laminin S) |
| LAMB3 | ENSG00000196878 | Laminin, beta 3 |
| LAMB4 | ENSG00000091128 | Laminin, beta 4 |
| LAMC1 | ENSG00000135862 | Laminin, gamma 1 (formerly LAMB2) |
| LAMC2 | ENSG00000058085 | Laminin, gamma 2 |
| LAMC3 | ENSG00000050555 | Laminin, gamma 3 |
| LAMP3 | ENSG00000078081 | Lysosomal-associated membrane protein 3 |
| LAT | ENSG00000213658 | Linker for activation of T cells |
| LAT2 | ENSG00000086730 | Linker for activation of T cells family, member 2 |
| LBP | ENSG00000129988 | Lipopolysaccharide binding protein |
| LCAT | ENSG00000213398 | Lecithin-cholesterol acyltransferase |
| LCN1 | ENSG00000160349 | Lipocalin 1 |
| LCN10 | ENSG00000187922 | Lipocalin 10 |
| LCN12 | ENSG00000184925 | Lipocalin 12 |
| LCN15 | ENSG00000177984 | Lipocalin 15 |
| LCN2 | ENSG00000148346 | Lipocalin 2 |
| LCN6 | ENSG00000267206 | Lipocalin 6 |
| LCN8 | ENSG00000204001 | Lipocalin 8 |
| LCN9 | ENSG00000148386 | Lipocalin 9 |
| LCORL | ENSG00000178177 | Ligand dependent nuclear receptor corepressor-like |
| LDLR | ENSG00000130164 | Low density lipoprotein receptor |
| LDLRAD2 | ENSG00000187942 | Low density lipoprotein receptor class A domain containing 2 |
| LEAP2 | ENSG00000164406 | Liver expressed antimicrobial peptide 2 |
| LECT2 | ENSG00000145826 | Leukocyte cell-derived chemotaxin 2 |
| LEFTY1 | ENSG00000243709 | Left-right determination factor 1 |
| LEFTY2 | ENSG00000143768 | Left-right determination factor 2 |
| LEP | ENSG00000174697 | Leptin |
| LFNG | ENSG00000106003 | LFNG O-fucosylpeptide 3-beta-N-acetylglucosaminyltransferase |
| LGALS3BP | ENSG00000108679 | Lectin, galactoside-binding, soluble, 3 binding protein |
| LGI1 | ENSG00000108231 | Leucine-rich, glioma inactivated 1 |
| LGI2 | ENSG00000153012 | Leucine-rich repeat LGI family, member 2 |
| LGI3 | ENSG00000168481 | Leucine-rich repeat LGI family, member 3 |
| LGI4 | ENSG00000153902 | Leucine-rich repeat LGI family, member 4 |
| LGMN | ENSG00000100600 | Legumain |
| LGR4 | ENSG00000205213 | Leucine-rich repeat containing G protein-coupled receptor 4 |
| LHB | ENSG00000104826 | Luteinizing hormone beta polypeptide |
| LHCGR | ENSG00000138039 | Luteinizing hormone/choriogonadotropin receptor |
| LIF | ENSG00000128342 | Leukemia inhibitory factor |
| LIFR | ENSG00000113594 | Leukemia inhibitory factor receptor alpha |
| LILRA1 | ENSG00000104974 | Leukocyte immunoglobulin-like receptor, subfamily A (with TM domain), member 1 |
| LILRA2 | ENSG00000239998 | Leukocyte immunoglobulin-like receptor, subfamily A (with TM domain), member 2 |
| LILRB3 | ENSG00000204577 | Leukocyte immunoglobulin-like receptor, subfamily B (with TM and ITIM domains), member 3 |
| LIME1 | ENSG00000203896 | Lck interacting transmembrane adaptor 1 |
| LINGO1 | ENSG00000169783 | Leucine rich repeat and Ig domain containing 1 |
| LIPA | ENSG00000107798 | Lipase A, lysosomal acid, cholesterol esterase |
| LIPC | ENSG00000166035 | Lipase, hepatic |
| LIPF | ENSG00000182333 | Lipase, gastric |
| LIPG | ENSG00000101670 | Lipase, endothelial |
| LIPH | ENSG00000163898 | Lipase, member H |
| LIPK | ENSG00000204021 | Lipase, family member K |
| LIPM | ENSG00000173239 | Lipase, family member M |
| LIPN | ENSG00000204020 | Lipase, family member N |
| LMAN2 | ENSG00000169223 | Lectin, mannose-binding 2 |

TABLE 1-continued

Exemplary Human Secreted Proteins

| Gene | Ensembl ID | Gene description |
|---|---|---|
| LMNTD1 | ENSG00000152936 | Lamin tail domain containing 1 |
| LNX1 | ENSG00000072201 | Ligand of numb-protein X 1, E3 ubiquitin protein ligase |
| LOX | ENSG00000113083 | Lysyl oxidase |
| LOXL1 | ENSG00000129038 | Lysyl oxidase-like 1 |
| LOXL2 | ENSG00000134013 | Lysyl oxidase-like 2 |
| LOXL3 | ENSG00000115318 | Lysyl oxidase-like 3 |
| LOXL4 | ENSG00000138131 | Lysyl oxidase-like 4 |
| LPA | ENSG00000198670 | Lipoprotein, Lp(a) |
| LPL | ENSG00000175445 | Lipoprotein lipase |
| LPO | ENSG00000167419 | Lactoperoxidase |
| LRAT | ENSG00000121207 | Lecithin retinol acyltransferase (phosphatidylcholine--retinol O-acyltransferase) |
| LRCH3 | ENSG00000186001 | Leucine-rich repeats and calponin homology (CH) domain containing 3 |
| LRCOL1 | ENSG00000204583 | Leucine rich colipase-like 1 |
| LRFN4 | ENSG00000173621 | Leucine rich repeat and fibronectin type III domain containing 4 |
| LRFN5 | ENSG00000165379 | Leucine rich repeat and fibronectin type III domain containing 5 |
| LRG1 | ENSG00000171236 | Leucine-rich alpha-2-glycoprotein 1 |
| LRP1 | ENSG00000123384 | Low density lipoprotein receptor-related protein 1 |
| LRP11 | ENSG00000120256 | Low density lipoprotein receptor-related protein 11 |
| LRP1B | ENSG00000168702 | Low density lipoprotein receptor-related protein 1B |
| LRP2 | ENSG00000081479 | Low density lipoprotein receptor-related protein 2 |
| LRP4 | ENSG00000134569 | Low density lipoprotein receptor-related protein 4 |
| LRPAP1 | ENSG00000163956 | Low density lipoprotein receptor-related protein associated protein 1 |
| LRRC17 | ENSG00000128606 | Leucine rich repeat containing 17 |
| LRRC32 | ENSG00000137507 | Leucine rich repeat containing 32 |
| LRRC3B | ENSG00000179796 | Leucine rich repeat containing 3B |
| LRRC4B | ENSG00000131409 | Leucine rich repeat containing 4B |
| LRRC70 | ENSG00000186105 | Leucine rich repeat containing 70 |
| LRRN3 | ENSG00000173114 | Leucine rich repeat neuronal 3 |
| LRRTM1 | ENSG00000162951 | Leucine rich repeat transmembrane neuronal 1 |
| LRRTM2 | ENSG00000146006 | Leucine rich repeat transmembrane neuronal 2 |
| LRRTM4 | ENSG00000176204 | Leucine rich repeat transmembrane neuronal 4 |
| LRTM2 | ENSG00000166159 | Leucine-rich repeats and transmembrane domains 2 |
| LSR | ENSG00000105699 | Lipolysis stimulated lipoprotein receptor |
| LST1 | ENSG00000204482 | Leukocyte specific transcript 1 |
| LTA | ENSG00000226979 | Lymphotoxin alpha |
| LTBP1 | ENSG00000049323 | Latent transforming growth factor beta binding protein 1 |
| LTBP2 | ENSG00000119681 | Latent transforming growth factor beta binding protein 2 |
| LTBP3 | ENSG00000168056 | Latent transforming growth factor beta binding protein 3 |
| LTBP4 | ENSG00000090006 | Latent transforming growth factor beta binding protein 4 |
| LTBR | ENSG00000111321 | Lymphotoxin beta receptor (TNFR superfamily, member 3) |
| LTF | ENSG00000012223 | Lactotransferrin |
| LTK | ENSG00000062524 | Leukocyte receptor tyrosine kinase |
| LUM | ENSG00000139329 | Lumican |
| LUZP2 | ENSG00000187398 | Leucine zipper protein 2 |
| LVRN | ENSG00000172901 | Laeverin |
| LY6E | ENSG00000160932 | Lymphocyte antigen 6 complex, locus E |
| LY6G5B | ENSG00000240053 | Lymphocyte antigen 6 complex, locus G5B |
| LY6G6D | ENSG00000244355 | Lymphocyte antigen 6 complex, locus G6D |
| LY6G6E | ENSG00000255552 | Lymphocyte antigen 6 complex, locus G6E (pseudogene) |
| LY6H | ENSG00000176956 | Lymphocyte antigen 6 complex, locus H |
| LY6K | ENSG00000160886 | Lymphocyte antigen 6 complex, locus K |
| LY86 | ENSG00000112799 | Lymphocyte antigen 86 |
| LY96 | ENSG00000154589 | Lymphocyte antigen 96 |
| LYG1 | ENSG00000144214 | Lysozyme G-like 1 |
| LYG2 | ENSG00000185674 | Lysozyme G-like 2 |
| LYNX1 | ENSG00000180155 | Ly6/neurotoxin 1 |
| LYPD1 | ENSG00000150551 | LY6/PLAUR domain containing 1 |
| LYPD2 | ENSG00000197353 | LY6/PLAUR domain containing 2 |
| LYPD4 | ENSG00000273111 | LY6/PLAUR domain containing 4 |
| LYPD6 | ENSG00000187123 | LY6/PLAUR domain containing 6 |
| LYPD6B | ENSG00000150556 | LY6/PLAUR domain containing 6B |
| LYPD8 | ENSG00000259823 | LY6/PLAUR domain containing 8 |
| LYZ | ENSG00000090382 | Lysozyme |
| LYZL4 | ENSG00000157093 | Lysozyme-like 4 |
| LYZL6 | ENSG00000275722 | Lysozyme-like 6 |
| M6PR | ENSG00000003056 | Mannose-6-phosphate receptor (cation dependent) |
| MAD1L1 | ENSG00000002822 | MAD1 mitotic arrest deficient-like 1 (yeast) |
| MAG | ENSG00000105695 | Myelin associated glycoprotein |
| MAGT1 | ENSG00000102158 | Magnesium transporter 1 |
| MALSU1 | ENSG00000156928 | Mitochondrial assembly of ribosomal large subunit 1 |
| MAMDC2 | ENSG00000165072 | MAM domain containing 2 |
| MAN2B1 | ENSG00000104774 | Mannosidase, alpha, class 2B, member 1 |
| MAN2B2 | ENSG00000013288 | Mannosidase, alpha, class 2B, member 2 |

TABLE 1-continued

Exemplary Human Secreted Proteins

| Gene | Ensembl ID | Gene description |
|---|---|---|
| MANBA | ENSG00000109323 | Mannosidase, beta A, lysosomal |
| MANEAL | ENSG00000185090 | Mannosidase, endo-alpha-like |
| MANF | ENSG00000145050 | Mesencephalic astrocyte-derived neurotrophic factor |
| MANSC1 | ENSG00000111261 | MANSC domain containing 1 |
| MAP3K9 | ENSG00000006432 | Mitogen-activated protein kinase 9 |
| MASP1 | ENSG00000127241 | Mannan-binding lectin serine peptidase 1 (C4/C2 activating component of Ra-reactive factor) |
| MASP2 | ENSG00000009724 | Mannan-binding lectin serine peptidase 2 |
| MATN1 | ENSG00000162510 | Matrilin 1, cartilage matrix protein |
| MATN2 | ENSG00000132561 | Matrilin 2 |
| MATN3 | ENSG00000132031 | Matrilin 3 |
| MATN4 | ENSG00000124159 | Matrilin 4 |
| MATR3 | ENSG00000015479 | Matrin 3 |
| MATR3 | ENSG00000280987 | Matrin 3 |
| MAU2 | ENSG00000129933 | MAU2 sister chromatid cohesion factor |
| MAZ | ENSG00000103495 | MYC-associated zinc finger protein (purine-binding transcription factor) |
| MBD6 | ENSG00000166987 | Methyl-CpG binding domain protein 6 |
| MBL2 | ENSG00000165471 | Mannose-binding lectin (protein C) 2, soluble |
| MBNL1 | ENSG00000152601 | Muscleblind-like splicing regulator 1 |
| MCCC1 | ENSG00000078070 | Methylcrotonoyl-CoA carboxylase 1 (alpha) |
| MCCD1 | ENSG00000204511 | Mitochondrial coiled-coil domain 1 |
| MCEE | ENSG00000124370 | Methylmalonyl CoA epimerase |
| MCF2L | ENSG00000126217 | MCF.2 cell line derived transforming sequence-like |
| MCFD2 | ENSG00000180398 | Multiple coagulation factor deficiency 2 |
| MDFIC | ENSG00000135272 | MyoD family inhibitor domain containing |
| MDGA1 | ENSG00000112139 | MAM domain containing glycosylphosphatidylinositol anchor 1 |
| MDK | ENSG00000110492 | Midkine (neurite growth-promoting factor 2) |
| MED20 | ENSG00000124641 | Mediator complex subunit 20 |
| MEGF10 | ENSG00000145794 | Multiple EGF-like-domains 10 |
| MEGF6 | ENSG00000162591 | Multiple EGF-like-domains 6 |
| MEI1 | ENSG00000167077 | Meiotic double-stranded break formation protein 1 |
| MEI4 | ENSG00000269964 | Meiotic double-stranded break formation protein 4 |
| MEIS1 | ENSG00000143995 | Meis homeobox 1 |
| MEIS3 | ENSG00000105419 | Meis homeobox 3 |
| MEPE | ENSG00000152595 | Matrix extracellular phosphoglycoprotein |
| MESDC2 | ENSG00000117899 | Mesoderm development candidate 2 |
| MEST | ENSG00000106484 | Mesoderm specific transcript |
| MET | ENSG00000105976 | MET proto-oncogene, receptor tyrosine kinase |
| METRN | ENSG00000103260 | Meteorin, glial cell differentiation regulator |
| METRNL | ENSG00000176845 | Meteorin, glial cell differentiation regulator-like |
| METTL17 | ENSG00000165792 | Methyltransferase like 17 |
| METTL24 | ENSG00000053328 | Methyltransferase like 24 |
| METTL7B | ENSG00000170439 | Methyltransferase like 7B |
| METTL9 | ENSG00000197006 | Methyltransferase like 9 |
| MEX3C | ENSG00000176624 | Mex-3 RNA binding family member C |
| MFAP2 | ENSG00000117122 | Microfibrillar-associated protein 2 |
| MFAP3 | ENSG00000037749 | Microfibrillar-associated protein 3 |
| MFAP3L | ENSG00000198948 | Microfibrillar-associated protein 3-like |
| MFAP4 | ENSG00000166482 | Microfibrillar-associated protein 4 |
| MFAP5 | ENSG00000197614 | Microfibrillar associated protein 5 |
| MFGE8 | ENSG00000140545 | Milk fat globule-EGF factor 8 protein |
| MFI2 | ENSG00000163975 | Antigen p97 (melanoma associated) identified by monoclonal antibodies 133.2 and 96.5 |
| MFNG | ENSG00000100060 | MFNG O-fucosylpeptide 3-beta-N-acetylglucosaminyltransferase |
| MGA | ENSG00000174197 | MGA, MAX dimerization protein |
| MGAT2 | ENSG00000168282 | Mannosyl (alpha-1,6-)-glycoprotein beta-1,2-N-acetylglucosaminyltransferase |
| MGAT3 | ENSG00000128268 | Mannosyl (beta-1,4-)-glycoprotein beta-1,4-N-acetylglucosaminyltransferase |
| MGAT4A | ENSG00000071073 | Mannosyl (alpha-1,3-)-glycoprotein beta-1,4-N-acetylglucosaminyltransferase, isozyme A |
| MGAT4B | ENSG00000161013 | Mannosyl (alpha-1,3-)-glycoprotein beta-1,4-N-acetylglucosaminyltransferase, isozyme B |
| MGAT4D | ENSG00000205301 | MGAT4 family, member D |
| MGLL | ENSG00000074416 | Monoglyceride lipase |
| MGP | ENSG00000111341 | Matrix Gla protein |
| MGST2 | ENSG00000085871 | Microsomal glutathione S-transferase 2 |
| MIA | ENSG00000261857 | Melanoma inhibitory activity |
| MIA2 | ENSG00000150526 | Melanoma inhibitory activity 2 |
| MIA3 | ENSG00000154305 | Melanoma inhibitory activity family, member 3 |
| MICU1 | ENSG00000107745 | Mitochondrial calcium uptake 1 |
| MIER1 | ENSG00000198160 | Mesoderm induction early response 1, transcriptional regulator |
| MINOS1-NBL1 | ENSG00000270136 | MINOS1-NBL1 readthrough |
| MINPP1 | ENSG00000107789 | Multiple inositol-polyphosphate phosphatase 1 |

TABLE 1-continued

Exemplary Human Secreted Proteins

| Gene | Ensembl ID | Gene description |
|---|---|---|
| MLEC | ENSG00000110917 | Malectin |
| MLN | ENSG00000096395 | Motilin |
| MLXIP | ENSG00000175727 | MLX interacting protein |
| MLXIPL | ENSG00000009950 | MLX interacting protein-like |
| MMP1 | ENSG00000196611 | Matrix metallopeptidase 1 |
| MMP10 | ENSG00000166670 | Matrix metallopeptidase 10 |
| MMP11 | ENSG00000099953 | Matrix metallopeptidase 11 |
| MMP12 | ENSG00000262406 | Matrix metallopeptidase 12 |
| MMP13 | ENSG00000137745 | Matrix metallopeptidase 13 |
| MMP14 | ENSG00000157227 | Matrix metallopeptidase 14 (membrane-inserted) |
| MMP17 | ENSG00000198598 | Matrix metallopeptidase 17 (membrane-inserted) |
| MMP19 | ENSG00000123342 | Matrix metallopeptidase 19 |
| MMP2 | ENSG00000087245 | Matrix metallopeptidase 2 |
| MMP20 | ENSG00000137674 | Matrix metallopeptidase 20 |
| MMP21 | ENSG00000154485 | Matrix metallopeptidase 21 |
| MMP25 | ENSG00000008516 | Matrix metallopeptidase 25 |
| MMP26 | ENSG00000167346 | Matrix metallopeptidase 26 |
| MMP27 | ENSG00000137675 | Matrix metallopeptidase 27 |
| MMP28 | ENSG00000271447 | Matrix metallopeptidase 28 |
| MMP3 | ENSG00000149968 | Matrix metallopeptidase 3 |
| MMP7 | ENSG00000137673 | Matrix metallopeptidase 7 |
| MMP8 | ENSG00000118113 | Matrix metallopeptidase 8 |
| MMP9 | ENSG00000100985 | Matrix metallopeptidase 9 |
| MMRN1 | ENSG00000138722 | Multimerin 1 |
| MMRN2 | ENSG00000173269 | Multimerin 2 |
| MOXD1 | ENSG00000079931 | Monooxygenase, DBH-like 1 |
| MPO | ENSG00000005381 | Myeloperoxidase |
| MPPED1 | ENSG00000186732 | Metallophosphoesterase domain containing 1 |
| MPZL1 | ENSG00000197965 | Myelin protein zero-like 1 |
| MR1 | ENSG00000153029 | Major histocompatibility complex, class I-related |
| MRPL2 | ENSG00000112651 | Mitochondrial ribosomal protein L2 |
| MRPL21 | ENSG00000197345 | Mitochondrial ribosomal protein L21 |
| MRPL22 | ENSG00000082515 | Mitochondrial ribosomal protein L22 |
| MRPL24 | ENSG00000143314 | Mitochondrial ribosomal protein L24 |
| MRPL27 | ENSG00000108826 | Mitochondrial ribosomal protein L27 |
| MRPL32 | ENSG00000106591 | Mitochondrial ribosomal protein L32 |
| MRPL34 | ENSG00000130312 | Mitochondrial ribosomal protein L34 |
| MRPL35 | ENSG00000132313 | Mitochondrial ribosomal protein L35 |
| MRPL52 | ENSG00000172590 | Mitochondrial ribosomal protein L52 |
| MRPL55 | ENSG00000162910 | Mitochondrial ribosomal protein L55 |
| MRPS14 | ENSG00000120333 | Mitochondrial ribosomal protein S14 |
| MRPS22 | ENSG00000175110 | Mitochondrial ribosomal protein S22 |
| MRPS28 | ENSG00000147586 | Mitochondrial ribosomal protein S28 |
| MS4A14 | ENSG00000166928 | Membrane-spanning 4-domains, subfamily A, member 14 |
| MS4A3 | ENSG00000149516 | Membrane-spanning 4-domains, subfamily A, member 3 (hematopoietic cell-specific) |
| MSH3 | ENSG00000113318 | MutS homolog 3 |
| MSH5 | ENSG00000204410 | MutS homolog 5 |
| MSLN | ENSG00000102854 | Mesothelin |
| MSMB | ENSG00000263639 | Microseminoprotein, beta- |
| MSRA | ENSG00000175806 | Methionine sulfoxide reductase A |
| MSRB2 | ENSG00000148450 | Methionine sulfoxide reductase B2 |
| MSRB3 | ENSG00000174099 | Methionine sulfoxide reductase B3 |
| MST1 | ENSG00000173531 | Macrophage stimulating 1 |
| MSTN | ENSG00000138379 | Myostatin |
| MT1G | ENSG00000125144 | Metallothionein 1G |
| MTHFD2 | ENSG00000065911 | Methylenetetrahydrofolate dehydrogenase (NADP+ dependent) 2, methenyltetrahydrofolate cyclohydrolase |
| MTMR14 | ENSG00000163719 | Myotubularin related protein 14 |
| MTRNR2L11 | ENSG00000270188 | MT-RNR2-like 11 (pseudogene) |
| MTRR | ENSG00000124275 | 5-methyltetrahydrofolate-homocysteine methyltransferase reductase |
| MTTP | ENSG00000138823 | Microsomal triglyceride transfer protein |
| MTX2 | ENSG00000128654 | Metaxin 2 |
| MUC1 | ENSG00000185499 | Mucin 1, cell surface associated |
| MUC13 | ENSG00000173702 | Mucin 13, cell surface associated |
| MUC20 | ENSG00000176945 | Mucin 20, cell surface associated |
| MUC3A | ENSG00000169894 | Mucin 3A, cell surface associated |
| MUC5AC | ENSG00000215182 | Mucin 5AC, oligomeric mucus/gel-forming |
| MUC5B | ENSG00000117983 | Mucin 5B, oligomeric mucus/gel-forming |
| MUC6 | ENSG00000184956 | Mucin 6, oligomeric mucus/gel-forming |
| MUC7 | ENSG00000171195 | Mucin 7, secreted |
| MUCL1 | ENSG00000172551 | Mucin-like 1 |
| MXRA5 | ENSG00000101825 | Matrix-remodelling associated 5 |
| MXRA7 | ENSG00000182534 | Matrix-remodelling associated 7 |
| MYDGF | ENSG00000074842 | Myeloid-derived growth factor |

TABLE 1-continued

Exemplary Human Secreted Proteins

| Gene | Ensembl ID | Gene description |
|---|---|---|
| MYL1 | ENSG00000168530 | Myosin, light chain 1, alkali; skeletal, fast |
| MYOC | ENSG00000034971 | Myocilin, trabecular meshwork inducible glucocorticoid response |
| MYRFL | ENSG00000166268 | Myelin regulatory factor-like |
| MZB1 | ENSG00000170476 | Marginal zone B and B1 cell-specific protein |
| N4BP2L2 | ENSG00000244754 | NEDD4 binding protein 2-like 2 |
| NAA38 | ENSG00000183011 | N(alpha)-acetyltransferase 38, NatC auxiliary subunit |
| NAAA | ENSG00000138744 | N-acylethanolamine acid amidase |
| NAGA | ENSG00000198951 | N-acetylgalactosaminidase, alpha- |
| NAGLU | ENSG00000108784 | N-acetylglucosaminidase, alpha |
| NAGS | ENSG00000161653 | N-acetylglutamate synthase |
| NAPSA | ENSG00000131400 | Napsin A aspartic peptidase |
| NBL1 | ENSG00000158747 | Neuroblastoma 1, DAN family BMP antagonist |
| NCAM1 | ENSG00000149294 | Neural cell adhesion molecule 1 |
| NCAN | ENSG00000130287 | Neurocan |
| NCBP2-AS2 | ENSG00000270170 | NCBP2 antisense RNA 2 (head to head) |
| NCSTN | ENSG00000162736 | Nicastrin |
| NDNF | ENSG00000173376 | Neuron-derived neurotrophic factor |
| NDP | ENSG00000124479 | Norrie disease (pseudoglioma) |
| NDUFA10 | ENSG00000130414 | NADH dehydrogenase (ubiquinone) 1 alpha subcomplex, 10, 42 kDa |
| NDUFB5 | ENSG00000136521 | NADH dehydrogenase (ubiquinone) 1 beta subcomplex, 5, 16 kDa |
| NDUFS8 | ENSG00000110717 | NADH dehydrogenase (ubiquinone) Fe—S protein 8, 23 kDa (NADH-coenzyme Q reductase) |
| NDUFV1 | ENSG00000167792 | NADH dehydrogenase (ubiquinone) flavoprotein 1, 51 kDa |
| NECAB3 | ENSG00000125967 | N-terminal EF-hand calcium binding protein 3 |
| NELL1 | ENSG00000165973 | Neural EGFL like 1 |
| NELL2 | ENSG00000184613 | Neural EGFL like 2 |
| NENF | ENSG00000117691 | Neudesin neurotrophic factor |
| NETO1 | ENSG00000166342 | Neuropilin (NRP) and tolloid (TLL)-like 1 |
| NFASC | ENSG00000163531 | Neurofascin |
| NFE2L1 | ENSG00000082641 | Nuclear factor, erythroid 2-like 1 |
| NFE2L3 | ENSG00000050344 | Nuclear factor, erythroid 2-like 3 |
| NGEF | ENSG00000066248 | Neuronal guanine nucleotide exchange factor |
| NGF | ENSG00000134259 | Nerve growth factor (beta polypeptide) |
| NGLY1 | ENSG00000151092 | N-glycanase 1 |
| NGRN | ENSG00000182768 | Neugrin, neurite outgrowth associated |
| NHLRC3 | ENSG00000188811 | NHL repeat containing 3 |
| NID1 | ENSG00000116962 | Nidogen 1 |
| NID2 | ENSG00000087303 | Nidogen 2 (osteonidogen) |
| NKG7 | ENSG00000105374 | Natural killer cell granule protein 7 |
| NLGN3 | ENSG00000196338 | Neuroligin 3 |
| NLGN4Y | ENSG00000165246 | Neuroligin 4, Y-linked |
| NLRP5 | ENSG00000171487 | NLR family, pyrin domain containing 5 |
| NMB | ENSG00000197696 | Neuromedin B |
| NME1 | ENSG00000239672 | NME/NM23 nucleoside diphosphate kinase 1 |
| NME1-NME2 | ENSG00000011052 | NME1-NME2 readthrough |
| NME3 | ENSG00000103024 | NME/NM23 nucleoside diphosphate kinase 3 |
| NMS | ENSG00000204640 | Neuromedin S |
| NMU | ENSG00000109255 | Neuromedin U |
| NOA1 | ENSG00000084092 | Nitric oxide associated 1 |
| NODAL | ENSG00000156574 | Nodal growth differentiation factor |
| NOG | ENSG00000183691 | Noggin |
| NOMO3 | ENSG00000103226 | NODAL modulator 3 |
| NOS1AP | ENSG00000198929 | Nitric oxide synthase 1 (neuronal) adaptor protein |
| NOTCH3 | ENSG00000074181 | Notch 3 |
| NOTUM | ENSG00000185269 | Notum pectinacetylesterase homolog (*Drosophila*) |
| NOV | ENSG00000136999 | Nephroblastoma overexpressed |
| NPB | ENSG00000183979 | Neuropeptide B |
| NPC2 | ENSG00000119655 | Niemann-Pick disease, type C2 |
| NPFF | ENSG00000139574 | Neuropeptide FF-amide peptide precursor |
| NPFFR2 | ENSG00000056291 | Neuropeptide FF receptor 2 |
| NPHS1 | ENSG00000161270 | Nephrosis 1, congenital, Finnish type (nephrin) |
| NPNT | ENSG00000168743 | Nephronectin |
| NPPA | ENSG00000175206 | Natriuretic peptide A |
| NPPB | ENSG00000120937 | Natriuretic peptide B |
| NPPC | ENSG00000163273 | Natriuretic peptide C |
| NPS | ENSG00000214285 | Neuropeptide S |
| NPTX1 | ENSG00000171246 | Neuronal pentraxin I |
| NPTX2 | ENSG00000106236 | Neuronal pentraxin II |
| NPTXR | ENSG00000221890 | Neuronal pentraxin receptor |
| NPVF | ENSG00000105954 | Neuropeptide VF precursor |
| NPW | ENSG00000183971 | Neuropeptide W |
| NPY | ENSG00000122585 | Neuropeptide Y |
| NQO2 | ENSG00000124588 | NAD(P)H dehydrogenase, quinone 2 |

TABLE 1-continued

Exemplary Human Secreted Proteins

| Gene | Ensembl ID | Gene description |
|---|---|---|
| NRCAM | ENSG00000091129 | Neuronal cell adhesion molecule |
| NRG1 | ENSG00000157168 | Neuregulin 1 |
| NRN1L | ENSG00000188038 | Neuritin 1-like |
| NRP1 | ENSG00000099250 | Neuropilin 1 |
| NRP2 | ENSG00000118257 | Neuropilin 2 |
| NRTN | ENSG00000171119 | Neurturin |
| NRXN1 | ENSG00000179915 | Neurexin 1 |
| NRXN2 | ENSG00000110076 | Neurexin 2 |
| NT5C3A | ENSG00000122643 | 5'-nucleotidase, cytosolic IIIA |
| NT5DC3 | ENSG00000111696 | 5'-nucleotidase domain containing 3 |
| NT5E | ENSG00000135318 | 5'-nucleotidase, ecto (CD73) |
| NTF3 | ENSG00000185652 | Neurotrophin 3 |
| NTF4 | ENSG00000225950 | Neurotrophin 4 |
| NTM | ENSG00000182667 | Neurotrimin |
| NTN1 | ENSG00000065320 | Netrin 1 |
| NTN3 | ENSG00000162068 | Netrin 3 |
| NTN4 | ENSG00000074527 | Netrin 4 |
| NTN5 | ENSG00000142233 | Netrin 5 |
| NTNG1 | ENSG00000162631 | Netrin G1 |
| NTNG2 | ENSG00000196358 | Netrin G2 |
| NTS | ENSG00000133636 | Neurotensin |
| NUBPL | ENSG00000151413 | Nucleotide binding protein-like |
| NUCB1 | ENSG00000104805 | Nucleobindin 1 |
| NUCB2 | ENSG00000070081 | Nucleobindin 2 |
| NUDT19 | ENSG00000213965 | Nudix (nucleoside diphosphate linked moiety X)-type motif 19 |
| NUDT9 | ENSG00000170502 | Nudix (nucleoside diphosphate linked moiety X)-type motif 9 |
| NUP155 | ENSG00000113569 | Nucleoporin 155 kDa |
| NUP214 | ENSG00000126883 | Nucleoporin 214 kDa |
| NUP85 | ENSG00000125450 | Nucleoporin 85 kDa |
| NXPE3 | ENSG00000144815 | Neurexophilin and PC-esterase domain family, member 3 |
| NXPE4 | ENSG00000137634 | Neurexophilin and PC-esterase domain family, member 4 |
| NXPH1 | ENSG00000122584 | Neurexophilin 1 |
| NXPH2 | ENSG00000144227 | Neurexophilin 2 |
| NXPH3 | ENSG00000182575 | Neurexophilin 3 |
| NXPH4 | ENSG00000182379 | Neurexophilin 4 |
| NYX | ENSG00000188937 | Nyctalopin |
| OAF | ENSG00000184232 | Out at first homolog |
| OBP2A | ENSG00000122136 | Odorant binding protein 2A |
| OBP2B | ENSG00000171102 | Odorant binding protein 2B |
| OC90 | ENSG00000253117 | Otoconin 90 |
| OCLN | ENSG00000197822 | Occludin |
| ODAM | ENSG00000109205 | Odontogenic, ameloblast asssociated |
| OGG1 | ENSG00000114026 | 8-oxoguanine DNA glycosylase |
| OGN | ENSG00000106809 | Osteoglycin |
| OIT3 | ENSG00000138315 | Oncoprotein induced transcript 3 |
| OLFM1 | ENSG00000130558 | Olfactomedin 1 |
| OLFM2 | ENSG00000105088 | Olfactomedin 2 |
| OLFM3 | ENSG00000118733 | Olfactomedin 3 |
| OLFM4 | ENSG00000102837 | Olfactomedin 4 |
| OLFML1 | ENSG00000183801 | Olfactomedin-like 1 |
| OLFML2A | ENSG00000185585 | Olfactomedin-like 2A |
| OLFML2B | ENSG00000162745 | Olfactomedin-like 2B |
| OLFML3 | ENSG00000116774 | Olfactomedin-like 3 |
| OMD | ENSG00000127083 | Osteomodulin |
| OMG | ENSG00000126861 | Oligodendrocyte myelin glycoprotein |
| OOSP2 | ENSG00000149507 | Oocyte secreted protein 2 |
| OPCML | ENSG00000183715 | Opioid binding protein/cell adhesion molecule-like |
| OPTC | ENSG00000188770 | Opticin |
| ORAI1 | ENSG00000276045 | ORAI calcium release-activated calcium modulator 1 |
| ORM1 | ENSG00000229314 | Orosomucoid 1 |
| ORM2 | ENSG00000228278 | Orosomucoid 2 |
| ORMDL2 | ENSG00000123353 | ORMDL sphingolipid biosynthesis regulator 2 |
| OS9 | ENSG00000135506 | Osteosarcoma amplified 9, endoplasmic reticulum lectin |
| OSCAR | ENSG00000170909 | Osteoclast associated, immunoglobulin-like receptor |
| OSM | ENSG00000099985 | Oncostatin M |
| OSMR | ENSG00000145623 | Oncostatin M receptor |
| OSTN | ENSG00000188729 | Osteocrin |
| OTOA | ENSG00000155719 | Otoancorin |
| OTOG | ENSG00000188162 | Otogelin |
| OTOGL | ENSG00000165899 | Otogelin-like |
| OTOL1 | ENSG00000182447 | Otolin 1 |
| OTOR | ENSG00000125879 | Otoraplin |
| OTOS | ENSG00000178602 | Otospiralin |
| OVCH1 | ENSG00000187950 | Ovochymase 1 |
| OVCH2 | ENSG00000183378 | Ovochymase 2 (gene/pseudogene) |
| OVGP1 | ENSG00000085465 | Oviductal glycoprotein 1, 120 kDa |

TABLE 1-continued

Exemplary Human Secreted Proteins

| Gene | Ensembl ID | Gene description |
|---|---|---|
| OXCT1 | ENSG00000083720 | 3-oxoacid CoA transferase 1 |
| OXCT2 | ENSG00000198754 | 3-oxoacid CoA transferase 2 |
| OXNAD1 | ENSG00000154814 | Oxidoreductase NAD-binding domain containing 1 |
| OXT | ENSG00000101405 | Oxytocin/neurophysin I prepropeptide |
| P3H1 | ENSG00000117385 | Prolyl 3-hydroxylase 1 |
| P3H2 | ENSG00000090530 | Prolyl 3-hydroxylase 2 |
| P3H3 | ENSG00000110811 | Prolyl 3-hydroxylase 3 |
| P3H4 | ENSG00000141696 | Prolyl 3-hydroxylase family member 4 (non-enzymatic) |
| P4HA1 | ENSG00000122884 | Prolyl 4-hydroxylase, alpha polypeptide I |
| P4HA2 | ENSG00000072682 | Prolyl 4-hydroxylase, alpha polypeptide II |
| P4HA3 | ENSG00000149380 | Prolyl 4-hydroxylase, alpha polypeptide III |
| P4HB | ENSG00000185624 | Prolyl 4-hydroxylase, beta polypeptide |
| PAEP | ENSG00000122133 | Progestagen-associated endometrial protein |
| PAM | ENSG00000145730 | Peptidylglycine alpha-amidating monooxygenase |
| PAMR1 | ENSG00000149090 | Peptidase domain containing associated with muscle regeneration 1 |
| PAPL | ENSG00000183760 | Iron/zinc purple acid phosphatase-like protein |
| PAPLN | ENSG00000100767 | Papilin, proteoglycan-like sulfated glycoprotein |
| PAPPA | ENSG00000182752 | Pregnancy-associated plasma protein A, pappalysin 1 |
| PAPPA2 | ENSG00000116183 | Pappalysin 2 |
| PARP15 | ENSG00000173200 | Poly (ADP-ribose) polymerase family, member 15 |
| PARVB | ENSG00000188677 | Parvin, beta |
| PATE1 | ENSG00000171053 | Prostate and testis expressed 1 |
| PATE2 | ENSG00000196844 | Prostate and testis expressed 2 |
| PATE3 | ENSG00000236027 | Prostate and testis expressed 3 |
| PATE4 | ENSG00000237353 | Prostate and testis expressed 4 |
| PATL2 | ENSG00000229474 | Protein associated with topoisomerase II homolog 2 (yeast) |
| PAX2 | ENSG00000075891 | Paired box 2 |
| PAX4 | ENSG00000106331 | Paired box 4 |
| PCCB | ENSG00000114054 | Propionyl CoA carboxylase, beta polypeptide |
| PCDH1 | ENSG00000156453 | Protocadherin 1 |
| PCDH12 | ENSG00000113555 | Protocadherin 12 |
| PCDH15 | ENSG00000150275 | Protocadherin-related 15 |
| PCDHA1 | ENSG00000204970 | Protocadherin alpha 1 |
| PCDHA10 | ENSG00000250120 | Protocadherin alpha 10 |
| PCDHA11 | ENSG00000249158 | Protocadherin alpha 11 |
| PCDHA6 | ENSG00000081842 | Protocadherin alpha 6 |
| PCDHB12 | ENSG00000120328 | Protocadherin beta 12 |
| PCDHGA11 | ENSG00000253873 | Protocadherin gamma subfamily A, 11 |
| PCF11 | ENSG00000165494 | PCF11 cleavage and polyadenylation factor subunit |
| PCOLCE | ENSG00000106333 | Procollagen C-endopeptidase enhancer |
| PCOLCE2 | ENSG00000163710 | Procollagen C-endopeptidase enhancer 2 |
| PCSK1 | ENSG00000175426 | Proprotein convertase subtilisin/kexin type 1 |
| PCSK1N | ENSG00000102109 | Proprotein convertase subtilisin/kexin type 1 inhibitor |
| PCSK2 | ENSG00000125851 | Proprotein convertase subtilisin/kexin type 2 |
| PCSK4 | ENSG00000115257 | Proprotein convertase subtilisin/kexin type 4 |
| PCSK5 | ENSG00000099139 | Proprotein convertase subtilisin/kexin type 5 |
| PCSK9 | ENSG00000169174 | Proprotein convertase subtilisin/kexin type 9 |
| PCYOX1 | ENSG00000116005 | Prenylcysteine oxidase 1 |
| PCYOX1L | ENSG00000145882 | Prenylcysteine oxidase 1 like |
| PDDC1 | ENSG00000177225 | Parkinson disease 7 domain containing 1 |
| PDE11A | ENSG00000128655 | Phosphodiesterase 11A |
| PDE2A | ENSG00000186642 | Phosphodiesterase 2A, cGMP-stimulated |
| PDE7A | ENSG00000205268 | Phosphodiesterase 7A |
| PDF | ENSG00000258429 | Peptide deformylase (mitochondrial) |
| PDGFA | ENSG00000197461 | Platelet-derived growth factor alpha polypeptide |
| PDGFB | ENSG00000100311 | Platelet-derived growth factor beta polypeptide |
| PDGFC | ENSG00000145431 | Platelet derived growth factor C |
| PDGFD | ENSG00000170962 | Platelet derived growth factor D |
| PDGFRA | ENSG00000134853 | Platelet-derived growth factor receptor, alpha polypeptide |
| PDGFRB | ENSG00000113721 | Platelet-derived growth factor receptor, beta polypeptide |
| PDGFRL | ENSG00000104213 | Platelet-derived growth factor receptor-like |
| PDHA1 | ENSG00000131828 | Pyruvate dehydrogenase (lipoamide) alpha 1 |
| PDIA2 | ENSG00000185615 | Protein disulfide isomerase family A, member 2 |
| PDIA3 | ENSG00000167004 | Protein disulfide isomerase family A, member 3 |
| PDIA4 | ENSG00000155660 | Protein disulfide isomerase family A, member 4 |
| PDIA5 | ENSG00000065485 | Protein disulfide isomerase family A, member 5 |
| PDIA6 | ENSG00000143870 | Protein disulfide isomerase family A, member 6 |
| PDILT | ENSG00000169340 | Protein disulfide isomerase-like, testis expressed |
| PDYN | ENSG00000101327 | Prodynorphin |
| PDZD8 | ENSG00000165650 | PDZ domain containing 8 |
| PDZRN4 | ENSG00000165966 | PDZ domain containing ring finger 4 |
| PEAR1 | ENSG00000187800 | Platelet endothelial aggregation receptor 1 |
| PEBP4 | ENSG00000134020 | Phosphatidylethanolamine-binding protein 4 |
| PECAM1 | ENSG00000261371 | Platelet/endothelial cell adhesion molecule 1 |
| PENK | ENSG00000181195 | Proenkephalin |

TABLE 1-continued

Exemplary Human Secreted Proteins

| Gene | Ensembl ID | Gene description |
| --- | --- | --- |
| PET117 | ENSG00000232838 | PET117 homolog |
| PF4 | ENSG00000163737 | Platelet factor 4 |
| PF4V1 | ENSG00000109272 | Platelet factor 4 variant 1 |
| PFKP | ENSG00000067057 | Phosphofructokinase, platelet |
| PFN1 | ENSG00000108518 | Profilin 1 |
| PGA3 | ENSG00000229859 | Pepsinogen 3, group I (pepsinogen A) |
| PGA4 | ENSG00000229183 | Pepsinogen 4, group I (pepsinogen A) |
| PGA5 | ENSG00000256713 | Pepsinogen 5, group I (pepsinogen A) |
| PGAM5 | ENSG00000247077 | PGAM family member 5, serine/threonine protein phosphatase, mitochondrial |
| PGAP3 | ENSG00000161395 | Post-GPI attachment to proteins 3 |
| PGC | ENSG00000096088 | Progastricsin (pepsinogen C) |
| PGF | ENSG00000119630 | Placental growth factor |
| PGLYRP1 | ENSG00000008438 | Peptidoglycan recognition protein 1 |
| PGLYRP2 | ENSG00000161031 | Peptidoglycan recognition protein 2 |
| PGLYRP3 | ENSG00000159527 | Peptidoglycan recognition protein 3 |
| PGLYRP4 | ENSG00000163218 | Peptidoglycan recognition protein 4 |
| PHACTR1 | ENSG00000112137 | Phosphatase and actin regulator 1 |
| PHB | ENSG00000167085 | Prohibitin |
| PI15 | ENSG00000137558 | Peptidase inhibitor 15 |
| PI3 | ENSG00000124102 | Peptidase inhibitor 3, skin-derived |
| PIANP | ENSG00000139200 | PILR alpha associated neural protein |
| PIGK | ENSG00000142892 | Phosphatidylinositol glycan anchor biosynthesis, class K |
| PIGL | ENSG00000108474 | Phosphatidylinositol glycan anchor biosynthesis, class L |
| PIGT | ENSG00000124155 | Phosphatidylinositol glycan anchor biosynthesis, class T |
| PIGZ | ENSG00000119227 | Phosphatidylinositol glycan anchor biosynthesis, class Z |
| PIK3AP1 | ENSG00000155629 | Phosphoinositide-3-kinase adaptor protein 1 |
| PIK3IP1 | ENSG00000100100 | Phosphoinositide-3-kinase interacting protein 1 |
| PILRA | ENSG00000085514 | Paired immunoglobin-like type 2 receptor alpha |
| PILRB | ENSG00000121716 | Paired immunoglobin-like type 2 receptor beta |
| PINLYP | ENSG00000234465 | Phospholipase A2 inhibitor and LY6/PLAUR domain containing |
| PIP | ENSG00000159763 | Prolactin-induced protein |
| PIWIL4 | ENSG00000134627 | Piwi-like RNA-mediated gene silencing 4 |
| PKDCC | ENSG00000162878 | Protein kinase domain containing, cytoplasmic |
| PKHD1 | ENSG00000170927 | Polycystic kidney and hepatic disease 1 (autosomal recessive) |
| PLA1A | ENSG00000144837 | Phospholipase A1 member A |
| PLA2G10 | ENSG00000069764 | Phospholipase A2, group X |
| PLA2G12A | ENSG00000123739 | Phospholipase A2, group XIIA |
| PLA2G12B | ENSG00000138308 | Phospholipase A2, group XIIB |
| PLA2G15 | ENSG00000103066 | Phospholipase A2, group XV |
| PLA2G1B | ENSG00000170890 | Phospholipase A2, group IB (pancreas) |
| PLA2G2A | ENSG00000188257 | Phospholipase A2, group IIA (platelets, synovial fluid) |
| PLA2G2C | ENSG00000187980 | Phospholipase A2, group IIC |
| PLA2G2D | ENSG00000117215 | Phospholipase A2, group IID |
| PLA2G2E | ENSG00000188784 | Phospholipase A2, group IIE |
| PLA2G3 | ENSG00000100078 | Phospholipase A2, group III |
| PLA2G5 | ENSG00000127472 | Phospholipase A2, group V |
| PLA2G7 | ENSG00000146070 | Phospholipase A2, group VII (platelet-activating factor acetylhydrolase, plasma) |
| PLA2R1 | ENSG00000153246 | Phospholipase A2 receptor 1, 180 kDa |
| PLAC1 | ENSG00000170965 | Placenta-specific 1 |
| PLAC9 | ENSG00000189129 | Placenta-specific 9 |
| PLAT | ENSG00000104368 | Plasminogen activator, tissue |
| PLAU | ENSG00000122861 | Plasminogen activator, urokinase |
| PLAUR | ENSG00000011422 | Plasminogen activator, urokinase receptor |
| PLBD1 | ENSG00000121316 | Phospholipase B domain containing 1 |
| PLBD2 | ENSG00000151176 | Phospholipase B domain containing 2 |
| PLG | ENSG00000122194 | Plasminogen |
| PLGLB1 | ENSG00000183281 | Plasminogen-like B1 |
| PLGLB2 | ENSG00000125551 | Plasminogen-like B2 |
| PLOD1 | ENSG00000083444 | Procollagen-lysine, 2-oxoglutarate 5-dioxygenase 1 |
| PLOD2 | ENSG00000152952 | Procollagen-lysine, 2-oxoglutarate 5-dioxygenase 2 |
| PLOD3 | ENSG00000106397 | Procollagen-lysine, 2-oxoglutarate 5-dioxygenase 3 |
| PLTP | ENSG00000100979 | Phospholipid transfer protein |
| PLXNA4 | ENSG00000221866 | Plexin A4 |
| PLXNB2 | ENSG00000196576 | Plexin B2 |
| PM20D1 | ENSG00000162877 | Peptidase M20 domain containing 1 |
| PMCH | ENSG00000183395 | Pro-melanin-concentrating hormone |
| PMEL | ENSG00000185664 | Premelanosome protein |
| PMEPA1 | ENSG00000124225 | Prostate transmembrane protein, androgen induced 1 |
| PNLIP | ENSG00000175535 | Pancreatic lipase |
| PNLIPRP1 | ENSG00000187021 | Pancreatic lipase-related protein 1 |
| PNLIPRP3 | ENSG00000203837 | Pancreatic lipase-related protein 3 |
| PNOC | ENSG00000168081 | Prepronociceptin |
| PNP | ENSG00000198805 | Purine nucleoside phosphorylase |

TABLE 1-continued

Exemplary Human Secreted Proteins

| Gene | Ensembl ID | Gene description |
|---|---|---|
| PNPLA4 | ENSG00000006757 | Patatin-like phospholipase domain containing 4 |
| PODNL1 | ENSG00000132000 | Podocan-like 1 |
| POFUT1 | ENSG00000101346 | Protein O-fucosyltransferase 1 |
| POFUT2 | ENSG00000186866 | Protein O-fucosyltransferase 2 |
| POGLUT1 | ENSG00000163389 | Protein O-glucosyltransferase 1 |
| POLL | ENSG00000166169 | Polymerase (DNA directed), lambda |
| POMC | ENSG00000115138 | Proopiomelanocortin |
| POMGNT2 | ENSG00000144647 | Protein O-linked mannose N-acetylglucosaminyltransferase 2 (beta 1,4-) |
| PON1 | ENSG00000005421 | Paraoxonase 1 |
| PON2 | ENSG00000105854 | Paraoxonase 2 |
| PON3 | ENSG00000105852 | Paraoxonase 3 |
| POSTN | ENSG00000133110 | Periostin, osteoblast specific factor |
| PPBP | ENSG00000163736 | Pro-platelet basic protein (chemokine (C—X—C motif) ligand 7) |
| PPIB | ENSG00000166794 | Peptidylprolyl isomerase B (cyclophilin B) |
| PPIC | ENSG00000168938 | Peptidylprolyl isomerase C (cyclophilin C) |
| PPOX | ENSG00000143224 | Protoporphyrinogen oxidase |
| PPP1CA | ENSG00000172531 | Protein phosphatase 1, catalytic subunit, alpha isozyme |
| PPT1 | ENSG00000131238 | Palmitoyl-protein thioesterase 1 |
| PPT2 | ENSG00000221988 | Palmitoyl-protein thioesterase 2 |
| PPY | ENSG00000108849 | Pancreatic polypeptide |
| PRAC2 | ENSG00000229637 | Prostate cancer susceptibility candidate 2 |
| PRADC1 | ENSG00000135617 | Protease-associated domain containing 1 |
| PRAP1 | ENSG00000165828 | Proline-rich acidic protein 1 |
| PRB1 | ENSG00000251655 | Proline-rich protein BstNI subfamily 1 |
| PRB2 | ENSG00000121335 | Proline-rich protein BstNI subfamily 2 |
| PRB3 | ENSG00000197870 | Proline-rich protein BstNI subfamily 3 |
| PRB4 | ENSG00000230657 | Proline-rich protein BstNI subfamily 4 |
| PRCD | ENSG00000214140 | Progressive rod-cone degeneration |
| PRCP | ENSG00000137509 | Prolylcarboxypeptidase (angiotensinase C) |
| PRDM12 | ENSG00000130711 | PR domain containing 12 |
| PRDX4 | ENSG00000123131 | Peroxiredoxin 4 |
| PRELP | ENSG00000188783 | Proline/arginine-rich end leucine-rich repeat protein |
| PRF1 | ENSG00000180644 | Perforin 1 (pore forming protein) |
| PRG2 | ENSG00000186652 | Proteoglycan 2, bone marrow (natural killer cell activator, eosinophil granule major basic protein) |
| PRG3 | ENSG00000156575 | Proteoglycan 3 |
| PRG4 | ENSG00000116690 | Proteoglycan 4 |
| PRH1 | ENSG00000231887 | Proline-rich protein HaeIII subfamily 1 |
| PRH2 | ENSG00000134551 | Proline-rich protein HaeIII subfamily 2 |
| PRKAG1 | ENSG00000181929 | Protein kinase, AMP-activated, gamma 1 non-catalytic subunit |
| PRKCSH | ENSG00000130175 | Protein kinase C substrate 80K-H |
| PRKD1 | ENSG00000184304 | Protein kinase D1 |
| PRL | ENSG00000172179 | Prolactin |
| PRLH | ENSG00000071677 | Prolactin releasing hormone |
| PRLR | ENSG00000113494 | Prolactin receptor |
| PRNP | ENSG00000171867 | Prion protein |
| PRNT | ENSG00000180259 | Prion protein (testis specific) |
| PROC | ENSG00000115718 | Protein C (inactivator of coagulation factors Va and VIIIa) |
| PROK1 | ENSG00000143125 | Prokineticin 1 |
| PROK2 | ENSG00000163421 | Prokineticin 2 |
| PROL1 | ENSG00000171199 | Proline rich, lacrimal 1 |
| PROM1 | ENSG00000007062 | Prominin 1 |
| PROS1 | ENSG00000184500 | Protein S (alpha) |
| PROZ | ENSG00000126231 | Protein Z, vitamin K-dependent plasma glycoprotein |
| PRR27 | ENSG00000187533 | Proline rich 27 |
| PRR4 | ENSG00000111215 | Proline rich 4 (lacrimal) |
| PRRG2 | ENSG00000126460 | Proline rich Gla (G-carboxyglutamic acid) 2 |
| PRRT3 | ENSG00000163704 | Proline-rich transmembrane protein 3 |
| PRRT4 | ENSG00000224940 | Proline-rich transmembrane protein 4 |
| PRSS1 | ENSG00000204983 | Protease, serine, 1 (trypsin 1) |
| PRSS12 | ENSG00000164099 | Protease, serine, 12 (neurotrypsin, motopsin) |
| PRSS16 | ENSG00000112812 | Protease, serine, 16 (thymus) |
| PRSS2 | ENSG00000275896 | Protease, serine, 2 (trypsin 2) |
| PRSS21 | ENSG00000007038 | Protease, serine, 21 (testisin) |
| PRSS22 | ENSG00000005001 | Protease, serine, 22 |
| PRSS23 | ENSG00000150687 | Protease, serine, 23 |
| PRSS27 | ENSG00000172382 | Protease, serine 27 |
| PRSS3 | ENSG00000010438 | Protease, serine, 3 |
| PRSS33 | ENSG00000103355 | Protease, serine, 33 |
| PRSS35 | ENSG00000146250 | Protease, serine, 35 |
| PRSS36 | ENSG00000178226 | Protease, serine, 36 |
| PRSS37 | ENSG00000165076 | Protease, serine, 37 |
| PRSS38 | ENSG00000185888 | Protease, serine, 38 |
| PRSS42 | ENSG00000178055 | Protease, serine, 42 |
| PRSS48 | ENSG00000189099 | Protease, serine, 48 |

TABLE 1-continued

Exemplary Human Secreted Proteins

| Gene | Ensembl ID | Gene description |
|---|---|---|
| PRSS50 | ENSG00000206549 | Protease, serine, 50 |
| PRSS53 | ENSG00000151006 | Protease, serine, 53 |
| PRSS54 | ENSG00000103023 | Protease, serine, 54 |
| PRSS55 | ENSG00000184647 | Protease, serine, 55 |
| PRSS56 | ENSG00000237412 | Protease, serine, 56 |
| PRSS57 | ENSG00000185198 | Protease, serine, 57 |
| PRSS58 | ENSG00000258223 | Protease, serine, 58 |
| PRSS8 | ENSG00000052344 | Protease, serine, 8 |
| PRTG | ENSG00000166450 | Protogenin |
| PRTN3 | ENSG00000196415 | Proteinase 3 |
| PSAP | ENSG00000197746 | Prosaposin |
| PSAPL1 | ENSG00000178597 | Prosaposin-like 1 (gene/pseudogene) |
| PSG1 | ENSG00000231924 | Pregnancy specific beta-1-glycoprotein 1 |
| PSG11 | ENSG00000243130 | Pregnancy specific beta-1-glycoprotein 11 |
| PSG2 | ENSG00000242221 | Pregnancy specific beta-1-glycoprotein 2 |
| PSG3 | ENSG00000221826 | Pregnancy specific beta-1-glycoprotein 3 |
| PSG4 | ENSG00000243137 | Pregnancy specific beta-1-glycoprotein 4 |
| PSG5 | ENSG00000204941 | Pregnancy specific beta-1-glycoprotein 5 |
| PSG6 | ENSG00000170848 | Pregnancy specific beta-1-glycoprotein 6 |
| PSG7 | ENSG00000221878 | Pregnancy specific beta-1-glycoprotein 7 (gene/pseudogene) |
| PSG8 | ENSG00000124467 | Pregnancy specific beta-1-glycoprotein 8 |
| PSG9 | ENSG00000183668 | Pregnancy specific beta-1-glycoprotein 9 |
| PSMD1 | ENSG00000173692 | Proteasome 26S subunit, non-ATPase 1 |
| PSORS1C2 | ENSG00000204538 | Psoriasis susceptibility 1 candidate 2 |
| PSPN | ENSG00000125650 | Persephin |
| PTGDS | ENSG00000107317 | Prostaglandin D2 synthase 21 kDa (brain) |
| PTGIR | ENSG00000160013 | Prostaglandin I2 (prostacyclin) receptor (IP) |
| PTGS1 | ENSG00000095303 | Prostaglandin-endoperoxide synthase 1 (prostaglandin G/H synthase and cyclooxygenase) |
| PTGS2 | ENSG00000073756 | Prostaglandin-endoperoxide synthase 2 (prostaglandin G/H synthase and cyclooxygenase) |
| PTH | ENSG00000152266 | Parathyroid hormone |
| PTH2 | ENSG00000142538 | Parathyroid hormone 2 |
| PTHLH | ENSG00000087494 | Parathyroid hormone-like hormone |
| PTK7 | ENSG00000112655 | Protein tyrosine kinase 7 (inactive) |
| PTN | ENSG00000105894 | Pleiotrophin |
| PTPRA | ENSG00000132670 | Protein tyrosine phosphatase, receptor type, A |
| PTPRB | ENSG00000127329 | Protein tyrosine phosphatase, receptor type, B |
| PTPRC | ENSG00000081237 | Protein tyrosine phosphatase, receptor type, C |
| PTPRCAP | ENSG00000213402 | Protein tyrosine phosphatase, receptor type, C-associated protein |
| PTPRD | ENSG00000153707 | Protein tyrosine phosphatase, receptor type, D |
| PTPRF | ENSG00000142949 | Protein tyrosine phosphatase, receptor type, F |
| PTPRJ | ENSG00000149177 | Protein tyrosine phosphatase, receptor type, J |
| PTPRO | ENSG00000151490 | Protein tyrosine phosphatase, receptor type, O |
| PTPRS | ENSG00000105426 | Protein tyrosine phosphatase, receptor type, S |
| PTTG1IP | ENSG00000183255 | Pituitary tumor-transforming 1 interacting protein |
| PTX3 | ENSG00000163661 | Pentraxin 3, long |
| PTX4 | ENSG00000251692 | Pentraxin 4, long |
| PVR | ENSG00000073008 | Poliovirus receptor |
| PVRL1 | ENSG00000110400 | Poliovirus receptor-related 1 (herpesvirus entry mediator C) |
| PXDN | ENSG00000130508 | Peroxidasin |
| PXDNL | ENSG00000147485 | Peroxidasin-like |
| PXYLP1 | ENSG00000155893 | 2-phosphoxylose phosphatase 1 |
| PYY | ENSG00000131096 | Peptide YY |
| PZP | ENSG00000126838 | Pregnancy-zone protein |
| QPCT | ENSG00000115828 | Glutaminyl-peptide cyclotransferase |
| QPRT | ENSG00000103485 | Quinolinate phosphoribosyltransferase |
| QRFP | ENSG00000188710 | Pyroglutamylated RFamide peptide |
| QSOX1 | ENSG00000116260 | Quiescin Q6 sulfhydryl oxidase 1 |
| R3HDML | ENSG00000101074 | R3H domain containing-like |
| RAB26 | ENSG00000167964 | RAB26, member RAS oncogene family |
| RAB36 | ENSG00000100228 | RAB36, member RAS oncogene family |
| RAB9B | ENSG00000123570 | RAB9B, member RAS oncogene family |
| RAET1E | ENSG00000164520 | Retinoic acid early transcript 1E |
| RAET1G | ENSG00000203722 | Retinoic acid early transcript 1G |
| RAMP2 | ENSG00000131477 | Receptor (G protein-coupled) activity modifying protein 2 |
| RAPGEF5 | ENSG00000136237 | Rap guanine nucleotide exchange factor (GEF) 5 |
| RARRES1 | ENSG00000118849 | Retinoic acid receptor responder (tazarotene induced) 1 |
| RARRES2 | ENSG00000106538 | Retinoic acid receptor responder (tazarotene induced) 2 |
| RASA2 | ENSG00000155903 | RAS p21 protein activator 2 |
| RBM3 | ENSG00000102317 | RNA binding motif (RNP1, RRM) protein 3 |
| RBP3 | ENSG00000265203 | Retinol binding protein 3, interstitial |
| RBP4 | ENSG00000138207 | Retinol binding protein 4, plasma |
| RCN1 | ENSG00000049449 | Reticulocalbin 1, EF-hand calcium binding domain |
| RCN2 | ENSG00000117906 | Reticulocalbin 2, EF-hand calcium binding domain |
| RCN3 | ENSG00000142552 | Reticulocalbin 3, EF-hand calcium binding domain |

TABLE 1-continued

Exemplary Human Secreted Proteins

| Gene | Ensembl ID | Gene description |
|---|---|---|
| RCOR1 | ENSG00000089902 | REST corepressor 1 |
| RDH11 | ENSG00000072042 | Retinol dehydrogenase 11 (all-trans/9-cis/11-cis) |
| RDH12 | ENSG00000139988 | Retinol dehydrogenase 12 (all-trans/9-cis/11-cis) |
| RDH13 | ENSG00000160439 | Retinol dehydrogenase 13 (all-trans/9-cis) |
| RDH5 | ENSG00000135437 | Retinol dehydrogenase 5 (11-cis/9-cis) |
| RDH8 | ENSG00000080511 | Retinol dehydrogenase 8 (all-trans) |
| REG1A | ENSG00000115386 | Regenerating islet-derived 1 alpha |
| REG1B | ENSG00000172023 | Regenerating islet-derived 1 beta |
| REG3A | ENSG00000172016 | Regenerating islet-derived 3 alpha |
| REG3G | ENSG00000143954 | Regenerating islet-derived 3 gamma |
| REG4 | ENSG00000134193 | Regenerating islet-derived family, member 4 |
| RELN | ENSG00000189056 | Reelin |
| RELT | ENSG00000054967 | RELT tumor necrosis factor receptor |
| REN | ENSG00000143839 | Renin |
| REPIN1 | ENSG00000214022 | Replication initiator 1 |
| REPS2 | ENSG00000169891 | RALBP1 associated Eps domain containing 2 |
| RET | ENSG00000165731 | Ret proto-oncogene |
| RETN | ENSG00000104918 | Resistin |
| RETNLB | ENSG00000163515 | Resistin like beta |
| RETSAT | ENSG00000042445 | Retinol saturase (all-trans-retinol 13,14-reductase) |
| RFNG | ENSG00000169733 | RFNG O-fucosylpeptide 3-beta-N-acetylglucosaminyltransferase |
| RGCC | ENSG00000102760 | Regulator of cell cycle |
| RGL4 | ENSG00000159496 | Ral guanine nucleotide dissociation stimulator-like 4 |
| RGMA | ENSG00000182175 | Repulsive guidance molecule family member a |
| RGMB | ENSG00000174136 | Repulsive guidance molecule family member b |
| RHOQ | ENSG00000119729 | Ras homolog family member Q |
| RIC3 | ENSG00000166405 | RIC3 acetylcholine receptor chaperone |
| RIMS1 | ENSG00000079841 | Regulating synaptic membrane exocytosis 1 |
| RIPPLY1 | ENSG00000147223 | Ripply transcriptional repressor 1 |
| RLN1 | ENSG00000107018 | Relaxin 1 |
| RLN2 | ENSG00000107014 | Relaxin 2 |
| RLN3 | ENSG00000171136 | Relaxin 3 |
| RMDN1 | ENSG00000176623 | Regulator of microtubule dynamics 1 |
| RNASE1 | ENSG00000129538 | Ribonuclease, RNase A family, 1 (pancreatic) |
| RNASE10 | ENSG00000182545 | Ribonuclease, RNase A family, 10 (non-active) |
| RNASE11 | ENSG00000173464 | Ribonuclease, RNase A family, 11 (non-active) |
| RNASE12 | ENSG00000258436 | Ribonuclease, RNase A family, 12 (non-active) |
| RNASE13 | ENSG00000206150 | Ribonuclease, RNase A family, 13 (non-active) |
| RNASE2 | ENSG00000169385 | Ribonuclease, RNase A family, 2 (liver, eosinophil-derived neurotoxin) |
| RNASE3 | ENSG00000169397 | Ribonuclease, RNase A family, 3 |
| RNASE4 | ENSG00000258818 | Ribonuclease, RNase A family, 4 |
| RNASE6 | ENSG00000169413 | Ribonuclease, RNase A family, k6 |
| RNASE7 | ENSG00000165799 | Ribonuclease, RNase A family, 7 |
| RNASE8 | ENSG00000173431 | Ribonuclease, RNase A family, 8 |
| RNASE9 | ENSG00000188655 | Ribonuclease, RNase A family, 9 (non-active) |
| RNASEH1 | ENSG00000171865 | Ribonuclease H1 |
| RNASET2 | ENSG00000026297 | Ribonuclease T2 |
| RNF146 | ENSG00000118518 | Ring finger protein 146 |
| RNF148 | ENSG00000235631 | Ring finger protein 148 |
| RNF150 | ENSG00000170153 | Ring finger protein 150 |
| RNF167 | ENSG00000108523 | Ring finger protein 167 |
| RNF220 | ENSG00000187147 | Ring finger protein 220 |
| RNF34 | ENSG00000170633 | Ring finger protein 34, E3 ubiquitin protein ligase |
| RNLS | ENSG00000184719 | Renalase, FAD-dependent amine oxidase |
| RNPEP | ENSG00000176393 | Arginyl aminopeptidase (aminopeptidase B) |
| ROR1 | ENSG00000185483 | Receptor tyrosine kinase-like orphan receptor 1 |
| RP11-1236K1.1 | ENSG00000233050 | |
| RP11-14J7.7 | ENSG00000259060 | |
| RP11-196G11.1 | ENSG00000255439 | |
| RP11-350O14.18 | ENSG00000261793 | |
| RP11-520P18.5 | ENSG00000261667 | |
| RP11-812E19.9 | ENSG00000259680 | |
| RP11-903H12.5 | ENSG00000259171 | |
| RP11-977G19.10 | ENSG00000144785 | |
| RP4-576H24.4 | ENSG00000260861 | |
| RP4-608O15.3 | ENSG00000276911 | Complement factor H-related protein 2 |
| RPL3 | ENSG00000100316 | Ribosomal protein L3 |
| RPLP2 | ENSG00000177600 | Ribosomal protein, large, P2 |
| RPN2 | ENSG00000118705 | Ribophorin II |
| RPS27L | ENSG00000185088 | Ribosomal protein S27-like |
| RQCD1 | ENSG00000144580 | RCD1 required for cell differentiation1 homolog (S. pombe) |
| RS1 | ENSG00000102104 | Retinoschisin 1 |
| RSF1 | ENSG00000048649 | Remodeling and spacing factor 1 |
| RSPO1 | ENSG00000169218 | R-spondin 1 |

TABLE 1-continued

Exemplary Human Secreted Proteins

| Gene | Ensembl ID | Gene description |
|---|---|---|
| RSPO2 | ENSG00000147655 | R-spondin 2 |
| RSPO3 | ENSG00000146374 | R-spondin 3 |
| RSPO4 | ENSG00000101282 | R-spondin 4 |
| RSPRY1 | ENSG00000159579 | Ring finger and SPRY domain containing 1 |
| RTBDN | ENSG00000132026 | Retbindin |
| RTN4RL1 | ENSG00000185924 | Reticulon 4 receptor-like 1 |
| RTN4RL2 | ENSG00000186907 | Reticulon 4 receptor-like 2 |
| SAA1 | ENSG00000173432 | Serum amyloid A1 |
| SAA2 | ENSG00000134339 | Serum amyloid A2 |
| SAA4 | ENSG00000148965 | Serum amyloid A4, constitutive |
| SAP30 | ENSG00000164105 | Sin3A-associated protein, 30 kDa |
| SAR1A | ENSG00000079332 | Secretion associated, Ras related GTPase 1A |
| SARAF | ENSG00000133872 | Store-operated calcium entry-associated regulatory factor |
| SARM1 | ENSG00000004139 | Sterile alpha and TIR motif containing 1 |
| SATB1 | ENSG00000182568 | SATB homeobox 1 |
| SAXO2 | ENSG00000188659 | Stabilizer of axonemal microtubules 2 |
| SBSN | ENSG00000189001 | Suprabasin |
| SBSPON | ENSG00000164764 | Somatomedin B and thrombospondin, type 1 domain containing |
| SCARF1 | ENSG00000074660 | Scavenger receptor class F, member 1 |
| SCG2 | ENSG00000171951 | Secretogranin II |
| SCG3 | ENSG00000104112 | Secretogranin III |
| SCG5 | ENSG00000166922 | Secretogranin V |
| SCGB1A1 | ENSG00000149021 | Secretoglobin, family 1A, member 1 (uteroglobin) |
| SCGB1C1 | ENSG00000188076 | Secretoglobin, family 1C, member 1 |
| SCGB1C2 | ENSG00000268320 | Secretoglobin, family 1C, member 2 |
| SCGB1D1 | ENSG00000168515 | Secretoglobin, family 1D, member 1 |
| SCGB1D2 | ENSG00000124935 | Secretoglobin, family 1D, member 2 |
| SCGB1D4 | ENSG00000197745 | Secretoglobin, family 1D, member 4 |
| SCGB2A1 | ENSG00000124939 | Secretoglobin, family 2A, member 1 |
| SCGB2A2 | ENSG00000110484 | Secretoglobin, family 2A, member 2 |
| SCGB2B2 | ENSG00000205209 | Secretoglobin, family 2B, member 2 |
| SCGB3A1 | ENSG00000161055 | Secretoglobin, family 3A, member 1 |
| SCGB3A2 | ENSG00000164265 | Secretoglobin, family 3A, member 2 |
| SCN1B | ENSG00000105711 | Sodium channel, voltage gated, type I beta subunit |
| SCN3B | ENSG00000166257 | Sodium channel, voltage gated, type III beta subunit |
| SCPEP1 | ENSG00000121064 | Serine carboxypeptidase 1 |
| SCRG1 | ENSG00000164106 | Stimulator of chondrogenesis 1 |
| SCT | ENSG00000070031 | Secretin |
| SCUBE1 | ENSG00000159307 | Signal peptide, CUB domain, EGF-like 1 |
| SCUBE2 | ENSG00000175356 | Signal peptide, CUB domain, EGF-like 2 |
| SCUBE3 | ENSG00000146197 | Signal peptide, CUB domain, EGF-like 3 |
| SDC1 | ENSG00000115884 | Syndecan 1 |
| SDF2 | ENSG00000132581 | Stromal cell-derived factor 2 |
| SDF2L1 | ENSG00000128228 | Stromal cell-derived factor 2-like 1 |
| SDF4 | ENSG00000078808 | Stromal cell derived factor 4 |
| SDHAF2 | ENSG00000167985 | Succinate dehydrogenase complex assembly factor 2 |
| SDHAF4 | ENSG00000154079 | Succinate dehydrogenase complex assembly factor 4 |
| SDHB | ENSG00000117118 | Succinate dehydrogenase complex, subunit B, iron sulfur (Ip) |
| SDHD | ENSG00000204370 | Succinate dehydrogenase complex, subunit D, integral membrane protein |
| SEC14L3 | ENSG00000100012 | SEC14-like lipid binding 3 |
| SEC16A | ENSG00000148396 | SEC16 homolog A, endoplasmic reticulum export factor |
| SEC16B | ENSG00000120341 | SEC16 homolog B, endoplasmic reticulum export factor |
| SEC22C | ENSG00000093183 | SEC22 homolog C, vesicle trafficking protein |
| SEC31A | ENSG00000138674 | SEC31 homolog A, COPII coat complex component |
| SECISBP2 | ENSG00000187742 | SECIS binding protein 2 |
| SECTM1 | ENSG00000141574 | Secreted and transmembrane 1 |
| SEL1L | ENSG00000071537 | Sel-1 suppressor of lin-12-like (*C. elegans*) |
| SELM | ENSG00000198832 | Selenoprotein M |
| SELO | ENSG00000073169 | Selenoprotein O |
| SEMA3A | ENSG00000075213 | Sema domain, immunoglobulin domain (Ig), short basic domain, secreted, (semaphorin) 3A |
| SEMA3B | ENSG00000012171 | Sema domain, immunoglobulin domain (Ig), short basic domain, secreted, (semaphorin) 3B |
| SEMA3C | ENSG00000075223 | Sema domain, immunoglobulin domain (Ig), short basic domain, secreted, (semaphorin) 3C |
| SEMA3E | ENSG00000170381 | Sema domain, immunoglobulin domain (Ig), short basic domain, secreted, (semaphorin) 3E |
| SEMA3F | ENSG00000001617 | Sema domain, immunoglobulin domain (Ig), short basic domain, secreted, (semaphorin) 3F |
| SEMA3G | ENSG00000010319 | Sema domain, immunoglobulin domain (Ig), short basic domain, secreted, (semaphorin) 3G |
| SEMA4A | ENSG00000196189 | Sema domain, immunoglobulin domain (Ig), transmembrane domain (TM) and short cytoplasmic domain, (semaphorin) 4A |
| SEMA4B | ENSG00000185033 | Sema domain, immunoglobulin domain (Ig), transmembrane domain (TM) and short cytoplasmic domain, (semaphorin) 4B |

TABLE 1-continued

Exemplary Human Secreted Proteins

| Gene | Ensembl ID | Gene description |
|---|---|---|
| SEMA4C | ENSG00000168758 | Sema domain, immunoglobulin domain (Ig), transmembrane domain (TM) and short cytoplasmic domain, (semaphorin) 4C |
| SEMA4D | ENSG00000187764 | Sema domain, immunoglobulin domain (Ig), transmembrane domain (TM) and short cytoplasmic domain, (semaphorin) 4D |
| SEMA4F | ENSG00000135622 | Sema domain, immunoglobulin domain (Ig), transmembrane domain (TM) and short cytoplasmic domain, (semaphorin) 4F |
| SEMA4G | ENSG00000095539 | Sema domain, immunoglobulin domain (Ig), transmembrane domain (TM) and short cytoplasmic domain, (semaphorin) 4G |
| SEMA5A | ENSG00000112902 | Sema domain, seven thrombospondin repeats (type 1 and type 1-like), transmembrane domain (TM) and short cytoplasmic domain, (semaphorin) 5A |
| SEMA6A | ENSG00000092421 | Sema domain, transmembrane domain (TM), and cytoplasmic domain, (semaphorin) 6A |
| SEMA6C | ENSG00000143434 | Sema domain, transmembrane domain (TM), and cytoplasmic domain, (semaphorin) 6C |
| SEMA6D | ENSG00000137872 | Sema domain, transmembrane domain (TM), and cytoplasmic domain, (semaphorin) 6D |
| SEMG1 | ENSG00000124233 | Semenogelin I |
| SEMG2 | ENSG00000124157 | Semenogelin II |
| 15-Sep | ENSG00000183291 | 15 kDa selenoprotein |
| SEPN1 | ENSG00000162430 | Selenoprotein N, 1 |
| SEPP1 | ENSG00000250722 | Selenoprotein P, plasma, 1 |
| 9-Sep | ENSG00000184640 | Septin 9 |
| SERPINA1 | ENSG00000197249 | Serpin peptidase inhibitor, clade A (alpha-1 antiproteinase, antitrypsin), member 1 |
| SERPINA10 | ENSG00000140093 | Serpin peptidase inhibitor, clade A (alpha-1 antiproteinase, antitrypsin), member 10 |
| SERPINA11 | ENSG00000186910 | Serpin peptidase inhibitor, clade A (alpha-1 antiproteinase, antitrypsin), member 11 |
| SERPINA12 | ENSG00000165953 | Serpin peptidase inhibitor, clade A (alpha-1 antiproteinase, antitrypsin), member 12 |
| SERPINA3 | ENSG00000196136 | Serpin peptidase inhibitor, clade A (alpha-1 antiproteinase, antitrypsin), member 3 |
| SERPINA3 | ENSG00000273259 | Serpin peptidase inhibitor, clade A (alpha-1 antiproteinase, antitrypsin), member 3 |
| SERPINA4 | ENSG00000100665 | Serpin peptidase inhibitor, clade A (alpha-1 antiproteinase, antitrypsin), member 4 |
| SERPINA5 | ENSG00000188488 | Serpin peptidase inhibitor, clade A (alpha-1 antiproteinase, antitrypsin), member 5 |
| SERPINA6 | ENSG00000170099 | Serpin peptidase inhibitor, clade A (alpha-1 antiproteinase, antitrypsin), member 6 |
| SERPINA7 | ENSG00000123561 | Serpin peptidase inhibitor, clade A (alpha-1 antiproteinase, antitrypsin), member 7 |
| SERPINA9 | ENSG00000170054 | Serpin peptidase inhibitor, clade A (alpha-1 antiproteinase, antitrypsin), member 9 |
| SERPINB2 | ENSG00000197632 | Serpin peptidase inhibitor, clade B (ovalbumin), member 2 |
| SERPINC1 | ENSG00000117601 | Serpin peptidase inhibitor, clade C (antithrombin), member 1 |
| SERPIND1 | ENSG00000099937 | Serpin peptidase inhibitor, clade D (heparin cofactor), member 1 |
| SERPINE1 | ENSG00000106366 | Serpin peptidase inhibitor, clade E (nexin, plasminogen activator inhibitor type 1), member 1 |
| SERPINE2 | ENSG00000135919 | Serpin peptidase inhibitor, clade E (nexin, plasminogen activator inhibitor type 1), member 2 |
| SERPINE3 | ENSG00000253309 | Serpin peptidase inhibitor, clade E (nexin, plasminogen activator inhibitor type 1), member 3 |
| SERPINF1 | ENSG00000132386 | Serpin peptidase inhibitor, clade F (alpha-2 antiplasmin, pigment epithelium derived factor), member 1 |
| SERPINF2 | ENSG00000167711 | Serpin peptidase inhibitor, clade F (alpha-2 antiplasmin, pigment epithelium derived factor), member 2 |
| SERPING1 | ENSG00000149131 | Serpin peptidase inhibitor, clade G (C1 inhibitor), member 1 |
| SERPINH1 | ENSG00000149257 | Serpin peptidase inhibitor, clade H (heat shock protein 47), member 1, (collagen binding protein 1) |
| SERPINI1 | ENSG00000163536 | Serpin peptidase inhibitor, clade I (neuroserpin), member 1 |
| SERPINI2 | ENSG00000114204 | Serpin peptidase inhibitor, clade I (pancpin), member 2 |
| SETD8 | ENSG00000183955 | SET domain containing (lysine methyltransferase) 8 |
| SEZ6L2 | ENSG00000174938 | Seizure related 6 homolog (mouse)-like 2 |
| SFRP1 | ENSG00000104332 | Secreted frizzled-related protein 1 |
| SFRP2 | ENSG00000145423 | Secreted frizzled-related protein 2 |
| SFRP4 | ENSG00000106483 | Secreted frizzled-related protein 4 |
| SFRP5 | ENSG00000120057 | Secreted frizzled-related protein 5 |
| SFTA2 | ENSG00000196260 | Surfactant associated 2 |
| SFTPA1 | ENSG00000122852 | Surfactant protein A1 |
| SFTPA2 | ENSG00000185303 | Surfactant protein A2 |
| SFTPB | ENSG00000168878 | Surfactant protein B |
| SFTPD | ENSG00000133661 | Surfactant protein D |
| SFXN5 | ENSG00000144040 | Sideroflexin 5 |
| SGCA | ENSG00000108823 | Sarcoglycan, alpha (50 kDa dystrophin-associated glycoprotein) |

TABLE 1-continued

Exemplary Human Secreted Proteins

| Gene | Ensembl ID | Gene description |
|---|---|---|
| SGSH | ENSG00000181523 | N-sulfoglucosamine sulfohydrolase |
| SH3RF3 | ENSG00000172985 | SH3 domain containing ring finger 3 |
| SHBG | ENSG00000129214 | Sex hormone-binding globulin |
| SHE | ENSG00000169291 | Src homology 2 domain containing E |
| SHH | ENSG00000164690 | Sonic hedgehog |
| SHKBP1 | ENSG00000160410 | SH3KBP1 binding protein 1 |
| SIAE | ENSG00000110013 | Sialic acid acetylesterase |
| SIDT2 | ENSG00000149577 | SID1 transmembrane family, member 2 |
| SIGLEC10 | ENSG00000142512 | Sialic acid binding Ig-like lectin 10 |
| SIGLEC6 | ENSG00000105492 | Sialic acid binding Ig-like lectin 6 |
| SIGLEC7 | ENSG00000168995 | Sialic acid binding Ig-like lectin 7 |
| SIGLECL1 | ENSG00000179213 | SIGLEC family like 1 |
| SIGMAR1 | ENSG00000147955 | Sigma non-opioid intracellular receptor 1 |
| SIL1 | ENSG00000120725 | SIL1 nucleotide exchange factor |
| SIRPB1 | ENSG00000101307 | Signal-regulatory protein beta 1 |
| SIRPD | ENSG00000125900 | Signal-regulatory protein delta |
| SLAMF1 | ENSG00000117090 | Signaling lymphocytic activation molecule family member 1 |
| SLAMF7 | ENSG00000026751 | SLAM family member 7 |
| SLC10A3 | ENSG00000126903 | Solute carrier family 10, member 3 |
| SLC15A3 | ENSG00000110446 | Solute carrier family 15 (oligopeptide transporter), member 3 |
| SLC25A14 | ENSG00000102078 | Solute carrier family 25 (mitochondrial carrier, brain), member 14 |
| SLC25A25 | ENSG00000148339 | Solute carrier family 25 (mitochondrial carrier; phosphate carrier), member 25 |
| SLC2A5 | ENSG00000142583 | Solute carrier family 2 (facilitated glucose/fructose transporter), member 5 |
| SLC35E3 | ENSG00000175782 | Solute carrier family 35, member E3 |
| SLC39A10 | ENSG00000196950 | Solute carrier family 39 (zinc transporter), member 10 |
| SLC39A14 | ENSG00000104635 | Solute carrier family 39 (zinc transporter), member 14 |
| SLC39A4 | ENSG00000147804 | Solute carrier family 39 (zinc transporter), member 4 |
| SLC39A5 | ENSG00000139540 | Solute carrier family 39 (zinc transporter), member 5 |
| SLC3A1 | ENSG00000138079 | Solute carrier family 3 (amino acid transporter heavy chain), member 1 |
| SLC51A | ENSG00000163959 | Solute carrier family 51, alpha subunit |
| SLC52A2 | ENSG00000185803 | Solute carrier family 52 (riboflavin transporter), member 2 |
| SLC5A6 | ENSG00000138074 | Solute carrier family 5 (sodium/multivitamin and iodide cotransporter), member 6 |
| SLC6A9 | ENSG00000196517 | Solute carrier family 6 (neurotransmitter transporter, glycine), member 9 |
| SLC8A1 | ENSG00000183023 | Solute carrier family 8 (sodium/calcium exchanger), member 1 |
| SLC8B1 | ENSG00000089060 | Solute carrier family 8 (sodium/lithium/calcium exchanger), member B1 |
| SLC9A6 | ENSG00000198689 | Solute carrier family 9, subfamily A (NHE6, cation proton antiporter 6), member 6 |
| SLCO1A2 | ENSG00000084453 | Solute carrier organic anion transporter family, member 1A2 |
| SLIT1 | ENSG00000187122 | Slit guidance ligand 1 |
| SLIT2 | ENSG00000145147 | Slit guidance ligand 2 |
| SLIT3 | ENSG00000184347 | Slit guidance ligand 3 |
| SLITRK3 | ENSG00000121871 | SLIT and NTRK-like family, member 3 |
| SLPI | ENSG00000124107 | Secretory leukocyte peptidase inhibitor |
| SLTM | ENSG00000137776 | SAFB-like, transcription modulator |
| SLURP1 | ENSG00000126233 | Secreted LY6/PLAUR domain containing 1 |
| SMARCA2 | ENSG00000080503 | SWI/SNF related, matrix associated, actin dependent regulator of chromatin, subfamily a, member 2 |
| SMG6 | ENSG00000070366 | SMG6 nonsense mediated mRNA decay factor |
| SMIM7 | ENSG00000214046 | Small integral membrane protein 7 |
| SMOC1 | ENSG00000198732 | SPARC related modular calcium binding 1 |
| SMOC2 | ENSG00000112562 | SPARC related modular calcium binding 2 |
| SMPDL3A | ENSG00000172594 | Sphingomyelin phosphodiesterase, acid-like 3A |
| SMPDL3B | ENSG00000130768 | Sphingomyelin phosphodiesterase, acid-like 3B |
| SMR3A | ENSG00000109208 | Submaxillary gland androgen regulated protein 3A |
| SMR3B | ENSG00000171201 | Submaxillary gland androgen regulated protein 3B |
| SNED1 | ENSG00000162804 | Sushi, nidogen and EGF-like domains 1 |
| SNTB1 | ENSG00000172164 | Syntrophin, beta 1 (dystrophin-associated protein A1, 59 kDa, basic component 1) |
| SNTB2 | ENSG00000168807 | Syntrophin, beta 2 (dystrophin-associated protein A1, 59 kDa, basic component 2) |
| SNX14 | ENSG00000135317 | Sorting nexin 14 |
| SOD3 | ENSG00000109610 | Superoxide dismutase 3, extracellular |
| SOST | ENSG00000167941 | Sclerostin |
| SOSTDC1 | ENSG00000171243 | Sclerostin domain containing 1 |
| SOWAHA | ENSG00000198944 | Sosondowah ankyrin repeat domain family member A |
| SPACA3 | ENSG00000141316 | Sperm acrosome associated 3 |
| SPACA4 | ENSG00000177202 | Sperm acrosome associated 4 |
| SPACA5 | ENSG00000171489 | Sperm acrosome associated 5 |
| SPACA5B | ENSG00000171478 | Sperm acrosome associated 5B |

TABLE 1-continued

Exemplary Human Secreted Proteins

| Gene | Ensembl ID | Gene description |
|---|---|---|
| SPACA7 | ENSG00000153498 | Sperm acrosome associated 7 |
| SPAG11A | ENSG00000178287 | Sperm associated antigen 11A |
| SPAG11B | ENSG00000164871 | Sperm associated antigen 11B |
| SPARC | ENSG00000113140 | Secreted protein, acidic, cysteine-rich (osteonectin) |
| SPARCL1 | ENSG00000152583 | SPARC-like 1 (hevin) |
| SPATA20 | ENSG00000006282 | Spermatogenesis associated 20 |
| SPESP1 | ENSG00000258484 | Sperm equatorial segment protein 1 |
| SPINK1 | ENSG00000164266 | Serine peptidase inhibitor, Kazal type 1 |
| SPINK13 | ENSG00000214510 | Serine peptidase inhibitor, Kazal type 13 (putative) |
| SPINK14 | ENSG00000196800 | Serine peptidase inhibitor, Kazal type 14 (putative) |
| SPINK2 | ENSG00000128040 | Serine peptidase inhibitor, Kazal type 2 (acrosin-trypsin inhibitor) |
| SPINK4 | ENSG00000122711 | Serine peptidase inhibitor, Kazal type 4 |
| SPINK5 | ENSG00000133710 | Serine peptidase inhibitor, Kazal type 5 |
| SPINK6 | ENSG00000178172 | Serine peptidase inhibitor, Kazal type 6 |
| SPINK7 | ENSG00000145879 | Serine peptidase inhibitor, Kazal type 7 (putative) |
| SPINK8 | ENSG00000229453 | Serine peptidase inhibitor, Kazal type 8 (putative) |
| SPINK9 | ENSG00000204909 | Serine peptidase inhibitor, Kazal type 9 |
| SPINT1 | ENSG00000166145 | Serine peptidase inhibitor, Kunitz type 1 |
| SPINT2 | ENSG00000167642 | Serine peptidase inhibitor, Kunitz type, 2 |
| SPINT3 | ENSG00000101446 | Serine peptidase inhibitor, Kunitz type, 3 |
| SPINT4 | ENSG00000149651 | Serine peptidase inhibitor, Kunitz type 4 |
| SPOCK1 | ENSG00000152377 | Sparc/osteonectin, cwcv and kazal-like domains proteoglycan (testican) 1 |
| SPOCK2 | ENSG00000107742 | Sparc/osteonectin, cwcv and kazal-like domains proteoglycan (testican) 2 |
| SPOCK3 | ENSG00000196104 | Sparc/osteonectin, cwcv and kazal-like domains proteoglycan (testican) 3 |
| SPON1 | ENSG00000262655 | Spondin 1, extracellular matrix protein |
| SPON2 | ENSG00000159674 | Spondin 2, extracellular matrix protein |
| SPP1 | ENSG00000118785 | Secreted phosphoprotein 1 |
| SPP2 | ENSG00000072080 | Secreted phosphoprotein 2, 24 kDa |
| SPRN | ENSG00000203772 | Shadow of prion protein homolog (zebrafish) |
| SPRYD3 | ENSG00000167778 | SPRY domain containing 3 |
| SPRYD4 | ENSG00000176422 | SPRY domain containing 4 |
| SPTY2D1-AS1 | ENSG00000247595 | SPTY2D1 antisense RNA 1 |
| SPX | ENSG00000134548 | Spexin hormone |
| SRGN | ENSG00000122862 | Serglycin |
| SRL | ENSG00000185739 | Sarcalumenin |
| SRP14 | ENSG00000140319 | Signal recognition particle 14 kDa (homologous Alu RNA binding protein) |
| SRPX | ENSG00000101955 | Sushi-repeat containing protein, X-linked |
| SRPX2 | ENSG00000102359 | Sushi-repeat containing protein, X-linked 2 |
| SSC4D | ENSG00000146700 | Scavenger receptor cysteine rich family, 4 domains |
| SSC5D | ENSG00000179954 | Scavenger receptor cysteine rich family, 5 domains |
| SSPO | ENSG00000197558 | SCO-spondin |
| SSR2 | ENSG00000163479 | Signal sequence receptor, beta (translocon-associated protein beta) |
| SST | ENSG00000157005 | Somatostatin |
| ST3GAL1 | ENSG00000008513 | ST3 beta-galactoside alpha-2,3-sialyltransferase 1 |
| ST3GAL4 | ENSG00000110080 | ST3 beta-galactoside alpha-2,3-sialyltransferase 4 |
| ST6GAL1 | ENSG00000073849 | ST6 beta-galactosamide alpha-2,6-sialyltranferase 1 |
| ST6GALNAC2 | ENSG00000070731 | ST6 (alpha-N-acetyl-neuraminyl-2,3-beta-galactosyl-1,3)-N-acetylgalactosaminide alpha-2,6-sialyltransferase 2 |
| ST6GALNAC5 | ENSG00000117069 | ST6 (alpha-N-acetyl-neuraminyl-2,3-beta-galactosyl-1,3)-N-acetylgalactosaminide alpha-2,6-sialyltransferase 5 |
| ST6GALNAC6 | ENSG00000160408 | ST6 (alpha-N-acetyl-neuraminyl-2,3-beta-galactosyl-1,3)-N-acetylgalactosaminide alpha-2,6-sialyltransferase 6 |
| ST8SIA2 | ENSG00000140557 | ST8 alpha-N-acetyl-neuraminide alpha-2,8-sialyltransferase 2 |
| ST8SIA4 | ENSG00000113532 | ST8 alpha-N-acetyl-neuraminide alpha-2,8-sialyltransferase 4 |
| ST8SIA6 | ENSG00000148488 | ST8 alpha-N-acetyl-neuraminide alpha-2,8-sialyltransferase 6 |
| STARD7 | ENSG00000084090 | StAR-related lipid transfer (START) domain containing 7 |
| STATH | ENSG00000126549 | Statherin |
| STC1 | ENSG00000159167 | Stanniocalcin 1 |
| STC2 | ENSG00000113739 | Stanniocalcin 2 |
| STMND1 | ENSG00000230873 | Stathmin domain containing 1 |
| STOML2 | ENSG00000165283 | Stomatin (EPB72)-like 2 |
| STOX1 | ENSG00000165730 | Storkhead box 1 |
| STRC | ENSG00000242866 | Stereocilin |
| SUCLG1 | ENSG00000163541 | Succinate-CoA ligase, alpha subunit |
| SUDS3 | ENSG00000111707 | SDS3 homolog, SIN3A corepressor complex component |
| SULF1 | ENSG00000137573 | Sulfatase 1 |
| SULF2 | ENSG00000196562 | Sulfatase 2 |
| SUMF1 | ENSG00000144455 | Sulfatase modifying factor 1 |
| SUMF2 | ENSG00000129103 | Sulfatase modifying factor 2 |
| SUSD1 | ENSG00000106868 | Sushi domain containing 1 |

TABLE 1-continued

Exemplary Human Secreted Proteins

| Gene | Ensembl ID | Gene description |
|---|---|---|
| SUSD5 | ENSG00000173705 | Sushi domain containing 5 |
| SVEP1 | ENSG00000165124 | Sushi, von Willebrand factor type A, EGF and pentraxin domain containing 1 |
| SWSAP1 | ENSG00000173928 | SWIM-type zinc finger 7 associated protein 1 |
| SYAP1 | ENSG00000169895 | Synapse associated protein 1 |
| SYCN | ENSG00000179751 | Syncollin |
| TAC1 | ENSG00000006128 | Tachykinin, precursor 1 |
| TAC3 | ENSG00000166863 | Tachykinin 3 |
| TAC4 | ENSG00000176358 | Tachykinin 4 (hemokinin) |
| TAGLN2 | ENSG00000158710 | Transgelin 2 |
| TAPBP | ENSG00000231925 | TAP binding protein (tapasin) |
| TAPBPL | ENSG00000139192 | TAP binding protein-like |
| TBL2 | ENSG00000106638 | Transducin (beta)-like 2 |
| TBX10 | ENSG00000167800 | T-box 10 |
| TCF12 | ENSG00000140262 | Transcription factor 12 |
| TCN1 | ENSG00000134827 | Transcobalamin I (vitamin B12 binding protein, R binder family) |
| TCN2 | ENSG00000185339 | Transcobalamin II |
| TCTN1 | ENSG00000204852 | Tectonic family member 1 |
| TCTN3 | ENSG00000119977 | Tectonic family member 3 |
| TDP2 | ENSG00000111802 | Tyrosyl-DNA phosphodiesterase 2 |
| TEK | ENSG00000120156 | TEK tyrosine kinase, endothelial |
| TEPP | ENSG00000159648 | Testis, prostate and placenta expressed |
| TEX101 | ENSG00000131126 | Testis expressed 101 |
| TEX264 | ENSG00000164081 | Testis expressed 264 |
| TF | ENSG00000091513 | Transferrin |
| TFAM | ENSG00000108064 | Transcription factor A, mitochondrial |
| TFF1 | ENSG00000160182 | Trefoil factor 1 |
| TFF2 | ENSG00000160181 | Trefoil factor 2 |
| TFF3 | ENSG00000160180 | Trefoil factor 3 (intestinal) |
| TFPI | ENSG00000003436 | Tissue factor pathway inhibitor (lipoprotein-associated coagulation inhibitor) |
| TFPI2 | ENSG00000105825 | Tissue factor pathway inhibitor 2 |
| TG | ENSG00000042832 | Thyroglobulin |
| TGFB1 | ENSG00000105329 | Transforming growth factor, beta 1 |
| TGFB2 | ENSG00000092969 | Transforming growth factor, beta 2 |
| TGFB3 | ENSG00000119699 | Transforming growth factor, beta 3 |
| TGFBI | ENSG00000120708 | Transforming growth factor, beta-induced, 68 kDa |
| TGFBR1 | ENSG00000106799 | Transforming growth factor, beta receptor 1 |
| TGFBR3 | ENSG00000069702 | Transforming growth factor, beta receptor III |
| THBS1 | ENSG00000137801 | Thrombospondin 1 |
| THBS2 | ENSG00000186340 | Thrombospondin 2 |
| THBS3 | ENSG00000169231 | Thrombospondin 3 |
| THBS4 | ENSG00000113296 | Thrombospondin 4 |
| THOC3 | ENSG00000051596 | THO complex 3 |
| THPO | ENSG00000090534 | Thrombopoietin |
| THSD4 | ENSG00000187720 | Thrombospondin, type I, domain containing 4 |
| THY1 | ENSG00000154096 | Thy-1 cell surface antigen |
| TIE1 | ENSG00000066056 | Tyrosine kinase with immunoglobulin-like and EGF-like domains 1 |
| TIMMDC1 | ENSG00000113845 | Translocase of inner mitochondrial membrane domain containing 1 |
| TIMP1 | ENSG00000102265 | TIMP metallopeptidase inhibitor 1 |
| TIMP2 | ENSG00000035862 | TIMP metallopeptidase inhibitor 2 |
| TIMP3 | ENSG00000100234 | TIMP metallopeptidase inhibitor 3 |
| TIMP4 | ENSG00000157150 | TIMP metallopeptidase inhibitor 4 |
| TINAGL1 | ENSG00000142910 | Tubulointerstitial nephritis antigen-like 1 |
| TINF2 | ENSG00000092330 | TERF1 (TRF1)-interacting nuclear factor 2 |
| TLL2 | ENSG00000095587 | Tolloid-like 2 |
| TLR1 | ENSG00000174125 | Toll-like receptor 1 |
| TLR3 | ENSG00000164342 | Toll-like receptor 3 |
| TM2D2 | ENSG00000169490 | TM2 domain containing 2 |
| TM2D3 | ENSG00000184277 | TM2 domain containing 3 |
| TM7SF3 | ENSG00000064115 | Transmembrane 7 superfamily member 3 |
| TM9SF1 | ENSG00000100926 | Transmembrane 9 superfamily member 1 |
| TMCO6 | ENSG00000113119 | Transmembrane and coiled-coil domains 6 |
| TMED1 | ENSG00000099203 | Transmembrane p24 trafficking protein 1 |
| TMED2 | ENSG00000086598 | Transmembrane p24 trafficking protein 2 |
| TMED3 | ENSG00000166557 | Transmembrane p24 trafficking protein 3 |
| TMED4 | ENSG00000158604 | Transmembrane p24 trafficking protein 4 |
| TMED5 | ENSG00000117500 | Transmembrane p24 trafficking protein 5 |
| TMED7 | ENSG00000134970 | Transmembrane p24 trafficking protein 7 |
| TMED7-TICAM2 | ENSG00000251201 | TMED7-TICAM2 readthrough |
| TMEM108 | ENSG00000144868 | Transmembrane protein 108 |
| TMEM116 | ENSG00000198270 | Transmembrane protein 116 |
| TMEM119 | ENSG00000183160 | Transmembrane protein 119 |

TABLE 1-continued

Exemplary Human Secreted Proteins

| Gene | Ensembl ID | Gene description |
|---|---|---|
| TMEM155 | ENSG00000164112 | Transmembrane protein 155 |
| TMEM168 | ENSG00000146802 | Transmembrane protein 168 |
| TMEM178A | ENSG00000152154 | Transmembrane protein 178A |
| TMEM179 | ENSG00000258986 | Transmembrane protein 179 |
| TMEM196 | ENSG00000173452 | Transmembrane protein 196 |
| TMEM199 | ENSG00000244045 | Transmembrane protein 199 |
| TMEM205 | ENSG00000105518 | Transmembrane protein 205 |
| TMEM213 | ENSG00000214128 | Transmembrane protein 213 |
| TMEM25 | ENSG00000149582 | Transmembrane protein 25 |
| TMEM30C | ENSG00000235156 | Transmembrane protein 30C |
| TMEM38B | ENSG00000095209 | Transmembrane protein 38B |
| TMEM44 | ENSG00000145014 | Transmembrane protein 44 |
| TMEM52 | ENSG00000178821 | Transmembrane protein 52 |
| TMEM52B | ENSG00000165685 | Transmembrane protein 52B |
| TMEM59 | ENSG00000116209 | Transmembrane protein 59 |
| TMEM67 | ENSG00000164953 | Transmembrane protein 67 |
| TMEM70 | ENSG00000175606 | Transmembrane protein 70 |
| TMEM87A | ENSG00000103978 | Transmembrane protein 87A |
| TMEM94 | ENSG00000177728 | Transmembrane protein 94 |
| TMEM95 | ENSG00000182896 | Transmembrane protein 95 |
| TMIGD1 | ENSG00000182271 | Transmembrane and immunoglobulin domain containing 1 |
| TMPRSS12 | ENSG00000186452 | Transmembrane (C-terminal) protease, serine 12 |
| TMPRSS5 | ENSG00000166682 | Transmembrane protease, serine 5 |
| TMUB1 | ENSG00000164897 | Transmembrane and ubiquitin-like domain containing 1 |
| TMX2 | ENSG00000213593 | Thioredoxin-related transmembrane protein 2 |
| TMX3 | ENSG00000166479 | Thioredoxin-related transmembrane protein 3 |
| TNC | ENSG00000041982 | Tenascin C |
| TNFAIP6 | ENSG00000123610 | Tumor necrosis factor, alpha-induced protein 6 |
| TNFRSF11A | ENSG00000141655 | Tumor necrosis factor receptor superfamily, member 11a, NFKB activator |
| TNFRSF11B | ENSG00000164761 | Tumor necrosis factor receptor superfamily, member 11b |
| TNFRSF12A | ENSG00000006327 | Tumor necrosis factor receptor superfamily, member 12A |
| TNFRSF14 | ENSG00000157873 | Tumor necrosis factor receptor superfamily, member 14 |
| TNFRSF18 | ENSG00000186891 | Tumor necrosis factor receptor superfamily, member 18 |
| TNFRSF1A | ENSG00000067182 | Tumor necrosis factor receptor superfamily, member 1A |
| TNFRSF1B | ENSG00000028137 | Tumor necrosis factor receptor superfamily, member 1B |
| TNFRSF25 | ENSG00000215788 | Tumor necrosis factor receptor superfamily, member 25 |
| TNFRSF6B | ENSG00000243509 | Tumor necrosis factor receptor superfamily, member 6b, decoy |
| TNFSF11 | ENSG00000120659 | Tumor necrosis factor (ligand) superfamily, member 11 |
| TNFSF12 | ENSG00000239697 | Tumor necrosis factor (ligand) superfamily, member 12 |
| TNFSF12-TNFSF13 | ENSG00000248871 | TNFSF12-TNFSF13 readthrough |
| TNFSF15 | ENSG00000181634 | Tumor necrosis factor (ligand) superfamily, member 15 |
| TNN | ENSG00000120332 | Tenascin N |
| TNR | ENSG00000116147 | Tenascin R |
| TNXB | ENSG00000168477 | Tenascin XB |
| TOMM7 | ENSG00000196683 | Translocase of outer mitochondrial membrane 7 homolog (yeast) |
| TOP1MT | ENSG00000184428 | Topoisomerase (DNA) I, mitochondrial |
| TOR1A | ENSG00000136827 | Torsin family 1, member A (torsin A) |
| TOR1B | ENSG00000136816 | Torsin family 1, member B (torsin B) |
| TOR2A | ENSG00000160404 | Torsin family 2, member A |
| TOR3A | ENSG00000186283 | Torsin family 3, member A |
| TPD52 | ENSG00000076554 | Tumor protein D52 |
| TPO | ENSG00000115705 | Thyroid peroxidase |
| TPP1 | ENSG00000166340 | Tripeptidyl peptidase I |
| TPSAB1 | ENSG00000172236 | Tryptase alpha/beta 1 |
| TPSB2 | ENSG00000197253 | Tryptase beta 2 (gene/pseudogene) |
| TPSD1 | ENSG00000095917 | Tryptase delta 1 |
| TPST1 | ENSG00000169902 | Tyrosylprotein sulfotransferase 1 |
| TPST2 | ENSG00000128294 | Tyrosylprotein sulfotransferase 2 |
| TRABD2A | ENSG00000186854 | TraB domain containing 2A |
| TRABD2B | ENSG00000269113 | TraB domain containing 2B |
| TREH | ENSG00000118094 | Trehalase (brush-border membrane glycoprotein) |
| TREM1 | ENSG00000124731 | Triggering receptor expressed on myeloid cells 1 |
| TREM2 | ENSG00000095970 | Triggering receptor expressed on myeloid cells 2 |
| TRH | ENSG00000170893 | Thyrotropin-releasing hormone |
| TRIM24 | ENSG00000122779 | Tripartite motif containing 24 |
| TRIM28 | ENSG00000130726 | Tripartite motif containing 28 |
| TRIO | ENSG00000038382 | Trio Rho guanine nucleotide exchange factor |
| TRNP1 | ENSG00000253368 | TMF1-regulated nuclear protein 1 |
| TSC22D4 | ENSG00000166925 | TSC22 domain family, member 4 |
| TSHB | ENSG00000134200 | Thyroid stimulating hormone, beta |
| TSHR | ENSG00000165409 | Thyroid stimulating hormone receptor |
| TSKU | ENSG00000182704 | Tsukushi, small leucine rich proteoglycan |
| TSLP | ENSG00000145777 | Thymic stromal lymphopoietin |
| TSPAN3 | ENSG00000140391 | Tetraspanin 3 |

TABLE 1-continued

Exemplary Human Secreted Proteins

| Gene | Ensembl ID | Gene description |
|---|---|---|
| TSPAN31 | ENSG00000135452 | Tetraspanin 31 |
| TSPEAR | ENSG00000175894 | Thrombospondin-type laminin G domain and EAR repeats |
| TTC13 | ENSG00000143643 | Tetratricopeptide repeat domain 13 |
| TTC19 | ENSG00000011295 | Tetratricopeptide repeat domain 19 |
| TTC9B | ENSG00000174521 | Tetratricopeptide repeat domain 9B |
| TTLL11 | ENSG00000175764 | Tubulin tyrosine ligase-like family member 11 |
| TTR | ENSG00000118271 | Transthyretin |
| TWSG1 | ENSG00000128791 | Twisted gastrulation BMP signaling modulator 1 |
| TXNDC12 | ENSG00000117862 | Thioredoxin domain containing 12 (endoplasmic reticulum) |
| TXNDC15 | ENSG00000113621 | Thioredoxin domain containing 15 |
| TXNDC5 | ENSG00000239264 | Thioredoxin domain containing 5 (endoplasmic reticulum) |
| TXNRD2 | ENSG00000184470 | Thioredoxin reductase 2 |
| TYRP1 | ENSG00000107165 | Tyrosinase-related protein 1 |
| UBAC2 | ENSG00000134882 | UBA domain containing 2 |
| UBALD1 | ENSG00000153443 | UBA-like domain containing 1 |
| UBAP2 | ENSG00000137073 | Ubiquitin associated protein 2 |
| UBXN8 | ENSG00000104691 | UBX domain protein 8 |
| UCMA | ENSG00000165623 | Upper zone of growth plate and cartilage matrix associated |
| UCN | ENSG00000163794 | Urocortin |
| UCN2 | ENSG00000145040 | Urocortin 2 |
| UCN3 | ENSG00000178473 | Urocortin 3 |
| UGGT2 | ENSG00000102595 | UDP-glucose glycoprotein glucosyltransferase 2 |
| UGT1A10 | ENSG00000242515 | UDP glucuronosyltransferase 1 family, polypeptide A10 |
| UGT2A1 | ENSG00000173610 | UDP glucuronosyltransferase 2 family, polypeptide A1, complex locus |
| UGT2B11 | ENSG00000213759 | UDP glucuronosyltransferase 2 family, polypeptide B11 |
| UGT2B28 | ENSG00000135226 | UDP glucuronosyltransferase 2 family, polypeptide B28 |
| UGT2B4 | ENSG00000156096 | UDP glucuronosyltransferase 2 family, polypeptide B4 |
| UGT2B7 | ENSG00000171234 | UDP glucuronosyltransferase 2 family, polypeptide B7 |
| UGT3A1 | ENSG00000145626 | UDP glycosyltransferase 3 family, polypeptide A1 |
| UGT3A2 | ENSG00000168671 | UDP glycosyltransferase 3 family, polypeptide A2 |
| UGT8 | ENSG00000174607 | UDP glycosyltransferase 8 |
| ULBP3 | ENSG00000131019 | UL16 binding protein 3 |
| UMOD | ENSG00000169344 | Uromodulin |
| UNC5C | ENSG00000182168 | Unc-5 netrin receptor C |
| UPK3B | ENSG00000243566 | Uroplakin 3B |
| USP11 | ENSG00000102226 | Ubiquitin specific peptidase 11 |
| USP14 | ENSG00000101557 | Ubiquitin specific peptidase 14 (tRNA-guanine transglycosylase) |
| USP3 | ENSG00000140455 | Ubiquitin specific peptidase 3 |
| UTS2 | ENSG00000049247 | Urotensin 2 |
| UTS2B | ENSG00000188958 | Urotensin 2B |
| UTY | ENSG00000183878 | Ubiquitously transcribed tetratricopeptide repeat containing, Y-linked |
| UXS1 | ENSG00000115652 | UDP-glucuronate decarboxylase 1 |
| VASH1 | ENSG00000071246 | Vasohibin 1 |
| VCAN | ENSG00000038427 | Versican |
| VEGFA | ENSG00000112715 | Vascular endothelial growth factor A |
| VEGFB | ENSG00000173511 | Vascular endothelial growth factor B |
| VEGFC | ENSG00000150630 | Vascular endothelial growth factor C |
| VGF | ENSG00000128564 | VGF nerve growth factor inducible |
| VIP | ENSG00000146469 | Vasoactive intestinal peptide |
| VIPR2 | ENSG00000106018 | Vasoactive intestinal peptide receptor 2 |
| VIT | ENSG00000205221 | Vitrin |
| VKORC1 | ENSG00000167397 | Vitamin K epoxide reductase complex, subunit 1 |
| VLDLR | ENSG00000147852 | Very low density lipoprotein receptor |
| VMO1 | ENSG00000182853 | Vitelline membrane outer layer 1 homolog (chicken) |
| VNN1 | ENSG00000112299 | Vanin 1 |
| VNN2 | ENSG00000112303 | Vanin 2 |
| VNN3 | ENSG00000093134 | Vanin 3 |
| VOPP1 | ENSG00000154978 | Vesicular, overexpressed in cancer, prosurvival protein 1 |
| VPREB1 | ENSG00000169575 | Pre-B lymphocyte 1 |
| VPREB3 | ENSG00000128218 | Pre-B lymphocyte 3 |
| VPS37B | ENSG00000139722 | Vacuolar protein sorting 37 homolog B (S. cerevisiae) |
| VPS51 | ENSG00000149823 | Vacuolar protein sorting 51 homolog (S. cerevisiae) |
| VSIG1 | ENSG00000101842 | V-set and immunoglobulin domain containing 1 |
| VSIG10 | ENSG00000176834 | V-set and immunoglobulin domain containing 10 |
| VSTM1 | ENSG00000189068 | V-set and transmembrane domain containing 1 |
| VSTM2A | ENSG00000170419 | V-set and transmembrane domain containing 2A |
| VSTM2B | ENSG00000187135 | V-set and transmembrane domain containing 2B |
| VSTM2L | ENSG00000132821 | V-set and transmembrane domain containing 2 like |
| VSTM4 | ENSG00000165633 | V-set and transmembrane domain containing 4 |
| VTN | ENSG00000109072 | Vitronectin |
| VWA1 | ENSG00000179403 | Von Willebrand factor A domain containing 1 |
| VWA2 | ENSG00000165816 | Von Willebrand factor A domain containing 2 |
| VWA5B2 | ENSG00000145198 | Von Willebrand factor A domain containing 5B2 |

TABLE 1-continued

Exemplary Human Secreted Proteins

| Gene | Ensembl ID | Gene description |
|---|---|---|
| VWA7 | ENSG00000204396 | Von Willebrand factor A domain containing 7 |
| VWC2 | ENSG00000188730 | Von Willebrand factor C domain containing 2 |
| VWC2L | ENSG00000174453 | Von Willebrand factor C domain containing protein 2-like |
| VWCE | ENSG00000167992 | Von Willebrand factor C and EGF domains |
| VWDE | ENSG00000146530 | Von Willebrand factor D and EGF domains |
| VWF | ENSG00000110799 | Von Willebrand factor |
| WDR25 | ENSG00000176473 | WD repeat domain 25 |
| WDR81 | ENSG00000167716 | WD repeat domain 81 |
| WDR90 | ENSG00000161996 | WD repeat domain 90 |
| WFDC1 | ENSG00000103175 | WAP four-disulfide core domain 1 |
| WFDC10A | ENSG00000180305 | WAP four-disulfide core domain 10A |
| WFDC10B | ENSG00000182931 | WAP four-disulfide core domain 10B |
| WFDC11 | ENSG00000180083 | WAP four-disulfide core domain 11 |
| WFDC12 | ENSG00000168703 | WAP four-disulfide core domain 12 |
| WFDC13 | ENSG00000168634 | WAP four-disulfide core domain 13 |
| WFDC2 | ENSG00000101443 | WAP four-disulfide core domain 2 |
| WFDC3 | ENSG00000124116 | WAP four-disulfide core domain 3 |
| WFDC5 | ENSG00000175121 | WAP four-disulfide core domain 5 |
| WFDC6 | ENSG00000243543 | WAP four-disulfide core domain 6 |
| WFDC8 | ENSG00000158901 | WAP four-disulfide core domain 8 |
| WFIKKN1 | ENSG00000127578 | WAP, follistatin/kazal, immunoglobulin, kunitz and netrin domain containing 1 |
| WFIKKN2 | ENSG00000173714 | WAP, follistatin/kazal, immunoglobulin, kunitz and netrin domain containing 2 |
| WIF1 | ENSG00000156076 | WNT inhibitory factor 1 |
| WISP1 | ENSG00000104415 | WNT1 inducible signaling pathway protein 1 |
| WISP2 | ENSG00000064205 | WNT1 inducible signaling pathway protein 2 |
| WISP3 | ENSG00000112761 | WNT1 inducible signaling pathway protein 3 |
| WNK1 | ENSG00000060237 | WNK lysine deficient protein kinase 1 |
| WNT1 | ENSG00000125084 | Wingless-type MMTV integration site family, member 1 |
| WNT10B | ENSG00000169884 | Wingless-type MMTV integration site family, member 10B |
| WNT11 | ENSG00000085741 | Wingless-type MMTV integration site family, member 11 |
| WNT16 | ENSG00000002745 | Wingless-type MMTV integration site family, member 16 |
| WNT2 | ENSG00000105989 | Wingless-type MMTV integration site family member 2 |
| WNT3 | ENSG00000108379 | Wingless-type MMTV integration site family, member 3 |
| WNT3A | ENSG00000154342 | Wingless-type MMTV integration site family, member 3A |
| WNT5A | ENSG00000114251 | Wingless-type MMTV integration site family, member 5A |
| WNT5B | ENSG00000111186 | Wingless-type MMTV integration site family, member 5B |
| WNT6 | ENSG00000115596 | Wingless-type MMTV integration site family, member 6 |
| WNT7A | ENSG00000154764 | Wingless-type MMTV integration site family, member 7A |
| WNT7B | ENSG00000188064 | Wingless-type MMTV integration site family, member 7B |
| WNT8A | ENSG00000061492 | Wingless-type MMTV integration site family, member 8A |
| WNT8B | ENSG00000075290 | Wingless-type MMTV integration site family, member 8B |
| WNT9A | ENSG00000143816 | Wingless-type MMTV integration site family, member 9A |
| WNT9B | ENSG00000158955 | Wingless-type MMTV integration site family, member 9B |
| WSB1 | ENSG00000109046 | WD repeat and SOCS box containing 1 |
| WSCD1 | ENSG00000179314 | WSC domain containing 1 |
| WSCD2 | ENSG00000075035 | WSC domain containing 2 |
| XCL1 | ENSG00000143184 | Chemokine (C motif) ligand 1 |
| XCL2 | ENSG00000143185 | Chemokine (C motif) ligand 2 |
| XPNPEP2 | ENSG00000122121 | X-prolyl aminopeptidase (aminopeptidase P) 2, membrane-bound |
| XXbac-BPG116M5.17 | ENSG00000244255 | |
| XXbac-BPG181M17.5 | ENSG00000248993 | |
| XXbac-BPG32J3.20 | ENSG00000204422 | |
| XXYLT1 | ENSG00000173950 | Xyloside xylosyltransferase 1 |
| XYLT1 | ENSG00000103489 | Xylosyltransferase I |
| XYLT2 | ENSG00000015532 | Xylosyltransferase II |
| ZFYVE21 | ENSG00000100711 | Zinc finger, FYVE domain containing 21 |
| ZG16 | ENSG00000174992 | Zymogen granule protein 16 |
| ZG16B | ENSG00000162078 | Zymogen granule protein 16B |
| ZIC4 | ENSG00000174963 | Zic family member 4 |
| ZNF207 | ENSG00000010244 | Zinc finger protein 207 |
| ZNF26 | ENSG00000198393 | Zinc finger protein 26 |
| ZNF34 | ENSG00000196378 | Zinc finger protein 34 |
| ZNF419 | ENSG00000105136 | Zinc finger protein 419 |
| ZNF433 | ENSG00000197647 | Zinc finger protein 433 |
| ZNF449 | ENSG00000173275 | Zinc finger protein 449 |
| ZNF488 | ENSG00000265763 | Zinc finger protein 488 |
| ZNF511 | ENSG00000198546 | Zinc finger protein 511 |
| ZNF570 | ENSG00000171827 | Zinc finger protein 570 |
| ZNF691 | ENSG00000164011 | Zinc finger protein 691 |
| ZNF98 | ENSG00000197360 | Zinc finger protein 98 |
| ZPBP | ENSG00000042813 | Zona pellucida binding protein |

TABLE 1-continued

Exemplary Human Secreted Proteins

| Gene | Ensembl ID | Gene description |
|---|---|---|
| ZPBP2 | ENSG00000186075 | Zona pellucida binding protein 2 |
| ZSCAN29 | ENSG00000140265 | Zinc finger and SCAN domain containing 29 |

In some embodiments of the disclosure, T cells are modified to express therapeutic proteins, including secreted proteins and secreted human proteins. In some embodiments of the methods of the disorder, compositions comprising CAR-T cells modified to express or to secrete a human protein are used to treat a clotting disorder. Blood clotting occurs through a multistep process known as the coagulation cascade. In the extrinsic pathway, Tissue Factor (also known as factor III or thromboplastin) comes into contact with factor VII to form an activated VIIa complex. This initiates a coagulation protease cascade, converting the inactive Factor X to an active protease Factor Xa, which, with activated Factor V, produces thrombin (IIa) from Prothrombin (II). In the intrinsic pathway, collagen forms a complex with high-molecular-weight-kininogen, prekallikrein and Factor XII, leading to the conversion of Factor XII into Factor XIIa. Factor XIIa converts Factor XI into Factor XIa, and Factor XIa activates Factor IX to produce Factor IXa, which, together with FVIIIa form the tenase complex, which activates Factor X, which helps convert Prothrombin (II) into Thrombin (IIa). Thrombin in turn leads to the conversion of Fibrinogen (I) into Fibrin, which together with Factor XIIIa forms a cross-linked fibrin clot. Many clotting disorders are the result of low levels of secreted proteins in the blood that are involved in the coagulation cascade. Clotting disorders can drastically increase the amount of blood leaving the body upon injury, or cause bleeding to occur under the skin or in vital organs. These disorders are frequently genetic. Exemplary, but non-limiting diseases caused by deficiencies in clotting factors include Hemophilias, von Willebrand disease and deficiencies in Antithrombin III, protein C or protein S. Hemophila A and B are X-linked, and are caused by insufficient levels of clotting factor VIII and factor IX (FIX) respectively. Hemophila C is caused by insufficient factor XI. Factor II, VII, X or XII deficiencies can also cause bleeding disorders. Von Willebrand disease is due to a low level of the von Willebrand clotting factor in the blood. In some cases, deficiencies in blood proteins that regulate clotting lead can lead to too much clotting. Factor V Leiden is a genetic disorder, where the factor V Leiden protein overreacts, causing the blood to clot too often or too much. Deficiencies in Antithrombin III, protein C or protein S, which help regulate bleeding, can also cause excessive clotting. Currently, clotting disorders such as Hemophilia are treated with blood transfusions or infusions of the missing clotting factor (replacement therapy). However, complications of replacement therapy include developing antibodies to the clotting factor, contracting viral infections from blood derived products and damage to joints. There thus exists a need for additional therapies.

In some embodiments of the disclosure, T cells are modified to express therapeutic proteins, including secreted proteins and secreted human proteins. In some embodiments of the methods of the disorder, compositions comprising CAR-T cells modified to express or to secrete a human protein are used for enzyme replacement therapy. Enzyme replacement therapy typically involves intravenous infusions of therapeutically effective amounts of compositions comprising enzymes that balance underlying enzyme deficiencies that cause the symptoms of the disease. The missing enzyme activity is thus supplied exogenously in this manner. Exemplary diseases that can be treated by modified T cells of the disclosure include, but are not limited to, lysosomal storage diseases Gaucher's disease (glucocerebrosidase enzyme), Fabry disease, mucopolysaccharidosis I (MPS I), mucopolysaccharidosis I (MPS II, or Hunter syndrome, caused by iduronate-2-sulfatase deficiency), mucopolysaccharidosis VI (MPS VI, caused by arylsulfatase B deficiency) and Pompe disease (or glycogen storage disease type II, caused by a deficiency in acid alpha-glucosidase). Additional diseases treatable with enzyme replacement therapy include but are not limited to Adenosine deaminase (ADA) deficiency, Hyperammonemia due to the deficiency of the hepatic enzyme N-acetylglutamate synthetase (NAGS), Hypophosphatasia, Lysosomal acid lipase deficiency, Morquio Syndrome A, Wolman LAL Lysosomal Acid Lipase deficiency, A1AT (Alpha1-Antitrypsin) deficiency and Urea cycle disorder. Enzymes supplied to patients during enzyme replacement therapy include, but are not limited to Alpha1-Antitrypsin, β-Glucocerebrosidase, Adenosine Deaminase, Alpha-Galactosidase A, α-L-Iduronidase, Iduronate-2-Sulfatase, N-Acetylgalactosamine-6 Sulfatase, -Acetylgalactosamine-4 Sulfatase and Lysosomal Acid Lipase.

In some embodiments of the disclosure, T cells are modified to express therapeutic proteins, including secreted proteins and secreted human proteins. In some embodiments of the methods of the disorder, compositions comprising CAR-T cells modified to express or to secrete a human protein are used to produce human antibodies. In some embodiments, the disease to be treated by modified T cells expressing secreted proteins is a disease that can be treated through the intravenous infusion or injection of an antibody or an antibody fragment. Antibody based therapies are used in the treatment of many types of diseases in addition to cancer, including immune-based diseases such as arthritis and asthma, and infections, as well as other diseases. Exemplary, but non-limiting list of diseases that can be treated with the modified T cells of the disclosure include platelet aggregation, Clostridium difficile infection, Rheumatoid arthritis, Crohn's Disease, Plaque Psoriasis, Psoriatic Arthritis, Ankylosing Spondylitis, Juvenile Idiopathic Arthritis, Alzheimer's disease, sepsis, Multiple Sclerosis, hypercholesterolemia, systemic lupus erythematosus, prevention of organ transplant rejections, viral infections, asthma, severe allergic disorders, retinopathy, osteoporosis, inflammatory bowel diseases, inflammatory diseases, influenza A, paroxysmal nocturnal hemoglobinuria, sepsis caused by Gram-negative bacteria, psoriasis, invasive Candida infection, ulcerative colitis, hypocholesterolemia, respiratory syncytial virus infection, focal segmental glomerulosclerosis, graft versus host disease, ankylosing spondylitis, HIV infection, ulcerative colitis, autoimmune diseases, chronic asthma, reduction of scarring after glaucoma surgery, hypercholesterolemia, white blood cell diseases, systemic scleroderma, respiratory syncytial virus (prevention), lupus erythematosus, diabetes mellitus type 1, inflammation, *Pseudomonas aeruginosa* infection, macular degeneration, anthrax, cytomegalovirus infection, inflammations of the airways, skin and gastrointestinal tract, systemic lupus erythematosus, rheumatic diseases, uveitis, cytomegalovirus infection, dermatomyositis, polymyositis, fibrosis, choroidal and retinal neovascularization, muscular dystrophy, *Staphylococcus aureus* infection, lupus nephritis, follicular lymphoma, chronic hepatitis B and ulcerative colitis.

Infusion of Modified Cells as Adoptive Cell Therapy

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises between $2\times10^5$ and $5\times10^8$ cells per kg of body weight of the patient per administration, or any range, value or fraction thereof.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises between $0.2\times10^6$ to $20\times10^6$ cells per kg of body weight of the patient per administration. In certain embodiments, a therapeutically effective dose of a composition of the disclosure or of compositions comprising modified cells of the disclosure comprises $0.2\times10^6$ cells per kg of body weight of the patient per administration, $2\times10^6$ cells per kg of body weight of the patient per administration, $20\times10^6$ cells per kg of body weight of the patient per administration, or any cells per kg of body weight of the patient per administration in between.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $1\times10^6$ cells or about $1\times10^6$ cells per kg of body weight of the patient per administration.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $3\times10^6$ cells or about $3\times10^6$ cells per kg of body weight of the patient per administration.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises between $0.7\times10^6$ to $6.7\times10^6$ cells per kg of body weight of the patient per administration. In certain embodiments, a therapeutically effective dose of a composition of the disclosure or of compositions comprising modified cells of the disclosure comprises $0.7\times10^6$ cells per kg of body weight of the patient per administration, $6.7\times10^6$ cells per kg of body weight of the patient per administration or any cells per kg of body weight of the patient per administration in between.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises between $0.7\times10^6$ to $16\times10^6$ cells per kg of body weight of the patient per administration. In certain embodiments, a therapeutically effective dose of a composition of the disclosure or of compositions comprising modified cells of the disclosure comprises $0.7\times10^6$ cells per kg of body weight of the patient per administration, $2\times10^6$ cells per kg of body weight of the patient per administration, $6\times10^6$ cells per kg of body weight of the patient per administration, $10.7\times10^6$ cells per kg of body weight of the patient per administration, $16\times10^6$ cells per kg of body weight of the patient per administration or any cells per kg of body weight of the patient per administration in between.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $1.2\times10^6$ to $7.1\times10^6$ cells per kg of body weight of the patient per administration. In certain embodiments, a therapeutically effective dose of a composition of the disclosure or of compositions comprising modified cells of the disclosure comprises $1.2\times10^6$ cells per kg of body weight of the patient per administration, $7.1\times10^6$ cells per kg of body weight of the patient per administration or any number of cells per kg of body weight of the patient per administration. In certain embodiments, a therapeutically effective dose of a composition of the disclosure or of compositions comprising modified cells of the disclosure comprises between $2\times10^6$ to $3\times10^6$ cells per kg of body weight of the patient per administration.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $1106\times10^6$ to $2106\times10^6$ cells per kg of body weight of the patient per administration. In certain embodiments, a therapeutically effective dose of a composition of the disclosure or of compositions comprising modified cells of the disclosure comprises $1106\times10^6$ cells per kg of body weight of the patient per administration, $2106\times10^6$ cells per kg of body weight of the patient per administration or any number of cells per kg of body weight of the patient per administration in between. In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises $0.7\times10^6$ to $1.3\times10^6$ cells per kg of body weight of the patient per administration. In certain embodiments, a therapeutically effective dose of a composition of the disclosure or of compositions comprising modified cells of the disclosure comprises $0.7\times10^6$ cells per kg of body weight of the patient per administration, $1.3\times10^6$ cells per kg of body weight of the patient per administration or any number of cells per kg of body weight of the patient per administration in between.

In certain embodiments of the disclosure, modified cells of the disclosure are delivered to a patient via injection or intravenous infusion. In certain embodiments, a therapeutically effective dose of a composition of the disclosure or of compositions comprising modified cells of the disclosure comprises a single or multiple doses. In certain embodiments, a therapeutically effective dose of a composition of the disclosure or of compositions comprising modified cells of the disclosure comprises a split dose. In certain embodiments, a therapeutically effective dose of a composition of the disclosure or of compositions comprising modified cells of the disclosure comprises an initial dose and a maintenance dose.

In certain embodiments of the disclosure, the modified cells are T cells and the T cells may be sorted according to T cell markers prior to either in vitro expansion or formulation with a pharmaceutically acceptable carrier. In some embodiments, modified T cells may be sorted on using CD8+ and/or CD4+ markers.

Nucleic Acid Molecules

Nucleic acid molecules of the disclosure encoding protein scaffolds can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one protein scaffold; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold, Centyrin, CAR, CARTyrin, transposon, and/or transposase as described herein and/or as known in the art. Of course, the genetic code is well known in the art. Thus, it would be routine for one skilled in the art to generate such degenerate nucleic acid variants that code for specific protein scaffolds of the present invention. See, e.g., Ausubel, et al., supra, and such nucleic acid variants are included in the present invention.

As indicated herein, nucleic acid molecules of the disclosure which comprise a nucleic acid encoding a protein scaffold, Centyrin, CAR, CARTyrin, transposon, and/or transposase can include, but are not limited to, those encoding the amino acid sequence of a protein scaffold, Centyrin, CAR, CARTyrin, transposon, and/or transposase fragment, by itself; the coding sequence for the entire protein scaffold, Centyrin, CAR, CARTyrin, transposon, and/or transposase or a portion thereof; the coding sequence for a protein scaffold, Centyrin, CAR, CARTyrin, transposon, and/or transposase, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold, Centyrin, CAR, CARTyrin, transposon, and/or transposase can be fused to a marker sequence, such as a sequence encoding a peptide that facilitates purification of the fused protein scaffold, Centyrin, CAR, CARTyrin, transposon, and/or transposase comprising a protein scaffold fragment or portion.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra).

Vectors and Host Cells

The disclosure also relates to vectors that include isolated nucleic acid molecules of the disclosure, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

For example, the PB-EF1a vector may be used. The vector comprises the following nucleotide sequence:

(SEQ ID NO: 35)
tgtacatagattaaccctagaaagataatcatattgtgacgtacgttaaa gataatcatgcgtaaaattgacgcatgtgttttatcggtctgtatatcga ggtttatttattaatttgaatagatattaagttttattatatttacactt acatactaataataaattcaacaaacaatttatttatgtttatttattta ttaaaaaaaacaaaaactcaaaatttcttctataaagtaacaaaactttt tatcgaatacctgcagcccgggggatgcagagggacagcccccccccaaa gcccccagggatgtaattacgtccctcccccgctaggggggcagcagcgag ccgcccgggctccgctccggtccggcgctcccccgcatcccgagccg gcagcgtgcggggacagcccgggcacggggaaggtggcacgggatcgctt tcctctgaacgcttctcgctgctctttgagcctgcagacacctggggga tacggggaaaagttgactgtgcctttcgatcgaaccatggacagttagct -continued ttgcaaagatggataaagtttaaacagagaggaatctttgcagctaatg
gaccttctaggtcttgaaaggagtgggaattggctccggtgcccgtcagt
gggcagagcgcacatcgcccacagtccccgagaagttggggggaggggtc
ggcaattgaaccggtgcctagagaaggtggcgcggggtaaactgggaaag
tgatgtcgtgtactggctccgccttttcccgagggtgggggagaaccgt
atataagtgcagtagtcgccgtgaacgttcttttcgcaacgggtttgcc
gccagaacacaggtaagtgccgtgtgtggttcccgcgggcctggcctctt
tacgggttatgcccttgcgtgccttgaattacttccacctggctgcagt
acgtgattcttgatcccgagcttcgggttggaagtgggtgggagagttcg
aggccttgcgcttaaggagccccttcgcctcgtgcttgagttgaggcctg
gcctgggcgctggggccgccgcgtgcgaatctggtggcaccttcgcgcct
gtctcgctgctttcgataagtctctagccattaaaattttgatgacct
gctgcgacgcttttttctggcaagatagtcttgtaaatgcgggccaaga
tctgcacactggtatttcggttttgggccgcgggcggcgacggggccc
gtgcgtcccagcgcacatgttcggcgaggcggggcctgcgagcgcggcca
ccgagaatcggacggggtagtctcaagctggccggcctgctctggtgcc
tggcctcgcgccgccgtgtatcgcccgccctgggcggcaaggctggcc
ggtcggcaccagttgcgtgagcggaaagatggccgcttcccggccctgct
gcagggagctcaaaatggaggacgcggcgctcgggagagcgggcgggtga
gtcacccacacaaaggaaaagggccttcccgtcctcagccgtcgcttcat
gtgactccacggagtaccgggcgccgtccaggcacctcgattagttctcg
agcttttggagtacgtcgtctttaggttgggggggagggttttatgcgat
ggagtttccccacactgagtgggtggagactgaagttaggccagcttggc
acttgatgtaattctccttggaattgcccttttgagtttggatcttgg
ttcattctcaagcctcagacagtggttcaaagttttttcttccattca
ggtgtcgtgagaattctaatacgactcactatagggtgtgctgtctcatc
attttggcaaagattggccaccaagcttgtcctgcaggagggtcgacgcc
tctagacgggcggccgctccggatccacgggtaccgatcacatatgcctt
taattaaacactagttctatagtgtcacctaaattccctttagtgaggt
taatggccgtaggccgccagaattgggtccagacatgataagatacattg
atgagtttggacaaaccacaactagaatgcagtgaaaaaaatgctttatt
tgtgaaatttgtgatgctattgctttatttgtaaccattataagctgcaa
taaacaagttaacaacaacaattgcattcattttatgtttcaggttcagg
gggaggtgtgggaggttttttcggactctaggacctgcgcatgcgcttgg
cgtaatcatggtcatagctgtttcctgtttcccgtatcccccaggtg
tctgcaggctcaaagagcagcgagaagcgttcagaggaaagcgatcccgt
gccaccttcccgtgcccgggctgtcccgcacgctgccggctcgggat
gcggggggagcgccggaccggagcggagcccggggcggctcgctgctgcc
ccctagcggggagggacgtaattacatccctggggcttggggggggg
ctgtccctctcaccgcggtggagctccagcttttgttcgaattgggcc
ccctcgagggtatcgatgatatctataacaagaaaatatatatataata -continued agttatcacgtaagtagaacatgaaataacaatataattatcgtatgagt
taaatcttaaaagtcacgtaaaagataatcatgcgtcattttgactcacg
cggtcgttatagttcaaaatcagtgacacttaccgcattgacaagcacgc
ctcacgggagctccaagcggcgactgagatgtcctaaatgcacagcgacg
gattcgcgctatttagaaagagagagcaatatttcaagaatgcatgcgtc
aattttacgcagactatctttctagggttaatctagctagccttaagggc
gcctattgcgttgcgctcactgcccgctttccagtcgggaaacctgtcgt
gccagctgcattaatgaatcggccaacgcgcggggagaggcggtttgcgt
attgggcgctcttccgcttcctcgctcactgactcgctgcgctcggtcgt
tcggctgcggcgagcggtatcagctcactcaaaggcggtaatacggttat
ccacagaatcaggggataacgcaggaaagaacatgaccaaaatcccttaa
cgtgagttttcgttccactgagcgtcagaccccgtagaaaagatcaaagg
atcttcttgagatcctttttttctgcgcgtaatctgctgcttgcaaacaa
aaaaaccaccgctaccagcggtggtttgtttgccggatcaagagctacca
actcttttccgaaggtaactggcttcagcagagcgcagataccaaatac
tgttcttctagtgtagccgtagttaggccaccacttcaagaactctgtag
caccgcctacatacctcgctctgctaatcctgttaccagtggctgctgcc
agtggcgataagtcgtgtcttaccgggttggactcaagacgatagttacc
ggataaggcgcagcggtcgggctgaacggggggttcgtgcacacagccca
gcttggagcgaacgacctacaccgaactgagatacctacagcgtgagcta
tgagaaagcgccacgcttcccgaagggagaaaggcggacaggtatccggt
aagcggcagggtcggaacaggagagcgcacgagggagcttccaggggggaa
acgcctggtatctttatagtcctgtcgggtttcgccacctctgacttgag
cgtcgattttgtgatgctcgtcaggggggcggagcctatggaaaaacgc
cagcaacgcggcctttttacggttcctggccttttgctggccttttgctc
acatgagattatcaaaaaggatcttcacctagatcctttttaaattaaaaa
tgaagttttaaatcaatctaaagtatatatgagtaaacttggtctgacag
tcagaagaactcgtcaagaaggcgatagaaggcgatgcgctgcgaatcgg
gagcggcgataccgtaaagcacgaggaagcggtcagcccattcgccgcca
agctcttcagcaatatcacgggtagccaacgctatgtcctgatagcggtc
cgccacacccagccggccacagtcgatgaatccagaaaagcggccatttt
ccaccatgatattcggcaagcaggcatcgccatgggtcacgacgagatcc
tcgccgtcgggcatgctcgccttgagcctggcgaacagttcggctggcgc
gagcccctgatgctcttcgtccagatcatcctgatcgacaagaccggctt
ccatccgagtacgtgctcgctcgatgcgatgtttcgcttggtggtcgaat
gggcaggtagccggatcaagcgtatgcagccgccgcattgcatcagccat
gatggatacttctcggcaggagcaaggtgagatgacaggagatcctgcc
ccggcacttcgcccaatagcagccagtcccttcccgcttcagtgacaacg
tcgagcacagctgcgcaaggaacgcccgtcgtggccagccacgatagccg
cgctgcctcgtcttgcagttcattcagggcaccggacaggtcggtcttga
caaaaagaaccgggcgcccctgcgctgacagccggaacacggcggcatca

```
-continued
gagcagccgattgtctgttgtgcccagtcatagccgaatagcctctccac ccaagcggccggagaacctgcgtgcaatccatcttgttcaatcataatat tattgaagcatttatcagggttcgtctcgtcccggtctcctcccaatgca tgtcaatattggccattagccatattattcattggttatatagcataaat caatattggctattggccattgcatacgttgtatctatatcataata.
```

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, "cluster of designation" or "classification determinant" proteins (often abbreviated as "CD") such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one protein scaffold of the disclosure can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the disclosure. Alternatively, nucleic acids of the disclosure can be expressed in a host cell by turning on (by manipulation) in a host cell that contains endogenous DNA encoding a protein scaffold of the disclosure. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of a Protein Scaffold

A protein scaffold can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Protein scaffolds of the disclosure include naturally purified products, products of chemical synthetic procedures, and products produced by recombinant techniques from a prokaryotic or eukaryotic host, including, for example, *E. coli*, yeast, higher plant, insect and mammalian cells. Depending upon the host employed in a recombinant production procedure, the protein scaffold of the disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Variants

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the disclosure can include one or more amino acid substitutions, deletions or additions, either from natural mutations or human manipulation, as specified herein. Amino acids in a protein scaffold of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, a bacteriophage, a bacterial artificial chromosome or a yeast artificial chromosome. A vector can be a DNA or RNA vector. A vector can be a self-replicating extrachromosomal vector, and preferably, is a DNA plasmid.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (Kyte et al., J. Mol. Biol. 157: 105-132 (1982)). The hydropathic index of an amino acid is based on a consideration of its hydrophobicity and charge. Amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the invention. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
| | Polar - uncharged | C S T M N Q |
| | Polar - charged | D E K R |
| | Aromatic | H F W Y |
| | Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |

TABLE C-continued

Conservative Substitutions III

| Original Residue | Exemplary Substitution |
|---|---|
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

EXAMPLES

Example 1: Production of Stem-Like Modified T-Cells

The following is an illustrative but nonlimiting example of one protocol for modifying T cells to express a chimeric antigen receptor (CAR) under conditions that induce or preserve desirable stem-like properties of the T cells.

Day 0: Nucleofection of T Cells

Pre-warm ImmunoCult™-XF T cell expansion medium (Stemcell Technologies, Cat #: 10981) in 37° C., 5% $CO_2$, high humidity incubator. For $5×10^6$ T cells/reaction (100 μL cuvette size) warm 3 mL of media/reaction in a single well of a 6-well plate. For $25×10^6$ T cells/reaction (100 μL cuvette size) warm 20 mL of media/reaction in a G-Rex10 (Wilson Wolf, Cat #: 80040S).

Warm P3 primary cell solution (Lonza, Cat #: PBP3-02250) up to room temperature and add supplement if necessary.

Turn on the core unit (Lonza, Cat #: AAF-1002B) of the 4D-Nucleofector™ System, which controls the X-unit (Lonza, Cat #: AAF-1002X). Program the number of nucleofections required to use P3 buffer. Program EO-210.

Label cuvettes, pre-open transfer pipettes (supplied with the Lonza P3 kit), and prepare proper dilutions of nucleic acids prior to working with the cells.

For a transposon plasmid, make a 0.5 μg/μL solution in nuclease free $H_2O$.

Count CD14, CD56, and CD19 depleted cells collected using the CliniMACs Prodigy and calculate the volume needed for the required cell number.

Centrifuge T cells at 90 g for 10 minutes with brake at 7 on a Heraeus Multifuge X3R benchtop centrifuge (Thermofisher Scientific). If performing multiple reactions using the same number of cells/reaction, centrifuge all the necessary cells in a single centrifuge tube. Either a 15 mL (Fisher, Cat #: 14-959-49B) or 50 mL (Fisher, Cat #: 14-959-49A) conical tube can be used depending on volume. During centrifugation add nucleic acids directly to the bottom of cuvettes that come with the P3 primary cell solution box (Lonza, Cat #: PBP3-02250). Add 2 μL of the 0.5 μg/μL transposon plasmid solution made in step 4 for a total of 1 μg transposon to one of the bottom corners of the cuvette. Add 5 μg of Super piggyBac™ (SPB) transposase mRNA to the other corner of the cuvette.

Because mRNA can be rapidly degraded, it is optimal to minimize the time it is in contact with other nucleic acid solutions and with cells prior to electroporation due to the potential presence of RNases. This is why, for example, the transposon and transposase are delivered to opposite corners of the cuvette to prevent mixing. In addition, it is optimal to keep the total volume of nucleic acids under 10 μL (10%) of the total reaction volume.

The amount of both transposon (1 μg) and transposase (5 μg) stays the same regardless of the number of cells/reaction. Transposition efficiencies remain unchanged between $5×10^6$ cells/100 μL reaction and $25×10^6$ cells/100 μL reaction.

Following centrifugation, completely aspirate off the media without disturbing the cell pellet.

Suspend the cell pellet in 100 μL of room temperature P3 buffer containing the supplement/reaction.

Transfer 100 μL of cells in P3 buffer to a cuvette containing the appropriate nucleic acids, optimally, taking care not to introduce any air bubbles into the solution. It is recommended that only up to 2 cuvettes should loaded with cells at a time. After the addition of cells to the cuvette, it is optimal to work quickly and efficiently to reduce contact time of mRNA with cells prior to nucleofection. While no decrease in transposition efficiency has observed for cells resting in P3 buffer for up to 10 minutes, it is recommended to minimize the amount of time cells remain in P3.

Mix the contents of the cuvette by flicking several times and load up to two cuvettes into the 4D-Nucleofector™ X-unit.

Pulse the cells with program EO-210 and ensure there was no error recorded by the machine.

Immediately transfer the nucleofected cells into either the 6-well plate or G-Rex10 using the transfer pipettes provided with the Lonza P3 kit. To transfer the cells, first draw up a small amount of pre-warmed media into the transfer pipette from either the 6-well plate or the G-Rex flask. Then pipette the media into the cuvette and transfer the entire contents of the cuvette using the pipette into the final culture dish. It is recommended not to pipette the cells up and down in either the cuvette or the final culture dish.

Repeat protocol from the transfer of cells in P3 buffer to a cuvette containing the appropriate nucleic acids through the mixing, pulsing, and transfer of the nucleofected cells into either the 6-well plate or G-Rex10 for any remaining reactions.

Place cells in incubator at 37° C., 5% $CO_2$, high humidity.

Day 2: T Cell Activation

Add 25 μL/mL of ImmunoCult™ Human CD3/CD28/CD2 T cell Activator (Stemcell Technologies, Cat #: 10970) to the nucleofected cells.

Mix cells gently by pipetting.

Place cells back into the incubator at 37° C., 5% $CO_2$, high humidity.

For Cells being Grown in G-Rex Flask:

It is essential not to disturb the cultures until visible cell clumping is observed. Thus, it is recommended to separate the media additions and changes from the disruption/mixing/pipetting of the cells.

Culture Media Notes:

For growing cells in the G-Rex flask, media addition and/or changes should be done based off of glucose and other metabolite levels. If the glucose level (or another indicating metabolite) falls to a critical level (~100 mg/dL of glucose, for example) media volume should be doubled and/or replenished by a half-media change using pre-warmed ImmunoCult™-XF T cell expansion medium. Media addition should be performed slowly and care taken to disrupt the cells as little as possible. Half media changes should be performed at least 12 hours post mechanical disruption of the cell culture to allow the cells to fully settle to the bottom of the culture flask.

Cell Sampling and Disruption:

Cells should be left undisturbed during much of the culture period.

The first disruption of the cell culture following activation reagent addition should occur once large visible aggregates of cells have formed (aggregates will measure 3-4 squares by 3-4 squares of the grid that can be seen on the G-Rex membrane).

Once cell aggregates have reached the required size, they can be mechanically disrupted using a 10 mL serological pipette. This time point may occur between 11-14 days depending on donor and transposition efficiency. In certain circumstances, this time point may occur closer to day 14 than day 11, for example, when using a manual cassette, a large volume and/or a large cell number for nucleofection. A sampling of cells should be collected at this point for cell counts, viability, and flow analysis. Ideally the volume of culture medium at this point will have no more than doubled from the initial volume used (200 mL for a G-Rex100). It is recommended to collect all of the cells needed at once so that the cells do not need to be disturbed again.

Once the cells have been disrupted they should be left undisturbed for 12 hours in the same volume of media they started in. Cells should re-aggregate at this point; however, the aggregates will be smaller and more numerous. These aggregates should measure 1-2 squares by 1-2 squares on the G-Rex membrane grid.

Three days following the first disruption (day 14-17 depending on the culture) of the cells they can be pipetted a second time. Samples should be taken again for cell counts, viability, and flow cytometry. Once again the cells should be left undisturbed for at least 12 hours post sampling. It is recommended to collect all of the cells needed at once so that the cells do not need to be disturbed again.

Following this second disruption, the cells will likely not form any clumps and the rate of cell growth will slow considerably.

Cell harvest should be performed 3 days after the second disruption of cells between day 17 and day 20 of the culture.

Flow Cytometry

Flow should be run on Day 5, D-Day, D-Day+3, and D-Day+6.

For Day 5, D-Day, and D-Day+3 use the CD45, CD4, CD8, and CARTyrin flow panel

For D-Day+6, there are 3 target panels:
a. Panel 1: CD3, CD8, CD4, CARTyrin, CD45RA, CD45RO, CD62L
b. Panel 2: CD3, CD8, CD4, CARTyrin, CD25, CXCR4, PD-1
c. Panel 3: CD45, CD14, CD20, CD56, CD8, CD4, CD3

Example 2: Functional Characterization of CARTyrin+ Stem Memory T Cells

CARTyrins of the disclosure may be introduced to T cells using a plasmid DNA transposon encoding the CARTyrin that is flanked by two cis-regulatory insulator elements to help stabilize CARTyrin expression by blocking improper gene activation or silencing.

In certain embodiments of the methods of the disclosure, the piggyBac™ (PB) Transposon System may be used for stable integration of antigen-specific (including cancer antigen-specific) CARTyrin into resting pan T cells, whereby the transposon was co-delivered along with an mRNA transposase enzyme, called Super piggyBac™ (SPB), in a single electroporation reaction. Delivery of piggyBac™ transposon into untouched, resting primary human pan T cells resulted in 20-30% of cells with stable integration and expression of PB-delivered genes. Unexpectedly, a majority of these modified CARTyrin-expressing T cells were positive for expression of CD62L and CD45RA, markers commonly associated with stem memory T-cells ($T_{SCM}$ cells). To confirm that this phenotype was retained upon CAR-T cell stimulation and expansion, the modified CARTyrin-expressing T cells positive for expression of CD62L and CD45RA were activated via stimulation of CD3 and CD28. As a result of stimulation of CD3 and CD28, >60% of CARTyrin+ T cells exhibited a stem-cell memory phenotype. Furthermore, these cells, which expressed a CARTyrin specific for a cancer antigen, were fully capable of expressing potent anti-tumor effector function.

To determine whether or not the PB system directly contributed to enhancing the expression of stem-like markers, the phenotype of CAR-T cells generated either by PB transposition or lentiviral (LV) transduction was compared. To do this, a new vector was constructed by subcloning the CARTyrin transgene into a common LV construct for production of virus. Following introduction of the CARTyrin to untouched resting T cells either by PB-transposition or LV-transduction, the CARTyrin+ cells were expanded and then allowed to return to a resting state. A variety of phenotypic and functional characteristics were measured including kinetic analysis of memory and exhaustion-associated markers, secondary proliferation in response to homeostatic cytokine or tumor-associated Ag, cytokine production, and lytic capability in response to target tumor cells. Unlike the PB-transposed CARTyrin+ T cells, the LV-transduced CARTyrin+ T cells did not exhibit an augmented memory phenotype. In addition, PB-transposed cells exhibited a comparable or greater capability for secondary proliferation and killing of target tumor cells. Together, these data demonstrate that CAR-T cells produced by PB transposition are predominantly $T_{SCM}$ cells, a highly desirable product phenotype in the CAR-T field. Furthermore, these CARTyrin T cells exhibit strong anti-tumor activity and may give rise to cells that persist longer in vivo due to the use of a Centyrin-based CAR, which may be less prone to tonic signaling and functional exhaustion.

Figure 10A:
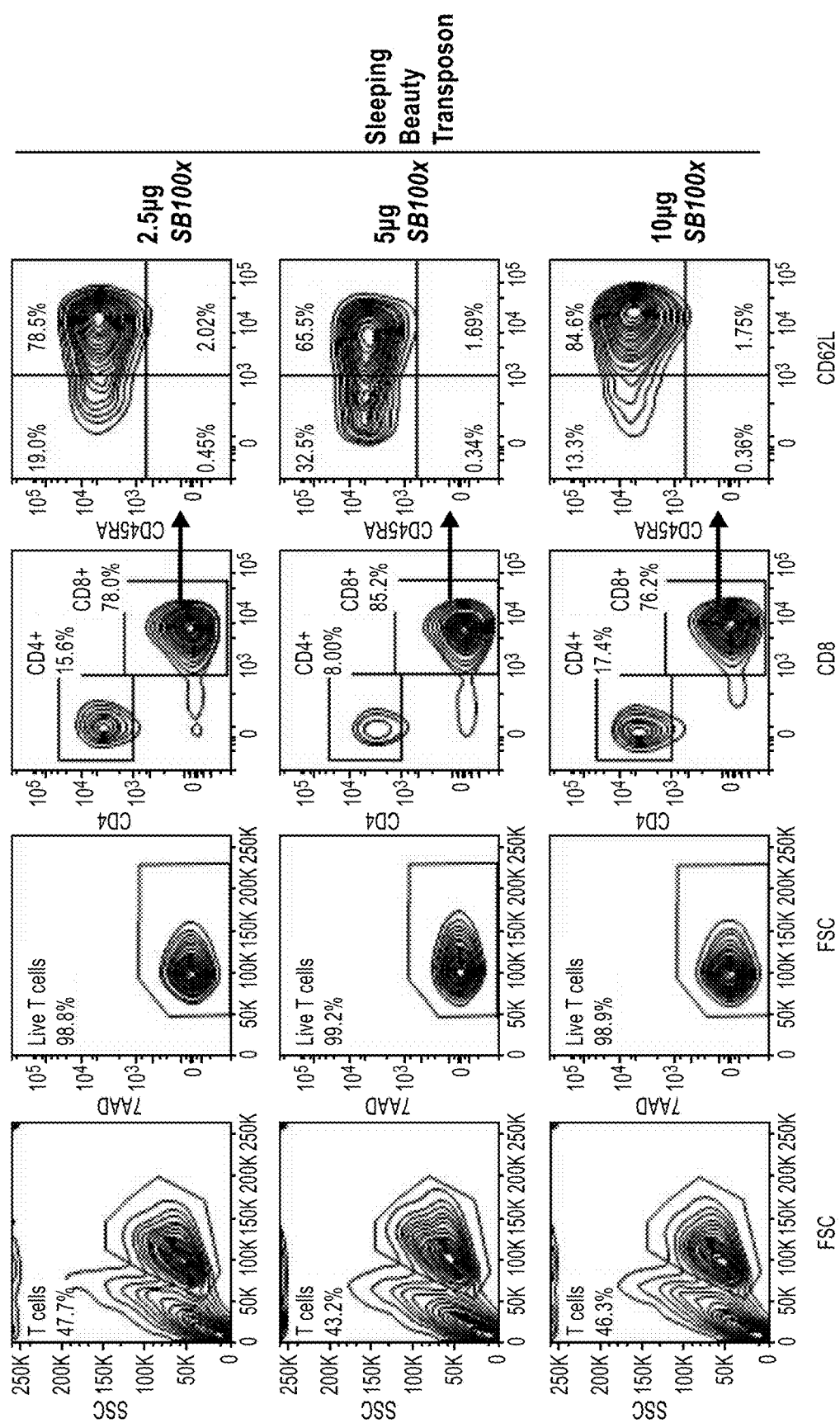
FIGS. 10A-B is a series of Fluorescence Activated Cell Sorting (FACs) plots characterizing T and $T_{SCM}$ cell markers in human pan T cells transformed with the Sleeping Beauty (SB100x) transposition system and the methods of the disclosure. Sleeping Beauty (SB100x) Transposition yields predominately $T_{SCM}$ phenotype using Poseida manufacture process. Human pan T cells were transposed using 1 μg of either a Sleeping Beauty or piggyBac transposon plasmid and SB100x or SPB mRNA, respectively as shown. Following transposition, cells were expanded ex vivo and all non-transposed cells were depleted using the Poseida manufacture drug selection system. Following 18 days in culture, cells were stained with the phenotypic markers CD4, CD8, CD45RA, and CD62L. Stem cell memory phenotype ($T_{SCM}$) is defined by CD45RA and CD62L double positive cells and make up >65% of the cells in all of samples. All panels in a column share common x-axis and y-axis parameters. In each row of FIG. 10A, from top to bottom, are shown data from T cells transposed with (top), 2.5 microgram (μg) of the Sleeping Beauty transposon SB100x, (second from top) 5 μg of SB100x and ($3^{rd}$ from top) 10 μg of SB100x. In each row of FIG. 10B, from top to bottom are shown data from T cells transposed with (top) 5 μg of the piggyBac transposon P-BCMA-101 and (bottom), an unstained control.
Figure 10B:
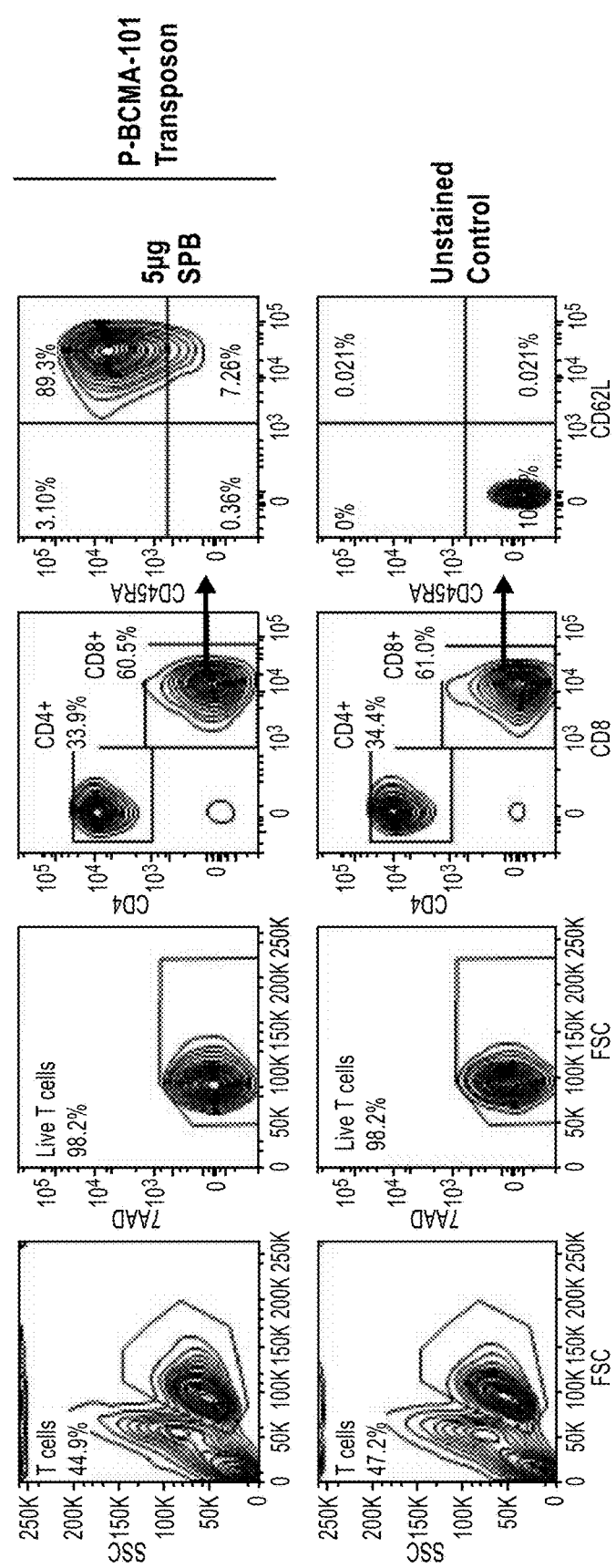

Example 3: Sleeping Beauty Transposition Yields Predominantly $T_{SCM}$ Phenotype Sleeping Beauty (SB100x) Transposition yielded a predominately $T_{SCM}$ phenotype using the methods of the disclosure. Human pan T cells were transposed using 1 μg of either a Sleeping Beauty or piggyBac transposon plasmid and SB100x or SPB mRNA, respectively as shown in FIG. 10. Following transposition, cells were expanded ex vivo and all non-transposed cells were depleted using a drug selection system. Following 18 days in culture, cells were stained with the phenotypic markers CD4, CD8, CD45RA, and CD62L. Stem cell memory phenotype ($T_{SCM}$) is defined by CD45RA and CD62L double positive cells and make up >65% of the cells in all of samples.

Example 4: Expression of Factor IX in Modified T-Cells

Figure 11:
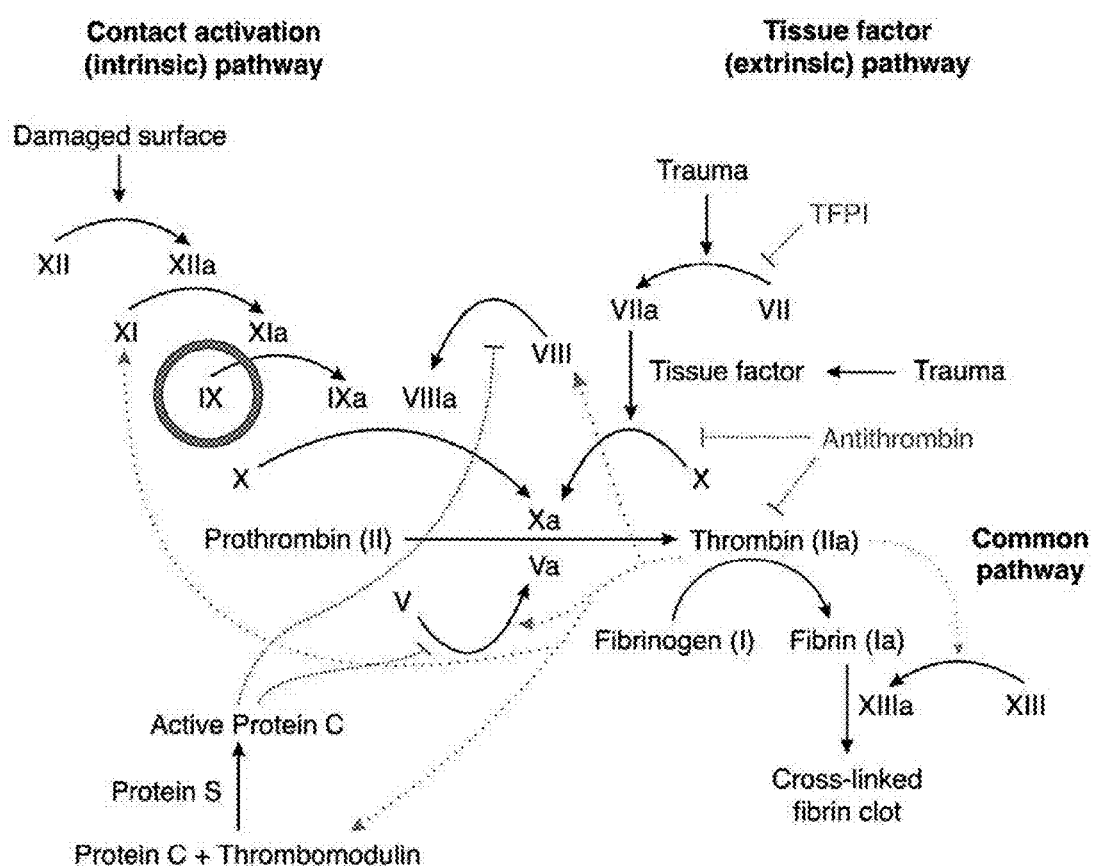
FIG. 11 is a schematic diagram showing the human coagulation pathway leading to blood clotting. Contact activation, for example by damaging an endothelium, activates an intrinsic clotting pathway. Tissue factors activate an extrinsic clotting pathway, for example following trauma. Both pathways converge onto the conversion of Prothrombin into Thrombin, which catalyzes the conversion of fibrinogen into fibrin. Polymerized fibrin together with platelets forms a clot. In the absence of Factor IX (circled), clotting is defective. Factor VIII (FVIII) deficiency leads to development of Hemophilia A. Factor IX (FIX) deficiency leads to development of Hemophilia B. Hemophilia B is a rare disease, occurring with a frequency of about one in between 25,000 and 30,000. Sixty percent of hemophilia B cases are severe. Fewer than one percent of individuals with Hemophilia B have normal FIX levels. Prior to the compositions and methods of the disclosure, the standard treatment for hemophilia B involved an infusion of recombinant FIX every 2 to 3 days, at an expense of approximately $250,000 per year. In sharp contrast to this standard treatment option, $T_{SCM}$ cells of the disclosure are maintained in humans for several decades.

Genetic deficiencies in Factor IX (FIG. 11) lead to a life threatening disease called Hemophila B. Hemophila B is a rare disease that affects 1 in 25,000 to 1 in 30,000 people. Current Hemophilia B treatments involve an infusion of recombinant Factor IX protein every 2-3 days, at a cost of around $250,000 per year.

Figure 12:
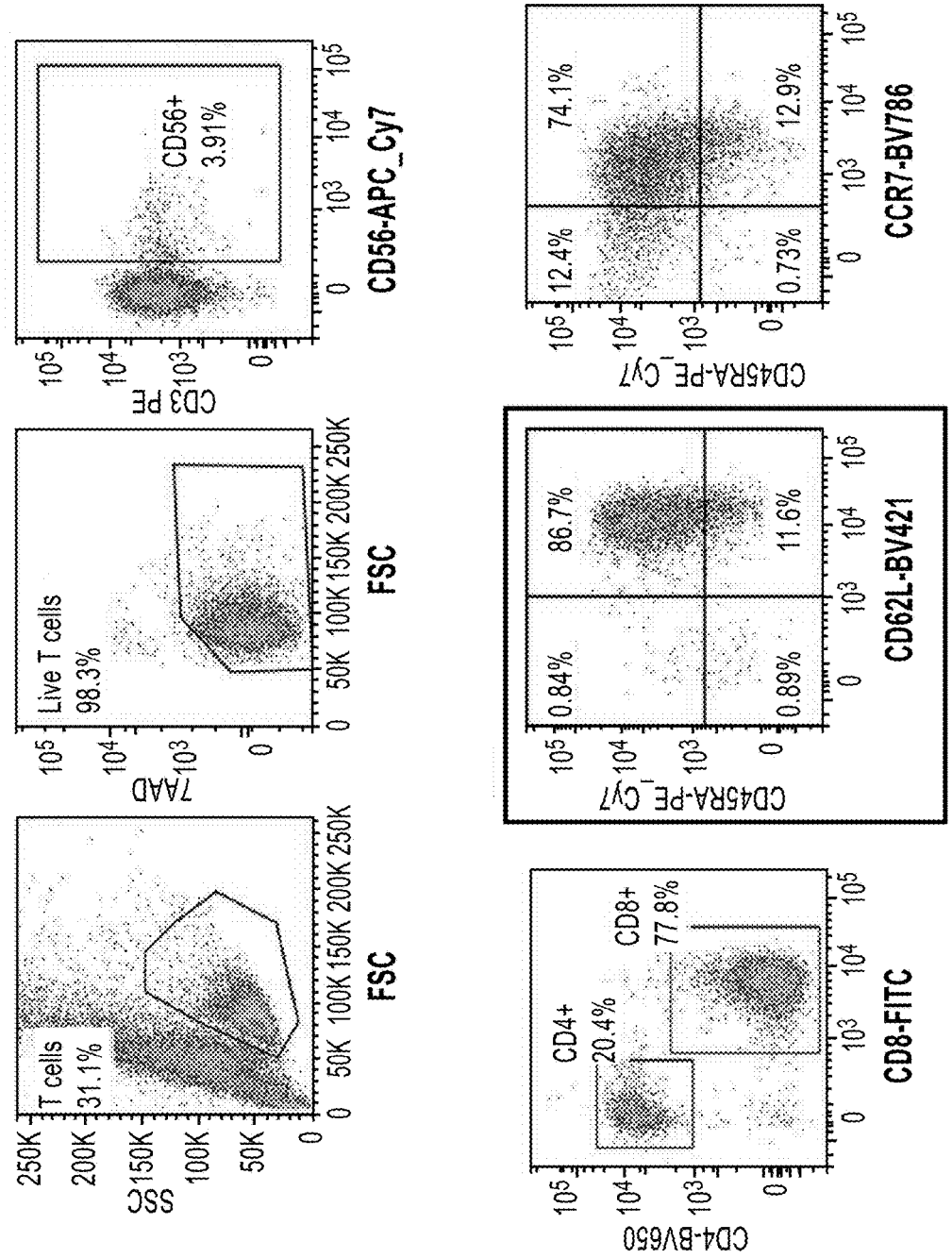
FIG. 12 is a series of Fluorescence-Activated Cell Sorting (FACS plots) depicting FIX-secreting T cells. T cells encoding a human Factor IX transgene showed a $T_{SCM}$ phenotype in approximately 80% of cells. The 6 panels are described in order from left to right. (1) Forward scatter (FSC) on the x-axis versus side scatter (SSC) on the y-axis. The x-axis is from 0 to 250 thousand (abbreviated k) in increments of 50 k, the y-axis is for 0 to 250 k, in increments of 50 k. (2) FSC on the x-axis versus the cell viability marker 7 aminoactinomycin D (7AAD). The x-axis is labeled from 0 to 250 k in increments of 50 k. The y-axis reads, from top to bottom, $-10^3$, 0, $10^3$, $10^4$, $10^5$. (3) On the x-axis is shown anti-CD56-APC conjugated to a Cy7 dye (CDC56-APC-Cy7), units from 0 to $10^5$ incrementing in powers of 10. On the y-axis is shown anti-CD3 conjugated to phycoerythrin (PE), units from 0 to $10^5$ incrementing in powers of 10. (4) On the x-axis is shown anti-CD8 conjugated to fluorescein isothiocyanate (FITC), units from 0 to $10^5$ incrementing in powers of 10. On the y-axis is shown anti-CD4 conjugated to Brilliant Violet 650 dye (BV650), units from 0 to $10^5$ incrementing in powers of 10. (5) On the x-axis is shown an anti CD62L antibody conjugated to a Brilliant Violet 421 dye (BV421), units from 0 to $10^5$ incrementing in powers of 10. On the y-axis is shown an anti-CD45RA antibody conjugated to PE and Cy7, units from 0 to $10^5$ incrementing in powers of 10. This panel is boxed. (6) On the x-axis is shown an anti-CCR7 antibody conjugated to Brilliant Violet 786 (BV786), units from 0 to $10^5$ incrementing in powers of 10. On the y-axis is shown anti-CD45RA conjugated to PE and Cy7, units from 0 to $10^5$ incrementing in powers of 10.
Figure 13A:
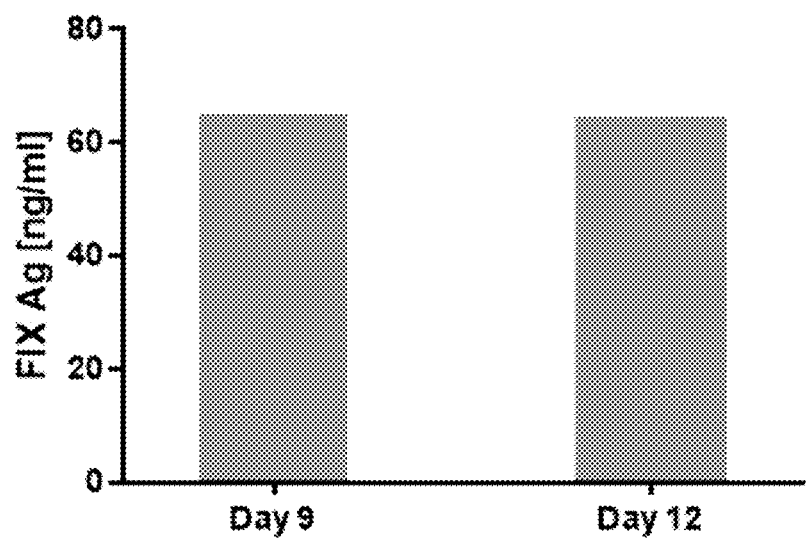
FIG. 13A is a graph showing human Factor IX secretion during production of modified T cells of the disclosure. On the y-axis, Factor IX concentration in nanograms (ng) per milliliter (mL) from 0 to 80 in increments of 20. On the x-axis are shown 9 day and 12 day T cells.
Figure 13B:
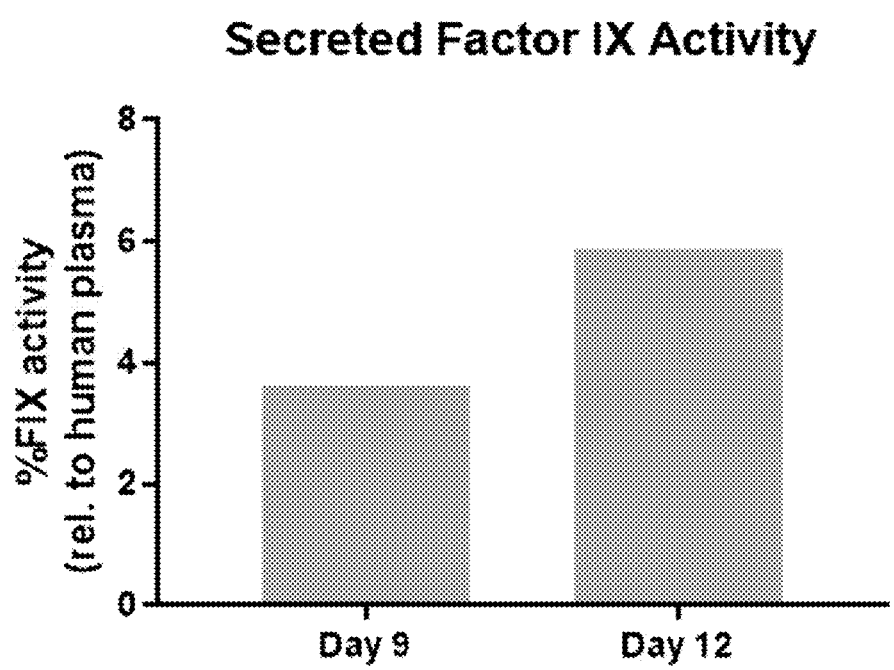
FIG. 13B is a graph showing the clotting activity of the secreted Factor IX produced by the T cells. On the y-axis is shown percent Factor IX activity relative to human plasma, from 0 to 8 in increments of 2. On the x-axis are 9 and 12 day T cells.
Figure 14A:
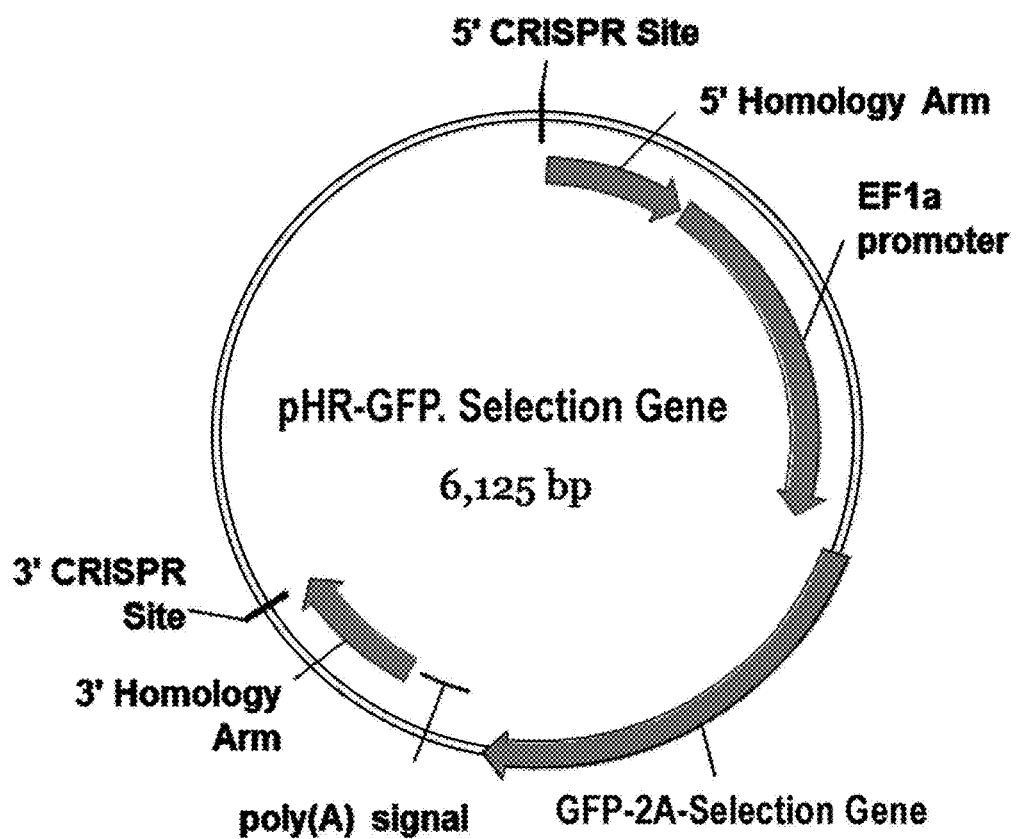
Figure 14B:
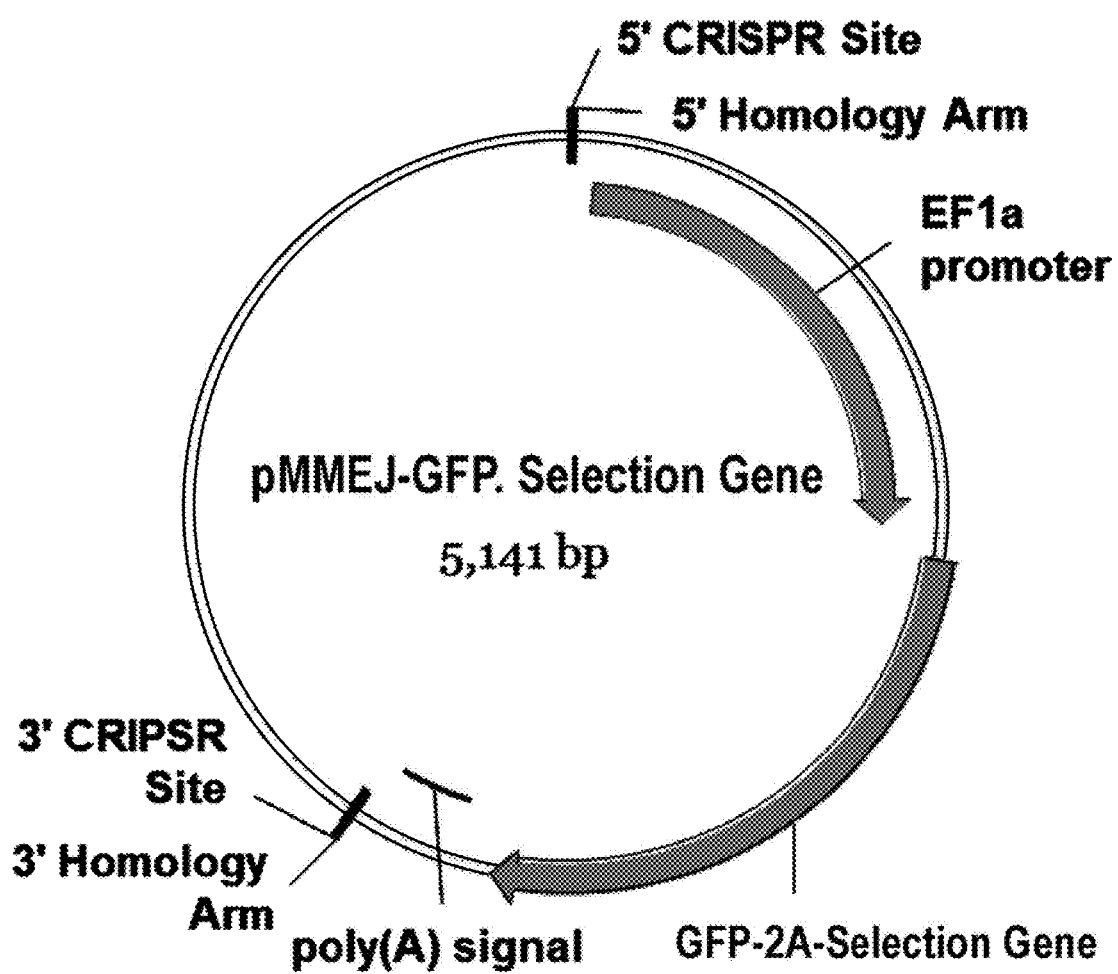
Figure 14C:
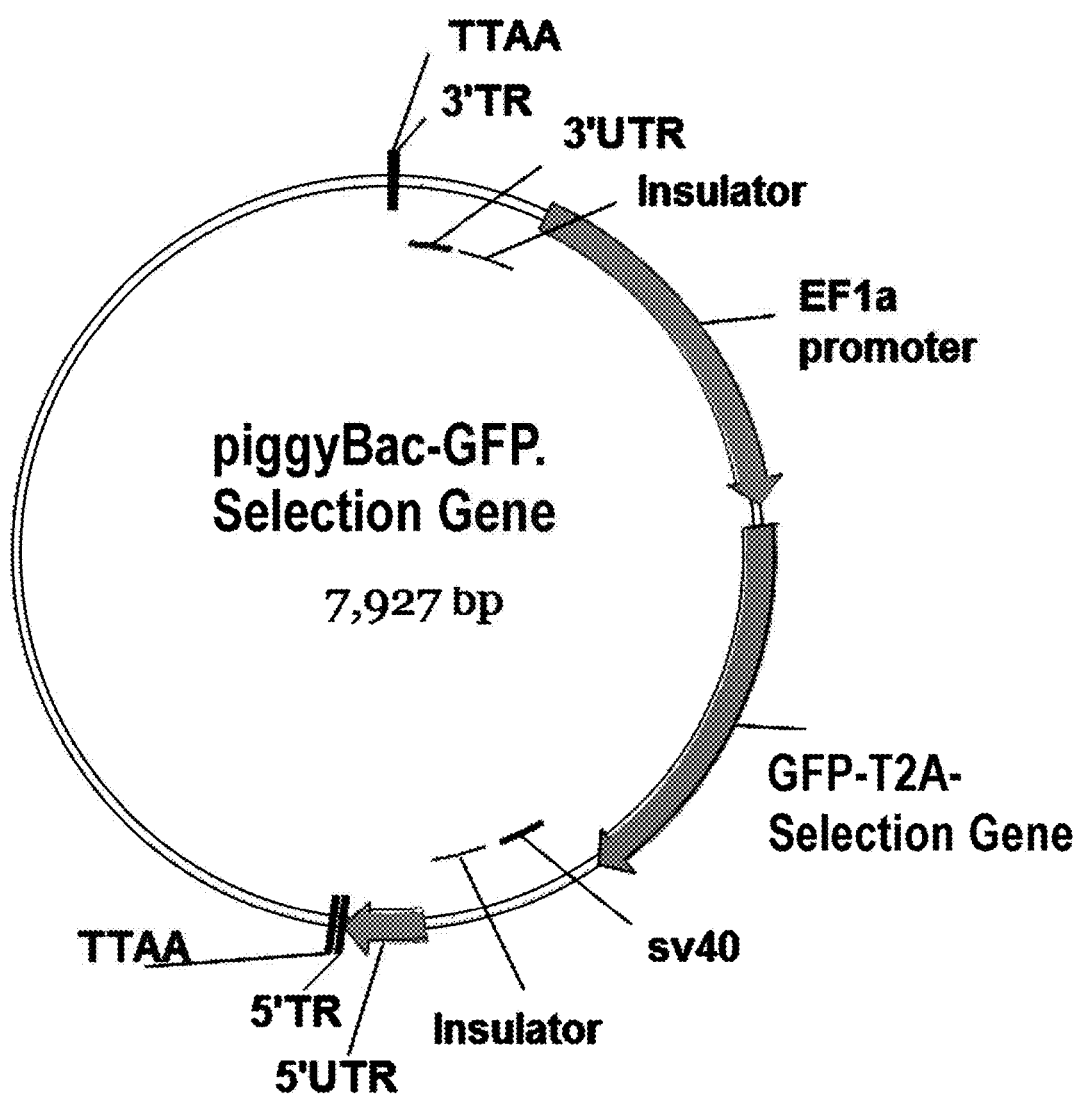
Figure 15:
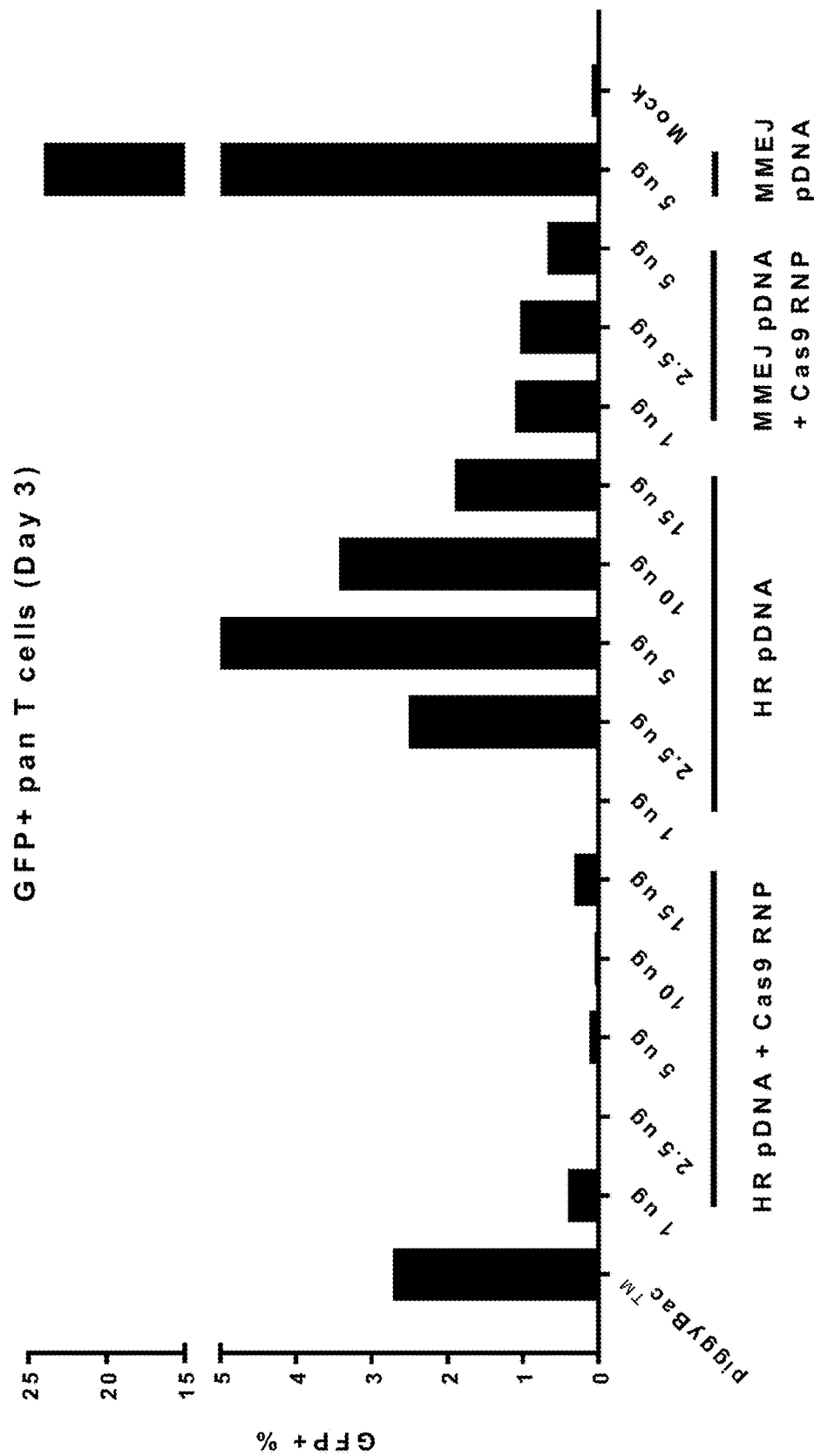
FIG. 15 is a graph showing transgene (GFP) expression in primary human pan T cells 3 days post-nucleofection. HR or MMEJ donor plasmids were co-delivered with or without CRISPR ribonucleoprotein (RNP) targeting reagents into pan T cells via nucleofection. T cells receiving donor plasmids alone were included as controls. Pan T cells were also modified using the piggyBac™ transposon delivery system. T cells were activated via TCR stimulation on Day 0 and GFP+ T cell percentage was accessed at day 3 post-nucleofection by flow cytometry and data are summarized in bar graph.
Figure 16:
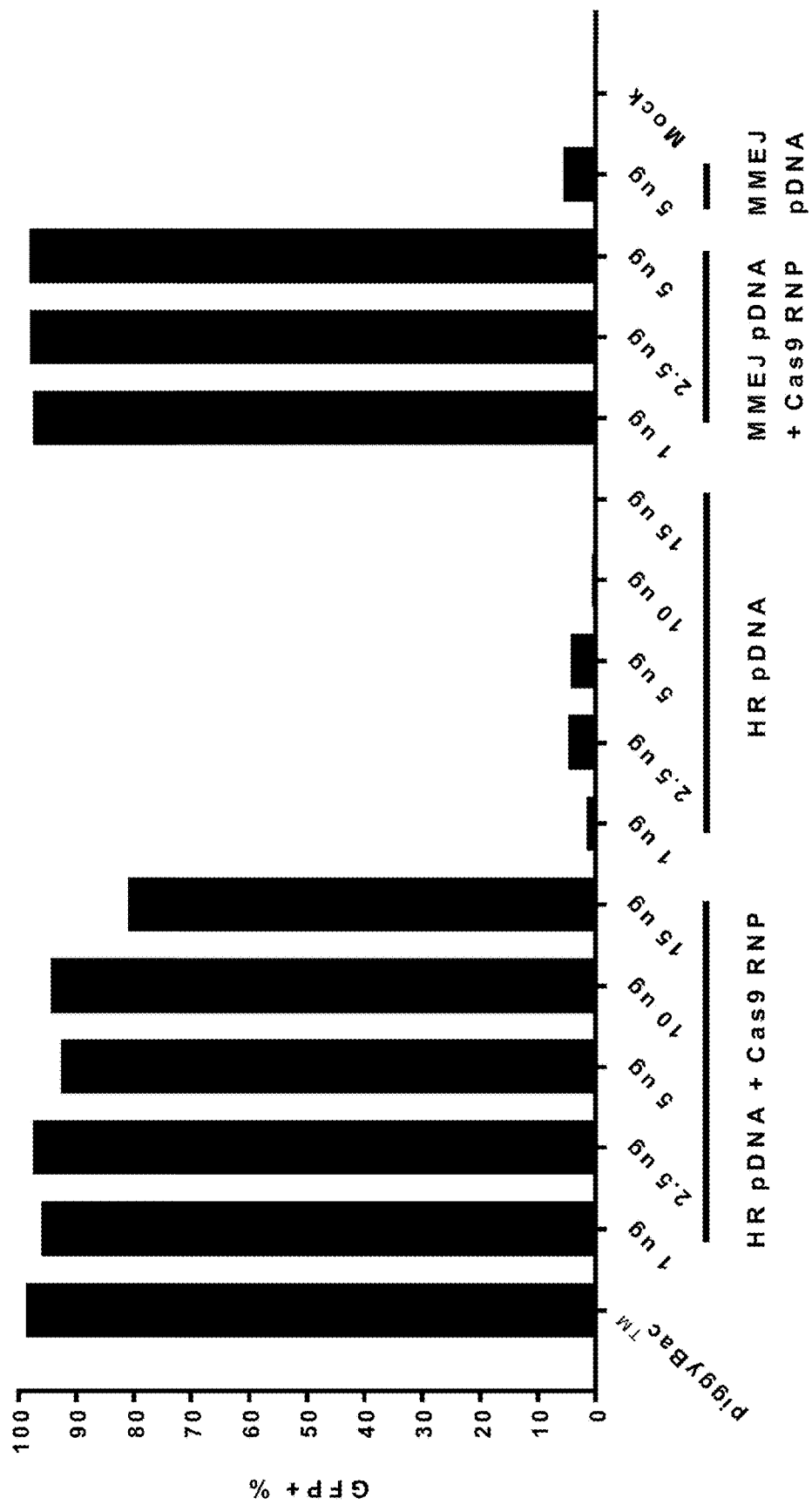
FIG. 16 is a graph showing transgene (GFP) expression in primary human pan T cells 11 days post-nucleofection and selection. Activated T cells with stably integrated transgenes were selected by methotrexate addition using the DHFR selection gene encoded in the bi-cistronic GFP-2A-DHFR integration cassettes. GFP+ cell percentage was assessed at Day 11 post-nucleofection and data are summarized in bar graph. GFP+ cells were highly enriched via selection in pan T cells receiving transposition reagents, RNP plus HR or MMEJ donor plasmids, but not in T cells receiving donor plasmids alone.
Figure 17A:
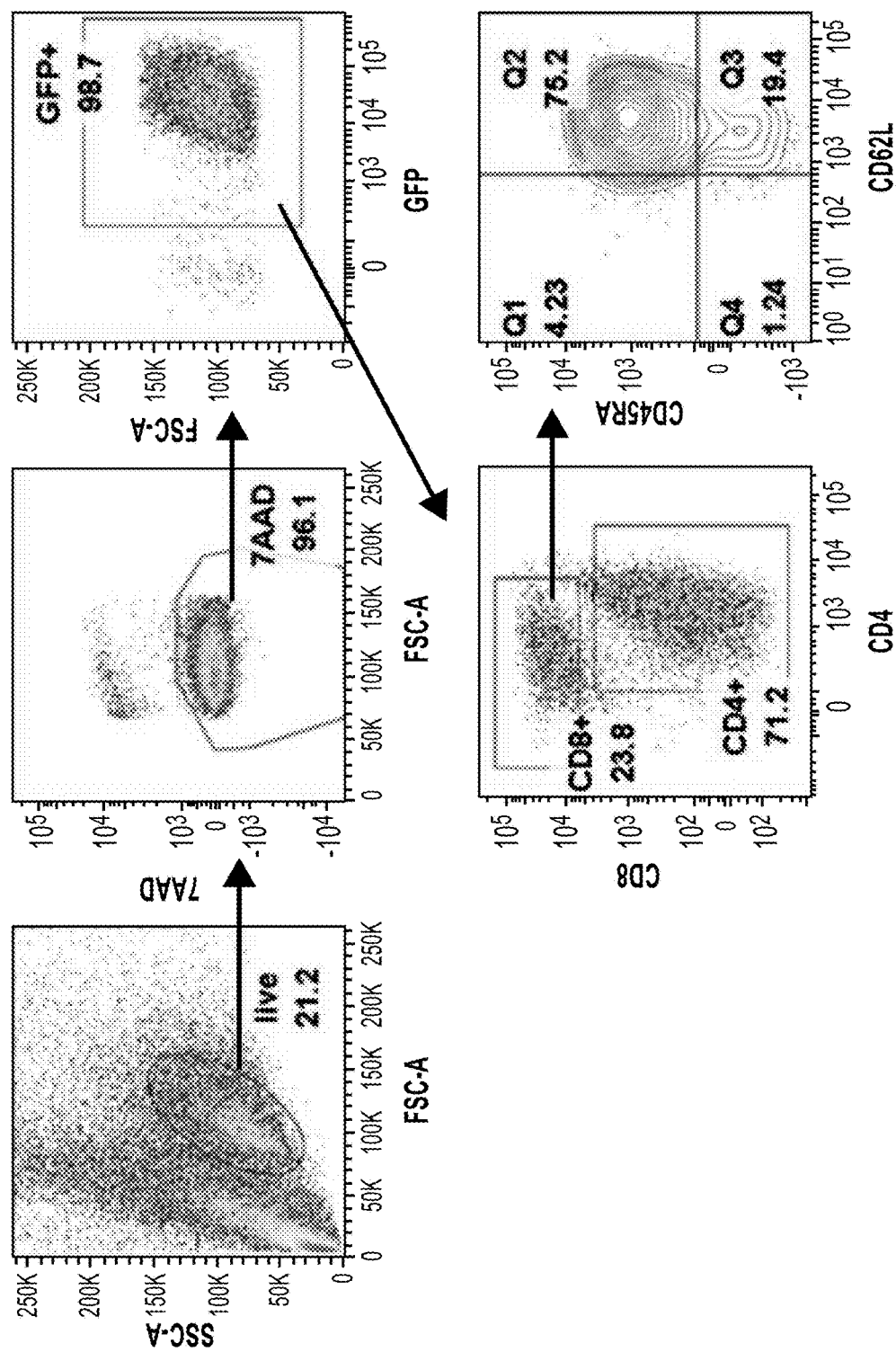
FIGS. 17A-C is a series of graphs showing the phenotype of primary human pan T cells modified by HR and MMEJ at the AAVS1 site. The phenotype of GFP+CD8+ pan T cells was analyzed at Day 11 post-nucleofection by flow cytometry. A) Cells were stained with 7AAD (cell viability), CD4, CD8, CD45RA and CD62L, and FACS plots show gating strategy. CD8+ T cell subsets were defined by expression of CD45RA+CD62L+(stem cell memory T cells ($T_{SCM}$)), CD45RA-CD62L+(central memory T cells ($T_{CM}$)), CD45RA-CD62L- (effector memory T cells (Tem)), and CD45RA+CD62L- (T effectors (Teff)). B) Percentage of total GFP+ CD8+ T cells in each T cell subset is summarized in bar graph. An enriched population of GFP+ $T_{SCM}$ was achieved in all cases using either the piggyBac™ transposon system, or HR and MMEJ in combination with Cas9 RNP. C) The total number of pan T cells was analyzed at day 13 post-nucleofection and data are summarized in bar graph.
Figure 17B:
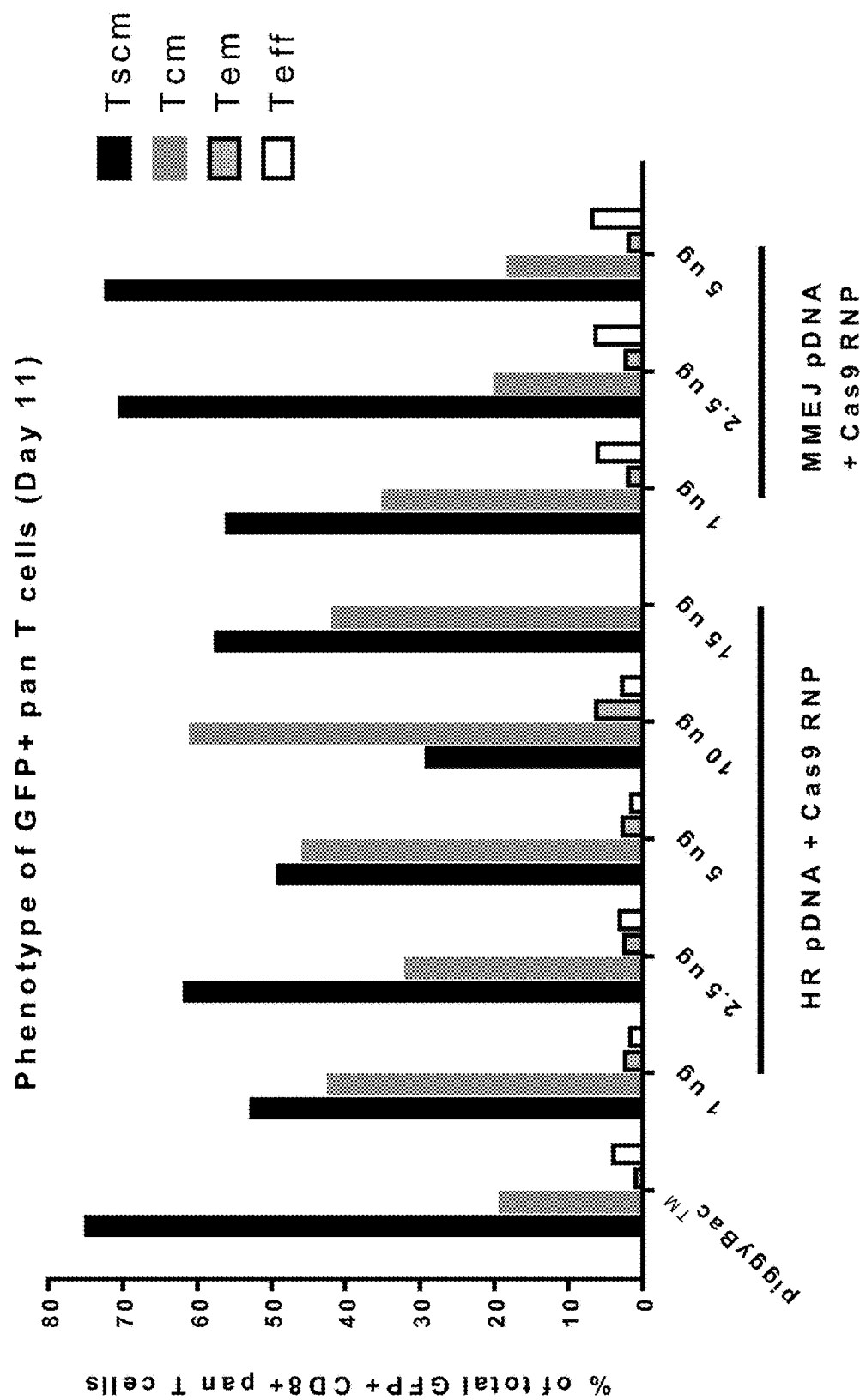
Figure 17C:
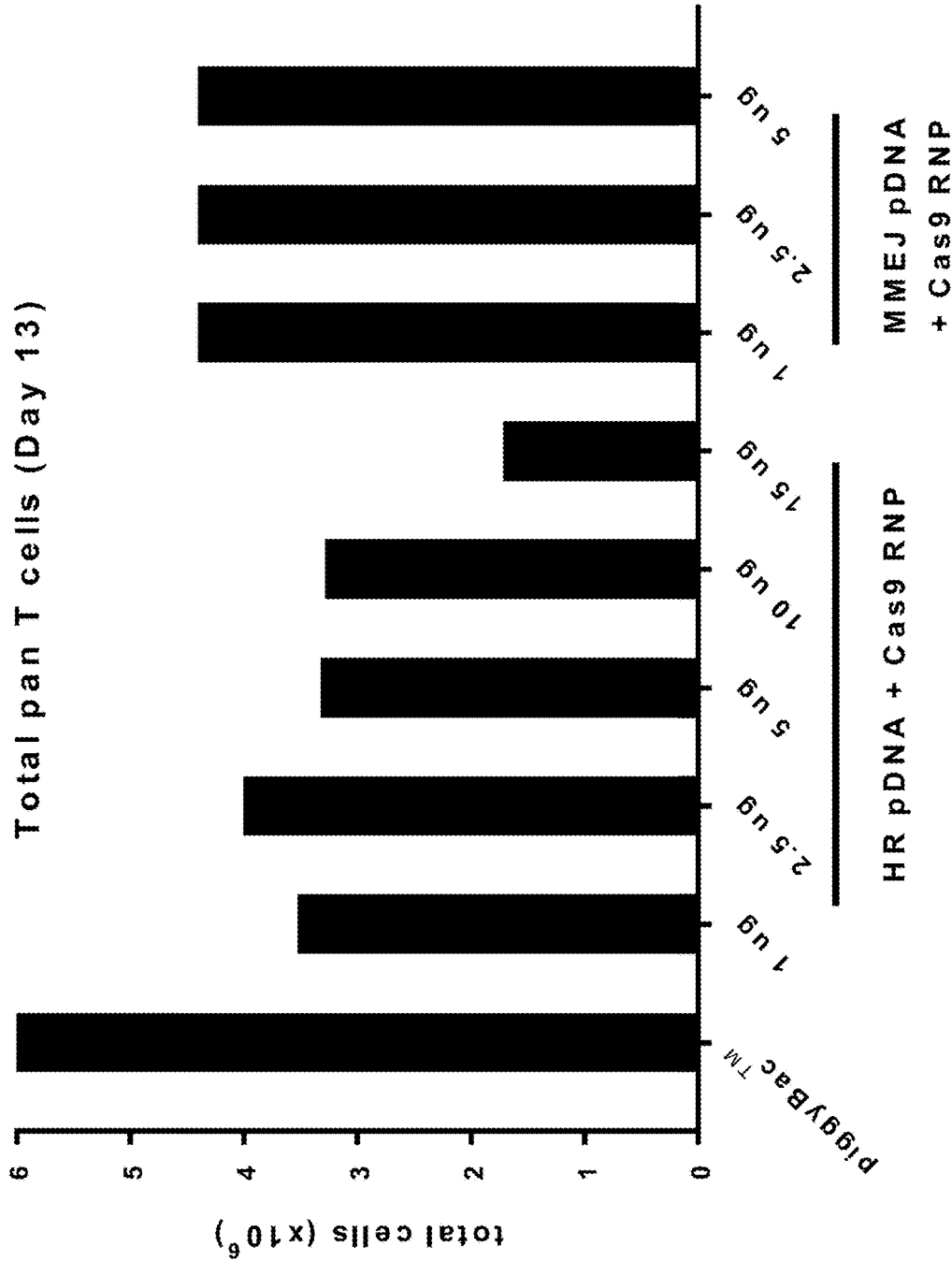
Figure 18A:
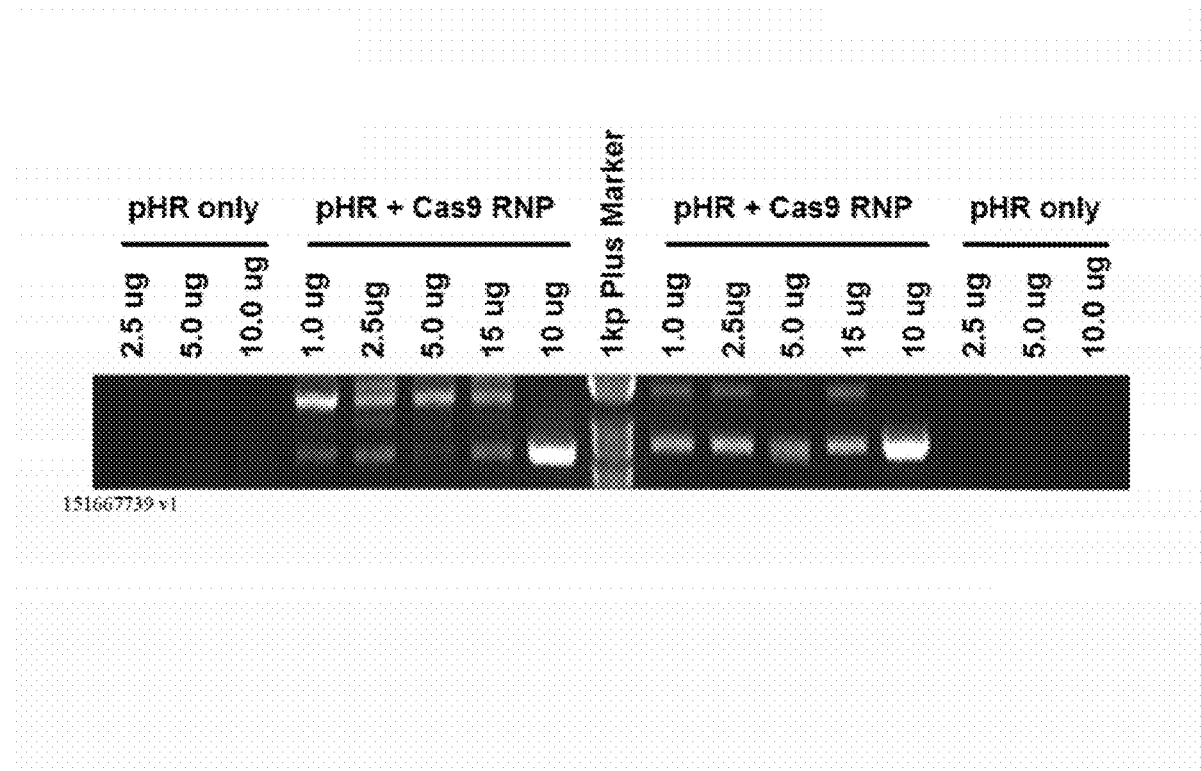
FIGS. 18A-B is a pair of photographs of gel electrophoresis results showing site-specific integration into the AAVS1 site. Selected cells from each group were harvested and genomic DNA was extracted and used as template for PCR to confirm site-specific integration into the AAVS1 site for A) HR and B) MMEJ. Two pairs of primers individually amplify the 5'-end junction (with one primer priming the promoter region of the insertion EF1a-2r CACCGGAGCCAATTCCCACT (SEQ ID NO: 36) and the other priming the AAVS1 region beyond the 500 bp homologue arm at the 5'-end AAVS-3r CTGCACCACGTGATGTCCTC (SEQ ID NO: 37), yielding a 0.73 kb DNA fragment for both HR or MMEJ) and 3'-end junction (with one primer priming the polyA signaling region SV40 pA-1r GTAACCATTATAAGCTGCAATAAACAAG (SEQ ID NO: 38) and the other priming the AAVS1 region beyond the 500 bp 5'-homologue arm AAVS-2f CTGGGGACTCTTTAAGGAAAGAAG (SEQ ID NO: 39), yielding a 0.76 kb DNA fragment for HR or MMEJ) of the AAVS1 target site. PCR products were displayed on Agarose gel. Non-specific bands in HR samples are the result of only a single round of PCR and would likely have been resolved given additional rounds.
Figure 18B:
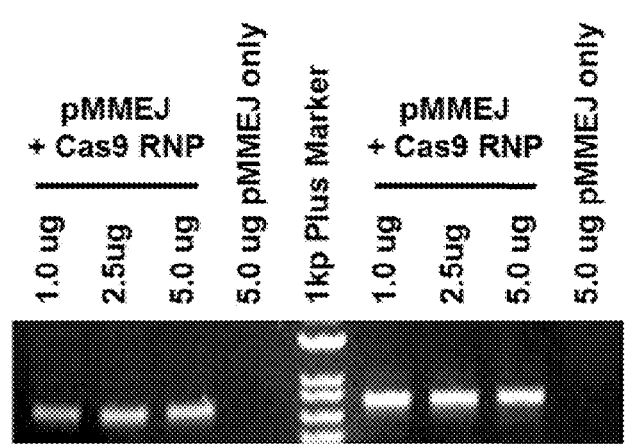

Stem memory T cells ($T_{SCM}$ cells) are maintained in humans for several decades, and are therefore an ideal vehicle to secrete Factor IX, supplying the Factor IX missing in Hemophilia B patients without the need for frequent transfusions. T cells were transformed with PiggyBac to secrete Factor IX. When transgenic T cells encoding a human Factor IX transgene were examined for T and $T_{SCM}$ cell markers using FACS, approximately 80% of all cells showed a $T_{SCM}$ phenotype (FIG. 12). These modified T cells were able to secrete human Factor IX (FIG. 13A), and this secreted Factor IX provided clotting activity (FIG. 13B).

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Other Embodiments

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A composition comprising a population of modified T-cells,
wherein a plurality of modified T-cells of the population comprise a non-naturally occurring antigen receptor or a sequence encoding the same,
wherein at least 25% of the population of modified T-cells expresses one or more cell-surface marker(s) of a stem memory T cell ($T_{SCM}$) or a $T_{SCM}$-like cell; and wherein the one or more cell-surface marker(s) comprise CD45RA and CD62L.

2. The composition of claim 1, wherein at least 25% of the modified T cells of the population express one or more of CD127, CD45RO, CD95 and IL-2Rβ.

3. The composition of claim 1, wherein the non-naturally occurring antigen receptor is a non-naturally occurring T-Cell Receptor (TCR).

4. The composition of claim 3, wherein the non-naturally occurring T-cell receptor comprises one or more mutation(s) compared to a wild-type TCR.

5. The composition of claim 3, wherein the non-naturally occurring T-cell receptor is a recombinant TCR.

6. The composition of claim 1, wherein the non-naturally occurring antigen receptor is a Chimeric Antigen Receptor (CAR).

7. The composition of claim 6, wherein the CAR comprises
   (a) an ectodomain comprising an antigen recognition region, wherein the antigen recognition region comprises one or more sequences that each specifically bind an antigen;
   (b) a transmembrane domain, and
   (c) an endodomain comprising at least one costimulatory domain.

8. The composition of claim 7, wherein the antigen recognition region comprises at least one of a single chain variable fragment (scFv), a single domain antibody, a VHH, an antibody mimetic, a protein scaffold or a Centyrin.

9. The composition of claim 7, wherein the antigen recognition region comprises at least one single chain variable fragment (scFv).

10. The composition of claim 7, wherein the antigen recognition region comprises at least one VHH.

11. The composition of claim 7, wherein the antigen recognition region comprises at least one Centyrin.

12. The composition of claim 1, wherein the plurality of modified T-cells of the population further comprise a genomic editing composition.

13. The composition of claim 12, wherein the genomic editing composition comprises a sequence encoding a DNA binding domain and a sequence encoding a nuclease domain.

14. The composition of claim 12, wherein the plurality of modified T-cells of the population further comprise a donor sequence composition.

15. The composition of claim 14, wherein the donor sequence composition comprises a sequence encoding the non-naturally occurring antigen receptor.

16. The composition of claim 15, wherein the sequence encoding the non-naturally occurring antigen receptor comprises a single-stranded or double-stranded DNA molecule.

17. The composition of claim 14, wherein the donor sequence composition is inserted into a specific site in the genome contacted with the composition by homologous recombination or by endogenous DNA repair mechanisms.

18. The composition of claim 1, wherein the plurality of modified T-cells of the population further comprise a transposon comprising a sequence encoding the non-naturally occurring antigen receptor.

19. The composition of claim 18, wherein the plurality of modified T-cells of the population further comprise a transposase composition comprising a transposase or a sequence encoding the transposase.

20. The composition of claim 19, wherein the transposase composition comprises a piggyBac transposase or a sequence encoding a piggyBac or piggyBac-like transposase.

21. The composition of claim 1, wherein a genomic safe harbor site comprises a sequence encoding the non-naturally occurring antigen receptor.

22. The composition of claim 1, wherein the composition further comprises a T-cell expansion composition.

23. The composition of claim 22, wherein the composition or the T-cell expansion composition comprises one or more of octanoic acid, nicotinamide, 2,4,7,9-tetramethyl-5-decyn-4,7-diol (TMDD), diisopropyl adipate (DIPA), n-butyl-benzenesulfonamide, 1,2-benzenedicarboxylic acid, bis (2-methylpropyl) ester, palmitic acid, linoleic acid, oleic acid, stearic acid hydrazide, oleamide, a sterol or an alkane.

24. The composition of claim 1, wherein at least 30% of the modified T cells of the population express CD62L and CD45RA.

25. The composition of claim 1, wherein at least 30% of the modified T cells of the population express one or more of CD127, CD45RO, CD95 and IL-2Rβ.

26. The composition of claim 1, wherein one or more of a stem cell-like T cell, a stem cell memory T cell ($T_{SCM}$) and a central memory T cell ($T_{CM}$) comprise at least 75% of the population of modified T-cells.

27. The composition of claim 1, wherein central memory T cells ($T_{CMs}$) comprise at least 15% of the population of modified T-cells.

28. The composition of claim 1, further comprising a T-cell activator composition comprising one or more of an anti-human CD3 monospecific tetrameric antibody complex, an anti-human CD28 monospecific tetrameric antibody complex and an anti-human CD2 monospecific tetrameric antibody complex.

29. The composition of claim 28, comprising a plurality of activated and modified T cells.

30. The composition of claim 1, wherein at least 40% of the modified T-cells of the population express CD62L and CD45RA.

* * * * *

```
                               SEQUENCE LISTING

<160> NUMBER OF SEQ ID NOS: 48

<210> SEQ ID NO 1
<211> LENGTH: 89
<212> TYPE: PRT
<213> ORGANISM: Artificial Sequence
<220> FEATURE:
<223> OTHER INFORMATION: FN3 domain consensus sequence

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 90
<212> TYPE: PRT
<213> ORGANISM: Artificial Sequence
<220> FEATURE:
<223> OTHER INFORMATION: FN3 consensus sequence

<400> SEQUENCE: 2

Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Lys Gly Gly His Arg
65                  70                  75                  80

Ser Asn Pro Leu Ser Ala Glu Phe Thr Thr
                85                  90

<210> SEQ ID NO 3
<211> LENGTH: 270
<212> TYPE: DNA
<213> ORGANISM: Artificial Sequence
<220> FEATURE:
<223> OTHER INFORMATION: FN3 consensus sequence

<400> SEQUENCE: 3
atgctgcctg caccaaagaa cctggtggtg tctcatgtga cagaggatag tgccagactg      60
tcatggactg ctcccgacgc agccttcgat agttttatca tcgtgtaccg ggagaacatc     120
gaaaccggcg aggccattgt cctgacagtg ccagggtccg aacgctctta tgacctgaca     180
```

-continued

```
gatctgaagc ccggaactga gtactatgtg cagatcgccg gcgtcaaagg aggcaatatc    240
agcttccctc tgtccgcaat cttcaccaca                                     270
```

<210> SEQ ID NO 4
<211> LENGTH: 594
<212> TYPE: PRT
<213> ORGANISM: Trichoplusia ni

<400> SEQUENCE: 4

```
Met Gly Ser Ser Leu Asp Asp Glu His Ile Leu Ser Ala Leu Leu Gln
1               5                  10                  15

Ser Asp Asp Glu Leu Val Gly Glu Asp Ser Asp Ser Glu Ile Ser Asp
            20                  25                  30

His Val Ser Glu Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365
```

-continued

```
Gly Thr Val Arg Ser Asn Lys Arg Glu Ile Pro Glu Val Leu Lys Asn
        370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Asn Gln Thr Lys Gly Gly Val Asp Thr
            435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
    515                 520                 525

Arg Asp Asn Ile Ser Asn Ile Leu Pro Asn Glu Val Pro Gly Thr Ser
530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe
```

<210> SEQ ID NO 5
<211> LENGTH: 594
<212> TYPE: PRT
<213> ORGANISM: Artificial Sequence
<220> FEATURE:
<223> OTHER INFORMATION: Super Piggybac Transposase

<400> SEQUENCE: 5

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110
```

-continued

```
Asn Ile Val Arg Ser Gln Arg Gly Pro Thr Arg Met Cys Arg Asn Ile
            115                 120                 125
Tyr Asp Pro Leu Leu Cys Phe Lys Leu Phe Phe Thr Asp Glu Ile Ile
        130                 135                 140
Ser Glu Ile Val Lys Trp Thr Asn Ala Glu Ile Ser Leu Lys Arg Arg
145                 150                 155                 160
Glu Ser Met Thr Ser Ala Thr Phe Arg Asp Thr Asn Glu Asp Glu Ile
                165                 170                 175
Tyr Ala Phe Phe Gly Ile Leu Val Met Thr Ala Val Arg Lys Asp Asn
            180                 185                 190
His Met Ser Thr Asp Asp Leu Phe Asp Arg Ser Leu Ser Met Val Tyr
        195                 200                 205
Val Ser Val Met Ser Arg Asp Arg Phe Asp Phe Leu Ile Arg Cys Leu
210                 215                 220
Arg Met Asp Asp Lys Ser Ile Arg Pro Thr Leu Arg Glu Asn Asp Val
225                 230                 235                 240
Phe Thr Pro Val Arg Lys Ile Trp Asp Leu Phe Ile His Gln Cys Ile
                245                 250                 255
Gln Asn Tyr Thr Pro Gly Ala His Leu Thr Ile Asp Glu Gln Leu Leu
            260                 265                 270
Gly Phe Arg Gly Arg Cys Pro Phe Arg Val Tyr Ile Pro Asn Lys Pro
        275                 280                 285
Ser Lys Tyr Gly Ile Lys Ile Leu Met Met Cys Asp Ser Gly Thr Lys
290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
            340                 345                 350
Pro Leu Ala Lys Asn Leu Leu Gln Glu Pro Tyr Lys Leu Thr Ile Val
        355                 360                 365
Gly Thr Val Arg Ser Asn Lys Arg Glu Ile Pro Glu Val Leu Lys Asn
370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
            420                 425                 430
Pro Gln Met Val Met Tyr Tyr Asn Gln Thr Lys Gly Gly Val Asp Thr
        435                 440                 445
Leu Asp Gln Met Cys Ser Val Met Thr Cys Ser Arg Lys Thr Asn Arg
450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
            500                 505                 510
Ser Phe Met Arg Lys Arg Leu Glu Ala Pro Thr Leu Lys Arg Tyr Leu
        515                 520                 525
Arg Asp Asn Ile Ser Asn Ile Leu Pro Lys Glu Val Pro Gly Thr Ser
```

-continued

```
            530                 535                 540
Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
                580                 585                 590

Cys Phe

<210> SEQ ID NO 6
<211> LENGTH: 340
<212> TYPE: PRT
<213> ORGANISM: Artificial Sequence
<220> FEATURE:
<223> OTHER INFORMATION: Sleeping Beauty Transposase

<400> SEQUENCE: 6

Met Gly Lys Ser Lys Glu Ile Ser Gln Asp Leu Arg Lys Lys Ile Val
1               5                   10                  15

Asp Leu His Lys Ser Gly Ser Leu Gly Ala Ile Ser Lys Arg Leu
            20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Tyr Leu
50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
        130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
        210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
        290                 295                 300
```

```
Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 7
<211> LENGTH: 340
<212> TYPE: PRT
<213> ORGANISM: Artificial Sequence
<220> FEATURE:
<223> OTHER INFORMATION: hyperactive sleeping beauty transposase

<400> SEQUENCE: 7

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Tyr Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320
```

Glu Gly Tyr Pro Lys Arg Leu Thr Gln Val Lys Gln Phe Lys Gly Asn
                325                 330                 335

Ala Thr Lys Tyr
            340

<210> SEQ ID NO 8
<211> LENGTH: 21
<212> TYPE: PRT
<213> ORGANISM: Homo sapiens

<400> SEQUENCE: 8

Met Ala Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 63
<212> TYPE: DNA
<213> ORGANISM: Artificial Sequence
<220> FEATURE:
<223> OTHER INFORMATION: nucleotide sequence for human CD8alpha signal
      peptide

<400> SEQUENCE: 9
atggcactgc cagtcaccgc cctgctgctg cctctggctc tgctgctgca cgcagctaga       60
cca                                                                    63

<210> SEQ ID NO 10
<211> LENGTH: 24
<212> TYPE: PRT
<213> ORGANISM: Homo sapiens

<400> SEQUENCE: 10

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 11
<211> LENGTH: 72
<212> TYPE: DNA
<213> ORGANISM: Artificial Sequence
<220> FEATURE:
<223> OTHER INFORMATION: nucleotide sequence coding for human CD8alpha
      transmembrane domain

<400> SEQUENCE: 11
atctacattt gggcaccact ggccgggacc tgtggagtgc tgctgctgag cctggtcatc       60
acactgtact gc                                                          72

<210> SEQ ID NO 12
<211> LENGTH: 112
<212> TYPE: PRT
<213> ORGANISM: Homo sapiens

<400> SEQUENCE: 12

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

```
Asp Val Leu Asp Lys Arg Arg Gly Arg Asp Pro Glu Met Gly Gly Lys
             35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110
```

<210> SEQ ID NO 13
<211> LENGTH: 336
<212> TYPE: DNA
<213> ORGANISM: Artificial Sequenec
<220> FEATURE:
<223> OTHER INFORMATION: nucleotide sequence encoding the CD28
      costimulatory domain

<400> SEQUENCE: 13

```
cgcgtgaagt ttagtcgatc agcagatgcc ccagcttaca aacagggaca gaaccagctg      60
tataacgagc tgaatctggg ccgccgagag gaatatgacg tgctggataa gcggagagga     120
cgcgaccccg aaatgggagg caagcccagg cgcaaaaacc ctcaggaagg cctgtataac     180
gagctgcaga aggacaaaat ggcagaagcc tattctgaga tcggcatgaa gggggagcga     240
cggagaggca aagggcacga tgggctgtac cagggactga gcaccgccac aaaggacacc     300
tatgatgctc tgcatatgca ggcactgcct ccaagg                               336
```

<210> SEQ ID NO 14
<211> LENGTH: 42
<212> TYPE: PRT
<213> ORGANISM: Homo sapiens

<400> SEQUENCE: 14

```
Lys Arg Gly Arg Lys Lys Leu Leu Tyr Ile Phe Lys Gln Pro Phe Met
  1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
             35                  40
```

<210> SEQ ID NO 15
<211> LENGTH: 126
<212> TYPE: DNA
<213> ORGANISM: Artificial Sequence
<220> FEATURE:
<223> OTHER INFORMATION: nucleotide sequence encoding the 4-1BB
      costimulatory domain

<400> SEQUENCE: 15

```
aagagaggca ggaagaaact gctgtatatt ttcaaacagc ccttcatgcg ccccgtgcag      60
actacccagg aggaagacgg gtgctcctgt cgattccctg aggaagagga aggcgggtgt     120
gagctg                                                                126
```

<210> SEQ ID NO 16
<211> LENGTH: 45
<212> TYPE: PRT
<213> ORGANISM: Homo sapiens

<400> SEQUENCE: 16

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 17
<211> LENGTH: 135
<212> TYPE: DNA
<213> ORGANISM: Artificial Sequence
<220> FEATURE:
<223> OTHER INFORMATION: nucleotide sequence encoding human CD8alpha
      hinge

<400> SEQUENCE: 17
actaccacac cagcacctag accaccaact ccagctccaa ccatcgcgag tcagcccctg     60
agtctgagac ctgaggcctg caggccagct gcaggaggag ctgtgcacac caggggcctg    120
gacttcgcct gcgac                                                    135

<210> SEQ ID NO 18
<211> LENGTH: 18
<212> TYPE: PRT
<213> ORGANISM: Thosea asigna

<400> SEQUENCE: 18

Glu Gly Arg Gly Ser Leu Leu Thr Cys Gly Asp Val Glu Glu Asn Pro
1               5                   10                  15

Gly Pro

<210> SEQ ID NO 19
<211> LENGTH: 21
<212> TYPE: PRT
<213> ORGANISM: Artificial Sequence
<220> FEATURE:
<223> OTHER INFORMATION: GSG-T2A

<400> SEQUENCE: 19

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 20
<211> LENGTH: 63
<212> TYPE: DNA
<213> ORGANISM: Artificial Sequence
<220> FEATURE:
<223> OTHER INFORMATION: GSG-T2A

<400> SEQUENCE: 20
ggatctggag agggaagggg aagcctgctg acctgtggag acgtggagga aaacccagga     60
cca                                                                  63

<210> SEQ ID NO 21
<211> LENGTH: 20
<212> TYPE: PRT
<213> ORGANISM: Equine rhinitis A

<400> SEQUENCE: 21

Gln Cys Thr Asn Tyr Ala Leu Leu Lys Leu Ala Gly Asp Val Glu Ser
```

```
1               5                   10                  15

Asn Pro Gly Pro
            20

<210> SEQ ID NO 22
<211> LENGTH: 23
<212> TYPE: PRT
<213> ORGANISM: Artificial Sequence
<220> FEATURE:
<223> OTHER INFORMATION: GSG-E2A peptide

<400> SEQUENCE: 22

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 23
<211> LENGTH: 22
<212> TYPE: PRT
<213> ORGANISM: Foot and nout disease virus type O

<400> SEQUENCE: 23

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 24
<211> LENGTH: 25
<212> TYPE: PRT
<213> ORGANISM: Artificial Sequence
<220> FEATURE:
<223> OTHER INFORMATION: GSG-F2A peptide

<400> SEQUENCE: 24

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 25
<211> LENGTH: 19
<212> TYPE: PRT
<213> ORGANISM: Porcine teschovirus-1

<400> SEQUENCE: 25

Ala Thr Asn Phe Ser Leu Leu Lys Gln Ala Gly Asp Val Glu Glu Asn
1               5                   10                  15

Pro Gly Pro

<210> SEQ ID NO 26
<211> LENGTH: 22
<212> TYPE: PRT
<213> ORGANISM: Artificial Sequence
<220> FEATURE:
<223> OTHER INFORMATION: GSG-P2A peptide

<400> SEQUENCE: 26

Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 27
<211> LENGTH: 5296
<212> TYPE: DNA
<213> ORGANISM: Artificial Sequence
<220> FEATURE:
<223> OTHER INFORMATION: Helraiser transposon

<400> SEQUENCE: 27

```
tcctatataa taaaagagaa acatgcaaat tgaccatccc tccgctacgc tcaagccacg      60
cccaccagcc aatcagaagt gactatgcaa attacccaa caaagatggc agttaaattt      120
gcatacgcag gtgtcaagcg ccccaggagg caacggcggc cgcgggctcc caggaccttc     180
gctggccccg ggaggcgagg ccggccgcgc ctagccacac ccgcgggctc ccgggacctt     240
cgccagcaga gagcagagcg ggagagcggg cggagagcgg gaggtttgga ggacttggca     300
gagcaggagg ccgctggaca tagagcagag cgagagagag ggtggcttgg agggcgtggc     360
tccctctgtc accccagctt cctcatcaca gctgtggaaa ctgacagcag ggaggaggaa     420
gtcccacccc cacagaatca gccagaatca gccgttggtc agacagctct cagcggcctg     480
acagccagga ctctcattca cctgcatctc agaccgtgac agtagagagg tgggactatg     540
tctaaagaac aactgttgat acaacgtagc tctgcagccg aaagatgccg gcgttatcga     600
cagaaaatgt ctgcagagca acgtgcgtct gatcttgaaa gaaggcggcg cctgcaacag     660
aatgtatctg aagagcagct actggaaaaa cgtcgctctg aagccgaaaa acagcggcgt     720
catcgacaga aaatgtctaa agaccaacgt gcctttgaag ttgaaagaag gcggtggcga     780
cgacagaata tgtctagaga acagtcatca acaagtacta ccaataccgg taggaactgc     840
cttctcagca aaaatggagt acatgaggat gcaattctcg aacatagttg tggtggaatg     900
actgttcgat gtgaattttg cctatcacta aatttctctg atgaaaaacc atccgatggg     960
aaatttactc gatgttgtag caaagggaaa gtctgtccaa atgatataca ttttccagat    1020
tacccggcat atttaaaaag attaatgaca aacgaagatt ctgacagtaa aaatttcatg    1080
gaaaatattc gttccataaa tagttctttt gcttttgctt ccatgggtgc aaatattgca    1140
tcgccatcag gatatgggcc atactgtttt agaatacacg gacaagttta tcaccgtact    1200
ggaactttac atccttcgga tggtgtttct cggaagtttg ctcaactcta tattttggat    1260
acagccgaag ctacaagtaa aagattagca atgccagaaa accagggctg ctcagaaaga    1320
ctcatgatca acatcaacaa cctcatgcat gaaataaatg aattaacaaa atcgtacaag    1380
atgctacatg aggtagaaaa ggaagcccaa tctgaagcag cagcaaaagg tattgctccc    1440
acagaagtaa caatggcgat taaatacgat cgtaacagtg acccaggtag atataattct    1500
ccccgtgtaa ccgaggttgc tgtcatattc agaaacgaag atggagaacc tccttttgaa    1560
agggacttgc tcattcattg taaaccagat cccaataatc caaatgccac taaaatgaaa    1620
caaatcagta tcctgttttcc tacattagat gcaatgacat atcctattct ttttccacat    1680
ggtgaaaaag gctggggaac agatattgca ttaagactca gagacaacag tgtaatcgac    1740
aataatacta gacaaaatgt aaggacacga gtcacacaaa tgcagtatta tggatttcat    1800
ctctctgtgc gggacacgtt caatcctatt ttaaatgcag gaaaattaac tcaacagttt    1860
attgtggatt catattcaaa aatggaggcc aatcggataa atttcatcaa agcaaaccaa    1920
tctaagttga gagttgaaaa atatagtggt ttgatggatt atctcaaatc tagatctgaa    1980
aatgacaatg tgccgattgg taaaatgata atacttccat catctttga gggtagtccc    2040
```

```
agaaatatgc agcagcgata tcaggatgct atggcaattg taacgaagta tggcaagccc    2100
gatttattca taaccatgac atgcaacccc aaatgggcag atattacaaa caatttacaa    2160
cgctggcaaa aagttgaaaa cagacctgac ttggtagcca gagttttaa tattaagctg     2220
aatgctcttt taaatgatat atgtaaattc catttatttg gcaaagtaat agctaaaatt    2280
catgtcattg aatttcagaa acgcggactg cctcacgctc acatattatt gatattagat    2340
agtgagtcca aattacgttc agaagatgac attgaccgta tagttaaggc agaaattcca    2400
gatgaagacc agtgtcctcg acttttcaa attgtaaaat caaatatggt acatggacca     2460
tgtggaatac aaaatccaaa tagtccatgt atggaaaatg gaaatgttc aagggatat      2520
ccaaaagaat ttcaaaatgc gaccattgga aatattgatg gatatcccaa atacaaacga    2580
agatctggta gcaccatgtc tattggaaat aaagttgtcg ataacacttg gattgtccct    2640
tataacccgt atttgtgcct taaatataac tgtcatataa atgttgaagt ctgtgcatca    2700
attaaaagtg tcaaatattt atttaaatac atctataaag gcacgattg tgcaaatatt     2760
caaatttctg aaaaaaatat tatcaatcat gacgaagtac aggacttcat tgactccagg    2820
tatgtgagcg ctcctgaggc tgtttggaga cttttgcaa tgcgaatgca tgaccaatct     2880
catgcaatca caagattagc tattcatttg ccaaatgatc agaatttgta ttttcatacc    2940
gatgattttg ctgaagtttt agatagggct aaaaggcata actcgacttt gatggcttgg    3000
ttcttattga atagagaaga ttctgatgca cgtaattatt attattggga gattccacag    3060
cattatgtgt taataattc tttgtggaca aaacgccgaa agggtgggaa taaagtatta     3120
ggtagactgt tcactgtgag ctttagagaa ccagaacgat attaccttag acttttgctt    3180
ctgcatgtaa aaggtgcgat aagttttgag gatctgcgaa ctgtaggagg tgtaacttat    3240
gatacatttc atgaagctgc taaacaccga ggattattac ttgatgacac tatctggaaa    3300
gatacgattg acgatgcaat catccttaat atgcccaaac aactacggca acttttgca    3360
tatatatgtg tgtttggatg tccttctgct gcagacaaat tatgggatga gaataaatct    3420
cattttattg aagatttctg ttggaaatta caccgaagag aaggtgcctg tgtgaactgt    3480
gaaatgcatg cccttaacga aattcaggag gtattcacat tgcatggaat gaaatgttca    3540
catttcaaac ttccggacta tcctttatta atgaatgcaa atacatgtga tcaattgtac    3600
gagcaacaac aggcagaggt tttgataaat tctctgaatg atgaacagtt ggcagccttt    3660
cagactataa cttcagccat cgaagatcaa actgtacacc ccaaatgctt tttcttggat    3720
ggtccaggtg gtagtggaaa acatatctg tataaagttt taacacatta tattagaggt     3780
cgtggtggta ctgttttacc cacagcatct acaggaattg ctgcaaattt acttcttggt    3840
ggaagaacct tcattcccca atataaatta ccaattccat taaatgaaac ttcaatttct    3900
agactcgata taaagagtga agttgctaaa accattaaaa aggcccaact tctcattatt    3960
gatgaatgca ccatggcatc cagtcatgct ataaacgcca tagatagatt actaagagaa    4020
attatgaatt tgaatgttgc atttggtggg aaagttctcc ttctcggagg ggattttcga    4080
caatgtctca gtattgtacc acatgctatg cgatcggcca tagtacaaac gagtttaaag    4140
tactgtaatg tttggggatg tttcagaaag ttgtctctta aacaaatat gagatcagag     4200
gattctgctt atagtgaatg gttagtaaaa cttggagatg gcaaacttga tagcagtttt    4260
catttaggaa tggatattat tgaaatcccc catgaaatga tttgtaacgg atctattatt    4320
gaagctacct ttgaaaatag tatatctata gataatatta aaaatatatc taaacgtgca    4380
attctttgtc caaaaaatga gcatgttcaa aaattaaatg aagaaatttt ggatatactt    4440
```

-continued

```
gatggagatt tcacacata tttgagtgat gattccattg attaacaga tgatgctgaa    4500 aaggaaaatt tcccatcga atttcttaat agtattactc cttcgggaat gccgtgtcat    4560
aaattaaaat tgaaagtggg tgcaatcatc atgctattga gaaatcttaa tagtaaatgg    4620
ggtctttgta atggtactag atttattatc aaaagattac gacctaacat tatcgaagct    4680
gaagtattaa caggatctgc agagggagag gttgttctga ttccaagaat tgatttgtcc    4740
ccatctgaca ctggcctccc atttaaatta attcgaagac agtttcccgt gatgccagca    4800
tttgcgatga ctattaataa atcacaagga caaactctag acagagtagg aatattccta    4860
cctgaacccg ttttcgcaca tggtcagtta tatgttgctt tctctcgagt tcgaagagca    4920
tgtgacgtta aagttaaagt tgtaaatact tcatcacaag ggaaattagt caagcactct    4980
gaaagtgttt ttactcttaa tgtggtatac agggagatat tagaataagt ttaatcactt    5040
tatcagtcat tgtttgcatc aatgttgttt ttatatcatg ttttttgttgt tttatatca    5100 tgtctttgtt gttgttatat catgttgtta ttgtttattt attaataaat ttatgtatta    5160
ttttcatata cattttactc atttcctttc atctctcaca cttctattat agagaaaggg    5220
caaatagcaa tattaaaata tttcctctaa ttaattccct ttcaatgtgc acgaatttcg    5280
tgcaccgggc cactag                                                    5296
```

<210> SEQ ID NO 28
<211> LENGTH: 1496
<212> TYPE: PRT
<213> ORGANISM: Artificial Sequence
<220> FEATURE:
<223> OTHER INFORMATION: Helitron transposase

<400> SEQUENCE: 28

```
Met Ser Lys Glu Gln Leu Leu Ile Gln Arg Ser Ser Ala Ala Glu Arg
1               5                   10                  15

Cys Arg Arg Tyr Arg Gln Lys Met Ser Ala Glu Gln Arg Ala Ser Asp
            20                  25                  30

Leu Glu Arg Arg Arg Leu Gln Gln Asn Val Ser Glu Gln Leu
        35                  40                  45

Leu Glu Lys Arg Arg Ser Glu Ala Lys Gln Arg Arg His Arg Gln
    50                  55                  60

Lys Met Ser Lys Asp Gln Arg Ala Phe Glu Val Glu Arg Arg Trp
65                  70                  75                  80

Arg Arg Gln Asn Met Ser Arg Glu Gln Ser Ser Thr Ser Thr Thr Asn
            85                  90                  95

Thr Gly Arg Asn Cys Leu Leu Ser Lys Asn Gly Val His Glu Asp Ala
        100                 105                 110

Ile Leu Glu His Ser Cys Gly Gly Met Thr Val Arg Cys Glu Phe Cys
    115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
            165                 170                 175

Ser Lys Asn Phe Met Glu Asn Ile Arg Ser Ile Asn Ser Ser Phe Ala
        180                 185                 190

Phe Ala Ser Met Gly Ala Asn Ile Ala Ser Pro Ser Gly Tyr Gly Pro
    195                 200                 205
```

```
Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240

Asp Thr Ala Glu Ala Thr Ser Lys Arg Leu Ala Met Pro Glu Asn Gln
                245                 250                 255

Gly Cys Ser Glu Arg Leu Met Ile Asn Ile Asn Asn Leu Met His Glu
                260                 265                 270

Ile Asn Glu Leu Thr Lys Ser Tyr Lys Met Leu His Glu Val Glu Lys
            275                 280                 285

Glu Ala Gln Ser Glu Ala Ala Ala Lys Gly Ile Ala Pro Thr Glu Val
290                 295                 300

Thr Met Ala Ile Lys Tyr Asp Arg Asn Ser Asp Pro Gly Arg Tyr Asn
305                 310                 315                 320

Ser Pro Arg Val Thr Glu Val Ala Val Ile Phe Arg Asn Glu Asp Gly
                325                 330                 335

Glu Pro Pro Phe Glu Arg Asp Leu Leu Ile His Cys Lys Pro Asp Pro
                340                 345                 350

Asn Asn Pro Asn Ala Thr Lys Met Lys Gln Ile Ser Ile Leu Phe Pro
                355                 360                 365

Thr Leu Asp Ala Met Thr Tyr Pro Ile Leu Phe Pro His Gly Glu Lys
370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
                405                 410                 415

Tyr Tyr Gly Phe His Leu Ser Val Arg Asp Thr Phe Asn Pro Ile Leu
                420                 425                 430

Asn Ala Gly Lys Leu Thr Gln Gln Phe Ile Val Asp Ser Tyr Ser Lys
                435                 440                 445

Met Glu Ala Asn Arg Ile Asn Phe Ile Lys Ala Asn Gln Ser Lys Leu
450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
                485                 490                 495

Phe Glu Gly Ser Pro Arg Asn Met Gln Gln Arg Tyr Gln Asp Ala Met
                500                 505                 510

Ala Ile Val Thr Lys Tyr Gly Lys Pro Asp Leu Phe Ile Thr Met Thr
                515                 520                 525

Cys Asn Pro Lys Trp Ala Asp Ile Thr Asn Asn Leu Gln Arg Trp Gln
530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
                565                 570                 575

Val Ile Ala Lys Ile His Val Ile Glu Phe Gln Lys Arg Gly Leu Pro
                580                 585                 590

His Ala His Ile Leu Leu Ile Leu Asp Ser Glu Ser Lys Leu Arg Ser
                595                 600                 605

Glu Asp Asp Ile Asp Arg Ile Val Lys Ala Glu Ile Pro Asp Glu Asp
610                 615                 620
```

```
Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
            645                 650                 655

Cys Ser Lys Gly Tyr Pro Lys Glu Phe Gln Asn Ala Thr Ile Gly Asn
            660                 665                 670

Ile Asp Gly Tyr Pro Lys Tyr Lys Arg Arg Ser Gly Ser Thr Met Ser
            675                 680                 685

Ile Gly Asn Lys Val Val Asp Asn Thr Trp Ile Val Pro Tyr Asn Pro
690                 695                 700

Tyr Leu Cys Leu Lys Tyr Asn Cys His Ile Asn Val Glu Val Cys Ala
705                 710                 715                 720

Ser Ile Lys Ser Val Lys Tyr Leu Phe Lys Tyr Ile Tyr Lys Gly His
                725                 730                 735

Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
            755                 760                 765

Val Trp Arg Leu Phe Ala Met Arg Met His Asp Gln Ser His Ala Ile
770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
                805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
            835                 840                 845

Leu Trp Thr Lys Arg Arg Lys Gly Gly Asn Lys Val Leu Gly Arg Leu
850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
                900                 905                 910

Leu Leu Leu Asp Asp Thr Ile Trp Lys Asp Thr Ile Asp Asp Ala Ile
            915                 920                 925

Ile Leu Asn Met Pro Lys Gln Leu Arg Gln Leu Phe Ala Tyr Ile Cys
            930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
            980                 985                 990

Phe Thr Leu His Gly Met Lys Cys  Ser His Phe Lys Leu  Pro Asp Tyr
            995                 1000                1005

Pro Leu  Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035

Ala Ala  Phe Gln Thr Ile Thr  Ser Ala Ile Glu Asp  Gln Thr Val
```

-continued

```
            1040                1045                1050

His Pro Lys Cys Phe Phe Leu Asp Gly Pro Gly Gly Ser Gly Lys
    1055                1060                1065

Thr Tyr Leu Tyr Lys Val Leu Thr His Tyr Ile Arg Gly Arg Gly
    1070                1075                1080

Gly Thr Val Leu Pro Thr Ala Ser Thr Gly Ile Ala Ala Asn Leu
    1085                1090                1095

Leu Leu Gly Gly Arg Thr Phe His Ser Gln Tyr Lys Leu Pro Ile
    1100                1105                1110

Pro Leu Asn Glu Thr Ser Ile Ser Arg Leu Asp Ile Lys Ser Glu
    1115                1120                1125

Val Ala Lys Thr Ile Lys Lys Ala Gln Leu Leu Ile Ile Asp Glu
    1130                1135                1140

Cys Thr Met Ala Ser Ser His Ala Ile Asn Ala Ile Asp Arg Leu
    1145                1150                1155

Leu Arg Glu Ile Met Asn Leu Asn Val Ala Phe Gly Gly Lys Val
    1160                1165                1170

Leu Leu Leu Gly Gly Asp Phe Arg Gln Cys Leu Ser Ile Val Pro
    1175                1180                1185

His Ala Met Arg Ser Ala Ile Val Gln Thr Ser Leu Lys Tyr Cys
    1190                1195                1200

Asn Val Trp Gly Cys Phe Arg Lys Leu Ser Leu Lys Thr Asn Met
    1205                1210                1215

Arg Ser Glu Asp Ser Ala Tyr Ser Glu Trp Leu Val Lys Leu Gly
    1220                1225                1230

Asp Gly Lys Leu Asp Ser Ser Phe His Leu Gly Met Asp Ile Ile
    1235                1240                1245

Glu Ile Pro His Glu Met Ile Cys Asn Gly Ser Ile Ile Glu Ala
    1250                1255                1260

Thr Phe Gly Asn Ser Ile Ser Ile Asp Asn Ile Lys Asn Ile Ser
    1265                1270                1275

Lys Arg Ala Ile Leu Cys Pro Lys Asn Glu His Val Gln Lys Leu
    1280                1285                1290

Asn Glu Glu Ile Leu Asp Ile Leu Asp Gly Asp Phe His Thr Tyr
    1295                1300                1305

Leu Ser Asp Asp Ser Ile Asp Ser Thr Asp Ala Glu Lys Glu
    1310                1315                1320

Asn Phe Pro Ile Glu Phe Leu Asn Ser Ile Thr Pro Ser Gly Met
    1325                1330                1335

Pro Cys His Lys Leu Lys Leu Lys Val Gly Ala Ile Ile Met Leu
    1340                1345                1350

Leu Arg Asn Leu Asn Ser Lys Trp Gly Leu Cys Asn Gly Thr Arg
    1355                1360                1365

Phe Ile Ile Lys Arg Leu Arg Pro Asn Ile Ile Glu Ala Glu Val
    1370                1375                1380

Leu Thr Gly Ser Ala Glu Gly Glu Val Val Leu Ile Pro Arg Ile
    1385                1390                1395

Asp Leu Ser Pro Ser Asp Thr Gly Leu Pro Phe Lys Leu Ile Arg
    1400                1405                1410

Arg Gln Phe Pro Val Met Pro Ala Phe Ala Met Thr Ile Asn Lys
    1415                1420                1425

Ser Gln Gly Gln Thr Leu Asp Arg Val Gly Ile Phe Leu Pro Glu
    1430                1435                1440
```

-continued

```
Pro Val Phe Ala His Gly Gln Leu Tyr Val Ala Phe Ser Arg Val
    1445                1450                1455

Arg Arg Ala Cys Asp Val Lys Val Lys Val Val Asn Thr Ser Ser
    1460                1465                1470

Gln Gly Lys Leu Val Lys His Ser Glu Ser Val Phe Thr Leu Asn
    1475                1480                1485

Val Val Tyr Arg Glu Ile Leu Glu
    1490                1495

<210> SEQ ID NO 29
<211> LENGTH: 30
<212> TYPE: DNA
<213> ORGANISM: Artificial Sequence
<220> FEATURE:
<223> OTHER INFORMATION: Helraiser palindromic sequence

<400> SEQUENCE: 29
gtgcacgaat tcgtgcacc gggccactag                                    30

<210> SEQ ID NO 30
<211> LENGTH: 649
<212> TYPE: PRT
<213> ORGANISM: Oryzias latipes

<400> SEQUENCE: 30

Met Glu Glu Val Cys Asp Ser Ser Ala Ala Ser Ser Thr Val Gln
 1               5                  10                  15

Asn Gln Pro Gln Asp Gln Glu His Pro Trp Pro Tyr Leu Arg Glu Phe
                20                  25                  30

Phe Ser Leu Ser Gly Val Asn Lys Asp Ser Phe Lys Met Lys Cys Val
            35                  40                  45

Leu Cys Leu Pro Leu Asn Lys Glu Ile Ser Ala Phe Lys Ser Ser Pro
        50                  55                  60

Ser Asn Leu Arg Lys His Ile Glu Arg Met His Pro Asn Tyr Leu Lys
 65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
               100                 105                 110

Lys His Val Ser Pro Val Thr Val Asn Lys Ala Ile Leu Arg Tyr Ile
           115                 120                 125

Ile Gln Gly Leu His Pro Phe Ser Thr Val Asp Leu Pro Ser Phe Lys
       130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
```

```
            245                 250                 255
Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605

Ala Cys Glu Arg Leu Phe Ser Thr Ala Gly Leu Leu Phe Ser Pro Lys
    610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645
```

<210> SEQ ID NO 31

<211> LENGTH: 4682
<212> TYPE: DNA
<213> ORGANISM: Oryzias latipes

<400> SEQUENCE: 31

| | | | | | |
|---|---|---|---|---|---|
| cagaggtgta | aagtacttga | gtaattttac | ttgattactg | tacttaagta | ttattttgg | 60 |
| ggatttttac | tttacttgag | tacaattaaa | aatcaatact | tttactttta | cttaattaca | 120 |
| ttttttaga | aaaaaagta | cttttactc | cttacaattt | tatttacagt | caaaaagtac | 180 |
| ttatttttg | gagatcactt | cattctattt | tcccttgcta | ttaccaaacc | aattgaattg | 240 |
| cgctgatgcc | cagtttaatt | taaatgttat | ttattctgcc | tatgaaaatc | gttttcacat | 300 |
| tatatgaaat | tggtcagaca | tgttcattgg | tcctttggaa | gtgacgtcat | gtcacatcta | 360 |
| ttaccacaat | gcacagcacc | ttgacctgga | aattagggaa | attataacag | tcaatcagtg | 420 |
| gaagaaaatg | gaggaagtat | gtgattcatc | agcagctgcg | agcagcacag | tccaaaatca | 480 |
| gccacaggat | caagagcacc | cgtggccgta | tcttcgcgaa | ttctttttctt | taagtggtgt | 540 |
| aaataaagat | tcattcaaga | tgaaatgtgt | cctctgtctc | ccgcttaata | agaaatatc | 600 |
| ggccttcaaa | agttcgccat | caaacctaag | gaagcatatt | gaggtaagta | cattaagtat | 660 |
| tttgttttac | tgatagtttt | tttttttttt | tttttttttt | ttttttgggtg | tgcatgtttt | 720 |
| gacgttgatg | gcgcgccttt | tatatgtgta | gtaggcctat | tttcactaat | gcatgcgatt | 780 |
| gacaatataa | ggctcacgta | ataaaatgct | aaaatgcatt | tgtaattggt | aacgttaggt | 840 |
| ccacgggaaa | tttggcgcct | attgcagctt | tgaataatca | ttatcattcc | gtgctctcat | 900 |
| tgtgtttgaa | ttcatgcaaa | acacaagaaa | accaagcgag | aaatttttttt | ccaaacatgt | 960 |
| tgtattgtca | aaacggtaac | actttacaat | gaggttgatt | agttcatgta | ttaactaaca | 1020 |
| ttaaataacc | atgagcaata | catttgttac | tgtatctgtt | aatctttgtt | aacgttagtt | 1080 |
| aatagaaata | cagatgttca | ttgtttgttc | atgttagttc | acagtgcatt | aactaatgtt | 1140 |
| aacaagatat | aaagtattag | taaatgttga | aattaacatg | tatacgtgca | gttcattatt | 1200 |
| agttcatgtt | aactaatgta | gttaactaac | gaaccttatt | gtaaaagtgt | taccatcaaa | 1260 |
| actaatgtaa | tgaaatcaat | tcaccctgtc | atgtcagcct | tacagtcctg | tgttttttgtc | 1320 |
| aatataatca | gaaataaaat | taatgtttga | ttgtcactaa | atgctactgt | atttctaaaa | 1380 |
| tcaacaagta | tttaacatta | taaagtgtgc | aattggctgc | aaatgtcagt | tttattaaag | 1440 |
| ggttagttca | cccaaaaatg | aaaataatgt | cattaatgac | tcgccctcat | gtcgttccaa | 1500 |
| gcccgtaaga | cctccgttca | tcttcagaac | acagtttaag | atattttaga | tttagtccga | 1560 |
| gagctttctg | tgcctccatt | gagaatgtat | gtacggtata | ctgtccatgt | ccagaaaggt | 1620 |
| aataaaaaca | tcaaagtagt | ccatgtgaca | tcagtggggtt | agttagaatt | ttttgaagca | 1680 |
| tcgaatacat | tttggtccaa | aaataacaaa | acctacgact | ttattcggca | ttgtattctc | 1740 |
| ttccgggtct | gttgtcaatc | cgcgttcacg | acttcgcagt | gacgctacaa | tgctgaataa | 1800 |
| agtcgtaggt | tttgttatt | ttggaccaaa | atgtattttc | gatgcttcaa | ataattctac | 1860 |
| ctaacccact | gatgtcacat | ggactacttt | gatgttttta | ttacctttct | ggacatggac | 1920 |
| agtataccgt | acatacattt | tcagtggagg | gacagaaagc | tctcggacta | aatctaaaat | 1980 |
| atcttaaact | gtgttccgaa | gatgaacgga | ggtgttacgg | gcttggaacg | acatgagggt | 2040 |
| gagtcattaa | tgcatctctt | tcatttttgg | gtgaactaac | cctttaatgc | tgtaatcaga | 2100 |
| gagtgtatgt | gtaattgtta | catttattgc | atacaatata | aatattttatt | tgttgttttt | 2160 |
| acagagaatg | cacccaaatt | acctcaaaaa | ctactctaaa | ttgacagcac | agaagagaaa | 2220 |

-continued

```
gatcgggacc tccacccatg cttccagcag taagcaactg aaagttgact cagttttccc    2280
agtcaaacat gtgtctccag tcactgtgaa caaagctata ttaaggtaca tcattcaagg    2340
acttcatcct ttcagcactg ttgatctgcc atcatttaaa gagctgatta gtacactgca    2400
gcctggcatt tctgtcatta caaggcctac tttacgctcc aagatagctg aagctgctct    2460
gatcatgaaa cagaaagtga ctgctgccat gagtgaagtt gaatggattg caaccacaac    2520
ggattgttgg actgcacgta gaaagtcatt cattggtgta actgctcact ggatcaaccc    2580
tggaagtctt gaaagacatt ccgctgcact tgcctgcaaa agattaatgg gctctcatac    2640
ttttgaggta ctggccagtg ccatgaatga tatccactca gagtatgaaa tacgtgacaa    2700
ggttgtttgc acaaccacag acagtggttc caactttatg aaggctttca gagttttttgg   2760
tgtggaaaac aatgatatcg agactgaggc aagaaggtgt gaaagtgatg acactgattc    2820
tgaaggctgt ggtgagggaa gtgatggtgt ggaattccaa gatgcctcac gagtcctgga    2880
ccaagacgat ggcttcgaat tccagctacc aaaacatcaa aagtgtgcct gtcacttact    2940
taacctagtc tcaagcgttg atgcccaaaa agctctctca aatgaacact acaagaaact    3000
ctacagatct gtctttggca aatgccaagc tttatggaat aaaagcagcc gatcggctct    3060
agcagctgaa gctgttgaat cagaaagccg gcttcagctt ttaaggccaa accaaacgcg    3120
gtggaattca acttttatgg ctgttgacag aattcttcaa atttgcaaag aagcaggaga    3180
aggcgcactt cggaatatat gcacctctct tgaggttcca atgtaagtgt ttttcccctc    3240
tatcgatgta aacaaatgtg ggttgttttt gtttaatact ctttgattat gctgatttct    3300
cctgtaggtt taatccagca gaaatgctgt tcttgacaga gtgggccaac acaatgcgtc    3360
cagttgcaaa agtactcgac atcttgcaag cggaaacgaa tacacagctg gggtggctgc    3420
tgcctagtgt ccatcagtta agcttgaaac ttcagcgact ccaccattct ctcaggtact    3480
gtgacccact tgtggatgcc ctacaacaag gaatccaaac acgattcaag catatgtttg    3540
aagatcctga gatcatagca gctgccatcc ttctccctaa atttcggacc tcttggacaa    3600
atgatgaaac catcataaaa cgaggtaaat gaatgcaagc aacatacact tgacgaattc    3660
taatctgggc aacctttgag ccataccaaa attattcttt tatttattta tttttgcact    3720
ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgatttta    3900
gatgtagatg actgcacgta aatgtagtta atgacaaaat ccataaaatt tgttcccagt    3960
cagaagcccc tcaaccaaac ttttctttgt gtctgctcac tgtgcttgta ggcatggact    4020
acatcagagt gcatctggag cctttggacc acaagaagga attggccaac agttcatctg    4080
atgatgaaga tttttttcgct tctttgaaac cgacaacaca tgaagccagc aaagagttgg    4140
atggatatct ggcctgtgtt tcagacacca gggagtctct gctcacgttt cctgctattt    4200
gcagcctctc tatcaagact aatacacctc ttcccgcatc ggctgcctgt gagaggcttt    4260
tcagcactgc aggattgctt ttcagcccca aaagagctag gcttgacact aacaattttg    4320
agaatcagct tctactgaag ttaaatctga ggttttacaa ctttgagtag cgtgtactgg    4380
cattagattg tctgtcttat agtttgataa ttaaatacaa acagttctaa agcaggataa    4440
aaccttgtat gcatttcatt taatgttttt tgagattaaa gcttaaaca agaatctcta    4500
gttttctttc ttgcttttac ttttacttcc ttaatactca agtacaattt taatggagta    4560
```

-continued

```
cttttttact tttactcaag taagattcta gccagatact tttactttta attgagtaaa    4620
attttcccta agtacttgta ctttcacttg agtaaaattt ttgagtactt tttacacctc    4680
tg                                                                   4682
```

<210> SEQ ID NO 32
<211> LENGTH: 1053
<212> TYPE: PRT
<213> ORGANISM: Artificial Sequence
<220> FEATURE:
<223> OTHER INFORMATION: dSaCas9

<400> SEQUENCE: 32

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335
```

-continued

```
Ala Arg Lys Glu Ile Ile Glu Asn Ala Glu Leu Leu Asp Gln Ile Ala
        340                 345                 350
Lys Ile Leu Thr Ile Tyr Gln Ser Ser Glu Asp Ile Gln Glu Glu Leu
355                 360                 365
Thr Asn Leu Asn Ser Glu Leu Thr Gln Glu Glu Ile Glu Gln Ile Ser
370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
        450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
                500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Ala Ser Lys Lys Gly Asn Arg Thr Pro Phe Gln Tyr Leu
                580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
                660                 665                 670
Val Lys Ser Ile Asn Gly Gly Phe Thr Ser Phe Leu Arg Arg Lys Trp
            675                 680                 685
Lys Phe Lys Lys Glu Arg Asn Lys Gly Tyr Lys His His Ala Glu Asp
690                 695                 700
Ala Leu Ile Ile Ala Asn Ala Asp Phe Ile Phe Lys Glu Trp Lys Lys
705                 710                 715                 720
Leu Asp Lys Ala Lys Lys Val Met Glu Asn Gln Met Phe Glu Glu Lys
                725                 730                 735
Gln Ala Glu Ser Met Pro Glu Ile Glu Thr Glu Gln Glu Tyr Lys Glu
                740                 745                 750
Ile Phe Ile Thr Pro His Gln Ile Lys His Ile Lys Asp Phe Lys Asp
```

-continued

```
            755                 760                 765
Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 33
<211> LENGTH: 1368
<212> TYPE: PRT
<213> ORGANISM: Artificial Sequence
<220> FEATURE:
<223> OTHER INFORMATION: dCas9 with X at position 1, X can be any amino
      acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 33

Xaa Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

Gly Ala Leu Leu Phe Asp Ser Gly Glu Thr Ala Glu Ala Thr Arg Leu
            50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
```

```
                885                 890                 895
Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290
```

```
Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 34
<211> LENGTH: 199
<212> TYPE: PRT
<213> ORGANISM: Clostridium sp. 7_2_43FAA

<400> SEQUENCE: 34

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
                20                  25                  30

Phe Asp Ser Lys Gln Asn Arg Leu Phe Glu Met Lys Val Leu Glu Leu
            35                  40                  45

Leu Val Asn Glu Tyr Gly Phe Lys Gly Arg His Leu Gly Gly Ser Arg
        50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
        115                 120                 125

Val Lys Lys Tyr Tyr Phe Val Phe Ile Ser Gly Ser Phe Lys Gly Lys
130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Leu Glu Arg Ala Met Phe Asn Asn
            180                 185                 190

Ser Glu Phe Ile Leu Lys Tyr
        195

<210> SEQ ID NO 35
<211> LENGTH: 4897
<212> TYPE: DNA
<213> ORGANISM: Artificial Sequence
<220> FEATURE:
<223> OTHER INFORMATION: PB-EF1a vector

<400> SEQUENCE: 35
tgtacataga ttaaccctag aaagataatc atattgtgac gtacgttaaa gataatcatg     60
cgtaaaattg acgcatgtgt tttatcggtc tgtatatcga ggtttattta ttaatttgaa    120
tagatattaa gttttattat atttcacctt acatactaat aataaattca acaaacaatt    180
```

-continued

| | |
|---|---|
| tatttatgtt tatttattta ttaaaaaaaa acaaaaactc aaaatttctt ctataaagta | 240 |
| acaaaacttt tatcgaatac ctgcagcccg ggggatgcag agggacagcc cccccccaaa | 300 |
| gcccccaggg atgtaattac gtccctcccc cgctaggggg cagcagcgag ccgcccgggg | 360 |
| ctccgctccg gtccggcgct cccccccgcat ccccgagccg cagcgtgcg gggacagccc | 420 |
| gggcacgggg aaggtggcac gggatcgctt tcctctgaac gcttctcgct gctctttgag | 480 |
| cctgcagaca cctgggggga tacggggaaa agttgactgt gcctttcgat cgaaccatgg | 540 |
| acagttagct ttgcaaagat ggataaagtt ttaaacagag aggaatcttt gcagctaatg | 600 |
| gaccttctag gtcttgaaag gagtgggaat tggctccggt gcccgtcagt gggcagagcg | 660 |
| cacatcgccc acagtccccg agaagttggg gggaggggtc ggcaattgaa ccggtgccta | 720 |
| gagaaggtgg cgcggggtaa actgggaaag tgatgtcgtg tactggctcc gccttttttcc | 780 |
| cgagggtggg ggagaaccgt atataagtgc agtagtcgcc gtgaacgttc ttttttcgcaa | 840 |
| cgggtttgcc gccagaacac aggtaagtgc cgtgtgtggt tcccgcgggc ctggcctctt | 900 |
| tacgggttat ggcccttgcg tgccttgaat tacttccacc tggctgcagt acgtgattct | 960 |
| tgatcccgag cttcggggttg gaagtgggtg ggagagttcg aggccttgcg cttaaggagc | 1020 |
| ccccttcgcct cgtgcttgag ttgaggcctg gcctgggcgc tggggccgcc gcgtgcgaat | 1080 |
| ctggtggcac cttcgcgcct gtctcgctgc tttcgataag tctctagcca tttaaaattt | 1140 |
| ttgatgacct gctgcgacgc ttttttttctg gcaagatagt cttgtaaatg cgggccaaga | 1200 |
| tctgcacact ggtatttcgg ttttggggc cgcgggcggc gacggggccc gtgcgtccca | 1260 |
| gcgcacatgt tcggcgaggc ggggcctgcg agcgcggcca ccgagaatcg gacggggta | 1320 |
| gtctcaagct ggccggcctg ctctggtgcc tggcctcgcg ccgccgtgta tcgccccgcc | 1380 |
| ctgggcggca aggctggccc ggtcggcacc agttgcgtga gcgaaagat ggccgcttcc | 1440 |
| cggccctgct gcagggagct caaaatggag gacgcggcgc tcgggagagc gggcgggtga | 1500 |
| gtcacccaca caaaggaaaa gggcctttcc gtcctcagcc gtcgcttcat gtgactccac | 1560 |
| ggagtaccgg gcgccgtcca ggcacctcga ttagttctcg agcttttgga gtacgtcgtc | 1620 |
| tttaggttgg ggggagggggt tttatgcgat ggagtttccc cacactgagt gggtggagac | 1680 |
| tgaagttagg ccagcttggc acttgatgta attctccttg gaatttgccc ttttttgagtt | 1740 |
| tggatcttgg ttcattctca agcctcagac agtggttcaa agtttttttc ttccatttca | 1800 |
| ggtgtcgtga gaattctaat acgactcact ataggtgtg ctgtctcatc attttggcaa | 1860 |
| agattggcca ccaagcttgt cctgcaggag ggtcgacgcg tctagacggg cggccgctcc | 1920 |
| ggatccacgg gtaccgatca catatgcctt taattaaaca ctagttctat agtgtcacct | 1980 |
| aaattccctt tagtgagggt taatggccgt aggccgccaa aattgggtcc agacatgata | 2040 |
| agatacattg atgagtttgg acaaaccaca actagaatgc agtgaaaaaa atgctttatt | 2100 |
| tgtgaaattt gtgatgctat tgctttattt gtaaccatta taagctgcaa taaacaagtt | 2160 |
| aacaacaaca attgcattca ttttatgttt caggttcagg gggaggtgtg ggaggttttt | 2220 |
| tcggactcta ggacctgcgc atgcgcttgg cgtaatcatg gtcatagctg tttcctgttt | 2280 |
| tccccgtatc ccccaggtg tctgcaggct caaagagcag cgagaagcgt tcagaggaaa | 2340 |
| gcgatcccgt gccaccttcc ccgtgcccgg gctgtccccg cacgctgccg gctcggggat | 2400 |
| gcgggggggag cgcggaccg gagcggagcc ccgggcggct cgctgctgcc cctagcggg | 2460 |
| ggagggacgt aattacatcc ctgggggctt tgggggggggg ctgtccctct caccgcgtg | 2520 |
| gagctccagc ttttgttcga attggggccc cccctcgagg gtatcgatga tatctataac | 2580 |

```
aagaaaatat atatataata agttatcacg taagtagaac atgaaataac aatataatta    2640
tcgtatgagt taaatcttaa aagtcacgta aaagataatc atgcgtcatt ttgactcacg    2700
cggtcgttat agttcaaaat cagtgacact taccgcattg acaagcacgc ctcacgggag    2760
ctccaagcgg cgactgagat gtcctaaatg cacagcgacg gattcgcgct atttagaaag    2820
agagagcaat atttcaagaa tgcatgcgtc aattttacgc agactatctt tctagggtta    2880
atctagctag ccttaagggc gcctattgcg ttgcgctcac tgcccgcttt ccagtcggga    2940
aacctgtcgt gccagctgca ttaatgaatc ggccaacgcg cggggagagg cggtttgcgt    3000
attgggcgct cttccgcttc ctcgctcact gactcgctgc gctcggtcgt tcggctgcgg    3060
cgagcggtat cagctcactc aaaggcggta atacggttat ccacagaatc aggggataac    3120
gcaggaaaga acatgaccaa aatcccttaa cgtgagtttt cgttccactg agcgtcagac    3180
cccgtagaaa agatcaaagg atcttcttga gatcctttt ttctgcgcgt aatctgctgc    3240
ttgcaaacaa aaaaaccacc gctaccagcg gtggtttgtt tgccggatca agagctacca    3300 actcttttc cgaaggtaac tggcttcagc agagcgcaga taccaaatac tgttcttcta    3360
gtgtagccgt agttaggcca ccacttcaag aactctgtag caccgcctac atacctcgct    3420
ctgctaatcc tgttaccagt ggctgctgcc agtggcgata agtcgtgtct taccgggttg    3480
gactcaagac gatagttacc ggataaggcg cagcggtcgg gctgaacggg gggttcgtgc    3540
acacagccca gcttggagcg aacgacctac accgaactga gatacctaca gcgtgagcta    3600
tgagaaagcg ccacgcttcc cgaagggaga aaggcggaca ggtatccggt aagcggcagg    3660
gtcggaacag gagagcgcac gagggagctt ccagggggaa acgcctggta tctttatagt    3720
cctgtcgggt ttcgccacct ctgacttgag cgtcgatttt tgtgatgctc gtcaggggg     3780 cggagcctat ggaaaaacgc cagcaacgcg gccttttttac ggttcctggc cttttgctgg    3840
ccttttgctc acatgagatt atcaaaaagg atcttcacct agatcctttt aaattaaaaa    3900
tgaagtttta aatcaatcta agtatatat gagtaaactt ggtctgacag tcagaagaac    3960
tcgtcaagaa ggcgatagaa ggcgatgcgc tgcgaatcgg gagcggcgat accgtaaagc    4020
acgaggaagc ggtcagccca ttcgccgcca agctcttcag caatatcacg ggtagccaac    4080
gctatgtcct gatagcggtc cgccacaccc agccggccac agtcgatgaa tccagaaaag    4140
cggccatttt ccaccatgat attcggcaag caggcatcgc catgggtcac gacgagatcc    4200
tcgccgtcgg gcatgctcgc cttgagcctg gcgaacagtt cggctggcgc gagcccctga    4260
tgctcttcgt ccagatcatc ctgatcgaca agaccggctt ccatccgagt acgtgctcgc    4320
tcgatgcgat gtttcgcttg gtggtcgaat gggcaggtag ccggatcaag cgtatgcagc    4380
cgccgcattg catcagccat gatggatact ttctcggcag gagcaaggtg agatgacagg    4440
agatcctgcc ccggcacttc gcccaatagc agccagtccc ttcccgcttc agtgacaacg    4500
tcgagcacag ctgcgcaagg aacgcccgtc gtggccagcc acgatagccg cgctgcctcg    4560
tcttgcagtt cattcagggc accggacagg tcggtcttga caaaaagaac cgggcgcccc    4620
tgcgctgaca gccggaacac ggcggcatca gagcagccga ttgtctgttg tgcccagtca    4680
tagccgaata gcctctccac ccaagcggcc ggagaacctg cgtgcaatcc atcttgttca    4740
atcataatat tattgaagca tttatcaggg ttcgtctcgt cccggtctcc tcccaatgca    4800
tgtcaatatt ggccattagc catattattc attggttata tagcataaat caatattggc    4860
tattggccat tgcatacgtt gtatctatat cataata                             4897
```

<210> SEQ ID NO 36
<211> LENGTH: 20
<212> TYPE: DNA
<213> ORGANISM: Artificial Sequence
<220> FEATURE:
<223> OTHER INFORMATION: EF1a-2r primer

<400> SEQUENCE: 36
caccggagcc aattcccact                                          20

<210> SEQ ID NO 37
<211> LENGTH: 20
<212> TYPE: DNA
<213> ORGANISM: Artificial Sequence
<220> FEATURE:
<223> OTHER INFORMATION: AAVS-3r primer

<400> SEQUENCE: 37
ctgcaccacg tgatgtcctc                                          20

<210> SEQ ID NO 38
<211> LENGTH: 28
<212> TYPE: DNA
<213> ORGANISM: Artificial Sequence
<220> FEATURE:
<223> OTHER INFORMATION: SV40pA-1r primer

<400> SEQUENCE: 38
gtaaccatta taagctgcaa taaacaag                                 28

<210> SEQ ID NO 39
<211> LENGTH: 24
<212> TYPE: DNA
<213> ORGANISM: Artificial Sequence
<220> FEATURE:
<223> OTHER INFORMATION: AAVS-2f primer

<400> SEQUENCE: 39
ctggggactc tttaaggaaa gaag                                     24

<210> SEQ ID NO 40
<211> LENGTH: 1591
<212> TYPE: PRT
<213> ORGANISM: Artificial Sequence
<220> FEATURE:
<223> OTHER INFORMATION: dCas9-Clo051

<400> SEQUENCE: 40

Met Ala Pro Lys Lys Lys Arg Lys Val Glu Gly Ile Lys Ser Asn Ile
1               5                   10                  15

Ser Leu Leu Lys Asp Glu Leu Arg Gly Gln Ile Ser His Ile Ser His
            20                  25                  30

Glu Tyr Leu Ser Leu Ile Asp Leu Ala Phe Asp Ser Lys Gln Asn Arg
        35                  40                  45

Leu Phe Glu Met Lys Val Leu Glu Leu Leu Val Asn Glu Tyr Gly Phe
    50                  55                  60

Lys Gly Arg His Leu Gly Gly Ser Arg Lys Pro Asp Gly Ile Val Tyr
65                  70                  75                  80

Ser Thr Thr Leu Glu Asp Asn Phe Gly Ile Ile Val Asp Thr Lys Ala
                85                  90                  95

Tyr Ser Glu Gly Tyr Ser Leu Pro Ile Ser Gln Ala Asp Glu Met Glu
            100                 105                 110

```
Arg Tyr Val Arg Glu Asn Ser Asn Arg Asp Glu Val Asn Pro Asn
            115                 120                 125
Lys Trp Trp Glu Asn Phe Ser Glu Glu Val Lys Tyr Tyr Phe Val
    130                 135                 140
Phe Ile Ser Gly Ser Phe Lys Gly Lys Phe Glu Glu Gln Leu Arg Arg
145                 150                 155                 160
Leu Ser Met Thr Thr Gly Val Asn Gly Ser Ala Val Asn Val Asn
                165                 170                 175
Leu Leu Leu Gly Ala Glu Lys Ile Arg Ser Gly Glu Met Thr Ile Glu
            180                 185                 190
Glu Leu Glu Arg Ala Met Phe Asn Asn Ser Glu Phe Ile Leu Lys Tyr
            195                 200                 205
Gly Gly Gly Gly Ser Asp Lys Lys Tyr Ser Ile Gly Leu Ala Ile Gly
            210                 215                 220
Thr Asn Ser Val Gly Trp Ala Val Ile Thr Asp Glu Tyr Lys Val Pro
225                 230                 235                 240
Ser Lys Lys Phe Lys Val Leu Gly Asn Thr Asp Arg His Ser Ile Lys
                245                 250                 255
Lys Asn Leu Ile Gly Ala Leu Leu Phe Asp Ser Gly Glu Thr Ala Glu
            260                 265                 270
Ala Thr Arg Leu Lys Arg Thr Ala Arg Arg Tyr Thr Arg Arg Lys
            275                 280                 285
Asn Arg Ile Cys Tyr Leu Gln Glu Ile Phe Ser Asn Glu Met Ala Lys
            290                 295                 300
Val Asp Asp Ser Phe Phe His Arg Leu Glu Glu Ser Phe Leu Val Glu
305                 310                 315                 320
Glu Asp Lys Lys His Glu Arg His Pro Ile Phe Gly Asn Ile Val Asp
                325                 330                 335
Glu Val Ala Tyr His Glu Lys Tyr Pro Thr Ile Tyr His Leu Arg Lys
            340                 345                 350
Lys Leu Val Asp Ser Thr Asp Lys Ala Asp Leu Arg Leu Ile Tyr Leu
            355                 360                 365
Ala Leu Ala His Met Ile Lys Phe Arg Gly His Phe Leu Ile Glu Gly
370                 375                 380
Asp Leu Asn Pro Asp Asn Ser Asp Val Asp Lys Leu Phe Ile Gln Leu
385                 390                 395                 400
Val Gln Thr Tyr Asn Gln Leu Phe Glu Glu Asn Pro Ile Asn Ala Ser
                405                 410                 415
Gly Val Asp Ala Lys Ala Ile Leu Ser Ala Arg Leu Ser Lys Ser Arg
            420                 425                 430
Arg Leu Glu Asn Leu Ile Ala Gln Leu Pro Gly Glu Lys Lys Asn Gly
            435                 440                 445
Leu Phe Gly Asn Leu Ile Ala Leu Ser Leu Gly Leu Thr Pro Asn Phe
    450                 455                 460
Lys Ser Asn Phe Asp Leu Ala Glu Asp Ala Lys Leu Gln Leu Ser Lys
465                 470                 475                 480
Asp Thr Tyr Asp Asp Asp Leu Asp Asn Leu Leu Ala Gln Ile Gly Asp
                485                 490                 495
Gln Tyr Ala Asp Leu Phe Leu Ala Ala Lys Asn Leu Ser Asp Ala Ile
            500                 505                 510
Leu Leu Ser Asp Ile Leu Arg Val Asn Thr Glu Ile Thr Lys Ala Pro
            515                 520                 525
Leu Ser Ala Ser Met Ile Lys Arg Tyr Asp Glu His His Gln Asp Leu
```

-continued

```
            530                 535                 540
Thr Leu Leu Lys Ala Leu Val Arg Gln Gln Leu Pro Glu Lys Tyr Lys
545                 550                 555                 560
Glu Ile Phe Phe Asp Gln Ser Lys Asn Gly Tyr Ala Gly Tyr Ile Asp
                    565                 570                 575
Gly Gly Ala Ser Gln Glu Glu Phe Tyr Lys Phe Ile Lys Pro Ile Leu
                580                 585                 590
Glu Lys Met Asp Gly Thr Glu Glu Leu Leu Val Lys Leu Asn Arg Glu
            595                 600                 605
Asp Leu Leu Arg Lys Gln Arg Thr Phe Asp Asn Gly Ser Ile Pro His
610                 615                 620
Gln Ile His Leu Gly Glu Leu His Ala Ile Leu Arg Arg Gln Glu Asp
625                 630                 635                 640
Phe Tyr Pro Phe Leu Lys Asp Asn Arg Glu Lys Ile Glu Lys Ile Leu
                    645                 650                 655
Thr Phe Arg Ile Pro Tyr Tyr Val Gly Pro Leu Ala Arg Gly Asn Ser
                660                 665                 670
Arg Phe Ala Trp Met Thr Arg Lys Ser Glu Glu Thr Ile Thr Pro Trp
            675                 680                 685
Asn Phe Glu Glu Val Val Asp Lys Gly Ala Ser Ala Gln Ser Phe Ile
690                 695                 700
Glu Arg Met Thr Asn Phe Asp Lys Asn Leu Pro Asn Glu Lys Val Leu
705                 710                 715                 720
Pro Lys His Ser Leu Leu Tyr Glu Tyr Phe Thr Val Tyr Asn Glu Leu
                    725                 730                 735
Thr Lys Val Lys Tyr Val Thr Glu Gly Met Arg Lys Pro Ala Phe Leu
                740                 745                 750
Ser Gly Glu Gln Lys Lys Ala Ile Val Asp Leu Leu Phe Lys Thr Asn
            755                 760                 765
Arg Lys Val Thr Val Lys Gln Leu Lys Glu Asp Tyr Phe Lys Lys Ile
770                 775                 780
Glu Cys Phe Asp Ser Val Glu Ile Ser Gly Val Glu Asp Arg Phe Asn
785                 790                 795                 800
Ala Ser Leu Gly Thr Tyr His Asp Leu Leu Lys Ile Ile Lys Asp Lys
                    805                 810                 815
Asp Phe Leu Asp Asn Glu Glu Asn Glu Asp Ile Leu Glu Asp Ile Val
                820                 825                 830
Leu Thr Leu Thr Leu Phe Glu Asp Arg Glu Met Ile Glu Glu Arg Leu
            835                 840                 845
Lys Thr Tyr Ala His Leu Phe Asp Asp Lys Val Met Lys Gln Leu Lys
850                 855                 860
Arg Arg Arg Tyr Thr Gly Trp Gly Arg Leu Ser Arg Lys Leu Ile Asn
865                 870                 875                 880
Gly Ile Arg Asp Lys Gln Ser Gly Lys Thr Ile Leu Asp Phe Leu Lys
                    885                 890                 895
Ser Asp Gly Phe Ala Asn Arg Asn Phe Met Gln Leu Ile His Asp Asp
                900                 905                 910
Ser Leu Thr Phe Lys Glu Asp Ile Gln Lys Ala Gln Val Ser Gly Gln
            915                 920                 925
Gly Asp Ser Leu His Glu His Ile Ala Asn Leu Ala Gly Ser Pro Ala
            930                 935                 940
Ile Lys Lys Gly Ile Leu Gln Thr Val Lys Val Val Asp Glu Leu Val
945                 950                 955                 960
```

```
Lys Val Met Gly Arg His Lys Pro Glu Asn Ile Val Ile Glu Met Ala
                965                 970                 975
Arg Glu Asn Gln Thr Thr Gln Lys Gly Gln Lys Asn Ser Arg Glu Arg
            980                 985                 990
Met Lys Arg Ile Glu Glu Gly Ile Lys Glu Leu Gly Ser Gln Ile Leu
            995                 1000                1005
Lys Glu His Pro Val Glu Asn Thr Gln Leu Gln Asn Glu Lys Leu
        1010                1015                1020
Tyr Leu Tyr Tyr Leu Gln Asn Gly Arg Asp Met Tyr Val Asp Gln
        1025                1030                1035
Glu Leu Asp Ile Asn Arg Leu Ser Asp Tyr Asp Val Asp Ala Ile
        1040                1045                1050
Val Pro Gln Ser Phe Leu Lys Asp Asp Ser Ile Asp Asn Lys Val
        1055                1060                1065
Leu Thr Arg Ser Asp Lys Asn Arg Gly Lys Ser Asp Asn Val Pro
        1070                1075                1080
Ser Glu Glu Val Val Lys Lys Met Lys Asn Tyr Trp Arg Gln Leu
        1085                1090                1095
Leu Asn Ala Lys Leu Ile Thr Gln Arg Lys Phe Asp Asn Leu Thr
        1100                1105                1110
Lys Ala Glu Arg Gly Gly Leu Ser Glu Leu Asp Lys Ala Gly Phe
        1115                1120                1125
Ile Lys Arg Gln Leu Val Glu Thr Arg Gln Ile Thr Lys His Val
        1130                1135                1140
Ala Gln Ile Leu Asp Ser Arg Met Asn Thr Lys Tyr Asp Glu Asn
        1145                1150                1155
Asp Lys Leu Ile Arg Glu Val Lys Val Ile Thr Leu Lys Ser Lys
        1160                1165                1170
Leu Val Ser Asp Phe Arg Lys Asp Phe Gln Phe Tyr Lys Val Arg
        1175                1180                1185
Glu Ile Asn Asn Tyr His His Ala His Asp Ala Tyr Leu Asn Ala
        1190                1195                1200
Val Val Gly Thr Ala Leu Ile Lys Lys Tyr Pro Lys Leu Glu Ser
        1205                1210                1215
Glu Phe Val Tyr Gly Asp Tyr Lys Val Tyr Asp Val Arg Lys Met
        1220                1225                1230
Ile Ala Lys Ser Glu Gln Glu Ile Gly Lys Ala Thr Ala Lys Tyr
        1235                1240                1245
Phe Phe Tyr Ser Asn Ile Met Asn Phe Phe Lys Thr Glu Ile Thr
        1250                1255                1260
Leu Ala Asn Gly Glu Ile Arg Lys Arg Pro Leu Ile Glu Thr Asn
        1265                1270                1275
Gly Glu Thr Gly Glu Ile Val Trp Asp Lys Gly Arg Asp Phe Ala
        1280                1285                1290
Thr Val Arg Lys Val Leu Ser Met Pro Gln Val Asn Ile Val Lys
        1295                1300                1305
Lys Thr Glu Val Gln Thr Gly Gly Phe Ser Lys Glu Ser Ile Leu
        1310                1315                1320
Pro Lys Arg Asn Ser Asp Lys Leu Ile Ala Arg Lys Lys Asp Trp
        1325                1330                1335
Asp Pro Lys Lys Tyr Gly Gly Phe Asp Ser Pro Thr Val Ala Tyr
        1340                1345                1350
```

```
Ser Val Leu Val Ala Lys Val Glu Lys Gly Lys Ser Lys Lys
    1355                1360                1365

Leu Lys Ser Val Lys Glu Leu Leu Gly Ile Thr Ile Met Glu Arg
1370                1375                1380

Ser Ser Phe Glu Lys Asn Pro Ile Asp Phe Leu Glu Ala Lys Gly
    1385                1390                1395

Tyr Lys Glu Val Lys Lys Asp Leu Ile Ile Lys Leu Pro Lys Tyr
1400                1405                1410

Ser Leu Phe Glu Leu Glu Asn Gly Arg Lys Arg Met Leu Ala Ser
    1415                1420                1425

Ala Gly Glu Leu Gln Lys Gly Asn Glu Leu Ala Leu Pro Ser Lys
1430                1435                1440

Tyr Val Asn Phe Leu Tyr Leu Ala Ser His Tyr Glu Lys Leu Lys
    1445                1450                1455

Gly Ser Pro Glu Asp Asn Glu Gln Lys Gln Leu Phe Val Glu Gln
1460                1465                1470

His Lys His Tyr Leu Asp Glu Ile Ile Glu Gln Ile Ser Glu Phe
    1475                1480                1485

Ser Lys Arg Val Ile Leu Ala Asp Ala Asn Leu Asp Lys Val Leu
1490                1495                1500

Ser Ala Tyr Asn Lys His Arg Asp Lys Pro Ile Arg Glu Gln Ala
    1505                1510                1515

Glu Asn Ile Ile His Leu Phe Thr Leu Thr Asn Leu Gly Ala Pro
1520                1525                1530

Ala Ala Phe Lys Tyr Phe Asp Thr Thr Ile Asp Arg Lys Arg Tyr
    1535                1540                1545

Thr Ser Thr Lys Glu Val Leu Asp Ala Thr Leu Ile His Gln Ser
1550                1555                1560

Ile Thr Gly Leu Tyr Glu Thr Arg Ile Asp Leu Ser Gln Leu Gly
    1565                1570                1575

Gly Asp Gly Ser Pro Lys Lys Lys Arg Lys Val Ser Ser
1580                1585                1590

<210> SEQ ID NO 41
<211> LENGTH: 4073
<212> TYPE: DNA
<213> ORGANISM: Artificial Sequence
<220> FEATURE:
<223> OTHER INFORMATION: pHR-GFP- selection gene plasmid

<400> SEQUENCE: 41
ggggccacta gggacaggat cggcgtcttc actcgctggg ttcccttttc cttctccttc      60
tggggcctgt gccatctctc gtttcttagg atggccttct ccgacggatg tctcccttgc    120
gtcccgcctc cccttcttgt aggcctgcat catcaccgtt tttctggaca accccaaagt    180
accccgtctc cctggcttta gccacctctc catcctcttg ctttctttgc ctggacaccc    240
cgttctcctg tggattcggg tcacctctca ctcctttcat ttgggcagct cccctacccc    300
ccttacctct ctagtctgtg ctagctcttc agcccctg tcatggcatc ttccaggggt    360
ccgagagctc agctagtctt cttcctccaa cccgggcccc tatgtccact tcaggacagc    420
atgtttgctg cctccaggga tcctgtgtcc ccgagctggg accacttat attcccaggg      480 ccggttaatg tggctctggt tctgggtact tttatctgtc ccgacgtccg atcgaaccat    540
ggacagttag ctttgcaaag atggataaag ttttaaacag agaggaatct ttgcagctaa    600
tggaccttct aggtcttgaa aggagtggga attggctccg gtgcccgtca gtgggcagag    660
```

```
cgcacatcgc ccacagtccc cgagaagttg gggggagggg tcggcaattg aaccggtgcc    720
tagagaaggt ggcgcggggt aaactgggaa agtgatgtcg tgtactggct ccgccttttt    780 cccgaggggtg ggggagaacc gtatataagt gcagtagtcg ccgtgaacgt tcttttttcgc   840 aacgggtttg ccgccagaac acaggtaagt gccgtgtgtg gttcccgcgg gcctggcctc    900
tttacgggtt atggcccttg cgtgccttga attacttcca cctggctgca gtacgtgatt    960
cttgatcccg agcttcgggt tggaagtggg tgggagagtt cgaggccttg cgcttaagga   1020
gccccttcgc ctcgtgcttg agttgaggcc tggcctgggc gctggggccg ccgcgtgcga   1080
atctggtggc accttcgcgc ctgtctcgct gctttcgata agtctctagc catttaaaat   1140
ttttgatgac ctgctgcgac gctttttttc tggcaagata gtcttgtaaa tgcgggccaa   1200
gatctgcaca ctggtatttc ggttttgggg gccgcgggcg gcgacgggggc ccgtgcgtcc   1260 cagcgcacat gttcggcgag gcggggcctg cgagcgcggc caccgagaat cggacggggg   1320
tagtctcaag ctggccggcc tgctctggtg cctggcctcg cgccgccgtg tatcgccccg   1380
ccctgggcgg caaggctggc ccggtcggca ccagttgcgt gagcggaaag atggccgctt   1440
cccggccctg ctgcagggag ctcaaaatgg aggacgcggc gctcgggaga gcgggcgggt   1500
gagtcaccca cacaaaggaa aagggccttt ccgtcctcag ccgtcgcttc atgtgactcc   1560
acggagtacc gggcgccgtc caggcacctc gattagttct cgagcttttg gagtacgtcg   1620
tctttaggtt ggggggaggg gttttatgcg atggagtttc cccacactga gtgggtggag   1680
actgaagtta ggccagcttg gcacttgatg taattctcct tggaatttgc ccttttttgag   1740 tttggatctt ggttcattct caagcctcag acagtggttc aaagttttttt tcttccattt   1800 caggtgtcgt gagaattcta atacgactca ctatagggtg tgctgtctca tcattttggc   1860
aaagattggc caccaagctt accgccatgg tgagcaaggg cgaggagctg ttcaccgggg   1920
tggtgcccat cctggtcgag ctggacgcg acgtaaacgg ccacaagttc agcgtgtccg   1980
gcgagggcga gggcgatgcc acctacggca agctgaccct gaagttcatc tgcaccaccg   2040
gcaagctgcc cgtgccctgg cccacccctcg tgaccaccct gacctacggc gtgcagtgct   2100
tcagccgcta ccccgaccac atgaagcagc acgacttctt caagtccgcc atgcccgaag   2160
gctacgtcca ggagcgcacc atcttcttca aggacgacgg caactacaag acccgcgccg   2220
aggtgaagtt cgagggcgac accctggtga accgcatcga gctgaagggc atcgacttca   2280
aggaggacgg caacatcctg ggcacaagc tggagtacaa ctacaacagc cacaacgtct   2340
atatcatggc cgacaagcag aagaacggca tcaaggtgaa cttcaagatc cgccacaaca   2400
tcgaggacgg cagcgtgcag ctcgccgacc actaccagca gaacaccccc atcggcgacg   2460
gccccgtgct gctgcccgac aaccactacc tgagcaccca gtccgccctg agcaaagacc   2520
ccaacgagaa gcgtgatcac atggtcctgc tggagttcgt gaccgccgcc gggatcactc   2580
tcggcatgga cgagctgtac aaggaaggaa gaggcagcct gctgacatgt ggcgacgtgg   2640
aggagaaccc tggcccaatg gtgggcagcc tgaattgtat cgtggccgtg tcccagaaca   2700
tgggcatcgg caagaatggc gattttcctt ggccccctct gagaaatgag tccagatact   2760
ttcagaggat gaccacaacc agctccgtgg agggcaagca gaacctggtc atcatgggca   2820
agaagacatg gttctctatc ccagagaaga accgcccct gaagggccgg atcaatctgg   2880
tgctgagcag gagctgaag gagccacccc agggagcaca ctttctgtcc aggtctctgg   2940
acgatgccct gaagctgacc gagcagcctg agctggccaa caaggtggac atggtgtgga   3000
```

```
tcgtgggcgg ctctagcgtg tataaggagg ccatgaatca ccctggccac ctgaagctgt    3060
tcgtgacacg atcatgcag gactttgagt ccgatacctt ctttccagag atcgacctgg     3120
agaagtacaa gctgctgccc gagtatcctg gcgtgctgtc tgatgtgcag gaggagaagg    3180
gcatcaagta caagttcgag gtgtatgaga agaacgatta taacatatg cctttaatta    3240 aacactagtt ctatagtgtc acctaaattc cctttagtga gggttaatgg ccgtaggccg    3300
ccagaattgg gtccagacat gataagatac attgatgagt ttggacaaac cacaactaga    3360
atgcagtgaa aaaatgcttt atttgtgaa atttgtgatg ctattgcttt atttgtaacc     3420
attataagct gcaataaaca agttaacaac aacaattgca ttcattttat gtttcaggtt    3480 caggggagg tgtgggaggt ttttcggac tctaggacct gcgcatgcgc ttggggtacc      3540
taggatatcg acagaaaagc cccatcctta ggcctcctcc ttcctagtct cctgatattg    3600
ggtctaaccc ccacctcctg ttaggcagat tccttatctg gtgacacacc cccatttcct    3660
ggagccatct ctctccttgc cagaacctct aaggtttgct tacgatggag ccagagagga   3720
tcctgggagg gagagcttgg caggggtgg gagggaaggg gggatgcgt gacctgcccg      3780 gttctcagtg gccaccctgc gctaccctct cccagaacct gagctgctct gacgcggccg    3840
tctggtgcgt ttcactgatc ctggtgctgc agcttcctta cacttcccaa gaggagaagc    3900
agtttggaaa acaaaatca gaataagttg gtcctgagtt ctaactttgg ctcttcacct    3960
ttctagtccc caatttatat tgttcctccg tgcgtcagtt ttacctgtga gataaggcca    4020
gtagccagcc ccgtcctggc agggctgtgc ctctagggac aggattggtg acg           4073

<210> SEQ ID NO 42
<211> LENGTH: 3089
<212> TYPE: DNA
<213> ORGANISM: Artificial Sequence
<220> FEATURE:
<223> OTHER INFORMATION: pMMEJ-GFP-selection gene plasmid

<400> SEQUENCE: 42
ccaatcctgt ccctagtggc cccactgtgg ggacgtccga tcgaaccatg gacagttagc      60
tttgcaaaga tggataaagt tttaaacaga gaggaatctt tgcagctaat ggaccttcta    120
ggtcttgaaa ggagtgggaa ttggctccgg tgcccgtcag tgggcagagc gcacatcgcc    180
cacagtcccc gagaagttgg ggggaggggt cggcaattga accggtgcct agagaaggtg    240
gcgcggggta aactgggaaa gtgatgtcgt gtactggctc cgcctttttc ccgagggtgg    300
gggagaaccg tatataagtg cagtagtcgc cgtgaacgtt cttttcgca acgggtttgc     360 cgccagaaca caggtaagtg ccgtgtgtgg ttcccgcggg cctggcctct ttacgggtta    420
tggcccttgc gtgccttgaa ttacttccac ctggctgcag tacgtgattc ttgatcccga    480
gcttcgggtt ggaagtgggt gggagagttc gaggccttgc gcttaaggag ccccttcgcc    540
tcgtgcttga gttgaggcct ggcctgggcg ctggggccgc cgcgtgcgaa tctggtggca    600
ccttcgcgcc tgtctcgctg ctttcgataa gtctctagcc atttaaaatt tttgatgacc    660
tgctgcgacg cttttttttct ggcaagatag tcttgtaaat gcgggccaag atctgcacac    720
tggtatttcg gttttttgggg ccgcgggcgg cgacggggcc cgtgcgtccc agcgcacatg    780
ttcggcgagg cggggcctgc gagcgcggcc accgagaatc ggacggggt agtctcaagc     840 tggccggcct gctctggtgg ctggcctcgc gccgccgtgt atcgcccgc cctgggcggc      900 aaggctggcc cggtcggcac cagttgcgtg agcggaaaga tggccgcttc ccggccctgc    960
tgcagggagc tcaaaatgga ggacgcggcg ctcgggagag cgggcgggtg agtcacccac    1020
```

```
acaaaggaaa agggcctttc cgtcctcagc cgtcgcttca tgtgactcca cggagtaccg   1080
ggcgccgtcc aggcacctcg attagttctc gagcttttgg agtacgtcgt ctttaggttg   1140
gggggagggg ttttatgcga tggagtttcc ccacactgag tgggtggaga ctgaagttag   1200
gccagcttgg cacttgatgt aattctcctt ggaatttgcc ctttttgagt ttggatcttg   1260
gttcattctc aagcctcaga cagtggttca aagttttttt cttccatttc aggtgtcgtg   1320
agaattctaa tacgactcac tatagggtgt gctgtctcat cattttggca aagattggcc   1380
accaagctta ccgccatggt gagcaagggc gaggagctgt tcaccggggt ggtgcccatc   1440
ctggtcgagc tggacggcga cgtaaacggc cacaagttca gcgtgtccgg cgagggcgag   1500
ggcgatgcca cctacggcaa gctgaccctg aagttcatct gcaccaccgg caagctgccc   1560
gtgccctggc ccaccctcgt gaccaccctg acctacggcg tgcagtgctt cagccgctac   1620
cccgaccaca tgaagcagca cgacttcttc aagtccgcca tgcccgaagg ctacgtccag   1680
gagcgcacca tcttcttcaa ggacgacggc aactacaaga cccgcgccga ggtgaagttc   1740
gagggcgaca ccctggtgaa ccgcatcgag ctgaagggca tcgacttcaa ggaggacggc   1800
aacatcctgg ggcacaagct ggagtacaac tacaacagcc acaacgtcta tatcatggcc   1860
gacaagcaga agaacggcat caaggtgaac ttcaagatcc gccacaacat cgaggacggc   1920
agcgtgcagc tcgccgacca ctaccagcag aacaccccca tcggcgacgg ccccgtgctg   1980
ctgcccgaca accactacct gagcacccag tccgccctga gcaaagaccc caacgagaag   2040
cgtgatcaca tggtcctgct ggagttcgtg accgccgccg ggatcactct cggcatggac   2100
gagctgtaca aggaaggaag aggcagcctg ctgacatgtg gcgacgtgga ggagaaccct   2160
ggcccaatgg tgggcagcct gaattgtatc gtggccgtgt cccagaacat gggcatcggc   2220
aagaatggcg attttccttg gccccctctg agaaatgagt ccagatactt tcagaggatg   2280
accacaacca gctccgtgga gggcaagcag aacctggtca tcatgggcaa gaagacatgg   2340
ttctctatcc cagagaagaa ccgccccctg aagggccgga tcaatctggt gctgagcagg   2400
gagctgaagg agccacccca gggagcacac tttctgtcca ggtctctgga cgatgccctg   2460
aagctgaccg agcagcctga gctggccaac aaggtggaca tggtgtggat cgtgggcggc   2520
tctagcgtgt ataaggaggc catgaatcac cctggccacc tgaagctgtt cgtgacacgg   2580
atcatgcagg actttgagtc cgataccttc tttccagaga tcgacctgga gaagtacaag   2640
ctgctgcccg agtatcctgg cgtgctgtct gatgtgcagg aggagaaggg catcaagtac   2700
aagttcgagg tgtatgagaa gaacgattga taacatatgc ctttaattaa acactagttc   2760
tatagtgtca cctaaattcc ctttagtgag ggttaatggc cgtaggccgc cagaattggg   2820
tccagacatg ataagataca ttgatgagtt tggacaaacc acaactagaa tgcagtgaaa   2880
aaaatgcttt atttgtgaaa tttgtgatgc tattgcttta tttgtaacca ttataagctg   2940
caataaacaa gttaacaaca acaattgcat tcattttatg tttcaggttc agggggaggt   3000
gtgggaggtt ttttcggact ctaggacctg cgcatgcgct tggggtacct aggatatcgg   3060
atggggcttt tctgtcacca atcctgagg                                      3089
```

<210> SEQ ID NO 43
<211> LENGTH: 4
<212> TYPE: PRT
<213> ORGANISM: Artificial Sequence
<220> FEATURE:
<223> OTHER INFORMATION: A-B loop

```
<400> SEQUENCE: 43

Thr Glu Asp Ser
1

<210> SEQ ID NO 44
<211> LENGTH: 7
<212> TYPE: PRT
<213> ORGANISM: Artificial Sequence
<220> FEATURE:
<223> OTHER INFORMATION: B-C loop

<400> SEQUENCE: 44

Thr Ala Pro Asp Ala Ala Phe
1               5

<210> SEQ ID NO 45
<211> LENGTH: 6
<212> TYPE: PRT
<213> ORGANISM: Artificial Sequence
<220> FEATURE:
<223> OTHER INFORMATION: C-D loop

<400> SEQUENCE: 45

Ser Glu Lys Val Gly Glu
1               5

<210> SEQ ID NO 46
<211> LENGTH: 4
<212> TYPE: PRT
<213> ORGANISM: Artificial Sequence
<220> FEATURE:
<223> OTHER INFORMATION: D-E loop

<400> SEQUENCE: 46

Gly Ser Glu Arg
1

<210> SEQ ID NO 47
<211> LENGTH: 5
<212> TYPE: PRT
<213> ORGANISM: Artificial Sequence
<220> FEATURE:
<223> OTHER INFORMATION: E-F loop

<400> SEQUENCE: 47

Gly Leu Lys Pro Gly
1               5

<210> SEQ ID NO 48
<211> LENGTH: 7
<212> TYPE: PRT
<213> ORGANISM: Artificial Sequence
<220> FEATURE:
<223> OTHER INFORMATION: F-G loop

<400> SEQUENCE: 48

Lys Gly Gly His Arg Ser Asn
1               5
```